US009388405B2

(12) United States Patent
Carlock et al.

(10) Patent No.: US 9,388,405 B2
(45) Date of Patent: Jul. 12, 2016

(54) METHOD FOR IDENTIFYING A SUBPOPULATION OF MAMMALIAN CELLS WITH DISTINCTIVE RIBOSOME TRANSLATION PROFILES

(75) Inventors: Leon Carlock, Bloomfield, MI (US); Maria Cypher, Magnolia, TX (US)

(73) Assignee: Wayne State University, Detroit, MI (US)

(*) Notice: Subject to any disclaimer, the term of this patent is extended or adjusted under 35 U.S.C. 154(b) by 638 days.

(21) Appl. No.: 13/202,286

(22) PCT Filed: Feb. 18, 2010

(86) PCT No.: PCT/US2010/024634
§ 371 (c)(1),
(2), (4) Date: Sep. 30, 2011

(87) PCT Pub. No.: WO2010/096594
PCT Pub. Date: Aug. 26, 2010

(65) Prior Publication Data
US 2012/0107828 A1    May 3, 2012

Related U.S. Application Data

(60) Provisional application No. 61/153,642, filed on Feb. 18, 2009.

(51) Int. Cl.
*C12N 15/01* (2006.01)
*C12N 15/67* (2006.01)

(52) U.S. Cl.
CPC .............. *C12N 15/01* (2013.01); *C12N 15/67* (2013.01)

(58) Field of Classification Search
CPC combination set(s) only.
See application file for complete search history.

(56) References Cited

U.S. PATENT DOCUMENTS

| 6,994,967 | B1 | 2/2006 | Baltimore et al. |
| 2001/0007768 | A1 | 7/2001 | Howell et al. |
| 2004/0043468 | A1 | 3/2004 | Mauro et al. |
| 2006/0173168 | A1 | 8/2006 | Carlock et al. |
| 2008/0227707 | A1 | 9/2008 | Carlock et al. |

FOREIGN PATENT DOCUMENTS

| GB | 2 445 068 A | 6/2008 |
| WO | 01/55371 A1 | 8/2001 |
| WO | 01/72994 A2 | 10/2001 |
| WO | 2004/067728 A2 | 8/2004 |

OTHER PUBLICATIONS

Ludwig, Cell Line Engineering, 2006, supplement, pp. 14-23.*
Suzuki et al., Clinical Cancer Research, 1997, vol. 3, pp. 947-954.*
Kane et al., Recombinant Gene Expression Protocols, 1997, vol. 62, pp. 359-367.*
Stonely et al., Nucleic Acids Research, 2000, vol. 28, pp. 687-694.*
Costa, G. L., et al., "Targeting Rare Populations of Murine Antigen-Specific T Lymphocytes by Retroviral Transduction for Potential Application in Gene Therapy for Autoimmune Disease," The Journal of Immunology, Apr. 1, 2000, pp. 3581-3590, vol. 164, No. 7.
Ghattas, I. R., et al., "The Encephalomyocarditis Virus Internal Ribosome Entry Site Allows Efficient Coexpression of Two Genes from a Recombinant Provirus in Cultured Cells and in Embryos," Molecular and Cellular Biology, Dec. 1991, pp. 5848-5859, vol. 11, No. 12.
Nevins, T. A., et al., "Distinct Regulation of Internal Ribosome Entry Site-mediated Translation Following Cellular Stress is Mediated by Apoptotic Fragments of eIF4G Translation Initiation Factor Family Members eIF4GI and p97/DAP5/NAT1," The Journal of Biological Chemistry, Feb. 7, 2003, pp. 3572-3579, vol. 278, No. 6.
Supplementary European Search Report, EP 10744318.6, dated Sep. 3, 2012, 15 pages.
Anderson, W. F., "Prospects for Human Gene Therapy," Science, Oct. 26, 1984, pp. 401-409, vol. 226, No. 4673.
Baird, S. D., et al., "Searching for IRES," RNA, Oct. 2006, pp. 1755-1785, vol. 12, No. 10.
Bonnal, S., et al., "IRESdb: The Internal Ribosome Entry Site Database," Nucleic Acids Research, Jan. 1, 2003, pp. 427-428, vol. 31, No. 1.
Cornetta, K., et al., "Gene Transfer into Primates and Prospects for Gene Therapy in Humans," Progress in Nucleic Acid Research and Molecular Biology, 1989, pp. 311-322, vol. 36.
Doetschman, T., et al., "Establishment of Hamster Blastocyst-Derived Embryonic Stem (ES) Cells," Developmental Biology, May 1988, pp. 224-227, vol. 127, No. 1.
Eglitis, M. A., et al., "Retroviral Vectors for Introduction of Genes into Mammalian Cells," Jul.-Aug. 1988, pp. 608-614, vol. 6, No. 7.
Friedmann, T., "Progress Toward Human Gene Therapy," Science, Jun. 16, 1989, pp. 1275-1281, vol. 244, No. 4910.
Guhaniyogi, J., et al., "Regulation of mRNA Stability in Mammalian Cells," Gene, Mar. 7, 2001, pp. 11-23, vol. 265, Nos. 1-2.
Jang, S. K., et al., "A Segment of the 5' Nontranslated Region of Encephalomyocarditis Virus RNA Directs Internal Entry of Ribosomes During in Vitro Translation," Journal of Virology, pp. 2636-2643, Aug. 1988, vol. 62, No. 8.
Johnson, L. G., "Gene Therapy for Cystic Fibrosis," Chest, Supplement, Feb. 1995, pp. 77S-83S, vol. 107, No. 2.
Le Gal La Salle, G., et al., "An Adenovirus Vector for Gene Transfer into Neurons and Glia in the Brain," Science, Feb. 12, 1993, pp. 988-990, vol. 259.
Miller, A. D., et al., "Improved Retroviral Vectors for Gene Transfer and Expression," Biotechniques, Oct. 1989, pp. 980-990, vol. 7, No. 9.
Miller, A. D., et al., "Retrovirus Packaging Cells," Human Gene Therapy, 1990, pp. 5-14, vol. 1, No. 1.
Moen, R. C., "Directions in Gene Therapy," Blood Cells, 1991, pp. 407-416, vol. 17, No. 2.
Mount, S. M., "A Catalogue of Splice Junction Sequences," Nucleic Acids Research, 1982, pp. 459-472, vol. 10, No. 2.
Mountford, P. S., et al., "Internal Ribosome Entry Sites and Dicistronic RNAs in Mammalian Transgenesis," TIG, May 1995, pp. 179-184, vol. 11, No. 5.

(Continued)

*Primary Examiner* — Michele K Joike
*Assistant Examiner* — Mindy G Brown
(74) *Attorney, Agent, or Firm* — Senniger Powers LLP

(57) ABSTRACT

The present invention generally relates to subpopulations of mammalian cells with distinctive ribosome translational profiles, i.e. translational activities. The present invention further relates to methods for identifying and isolating such cells, kits comprising the same, or methods which utilize different translational activities of these subpopulations of mammalian cells.

14 Claims, 65 Drawing Sheets

(56) References Cited

OTHER PUBLICATIONS

Pain, B., et al., "Long-Term In Vitro Culture and Characterisation of Avian Embryonic Stem Cells with Multiple Morphogenetic Potentialities," Development, pp. 2339-2348, vol. 122.
Park, S., et al., "Generation of Dopaminergic Neurons in Vitro from Human Embryonic Stem Cells Treated with Neurotrophic Factors," Neuroscience Letters, 2004, pp. 99-103, vol. 359.
Perrier, A. L., et al., "Derivation of Midbrain Dopamine Neurons from Human Embryonic Stem Cells," PNAS, Aug. 24, 2004, pp. 12543-12548, vol. 101, No. 34.
Ridgway, A. A. G., "Mammalian Express Vectors," Vectors, A Survey of Molecular Cloning Vectors and Their Uses, Chapter 24, 1988, pp. 470-472.
Sharp, D., "Gene Therapy," The Lancet, May 25, 1991, pp. 1277-1278, vol. 337.
Sharp, P. A., "Splicing of Messenger RNA Precursors," Science, Feb. 13, 1987, pp. 766-771, vol. 235, No. 4790.
Shim, H., et al., "Isolation of Pluripotent Stem Cells from Cultured Porcine Primordial Germ Cells," Biology of Reproduction, Nov. 1997, pp. 1089-1095, vol. 57, No. 5.
Sukoyan, M. A., et al., "Embryonic Stem Cells Derived from Morulae, Inner Cell Mass, and Blastocysts of Mink: Comparisons of Their Pluripotencies," Molecular Reproduction and Development, Oct. 1993, pp. 148-158, vol. 36, No. 2.
Thomson, J. A., et al., "Isolation of a Primate Embryonic Stem Cell Line," Proceedings of the National Academy of Sciences of the United States of America, Aug. 15, 1995, pp. 7844-7848, vol. 92, No. 17.
Thomson, J. A., et al., "Pluripotent Cell Lines Derived from Common Marmoset (Callithrix jacchus) Blastocysts," Biology of Reproduction, Aug. 1996, pp. 254-259, vol. 55, No. 1.
Tolstoshev, P., et al., "Gene Expression Using Retroviral Vectors," Current Opinion in Biotechnology, Oct. 1990, pp. 55-61, vol. 1, No. 1.
Wheeler, M. B., "Development and Validation of Swine Embryonic Stem Cells: A Review," Reproduction, Fertility, and Development, 1994, pp. 563-568, vol. 6, No. 5.
Zhuang, Y., et al., "UACUAAC is the Preferred Branch Site for Mammalian mRNA Splicing," Proceedings of the National Academy of Sciences of the United States of America, Apr. 1989, pp. 2752-2756, vol. 86, No. 8.
Bandyopadhyay, S., et al., "A High-Throughput Drug Screen Targeted to the 5'Untranslated Region of Alzheimer Amyloid Precursor Protein mRNA," Journal of Biomolecular Screening, 2006, pp. 469-480, vol. 11, No. 5.
Conte, C., et al., "FGF2 Translationally Induced by Hypoxia Is Involved in Negative and Positive Feedback Loops with HIF-1alpha," PLoS ONE, Aug. 2008, e3078, 9 pages, vol. 3, No. 8.
Schiavi, A., et al., "Connexin43 mRNA Contains A Functional Internal Ribosome Entry Site," FEBS Letters, 1999, pp. 118-122, vol. 464.
Spriggs, K. A., et al., "Re-Programming of Translation Following Cell Stress Allows IRES-Mediated Translation to Predominate," Biology of the Cell, 2008, pp. 27-38, vol. 100, No. 1.

* cited by examiner

5-Assay Toxin Analyses of HCT116 mTRdm-fLUC 12-16 Subclone 30

5-Assay Toxin Analyses of HCT116 mTRdm-fLUC 12-16 Subclone 38

FIG. 2C

|   | UNT Sample 1 | UNT Sample 2 | UNT Sample 3 | Average | TPA Sample 1 | TPA Sample 2 | TPA Sample 3 | Average | Fold Induction |
|---|---|---|---|---|---|---|---|---|---|
| 1 | 67127 | 77337 | 62832 | 69099 | 192452 | 197245 | 213040 | 200912 | 2.9 |
| 2 | 620 | 3545 | 1315 | 1827 | 5317 | 13407 | 64 80 | 8401 | ??? |
| 3 | 22647 | 20810 | 24535 | 22664 | 177312 | 184675 | 154145 | 172044 | 7.6 |
| 3A | 103712 | 109960 | 78567 | 97413 | 685087 | 712162 | 749622 | 715624 | 7.3 |
| 4 | 765 | 1335 | 1337 | 1146 | 4757 | 5545 | 3952 | 4751 | 4.1 |
| 5 | 87 | 142 | 212 | 147 | 295 | 600 | 447 | 447 | ??? |
| 6 | 32 | 52 | 47 | 44 | 72 | 82 | 92 | 82 | XX |
| 7 | 21662 | 26500 | 31565 | 26576 | 461725 | 448515 | 475287 | 461842 | 17.4 |
| 8 | 133120 | 144270 | 148070 | 141820 | 946542 | 991710 | 869777 | 936010 | 6.6 |

| Class Assignment using Ranking Plot | | | |
|---|---|---|---|
| | Number | % Responders | Range (Fold Induction) |
| Class 1 | 25 of 43 | 58.1 | 2.4 - 5.0 |
| Class 2 | 13 of 43 | 30.2 | 5.4 - 12.3 |
| Class 3 | 5 of 43 | 11.6 | 15.9 - 128.5 |

| hTRdm-fLUC | | | |
|---|---|---|---|
| Fold Induction | Class # | Fold Induction | Class # |
| 0.8 | 1 | 3.8 | 1 |
| 1.1 | 1 | 4.1 | 1 |
| 1.2 | 1 | 4.1 | 1 |
| 1.3 | 1 | 4.2 | 1 |
| 1.4 | 1 | 4.3 | 1 |
| 1.6 | 1 | 4.6 | 1 |
| 1.6 | 1 | 4.6 | 1 |
| 1.7 | 1 | 4.6 | 1 |
| 1.8 | 1 | 4.8 | 1 |
| 1.8 | 1 | 5.4 | 2 |
| 1.8 | 1 | 5.5 | 2 |
| 1.9 | 1 | 5.5 | 2 |
| 2 | 1 | 5.6 | 2 |
| 2 | 1 | 5.9 | 2 |
| 2 | 1 | 6 | 2 |
| 2 | 1 | 6.1 | 2 |
| 2.1 | 1 | 6.1 | 2 |
| 2.2 | 1 | 6.1 | 2 |
| 2.3 | 1 | 6.2 | 2 |
| 2.4 | 1 | 6.6 | 2 |
| 2.4 | 1 | 6.7 | 2 |
| 2.5 | 1 | 7 | 2 |
| 2.5 | 1 | 7.3 | 2 |
| 2.5 | 1 | 7.6 | 2 |
| 2.6 | 1 | 8.4 | 2 |
| 2.6 | 1 | 8.7 | 2 |
| 2.9 | 1 | 9 | 2 |
| 2.9 | 1 | 9.9 | 2 |
| 2.9 | 1 | 10 | 2 |
| 3 | 1 | 10.1 | 2 |
| 3 | 1 | 10.2 | 2 |
| 3.2 | 1 | 11.2 | 2 |
| 3.3 | 1 | 11.6 | 2 |
| 3.3 | 1 | 11.8 | 2 |
| 3.3 | 1 | 11.8 | 2 |
| 3.4 | 1 | 12.3 | 2 |
| 3.4 | 1 | 14.7 | 3 |
| 3.5 | 1 | 17.4 | 3 |
| 3.6 | 1 | 17.8 | 3 |
| 3.7 | 1 | 24.5 | 3 |
| 3.8 | 1 | 26.6 | 3 |
| n=82 | | | |

| Class Assignment using Ranking Plot | | | |
|---|---|---|---|
| | Number | % Responders | Range (Fold Induction) |
| Class 1 | 50 of 82 | 61.0 | 0.8 - 4.8 |
| Class 2 | 27 of 82 | 32.9 | 5.4 - 12.3 |
| Class 3 | 5 of 82 | 6.1 | 14.7 - 26.6 |

| Class Assignment using Ranking Plot | | | |
|---|---|---|---|
| | Number | % Responders | Range (Fold Induction) |
| Class 1 | 51 of 65 | 78.5 | 1.0 - 4.9 |
| Class 2 | 13 of 65 | 20.0 | 5.7 - 10.4 |
| Class 3 | 1 of 65 | 1.5 | 14.8 |

| Class Assignment using Ranking Plot | | | |
|---|---|---|---|
| | Number | % Responders | Range (Fold Induction) |
| Class 1 | 34 of 39 | 87.2 | 1.2 - 4.3 |
| Class 2 | 4 of 39 | 10.3 | 5.2 - 12.3 |
| Class 3 | 1 of 39 | 2.6 | 23.4 |

| Tentative Class Assignment using Ranking Plot | | | |
|---|---|---|---|
|  | Number | % Responders | Range (Fold Induction) |
| Class 1 | 6 of 11 | 54.5 | 2.2 - 3.2 |
| Class 2 | 4 of 11 | 36.4 | 5.7 - 9.5 |
| Class 3 | 1 of 11 | 9.1 | 23.2 |

| Tentative Class Assignment using Ranking Plot | | | |
|---|---|---|---|
|  | Number | % Responders | Range (Fold Induction) |
| Class 1 | 31 of 36 | 86.1 | 1.5 - 4.2 |
| Class 2 | 3 of 36 | 8.3 | 5.3 - 12.6 |
| Class 3 | 2 of 36 | 5.6 | 15.2 - 23.1 |

| Tentative Class Assignment using Ranking Plot | | | |
|---|---|---|---|
| | Number | % Responders | Range (Fold Induction) |
| Class 1 | 27 of 92 | 29.3 | 1.4 - 4.9 |
| Class 2 | 19 of 92 | 20.7 | 5.2 - 14.0 |
| Class 3 | 46 of 92 | 50.0 | 14.8 - 135.6 |

| Tentative Class Assignment using Ranking Plot | | | |
|---|---|---|---|
|  | Number | % Responders | Range (Fold Induction) |
| Class 1 | 5 of 22 | 22.7 | 1.7 - 5.2 |
| Class 2 | 13 of 22 | 59.1 | 5.8 - 13.2 |
| Class 3 | 4 of 22 | 18.2 | 15.6 - 132.0 |

| Tentative Class Assignment using Ranking Plot | | | |
|---|---|---|---|
|  | Number | % Responders | Range (Fold Induction) |
| Class 1 | 10 of 65 | 15.4 | 1.3 - 4.2 |
| Class 2 | 33 of 65 | 50.8 | 5.8 - 13.9 |
| Class 3 | 22 of 65 | 33.8 | 14.1 - 132.0 |

| Tentative Class Assignment using Ranking Plot | | | |
|---|---|---|---|
| | Number | % Responders | Range (Fold Induction) |
| Class 1 | 20 of 21 | 95.2 | 1.0 - 2.4 |
| Class 2 | 1 of 21 | 4.8 | 6.6 |
| Class 3 | 0 of 21 | -- | -- |

| Tentative Class Assignment using Ranking Plot | | | |
|---|---|---|---|
| | Number | % Responders | Range (Fold Induction) |
| Class 1 | 11 of 12 | 91.7 | 1.0 - 3.9 |
| Class 2 | 0 of 12 | -- | -- |
| Class 3 | 1 of 12 | 8.3 | 17.2 |

HCT116 CMV-fLUC Class Assignment using Ranking Plot

| Tentative Class Assignment using Ranking Plot ||||
|---|---|---|---|
|  | Number | % Responders | Range (Fold Induction) |
| Class 1 | 6 of 6 | 100.0 | 1.7 - 3.8 |
| Class 2 | 0 of 6 | -- | -- |
| Class 3 | 0 of 6 | -- | -- |

HCT116 mTRdm-fLUC Class Assignment using Ranking Plot

| Tentative Class Assignment using Ranking Plot ||||
|---|---|---|---|
|  | Number | % Responders | Range (Fold Induction) |
| Class 1 | 29 of 39 | 74.4 | 0.7 - 4.3 |
| Class 2 | 8 of 39 | 20.5 | 5.2 - 13.5 |
| Class 3 | 2 of 39 | 5.1 | 14.3 - 46.9 |

| Tentative Class Assignment using Ranking Plot | | | |
|---|---|---|---|
|  | Number | % Responders | Range (Fold Induction) |
| Class 1 | 0 of 5 | -- | -- |
| Class 2 | 3 of 5 | 60.0 | 6.0 - 9.8 |
| Class 3 | 2 of 5 | 40.0 | 15.5 - 24.5 |

| mTRdm-fLUC HCT116 Cell Recovery measured using TPA+Taxol assay | |
|---|---|
| Clonal Name | Student's T-Test (High passage to Recovered) |
| 7-2 | p = 0.00395 |
| 12-16 | p = 0.0000011 |
| Sub #30 | p = 0.001146 |
| Sub #38 | p = 0.01889 |

| mTRdm-fLUC HCT116 Cell Recovery measured using TPA assay | |
|---|---|
| Clonal Name | Student's T-Test (High passage to Recovered) |
| 7-2 | p = 0.000018 |
| 12-16 | p = 0.0174 |
| Sub #30 | p = 0.0061 |
| Sub #38 | p = 0.0446 |

FIG. 15A
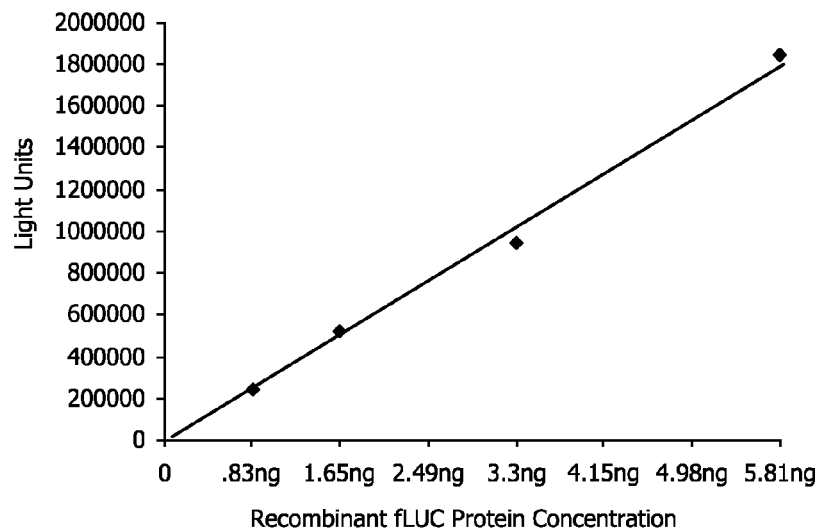
FIG. 15B
| Toxin Treatment | Graph Value 1/10 total cell number |
|---|---|
| dbcAMP | 2.2ng |
| TPA | 5.2ng |
| Taxol | 4.2ng |
| MG132 | 12.6ng |
| Calon | 3.4ng |
| dbcAMP+TPA | 2.0ng |
| dbcAMP+Taxol | 1.4ng |
| dbcAMP+MG132 | 4.7ng |
| dbcAMP+Calon | 1.7ng |
| TPA+Taxol | 53.0ng |
| TPA+MG132 | 23.5ng |
| TPA+Calon | 5.6ng |
| Taxol+MG132 | 3.9ng |
| Taxol+Calon | 7.6ng |
| MG132+Calon | 6.8ng |
FIG. 15C
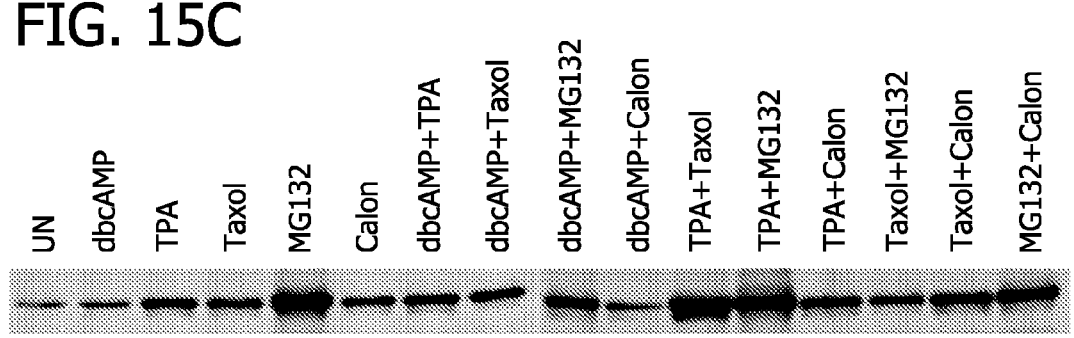

FIG. 26A

```
          1         10        20        30        40        50        60        70        80        90        100
          |         |         |         |         |         |         |         |         |         |         |
mDM       atggcttgttagagtgttgtgtctagatgtgctagagggccccctttgcttcccctggtgctggccactggatgtgttcttttgagtggcactgttctgtg
mPLP      atggcttgttagagtgttgtgtctagatgtgctagagggccccctttgcttcccctggtgctggccactggatgtgttcttttgagtggcactgttctgtg
mTRd      ttgagtgagtgagagtagtagtagtagtagtagggccccctttgcttcccctggtgctggccactggatgtgttcttttgagtggcactgttctgtg
mTRp      ttgagtgagtgagagtagtagtagtagtagtagggccccctttgcttcccctggtgctggccactggatgtgttcttttgagtggcactgttctgtg
hTRd      ttgagtgagtgagagtagtagtagtagtagtagggccccctttgcttcccctggtgctggccactggatgttttctttggggtggcactgttctgtg
hTRp      ttgagtgagtgagagtagtagtagtagtagtagggccccctttgcttcccctggtgctggccactggatgttttctttggggtggcactgttctgtg
hDM       atgggcttgttagagtgctgtgtgcaagatgctgtgcaagatgtcaagatgtcaagatggggccccctttgcttcccctggtgctggccactggatgttttctttggggtggcactgttctgtg
hPLP      atgggcttgttagagtgctgtgtgcaagatgctgtgcaagatggggccccctttgcttcccctggtgctggccactggatgttttctttggggtggcactgttctgtg 101       110       120       130       140       150       160       170       180       190       200
          |         |         |         |         |         |         |         |         |         |         |
mDM       gatgtggacatgaagctcactggtacagaaaagctaattgagacctatttctccaaaaactaccaggactatgagtatctcattaatgtgattcatgc
mPLP      gatgtggacatgaagctcactggtacagaaaagctaattgagacctatttctccaaaaactaccaggactatgagtatctcattaatgtgattcatgc
mTRd      gatgtggacatgaagctcactggtacagaaaagctaattgagacctatttctccaaaaactaccaggactatgagtatctcattaatgtgattcatgc
mTRp      gatgtggacatgaagctcactggtacagaaaagctaattgagacctatttctccaaaaactaccaggactatgagtatctcattaatgtgattcatgc
hTRd      gctgtggacatgaagccctcactggccactggcacagaaaagctaattgagacctatttctccaaaaactaccaggactatgagtatctcatcaatgtgattcatgc
hTRp      gctgtggacatgaagccctcactggccactggcacagaaaagctaattgagacctatttctccaaaaactaccaggactatgagtatctcatcaatgtgattcatgc
hDM       gctgtggacatgaagccctcactggccactggcacagaaaagctaattgagacctatttctccaaaaactaccaggactatgagtatctgatcaatgc
hPLP      gctgtggacatgaagccctcactggccactggcacagaaaagctaattgagacctatttctccaaaaactaccaggactatgagtatctgatcaatgc 201       210       220       230       240       250       260       270       280       290       300
          |         |         |         |         |         |         |         |         |         |         |
mDM       tttccagtatgtcatctatgaactgcctcttcttcttcttcttcttcttcttcttcttcttatgggccctcctgctgctgctgctgctgctgctgctgagggcttctacaccaccaccggcgctgtcaggcagatc
mPLP      tttccagtatgtcatctatgaactgcctcttcttcttcttcttcttcttcttcttcttatgggccctcctgctgctgctgctgctgctgctgctgagggcttctacaccaccaccggcgctgtcaggcagatc
mTRd      tttccagtatgtcatctatgaactgcctcttcttcttcttcttcttcttcttcttcttatgggccctcctgctgctgctgctgctgctgctgctgagggcttctacaccaccaccggcgctgtcaggcagatc
mTRp      tttccagtatgtcatctatgaactgcctcttcttcttcttcttcttcttcttcttcttatgggccctcctgctgctgctgctgctgctgctgctgagggcttctacaccaccaccggcgctgtcaggcagatc
hTRd      tttccagtatgtcatctatgaactgcctcttcttcttcttcttcttcttcttcttcttatgggccctcctgctgctgctgctgctgctgctgctgagggcttctacaccaccaccggcgctgtcaggcagatc
hTRp      tttccagtatgtcatctatgaactgcctcttcttcttcttcttcttcttcttcttcttatgggccctcctgctgctgctgctgctgctgctgctgagggcttctacaccaccaccggcgctgtcaggcagatc
hDM       cttccagtatgtcatctatgaactgcctcttcttcttcttcttcttcttcttcttcttatgggccctcctgctgctgctgctgctgctgctgctgagggcttctacaccaccaccggcgctgtcagtcagatc
hPLP      cttccagtatgtcatctatgaactgcctcttcttcttcttcttcttcttcttcttcttatgggccctcctgctgctgctgctgctgctgctgctgagggcttctacaccaccaccggcgctgtcagtcagatc
```

FIG. 26C

```
         610        620        630        640        650        660        670        680        690        700
          |          |          |          |          |          |          |          |          |          |
mDM   tgcgctgatgcagcagaatgtatggtgttctgccatggaatgcttccctggctcccaaccttctgtgcctccatctgcaaaacagctgagttcc
mPLP  tgcgctgatgcagcagaatgtatggtgttctgccatggaatgcttccctggctcccaaccttctgtgcctccatctgcaaaacagctgagttcc
mTRd  tgcgctgatgcagcagaatgtatggttgttctgccatggaatgcttccctggctcccaaccttctgtgcctccatctgcaaaacagctgagttcc
mTRp  tgcgctgatgcagcagattgtatggtgttctgccatggaatgcttccctggctcccaaccttctgtgcctccatctgcaaaacagctgagttcc
hTRd  tgtgctgacgcagcagaatgtatggtgttctgccatggaatgcttccctggctcccaaccttctgtgcctccatctgcaaaacagctgagttcc
hTRp  tgtgctgacgcagcagaatgtatggtgttctgccatggaatgcttccctggctcccaaccttctgtgcctccatctgcaaaacagctgagttcc
hDM   tgtgctgacgcagcagaatgtatggtgttctgccatggaatgcttccctggctcccaaccttctgtgcctccatctgcaaaacagctgagttcc
hPLP  tgtgctgacgcagcagaatgtatggtgttctgccatggaatgcttccctggctcccaaccttctgtgcctccatctgcaaaacagctgagttcc
                    |          |          |          |          |          |          |          |
                   500        510        520        530        540        550        560        570        580        590

710        720        730        740        750        760        770        780        790        800
          |          |          |          |          |          |          |          |          |          |
mDM   aaatgaccttccacctgtttattgctgctgcggccacactagtttccctgctcaccttcatgattgctgccacttacaacttcgccgt
mPLP  aaatgaccttccacctgtttattgctgctgcggccacactagtttccctgctcaccttcatgattgctgccacttacaacttcgccgt
mTRd  aattgaccttccacctgtttattgctgctgcggccacactagtttccctgctcaccttcatgattgctgccacttacaacttcgccgt
mTRp  aattgaccttccacctgtttattgctgctgcggccacactagtttccctgctcaccttcatgattgctgccacttacaacttcgccgt
hTRd  aattgaccttccacctgtttattgctgttgctgcggccacactagttcccctggttccctgctcaccttcatgattgctgccacttacaacttcgccgt
hTRp  aattgaccttccacctgtttattgctgttgctgcagccacactagttcccctggttccctgctcaccttcatgattgctgccacttacaacttcgccgt
hDM   aaatgaccttccacctgtttattgctgttgcagccacactagttcccctggttccctgctcaccttcatgattgctgccacttacaacttcgccgt
hPLP  aaatgaccttccacctgtttattgctgttgcagccacactagttcccctggttccctgctcaccttcatgattgctgccacttacaacttcgccgt
                    |          |          |          |          |          |          |          |
                   600        610        620        630        640        650        660        670        680        690

810        820        830        840        850
          |          |          |          |          |
mDM   ccttaaactcatgggccgaggccaccaagttctga
mPLP  ccttaaactcatgggccgaggccaccaagttctga
mTRd  ccttaaactcatgggccgaggccaccaagttc
mTRp  ccttaaactcatgggccgaggccaccaagttc
hTRd  ccttaaactcatgggccgaggccaccaagttc
hTRp  ccttaaactcatgggccgaggccaccaagttc
hDM   ccttaaactcatgggccgaggccaccaagttctga
hPLP  ccttaaactcatgggccgaggccaccaagttctgatacactggtttccctg
                    |          |          |          |
                   700        710        720        730        740
```

MCF7 mTR Bryostatin 1 Dose Response Assay

MCF7 mTRdm Bryostatin 2 Dose Response Assay

HEK293 CMV-fLUC Translation Inhibitors

HEK293 hTRdm-fLUC Translation Inhibitors

HEK293 mTRdm-fLUC Translation Inhibitors

| mTRdm-fLUC #45 Response to 25uM Translation Inhibitors | |
|---|---|
| Drug Comparison | Student's T-test (mTR #45 to hTR #13 Result) |
| TPA+25uM Cycloheximide | P = 0.01541 |
| TPA+25uM Anisomycin | P = 0.24151 |
| TPA+25uM Puromycin | P = 0.00006 |
| TPA+25uM Emetine | P = 0.00169 |

METHOD FOR IDENTIFYING A SUBPOPULATION OF MAMMALIAN CELLS WITH DISTINCTIVE RIBOSOME TRANSLATION PROFILES

FIELD OF THE INVENTION

The present invention generally relates to subpopulations of mammalian cells with distinctive ribosomal profiles, i.e. translational activities. The present invention further relates to methods for identifying and isolating such cells, kits comprising the same, or methods which utilize these subpopulations of mammalian cells.

BACKGROUND OF THE INVENTION

Normal biological activity in a living organism combines endogenous expression of genes that constitute an individual's genome with responses to the outside world. In higher eukaryotes, gene expression begins in the nucleus with transcription of genomic DNA into a pre-mRNA or "primary" RNA transcript. While still in the nucleus, the pre-mRNA is modified to include a 5' cap structure, forms heteronuclear ribonucleoprotein (hnRNP) complexes, acquires a 3' polyadenylate tail and undergoes splicing to remove intervening RNA sequences (e.g. introns). The mature mRNA is then exported to the cytoplasm where protein complexes direct (1) association with ribosomes via the 5' cap structure, termed Cap-dependent translation, or (2) interaction with cytosolic RNA binding proteins that facilitate mRNA storage, processing or degradation. Following ribosome-driven translation, sequential shortening of the 3'-polyadenylate tail results in transport of the mRNA body to a complex of ribonucleases (RNAses), termed the exosome, which degrades the aged mRNA and effectively terminates protein synthesis.

As expected, gene expression is a highly regulated process that must produce a desired gene product (typically a polypeptide) at a particular time, rate and quantity. In addition to transcriptional regulation, post-transcriptional processes such as mRNA decay and translation are key checkpoints in gene expression. It is not surprising that changes in a cellular expression profile, produced by genetic mutations or aberrant responses to external stimuli can cause severe abnormalities that often result in acute cell death or the manifestation of a chronic disease phenotype.

Extensive or prolonged cellular stimulation by environmental factors, such as altered nutrient levels, cytokines, hormones and temperature shifts, as well as environmental stresses like hypoxia, hypocalcemia, viral infection and tissue injury, results in the rapid attenuation of cap-dependent translation. This process is adaptive as it curtails global protein synthesis which is not needed for an immediate stress response and recovery. However, this translational abatement does not completely eliminate ribosome activity, since many products of stress response and recovery genes continue to be synthesized by an alternative process, termed cap-independent translation (reviewed in Guhaniyogi & Brewer, 2001, Gene 265 (1-2):11-23).

Cap-independent translation occurs by direct recruitment of ribosomes to specific RNA structures termed Internal Ribosome Entry Sites (IRESs). IRES elements have been identified in a number of eukaryotic mRNAs (Bonnal S et al., (2003) Nucleic Acids Res. 31:427-428) and ensure the efficient expression of proteins or fragments thereof during nuclear inactivity or acute cellular stress when "cap-dependent" translation initiation is inhibited (i.e., apoptosis, starvation, gamma-irradiation, hypoxia, mitosis, or terminal differentiation).

Bypassing the requirement for a 5' mRNA cap structure was initially described as a mechanism for translating viral RNAs irrespective of a near complete inhibition of cellular cap-dependent translation in infected cells (Jang et al., 1988, J. Virol., 62:2636-43). Generally, IRES sequences cannot be identified by sequence homology and well characterized IRES elements have been verified using functional assays (Mountford and Smith, 1995, TIG, 11(5): 179-184; Baird et al., 2006, NAR, 12(10):1755-85). Current evidence shows that the conformation of the IRES RNA and the binding of accessory proteins to specific mRNA sequences enable ribosome binding. In eukaryotic cells, IRES-directed translation has often been associated with ~5' untranslated regions (5'UTRs) of mRNAs that contain unusually long and thermodynamically stable RNA secondary structures with multiple short open reading frames (ORFs) that dramatically inhibit the initiation of ribosome-dependent translation. However, functional verification of IRES activity for many of these 5'UTR IRES elements has been complicated by the presence of transcriptional effector sequences cloned from the overlapping 5' gene promoter. Attempts to employ these 5'UTR elements in IRES reporter vectors have been complicated by this residual background transcriptional activity which masks any translational regulation produced by these sequences. Thus, the cap-independent translation and its regulation are still highly unexplored, as are the systems which utilize translation in general as a readout tool.

SUMMARY OF THE INVENTION

It is one object of the present invention to provide a method for identifying a desired subpopulation of mammalian cells. The method comprises treating a subset of mammalian cells with at least one toxin to form toxin-treated cells, the mammalian cells being stably transformed with a nucleic acid expression cassette comprising either: (1) a TR element encoding an mRNA molecule that is selectively translated in stressed and/or dying cells, and a nucleotide sequence operably linked to the TR element, which encodes a reporter gene and is translated from the TR element; or (2) a constitutive promoter and a nucleotide sequence operably linked to the promoter, which encodes a reporter gene; measuring a level of a reporter protein encoded by the reporter gene in the toxin-treated cells as compared to a level of the reporter protein expressed by a reference standard to identify whether the subset of mammalian cells exhibit the phenotype of the desired subpopulation of mammalian cells; isolating at least one cell from the mammalian cells to form a cell culture if the toxin-treated cells of the mammalian cells exhibit the phenotype of the desired subpopulation of the mammalian cells; growing the cell culture to form a subpopulation of mammalian cells; and optionally treating the subpopulation of mammalian cells with at least one toxin and repeating the measuring, isolating, and growing steps until the desired subpopulation of mammalian cells is identified.

It is another object of the present invention to provide a method for identifying whether or not mammalian cell translation is resistant to a substance or for determining whether or not a substance is toxic to mammalian cells. The method comprises stably transforming the mammalian cells with a nucleic acid expression cassette comprising either: (1) a TR element encoding an mRNA molecule that is selectively translated in stressed and/or dying cells, and a nucleotide sequence operably linked to the TR element, which encodes a reporter gene and is translated from the TR element; or (2) a constitutive promoter and a nucleotide sequence operably linked to the promoter, which encodes a reporter gene to form stably transformed cells; treating a subset of stably transformed mammalian cells with at least one toxin to form toxin-treated cells, measuring a level of a reporter protein encoded by the reporter gene in the toxin-treated cells as compared to a level of the reporter protein expressed by a reference standard to identify whether the subset of stably transformed mammalian cells exhibit the phenotype of the desired subpopulation of mammalian cells; isolating at least one cell from the stably transformed mammalian cells to form a cell culture if the toxin-treated cells of the mammalian cells exhibit the phenotype of the desired subpopulation of the mammalian cells; growing the cell culture to form a subpopulation of mammalian cells; optionally treating the subpopulation of mammalian cells with the at least one toxin and repeating the measuring, isolating, and growing steps until the desired subpopulation of mammalian cells is identified; contacting the desired subpopulation of the mammalian cells with the substance; and detecting presence or measuring levels of the reporter protein after the desired subpopulation of the mammalian cells is contacted with the substance, wherein the toxicity of the substance and resistance of mammalian cell translation to the substance correlates to the presence or the increase in the level of the reporter protein as compared to control mammalian cells that are not exposed to the substance, and lack of toxicity to the substance and lack of resistance of mammalian cell translation to the substance correlates to the absence or the decrease in the level of the reporter protein as compared to control mammalian cells that are not exposed to the substance.

It is still another object of the present invention to provide subpopulations of mammalian cells with distinctive ribosomal profiles obtained by the methods of the present invention. Related to that, the present invention further provides Class I, Class II, and Class III mammalian cells as defined herein.

Yet another object of the present invention is the provision of kits, which include instructions for the use of the kit along with Class I cells or lysates thereof, Class II cells or lysates thereof, or alternatively Class III cells or lysates thereof.

It is another object of the present invention to provide a method for recombinantly expressing a polypeptide of interest. The method comprises introducing a second nucleic acid expression cassette into the class III mammalian cells, the expression cassette comprising either (1) a TR element encoding a mRNA molecule that is selectively translated in stressed and/or dying cells, and a nucleotide sequence operably linked to the TR element, which encodes a reporter gene and is translated from the TR element; or (2) a constitutive promoter and a nucleotide sequence operably linked to the promoter, which encodes a reporter gene; growing the mammalian cells expressing the second nucleic acid expression cassette under conditions which allow for expression of the polypeptide of interest; and purifying the polypeptide of interest.

The present invention also relates to a mammalian cell used to produce a polypeptide of interest obtained by a method comprising the steps of introducing a second nucleic acid expression cassette into the class III mammalian cell, the expression cassette comprising either (1) a TR element encoding an mRNA molecule that is selectively translated in stressed and/or dying cells, and a nucleotide sequence operably linked to the TR element, which encodes a reporter gene and is translated from the TR element; or (2) a constitutive promoter and a nucleotide sequence operably linked to the promoter, which encodes a reporter gene; and growing the mammalian cell expressing the second nucleic acid expression cassette under conditions which allow for expression of the polypeptide of interest.

Still another object of the present invention is the provision of a method for identifying a protein involved in regulation of cap-independent translation. The method comprises treating mammalian cells with at least one toxin to form toxin-treated cells, the mammalian cells being stably transformed with a nucleic acid expression cassette comprising a TR element encoding an mRNA molecule that is selectively translated in stressed and/or dying cells, and a nucleotide sequence operably linked to the TR element, which encodes a reporter gene and is translated from the TR element; preparing a cell lysate from the toxin-treated cells; isolating mRNA encoding the TR element and the nucleotide sequence operably linked to the TR element; contacting the mRNA and protein from the cell lysate to form protein bound to the mRNA; and identifying the protein bound to the mRNA.

The present invention also provides a method for verifying that Class I, Class II, or Class III mammalian cells retain their translational phenotype. The method comprises treating a subset of the class I, class II or class III mammalian cells with toxin(s); measuring a level of a reporter protein encoded by the reporter gene in the subset of mammalian cells as compared to a level of the reporter protein expressed by a reference standard; verifying that the mammalian cells retain their phenotype wherein the class I cells are characterized by the expression of the reporter protein that is up to 500% greater than the expression of the reporter protein in the mammalian cells which have not been treated with the toxins, the class II cells are characterized by the expression of the reporter protein that is more than 500% to 1400% greater than the expression of the reporter protein in the mammalian cells which have not been treated with the toxins, and the class III cells are characterized by the expression of the reporter protein that is more than 1400% to about 75000% greater than the expression of the reporter protein in the mammalian cells which have not been treated with the toxins.

It is yet another object of the present invention to provide a method for determining the ability of a substance to inhibit protein translation in mammalian cells. The method comprises contacting Class I, II or III mammalian cells with the substance; and determining the expression of the reporter protein produced by the mammalian cells after contact with the substance as compared to the expression of the reporter protein by the cells which have not been treated with the substance, wherein reduction in the expression of the reporter protein produced by the substance-treated cells as compared to the expression of the reporter protein produced by the cells which have not been treated with the substance indicates that the substance inhibits protein translation.

It is another object of the present invention to provide a method for restoring a phenotype of a desired subpopulation of mammalian cells. The method comprises culturing at least a subset of the mammalian cells to form cultured cells, wherein the mammalian cells are stably transformed with a nucleic acid expression cassette comprising a nucleotide sequence for a selectable marker and either: (1) a TR element encoding an mRNA molecule that is selectively translated in stressed and/or dying cells, and a nucleotide sequence operably linked to the TR element, which encodes a reporter gene and is translated from the TR element; or (2) a constitutive promoter and a nucleotide sequence operably linked to the promoter, which encodes a reporter gene; treating the cultured cells with a substance to which the selectable marker provides resistance, such that the cultured cells which no longer contain the nucleic acid expression cassette die; growing the treated cells to form a subpopulation of mammalian cells; and optionally repeating the culturing, treating and growing steps until the phenotype of the desired subpopulation of mammalian cells is restored.

Other objects and features will be in part apparent and in part pointed out hereinafter.

BRIEF DESCRIPTION OF THE DRAWINGS

FIG. 1 shows the TR-specific responses of the human HCT116 cell line to the 5-Assay and 15-Assay procedures.

FIG. 1C shows the highly significant increase in TR-regulated translation in the combinatorial TPA+Taxol two-Toxin assay that was not observed in the single-Toxin 5-Assays.

FIG. 2 shows the application of Toxin Assay procedures for identifying and assigning translationally responsive HEK293 cells to defined Classes.

FIG. 2C illustrates an example of the plate reader results for nine subclones from the HEK293 hTRdm-fLUC pool. Triplicate samples were treated with no toxin (UNT) or the TPA single-Toxin assay (TPA). The plate reader values were averaged and expressed as the ratio of untreated to treated samples (Fold Induction). For samples with any raw value statistically out of the range of the remaining duplicate values, a questionable response is assigned and these samples are rescreened in a subsequent assay (marked with question marks). Samples exhibiting uniformly low values (at or near the plate reader background for a given Gain setting) are considered nonresponsive and removed from any continuing evaluation (marked with XX). In this example, 9 random samples returned 6 responding clones (Fold induction range of 4.1 to 17.4), 2 questionable clones and 1 clone exhibiting background values.

FIG. 2D Top panel shows a plot of 43 HEK293 mTRdm-fLUC cell subclones as a function of rank order, lowest to highest on the x-axis, to Fold Induction (y-axis) which is termed a Ranking Plot. The middle panel shows the same ranking plot with the maximal outlier species removed to highlight responding subclones with smaller translational responses. Table shows the Class assignment using the compilation of all Ranking Plot results to define Class designations. For the HEK293 mTRdm-fLUC cell pool, 25 of 43 responders (58.1%) displayed a low TR-specific toxin response with a Fold Induction value under 5.0 (termed Class I cells), 13 of 43 subclones (30.2%) exhibited a Class II phenotype (ranging from over 5.0 to 14.0) and 5 of 43 subclones (11.6%) exhibited a Class III phenotype (over 14.0 fold induction).

FIG. 2E Left Table demonstrates the Fold Inductions observed for 82 HEK293 hTRdm-fLUC cell subclones and a Class assignment. The top right panel shows a Ranking Plot of the 82 HEK293 hTRdm-fLUC cell subclones. The right table shows the Class assignment for the HEK293 hTRdm-fLUC cell pool. 50 of 82 responders (61.0%) displayed a Class I response, 27 of 82 subclones (32.9%) exhibited a Class II phenotype and 5 of 82 subclones (6.1%) exhibited a Class III phenotype.

FIG. 2F The top panel is a Ranking Plot showing the 65 HEK293 mTRplp-fLUC subclones. The bottom table shows the Class assignment for the HEK293 mTRplp-fLUC cell pool. 51 of 65 subclones (78.5%) were Class I cells, 13 of 65 (20.0%) exhibited a Class II phenotype and 1 of 65 (1.5%) displayed a Class III response.

FIG. 2G The top panel is a Ranking Plot showing the 39 HEK293 CMV-fLUC subclone responses. The bottom table shows the Class assignment for the HEK293 CMV-fLUC pool; 34 of 39 subclones (87.2%) showed a Class I response, 4 of 39 (10.3%) exhibited a Class II phenotype and 1 of 39 (2.6%) produced a Class III response.

FIG. 3 displays the application of the Toxin Assay procedure for identifying and assigning translationally responsive HEK293 cells to defined classes.

FIG. 4 displays the application of the Toxin Assay procedure for identifying and assigning translationally responsive U2OS cells to defined classes.

FIG. 5 displays the application of the Toxin Assay procedure for identifying and assigning translationally responsive MCF7 cells to defined Classes.

FIG. 6 displays the application of the Toxin Assay procedure for identifying and assigning translationally responsive DU145 cells to defined Classes.

FIG. 7 displays the application of the Toxin Assay procedure for identifying and assigning translationally responsive HCT116 cells to defined Classes.

FIG. 8 displays the application of the Toxin Assay procedure for identifying and assigning translationally responsive MDA231 cells to defined Classes.

FIG. 9 displays the application of the Toxin Assay procedure for identifying and assigning translationally responsive HepG2 cells to defined Classes.

FIG. 10 shows the application of the 15-Assay procedure to Class defined cell lines.

CMV-fLUC 1-21, 2-5 and 1-20 subclones exhibited increased fLUC levels, each subclone still expressed a Class I phenotype.

FIG. 11 shows the protocol for recovering a Class defined phenotype by colony formation and subcloning.

Figure 10A:
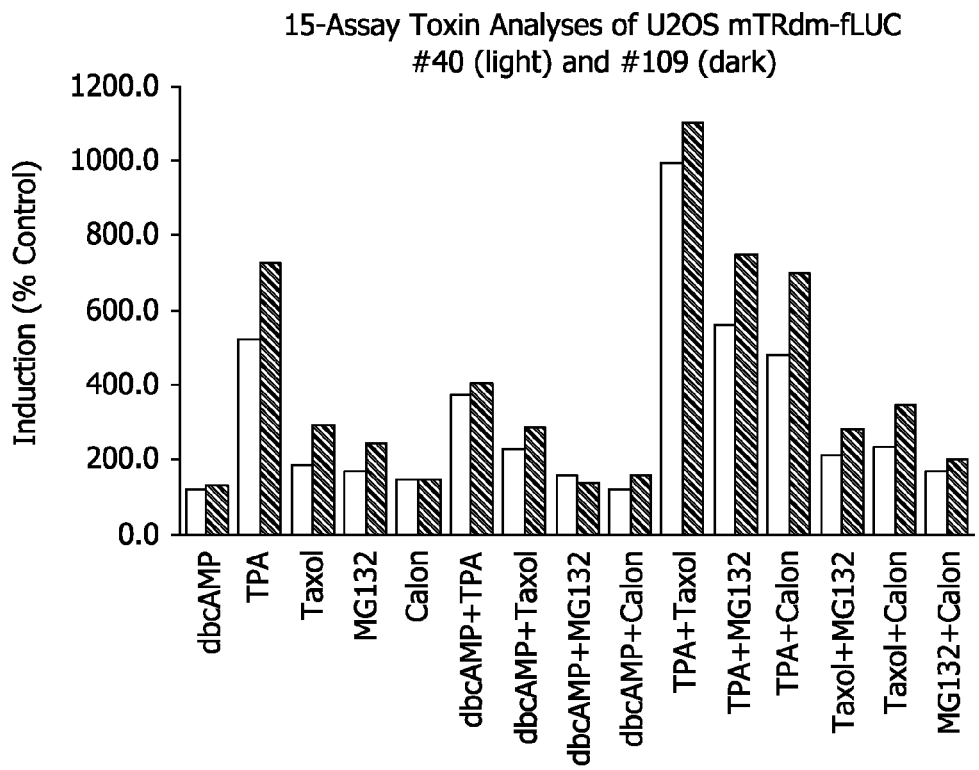
FIG. 10A shows a histogram of the U2OS mTRdm-fLUC #40 (light bar) and #109 (dark bar) subclones subjected to the 15-Assay procedure. Both subclones were assigned Class II designations in FIG. 4 using a single toxin assay but were reanalyzed using the Cell Count plating procedure as described in the examples. The composition and concentration of the toxins in this figure are described in Table 3. Both subclones continued to exhibit Class II responses. Of note, the Y axis in FIG. 10 is shown as induction in % of untreated Control instead of fold induction as in the previous figures. % induction can be converted to fold induction by dividing the % by 100 (e.g., 1000% of control is a 10 fold induction).
Figure 10B:
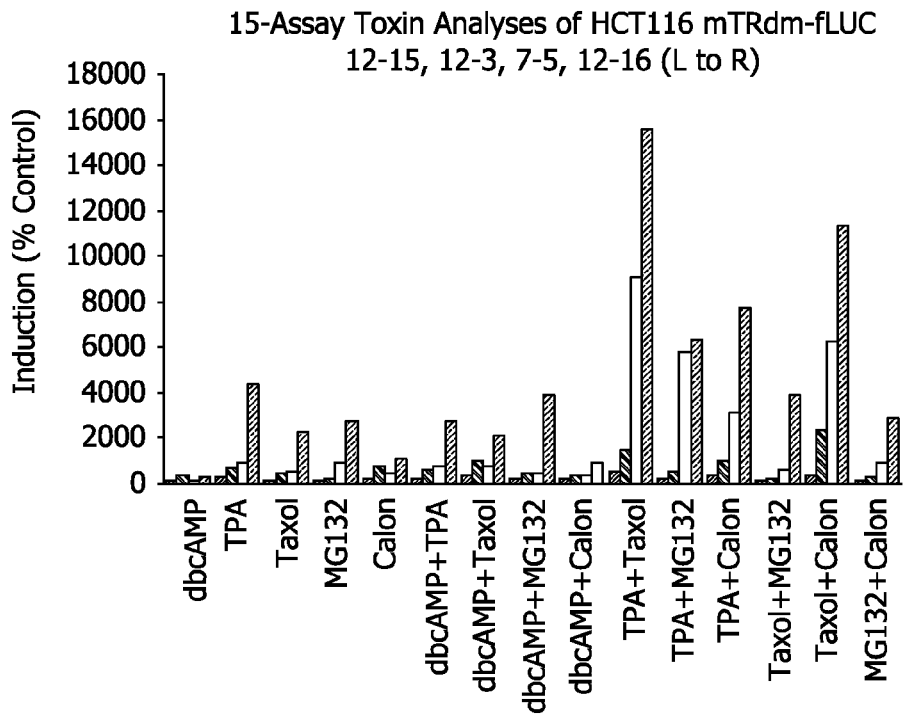
FIG. 10B shows a histogram of the reanalysis of four HCT116 mTRdm-fLUC subclones using the Cell Count plating procedure. These subclones had been previously assigned a Class I designation in FIG. 7 using a suboptimal single-Toxin assay. This histogram illustrates the enhanced TR responses produced in the 15-Assay procedure by the HCT116 mTRdm-fLUC 12-15, 12-3, 7-5 and 12-16 subclones (left to right) treated with the TPA+Taxol two-Toxin assay. Whereas the HCT116 mTRdm-fLUC 12-15 and 12-3 subclones continued to express a Class I phenotype, the HCT116 mTRdm-fLUC 7-5 and 12-16 subclones showed Class III phenotypes.
Figure 10F:
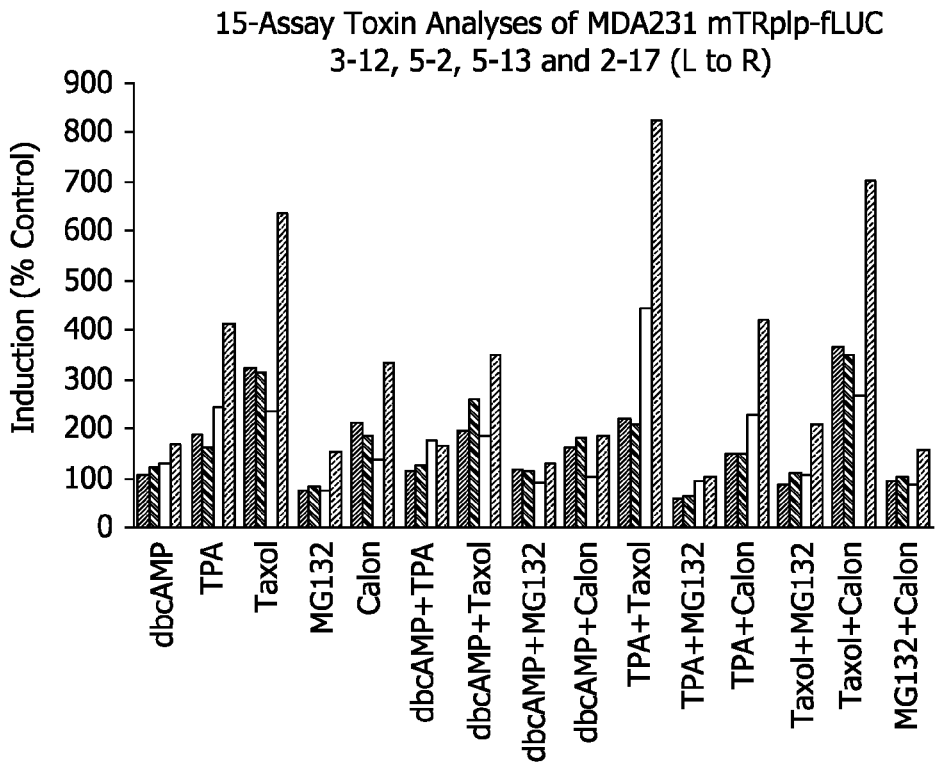
FIG. 10F shows a histogram of the reanalysis of four MDA231 mTRplp-fLUC subclones using the Cell Count plating procedure. These cells were previously assigned a Class I designation in FIG. 8B using a suboptimal single-Toxin assay. This histogram illustrates the TR responses produced in the 15-Assay procedure by the MDA231 mTRplp-fLUC 3-12, 5-2, 5-13 and 2-17 subclones (left to right). Whereas the MDA231 mTRplp-fLUC 3-12, 5-2 and 5-13 subclones expressed only a Class I phenotype, the MDA231 mTRplp-fLUC 2-17 subclone exhibited a Class II response in the TPA+Taxol two-Toxin assay.
Figure 10G:
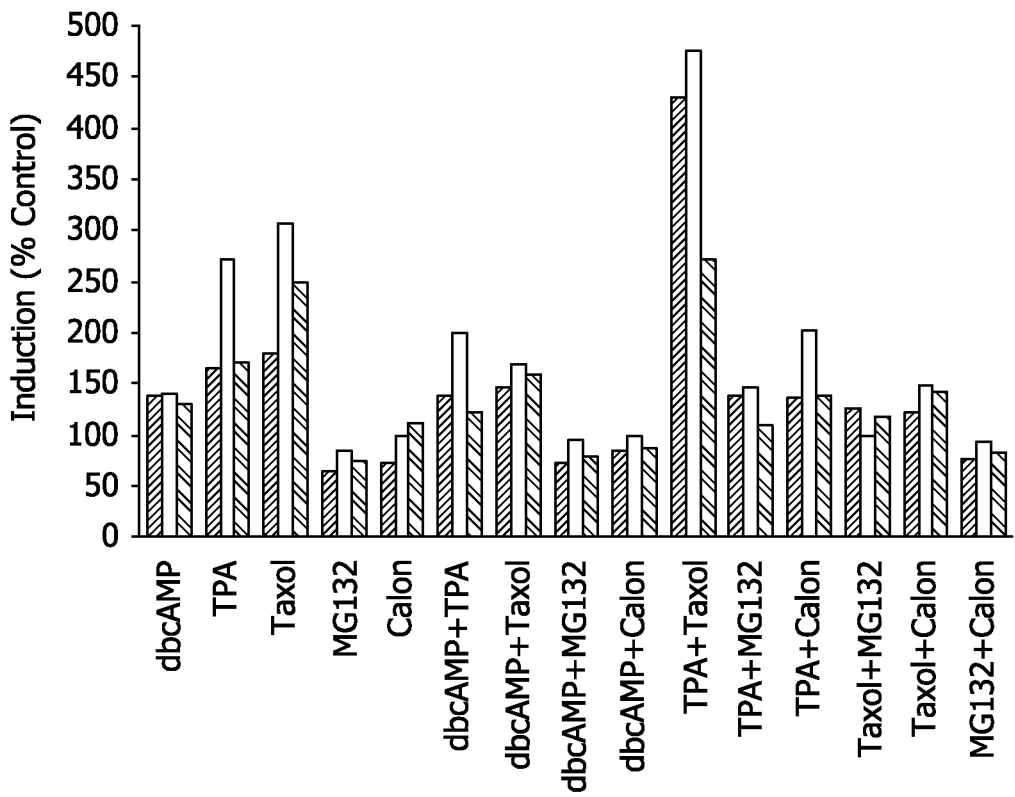
FIG. 10G shows a histogram of the reanalysis of three MDA231 CMV-fLUC subclones using the Cell Count plating procedure. These cells were previously assigned a Class I designation in FIG. 8C using a suboptimal single-Toxin assay. This histogram illustrates the fLUC activity produced in the 15-Assay protocol by the MDA231 CMV-fLUC 1-21, 2-5 and 1-20 subclones (left to right). Although the MDA231
Figure 11A:
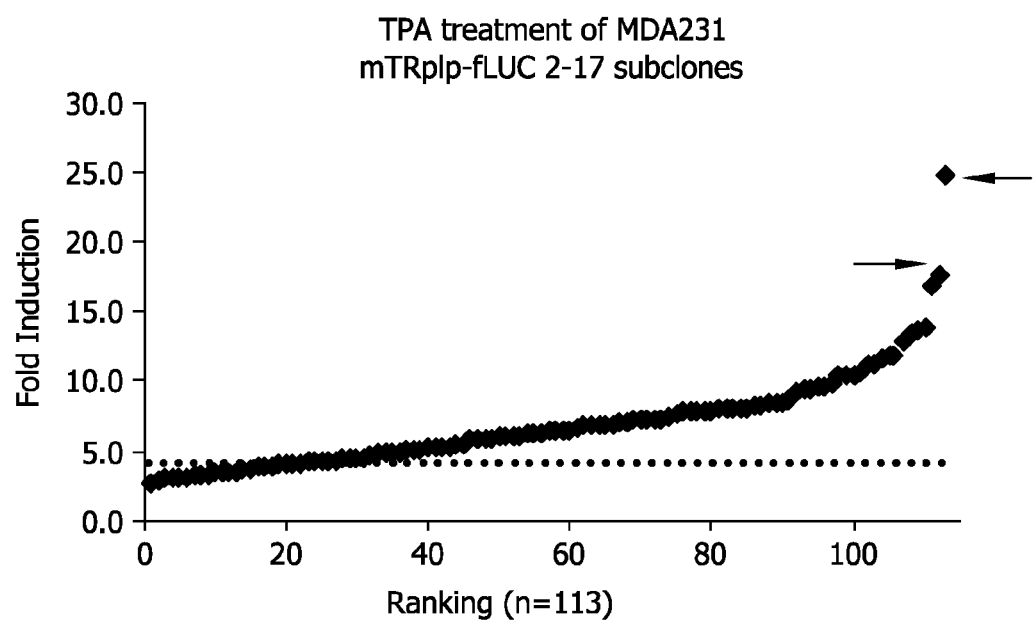
Figure 11A:
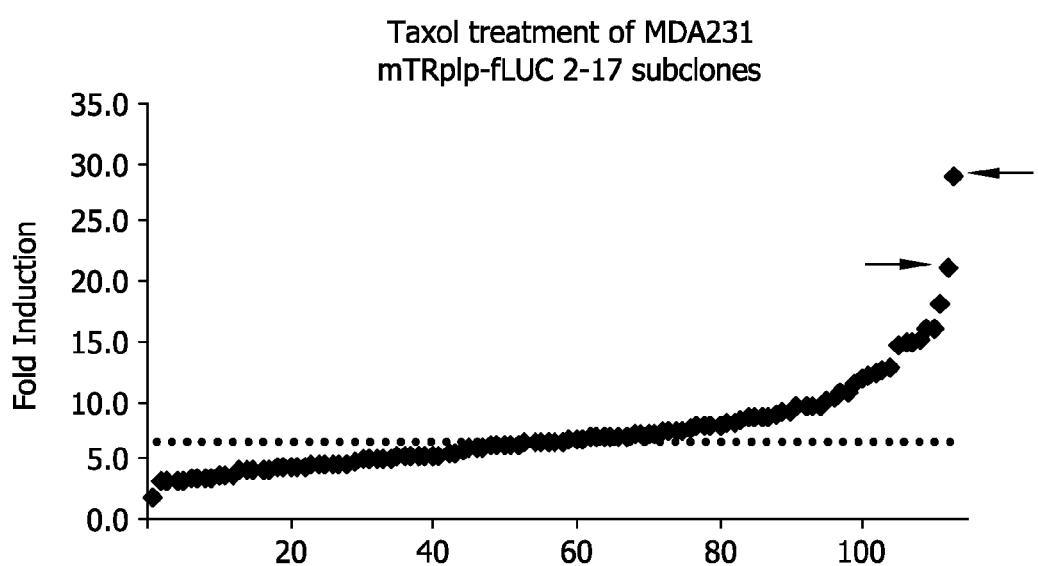

FIG. 11A The left panel is a Ranking plot produced by the 113 secondary subclones isolated from the Class II MDA231 mTRplp-fLUC 2-17 cell line (treated with a TPA single-Toxin assay). Subclones were isolated as described in the examples. The plot shows the TR responses as a function of rank order, lowest to highest on the x-axis, by Fold Induction (y-axis). Dotted line is the TPA-specific TR response as shown in FIG. 10F. A significant fraction of the subclones showed an increase in TR response compared to the parental cell line. Although the majority of subclones exhibited a Class II TR activity, a small fraction exhibited a Class III response. The right panel is an analysis of the 113 MDA231 mTRplp-fLUC 2-17 subclones using the Taxol single-Toxin assay. Dotted line shows the Taxol-specific TR activity from FIG. 10F. As before, a significant fraction of subclones displayed a Class II phenotype but a subset produced Class III responses. The two arrows indicate that the maximal responding subclones in each assay are the same cell lines.

Figure 11B:
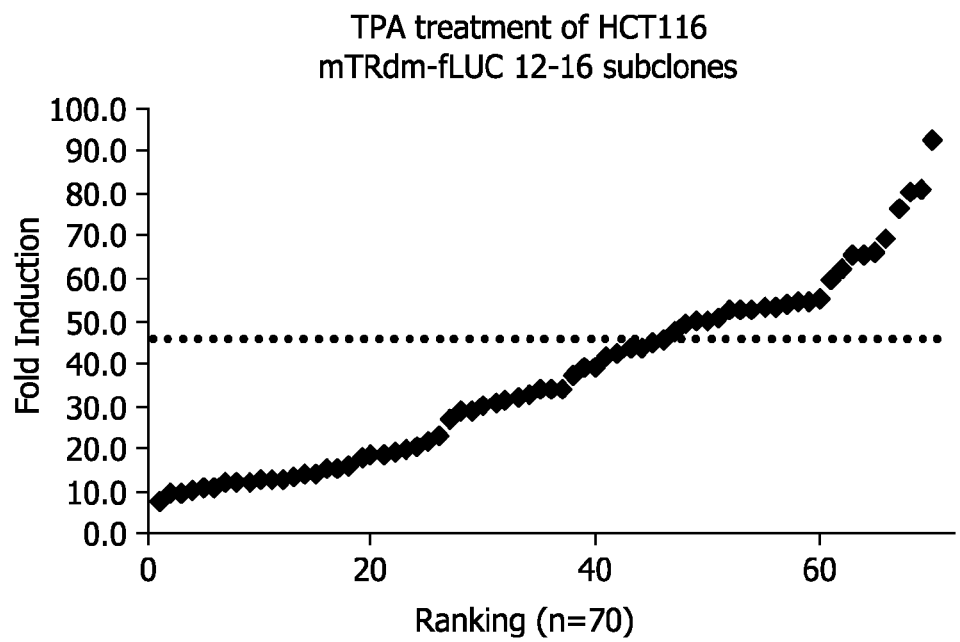
Figure 11B:
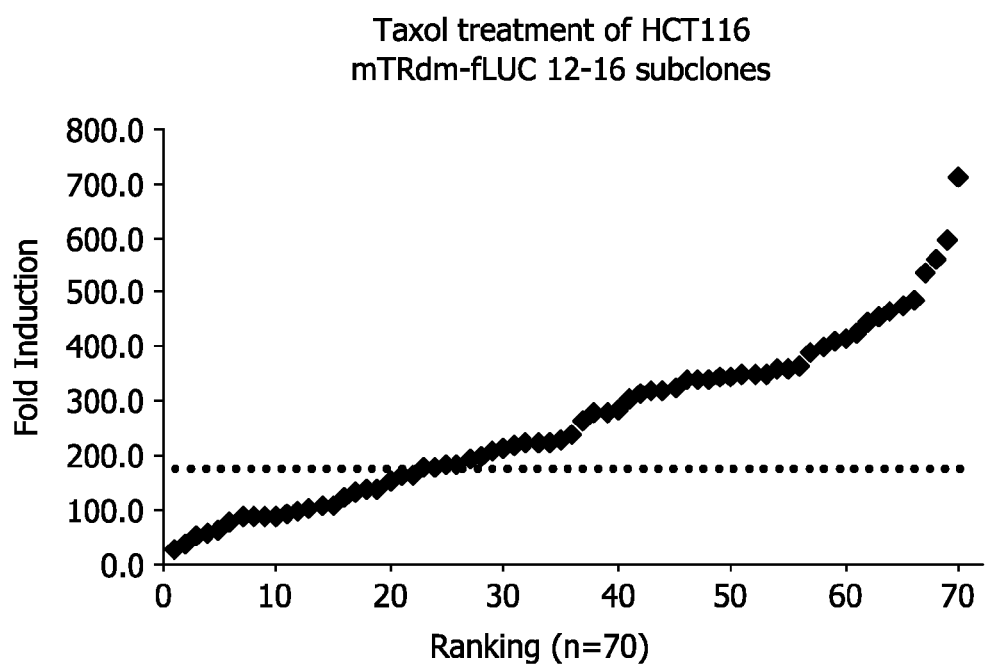

FIG. 11B The left panel is a Ranking plot produced from the 70 secondary subclones isolated from the Class III HCT116 mTRdm-fLUC 12-16 cell line (treated with a TPA single-Toxin assay). Dotted line is the TPA-specific TR response shown in FIG. 10B. Most of the subclones showed Class III TR activity, with a small group exhibiting significantly larger TR responses compared to the parental cells. The right panel is an analysis of the same 70 HCT116 mTRdm-fLUC 12-16 subclones using the Taxol single-Toxin assay. Dotted line shows the Taxol-specific TR activity from FIG. 10B. All subclones displayed a Class III response with a significant fraction exhibiting an enhanced TR activity compared to the parental cell line.

Figure 11C:
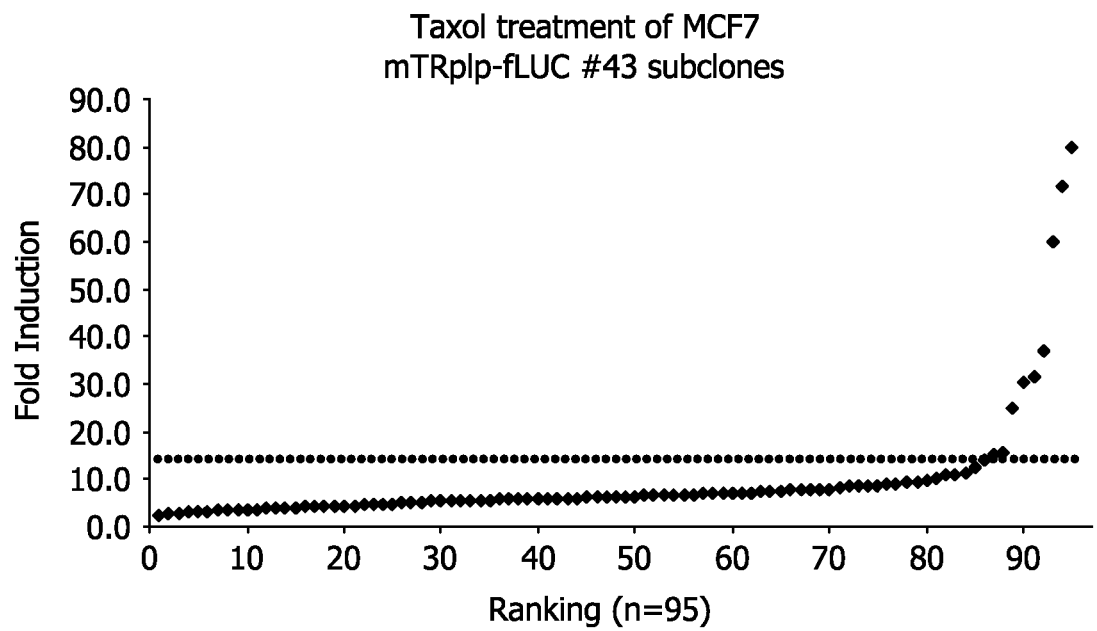

FIG. 11C shows a Ranking Plot of the 95 secondary subclones isolated from the MCF7 mTRplp-fLUC #43 cell line (treated with the Taxol single-Toxin assay). The MCF7 mTR-plp-fLUC #43 cell line was assigned a Class III designation in FIG. 5B. Dotted line is the TPA-specific TR response produced by the parental cell line in the 15-Assay procedure (not shown). A fraction of the secondary subclones clearly exhibit a Class III phenotype that is larger than the parental cell line.

Figure 5A:
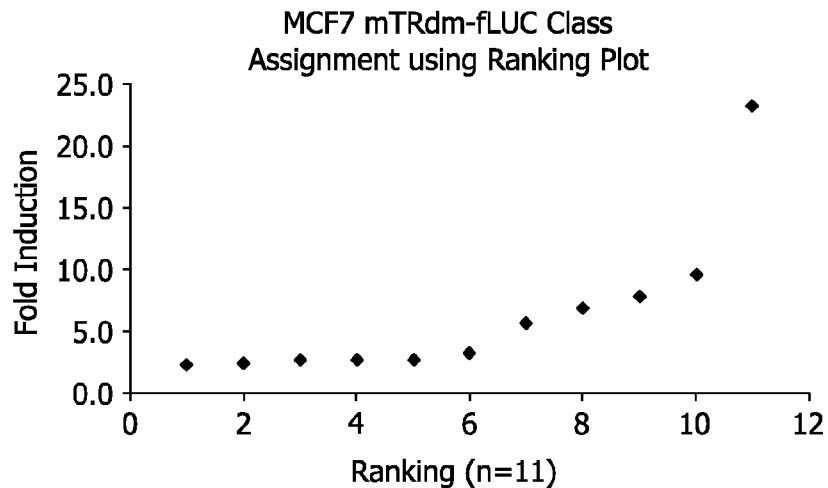
FIG. 5A The top panel is a Ranking plot of the 11 TR responses produced by a human breast adenocarcinoma MCF7 cell pool, stably transformed with the mouse mTRdm-fLUC (firefly luciferase) expression vector, following treatment with the TPA single-Toxin assay. The bottom table shows the Class designation for the MCF7 mTRdm-fLUC pool; 6 of 11 (54.5%) subclones showed a Class I response, 4 of 11 subclones (36.4%) exhibited a Class II response, and 1 of 11 responders (9.1%) displayed a Class III phenotype.
Figure 11D:
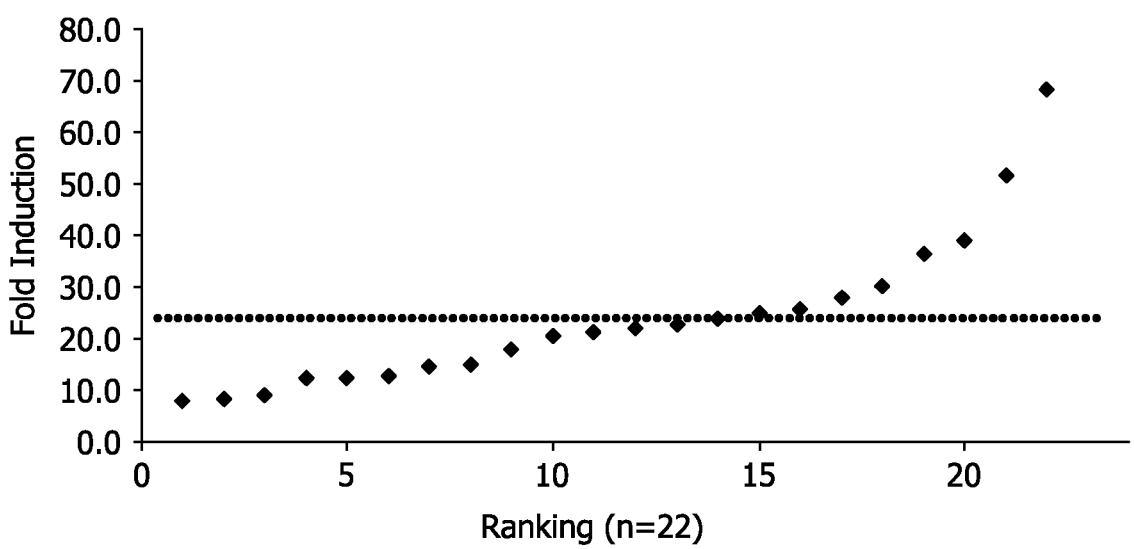

FIG. 11D shows a Ranking Plot of the 22 secondary subclones isolated from the MCF7 mTRdm-fLUC #64 cell line (treated with the Taxol single-Toxin assay). The MCF7 mTRdm-fLUC #64 cell line was given a Class III designation in FIG. 5A. Dotted line is the Taxol-specific TR response produced by the parental cell line in the 15-Assay protocol (not shown). A majority of the secondary subclones retained the Class III phenotype, and a significant fraction show enhanced TR activity compared to the parental cell line.

FIG. 12 shows the results for recovering a Class defined phenotype by reselection of the antibiotic resistance marker in the expression cassette.

Figure 12A:
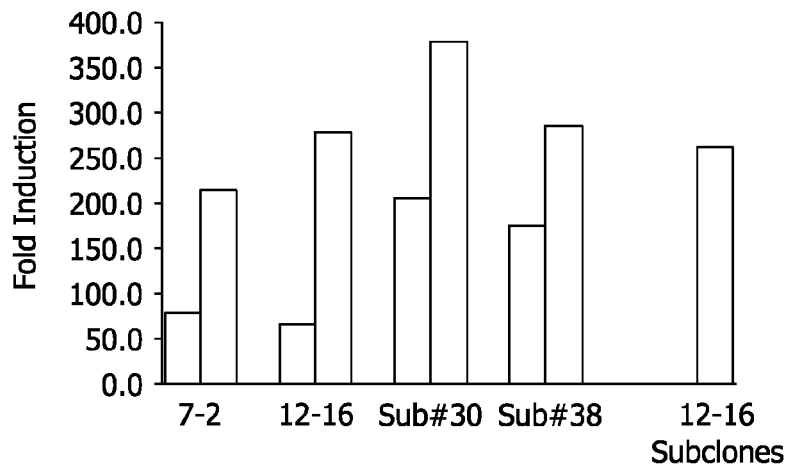

FIG. 12A shows a histogram of 4 HCT116 subclones all previously assigned a Class III phenotype. HCT116 mTRdm-fLUC 7-2 and 12-16 were primary HCT116 isolates. The HCT116 mTRdm-fLUC subclone #30 and subclone #38 were highly responsive secondary subclones isolated from the 12-16 primary cell line (FIG. 11B). The light bars show high passage cell lines (P10-P20) treated with the TPA+Taxol two-Toxin assay. The dark bars are the same cultures reselected with G418 to remove cells that segregated the TR expression plasmid, which have also been treated with the TPA+Taxol two-Toxin assay. For comparison, the average response produced by the 70 secondary 12-16 subclones (FIG. 11B) is shown by a bar on the far right. The bottom table shows the highly significant increases in TR-specific activity observed after reselection.

Figure 12B:
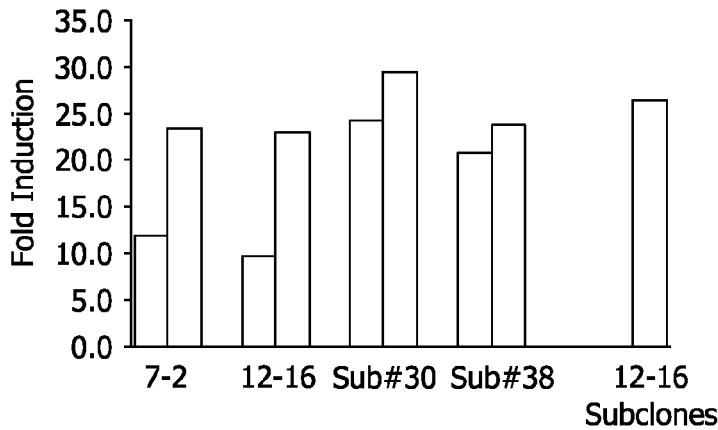

FIG. 12B shows a histogram of the TR activity produced by the described cell lines, which were treated with the TPA single-Toxin assay. The bottom table shows the highly significant increases in TR-specific responses following the reselection process.

FIG. 13 shows the regulation of basal cap-independent translation by mechanical manipulation.

Figure 13A:
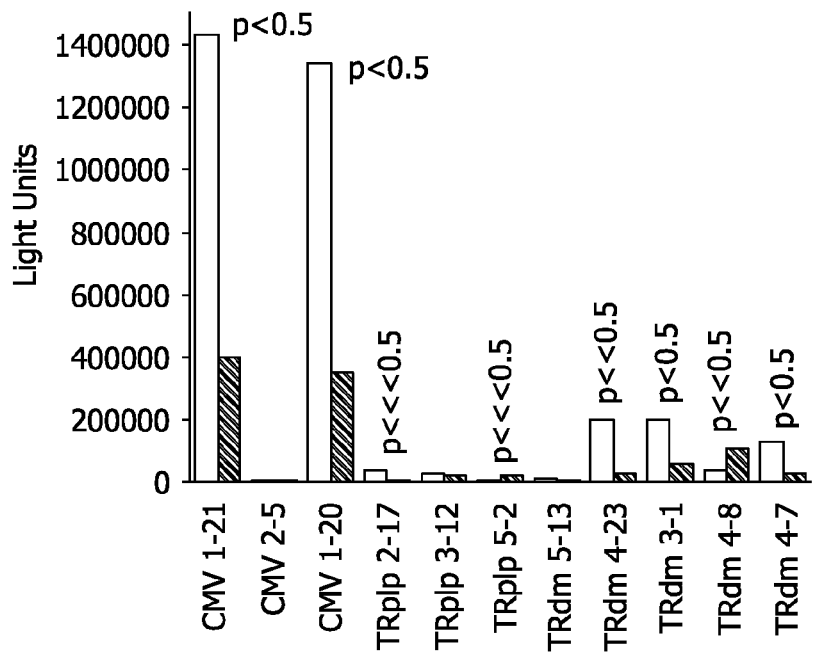

FIG. 13A shows a histogram of the basal translational activity produced by untreated MDA231 cell lines plated using the Confluence (light bar) and Cell Count (dark bar) procedures. Three MDA231 CMV-fLUC cell lines (1-21, 2-5, 1-20) were compared to four mTRplp-fLUC (2-17, 3-12, 5-2, 5-13) and four mTRdm-fLUC cell lines (4-23, 3-1, 4-8, 4-7). Cells were lysed, analyzed without toxin treatment, and plate reader values were plotted as relative Light Units. In general, each of the cell lines showed that the Confluence plating procedure (which maximizes cell number per square cm of culture area and results in a confluent, post-mitotic cell culture) resulted in significantly higher basal fLUC levels compared to the Cell Count protocol (which produces a subconfluent, mitotic cell culture).

Figure 13B:
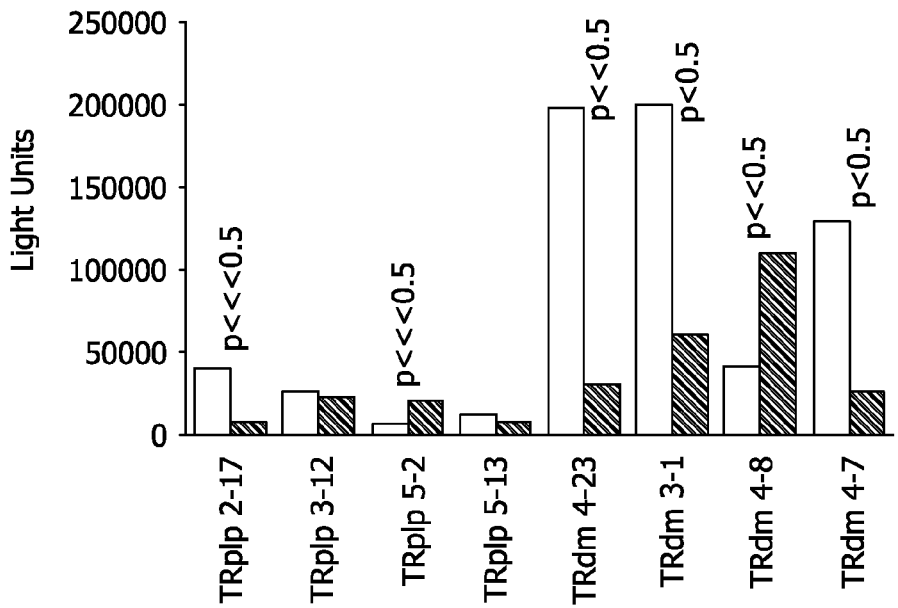

FIG. 13B shows a histogram of the same untreated cells with the CMV results removed to graphically enhance the lower values in the TR expressing cell lines. As before, the general trend was that the Confluence plating method introduced more cells into an assay and increased the basal level fLUC activity; however, two cell lines (mTRplp-fLUC 5-2 and mTRdm-fLUC 4-8) exhibited enhanced fLUC activity in untreated cells plated by the Cell Count procedure.

FIG. 14 shows the correlation of the TR-specific reporter activity produced in a standard toxin assay with TR-derived translated protein.

Figure 14A:
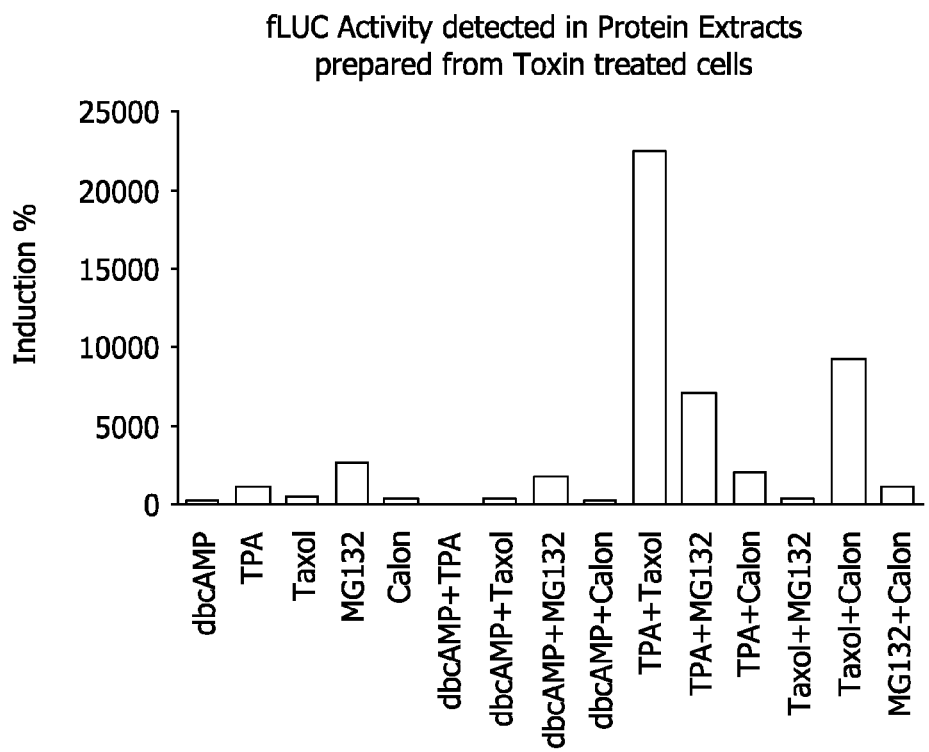
Figure 14A:
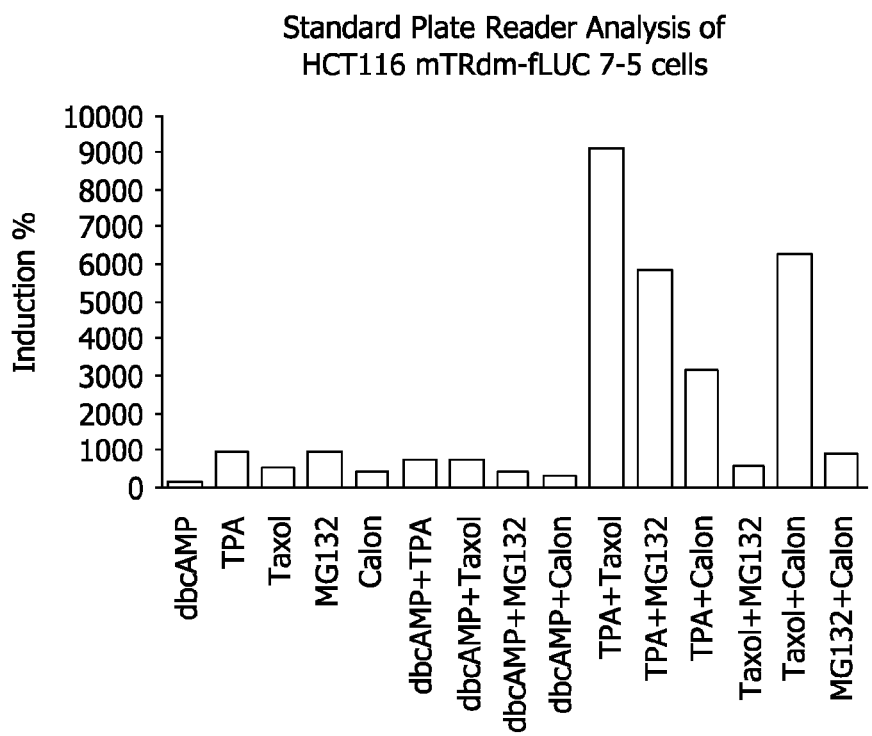

FIG. 14A The top panel shows a 15-Assay histogram of fLUC activity produced by cell extracts prepared from the Class III HCT116 mTRdm-fLUC 7-5 subclone. The bottom panel shows a 15-Assay histogram of the HCT116 mTRdm-fLUC 7-5 cell line used to assign a Class III designation. Equal number of cells was examined in each assay.

Figure 14B:
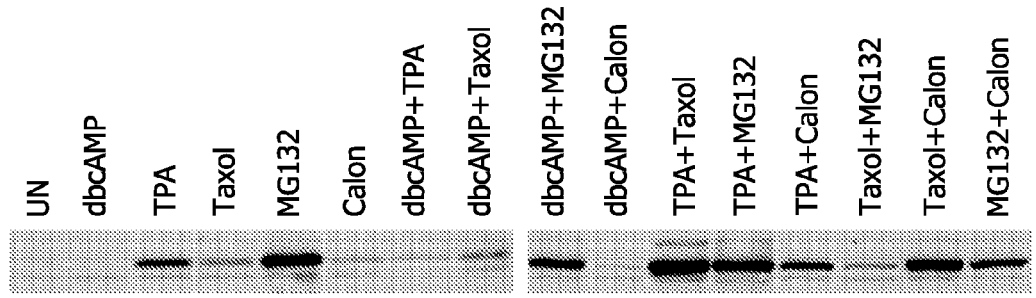

FIG. 14B shows a Western blot of the 15-Assay cell extracts described above developed using an anti-firefly luciferase antibody. Equal amounts of total protein were resolved in each gel lane.

Figure 14C:
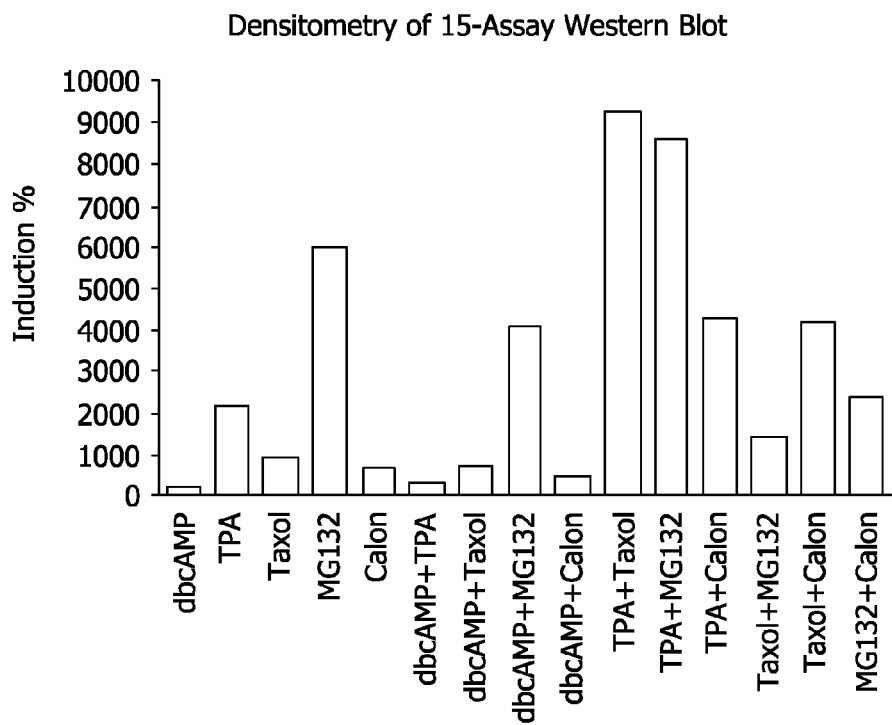
Figure 16:
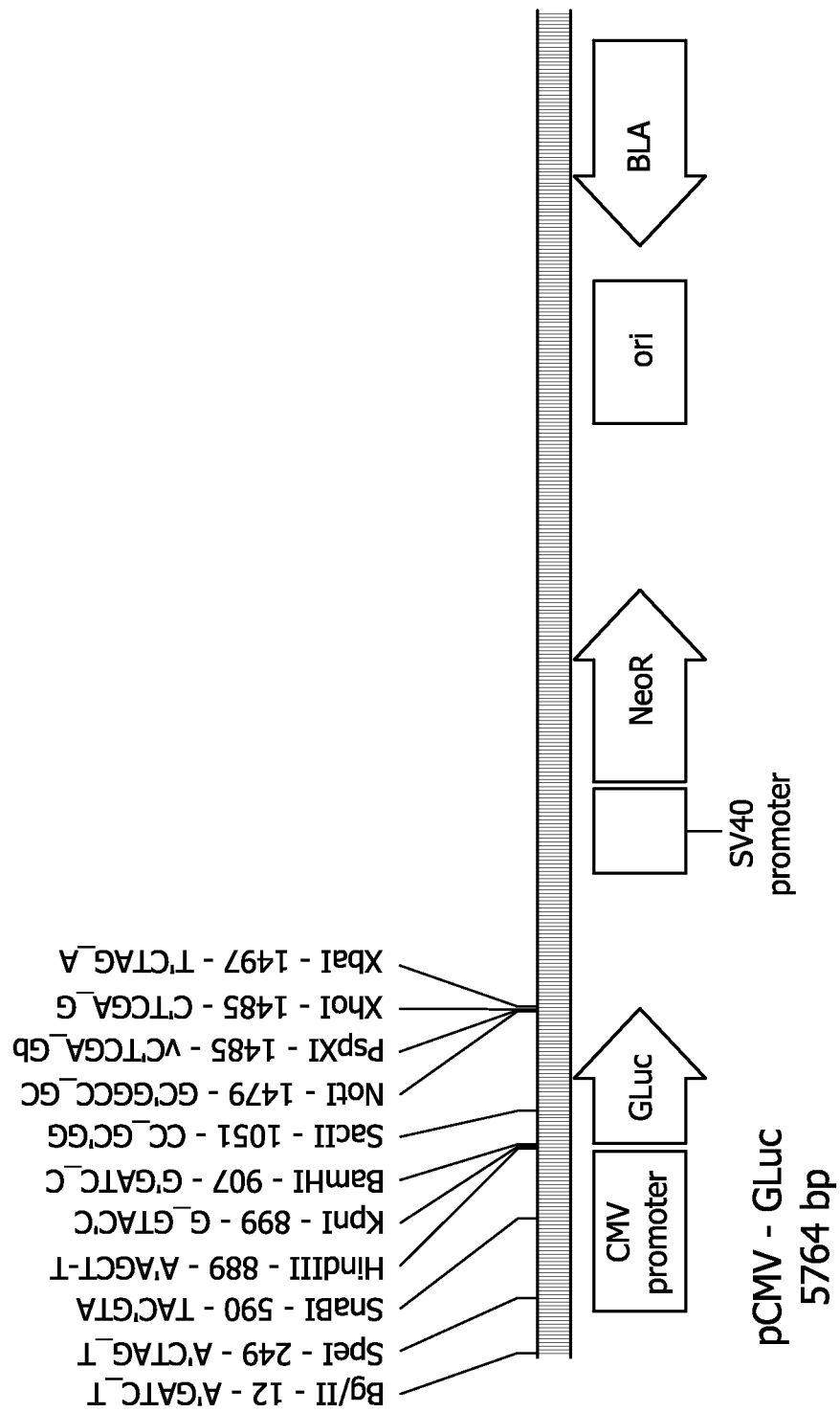
Figure 17:
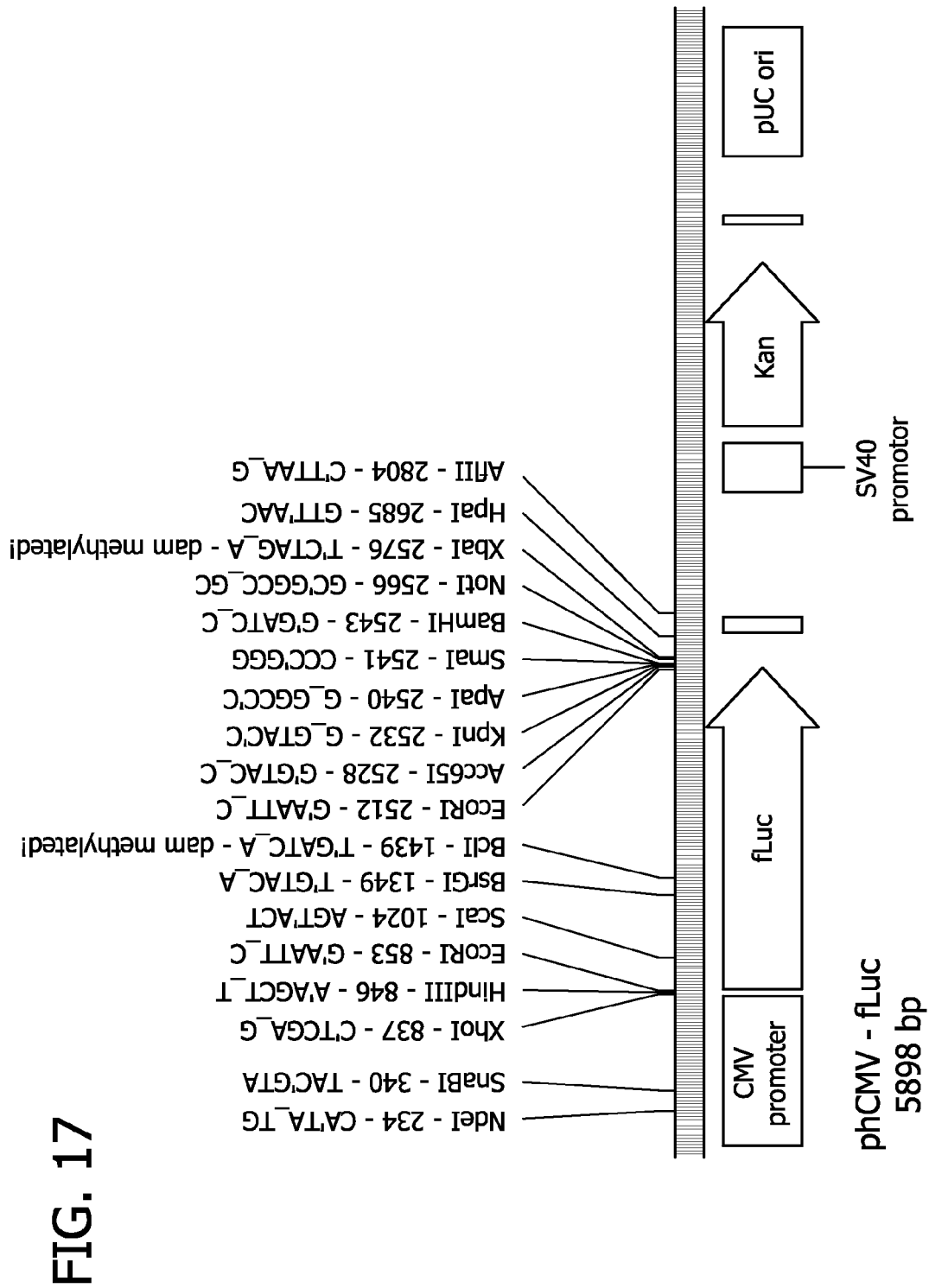
Figure 18:
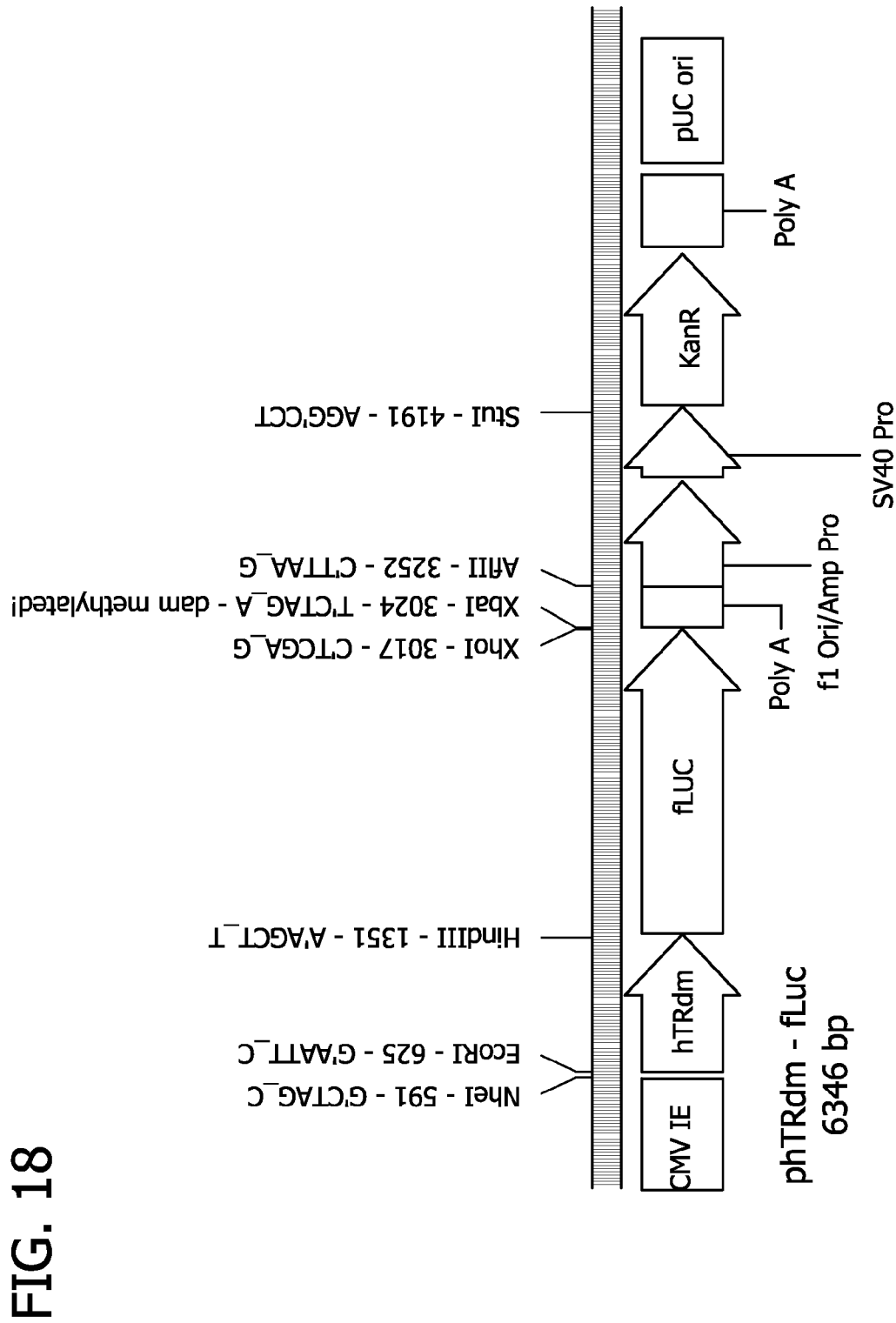
Figure 19:
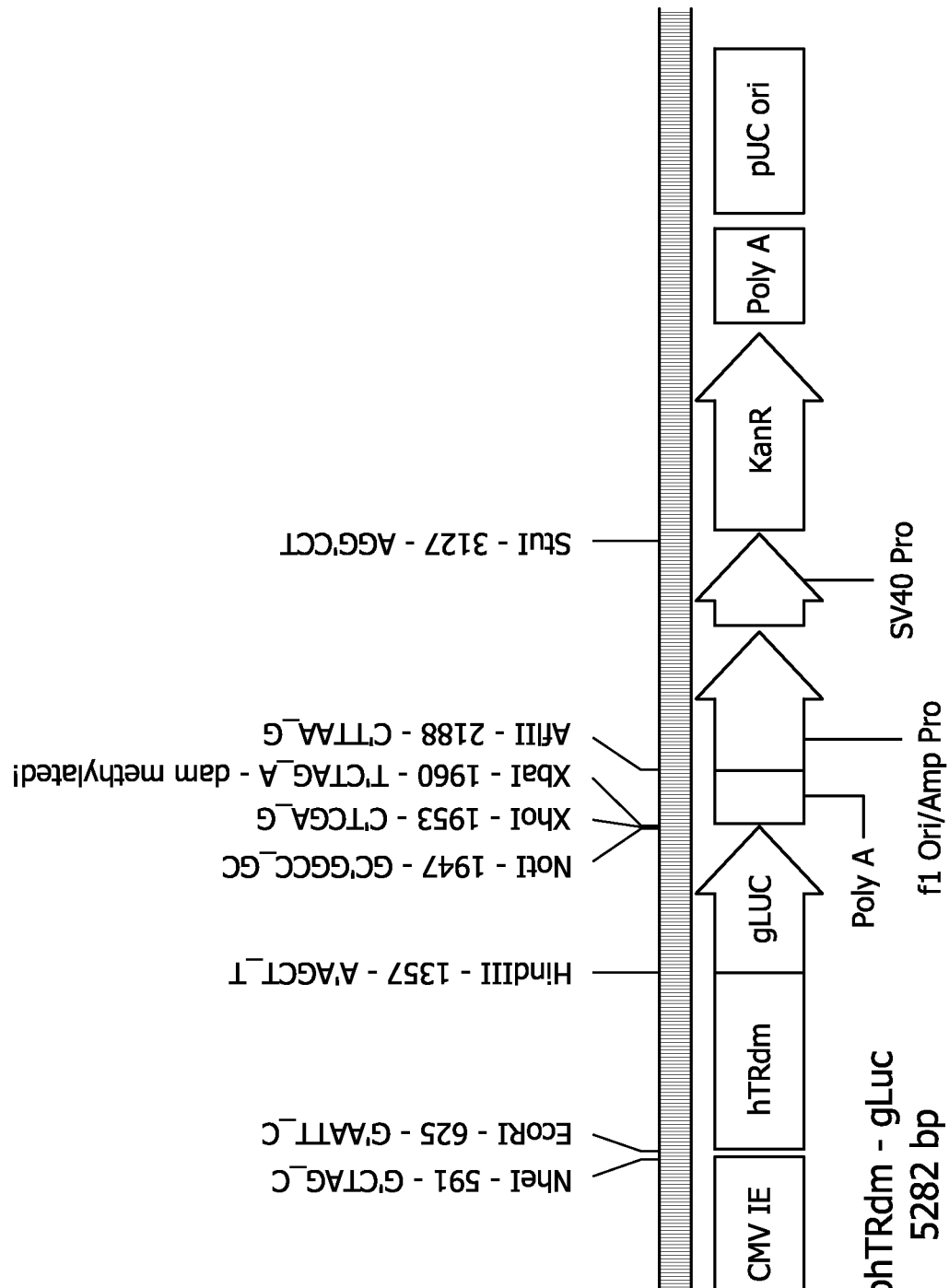
Figure 20:
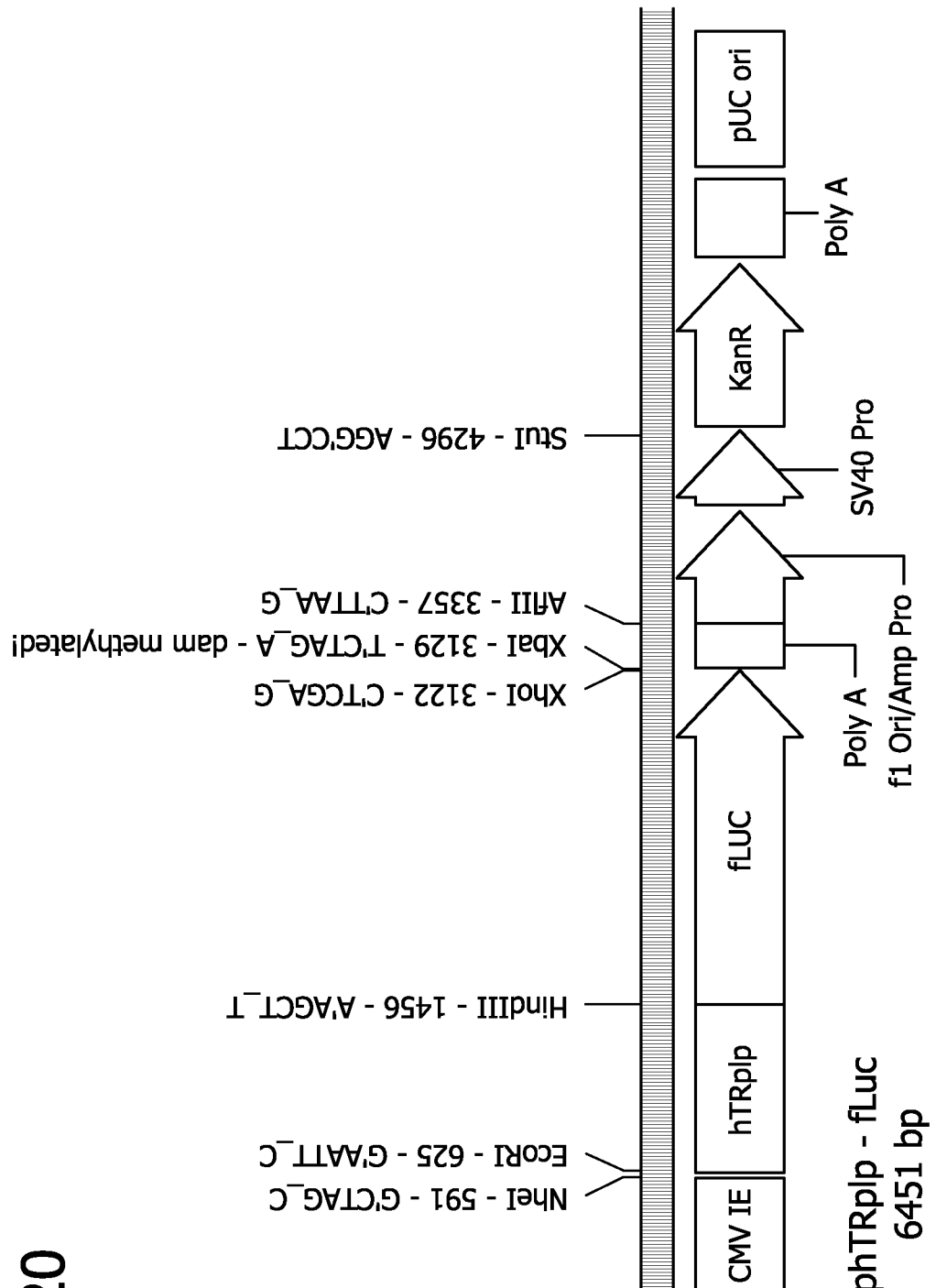
Figure 21:
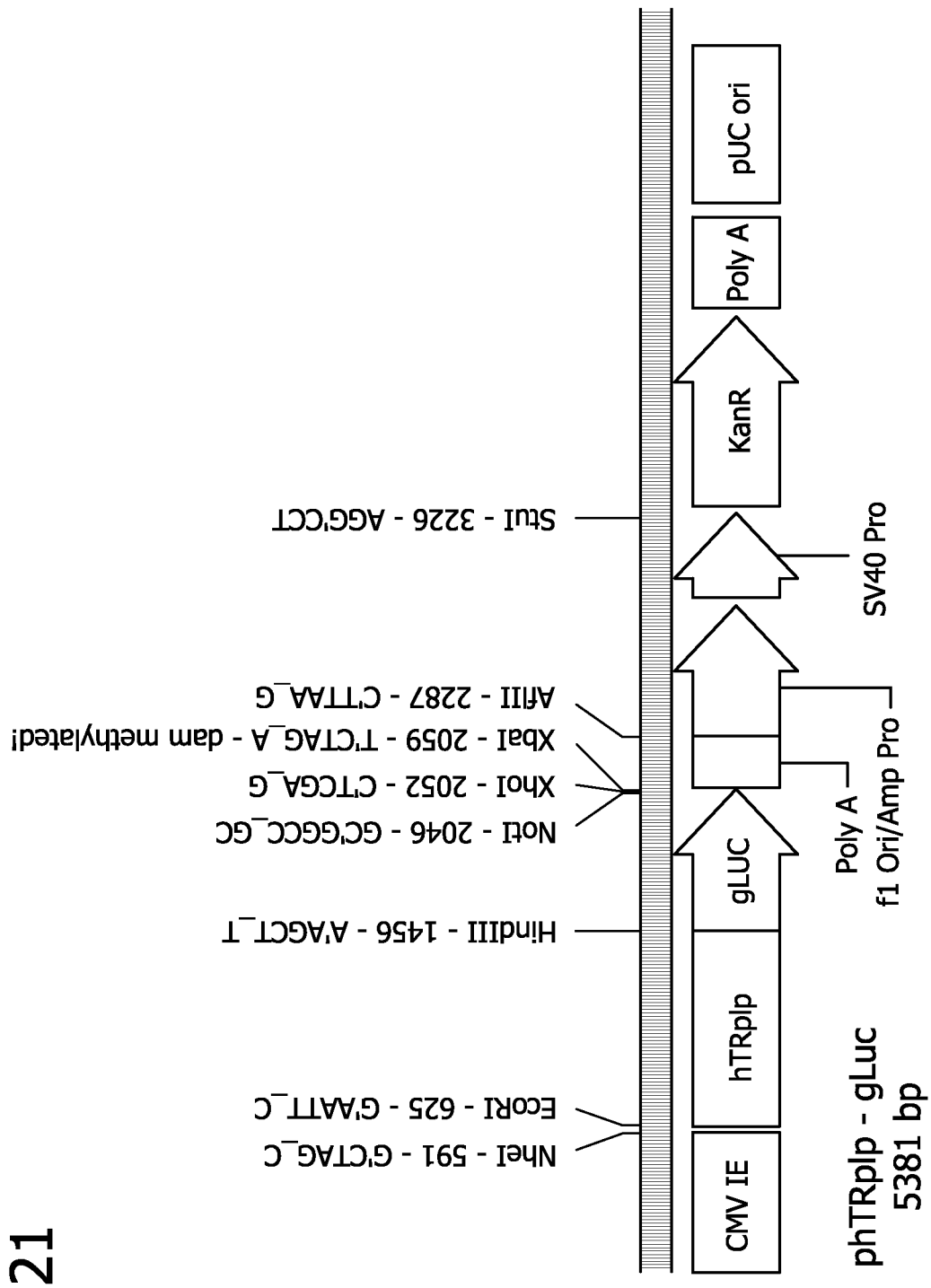
Figure 22:
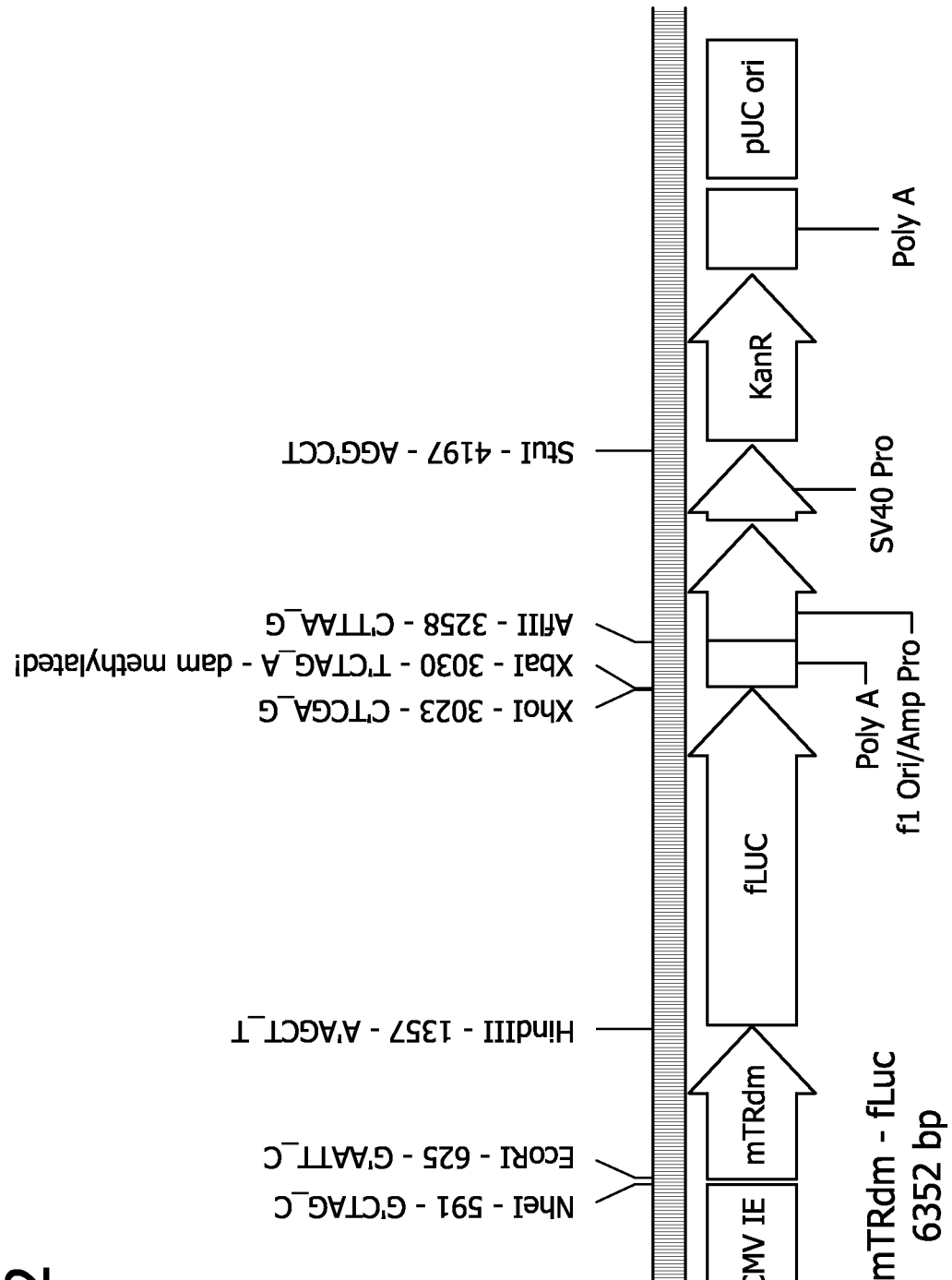
Figure 23:
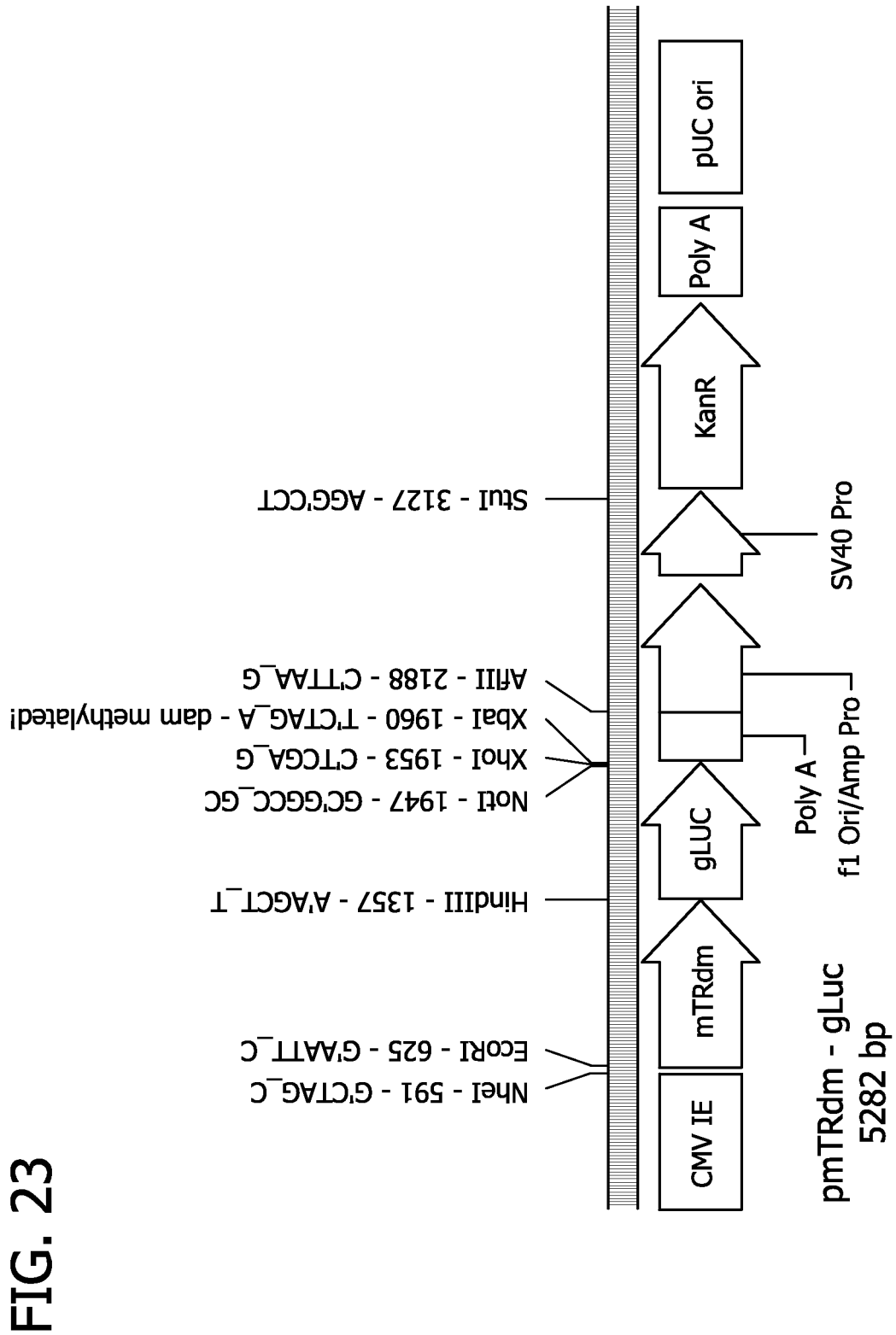
Figure 24:
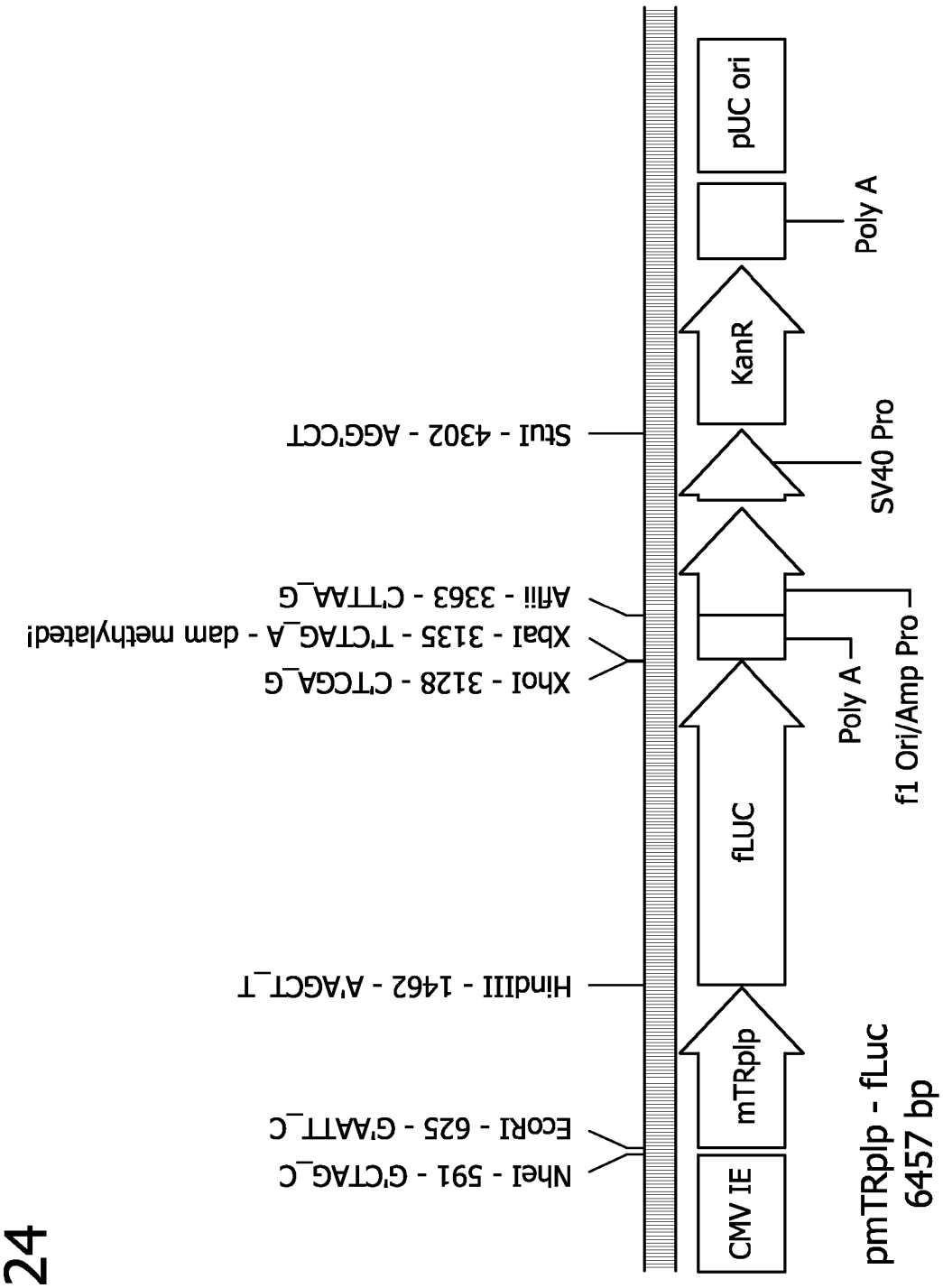
Figure 25:
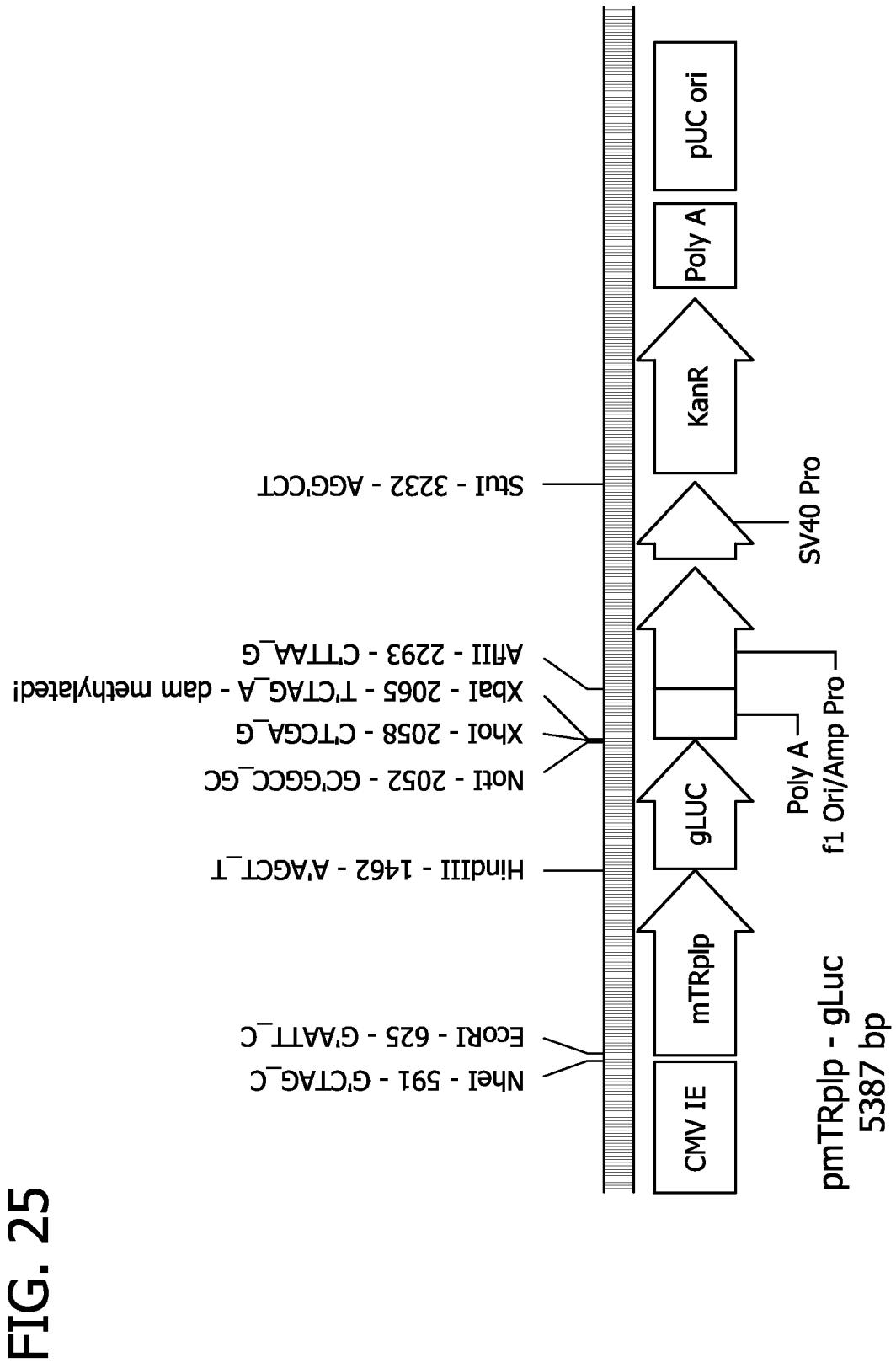

FIG. 14C shows a histogram of densitometry analysis of band intensities on the Western blot. High band intensities were outside the linear range of the x-ray film response and produced lower values compared to direct cell measurements.

FIG. 15 shows the correlation of the TR-specific reporter activity with TR-derived translation products.

FIG. 15A shows a dose-response graph of recombinant fLUC protein concentration (Sigma) as a function of relative Light Units. For this graph, serial dilutions of the fLUC protein were prepared and assayed using a standard plate reader procedure.

FIG. 15B shows a Table of cell extracts prepared from the Class III HCT116 mTRdm-fLUC 12-16 subclone using the 15-Assay procedure. A fixed cell number ($1/10$ of the total cell number) was taken from each extract and assayed in a plate reader assay. The relative Light Units produced by each sample extract could be graphically compared to a known protein concentration in FIG. 15A. The fLUC protein concentration for a Class III HCT116 mTRdm-fLUC 12-16 cell treated with a defined toxin assay for 6 hrs was defined using ⅟₁₀ of the total cell number and converted to a specific activity defined as Light Units/μg fLUC protein.

FIG. 15C is a Western blot of the protein extracts produced from the HCT116 mTRdm-fLUC 12-16 cells treated with the 15-Assay procedure. The band intensity (fLUC protein level) correlates well with the protein concentrations calculated above. Equal amounts of total protein were resolved in each gel lane.

FIGS. 16-25 are schematic drawings of plasmids pCMV-gLuc, pCMV-fLuc, phTRdm-fLuc, phTRdm-gLuc, phTRplp-fLuc, phTRplp-gLuc, pmTdm-fLuc, pmTRdm-gLuc, pmTRplp-fLuc and pmTRplp-gLuc, respectively. Functional plasmid elements (restriction enzyme sites, origins of replication, open reading frames, etc.) are represented with vertical lines, boxes and arrows as needed. mDM=murine DM20 cDNA; mP=murine PLP cDNA; mTRd=murine TRdm; mTRp=murine TRplp; hDM=human DM20; hP=human PLP; hTRd=human TRdm, hTRp=human TRplp, fLuc=firefly Luciferase; gLuc=Gaussia Luciferase.

Figure 26B:
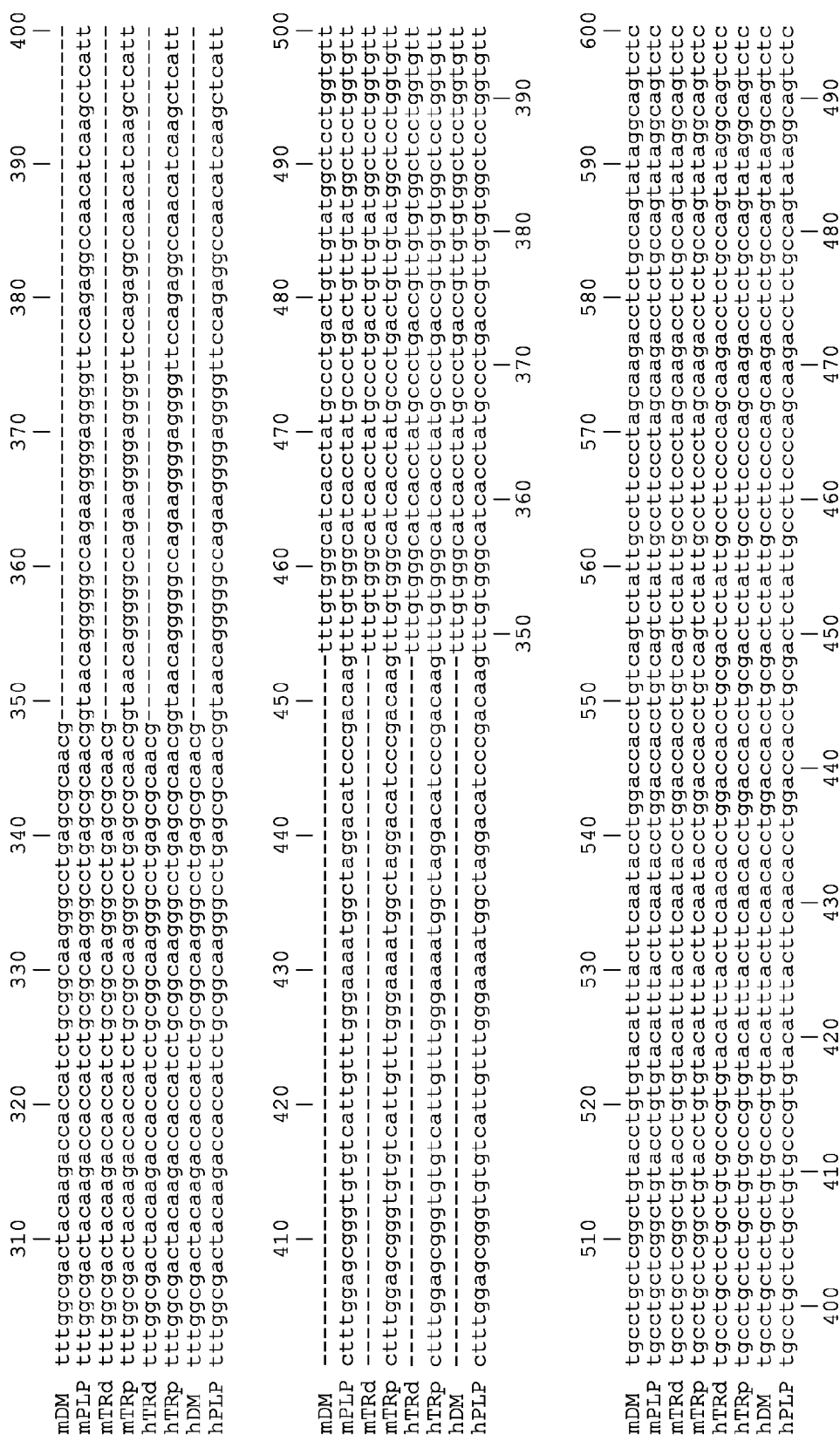

FIGS. 26A-C depict a sequence alignment chart of murine and human PLP/DM20 coding sequences and TR elements hereof. Key: mDM=murine DM20 cDNA [SEQ ID NO:7]; mP=murine PLP cDNA [SEQ ID NO: 6]; mTRd=murine TRdm [SEQ ID NO:1]; mTRp=murine TRplp [SEQ ID NO:2]; hDM=human DM20 [SEQ ID NO: 8]; hP=human PLP [SEQ ID NO:9]; hTRd=human TRdm [SEQ ID NO:3], and hTRp=human TRplp [SEQ ID NO:4]. Because DM20 sequences omit part of the sequence present in full-length PLP coding sequences, the numbering of DM20 sequences in FIG. 26 is discontinuous and, after the omitted segment, DM20 numbering is shown continuing below the aligned sequences. In describing sequences herein with reference to FIG. 26, in some cases dual numbering for PLP/DM20 nucleotide positions is utilized, e.g., residue 560/455; this usage refers to PLP and DM20 numbering in the alternative, with PLP numbering as shown above the aligned sequences, and DM20 numbering as shown below the aligned sequences.

FIG. 27 illustrates the application of the Toxin Assay procedures to differentiate toxin-specific effects (species-specific toxin actions) within the Protein Kinase C (PKC) activator group (genus-specific molecular target) in MCF7 breast cancer cells.

Figure 27A:
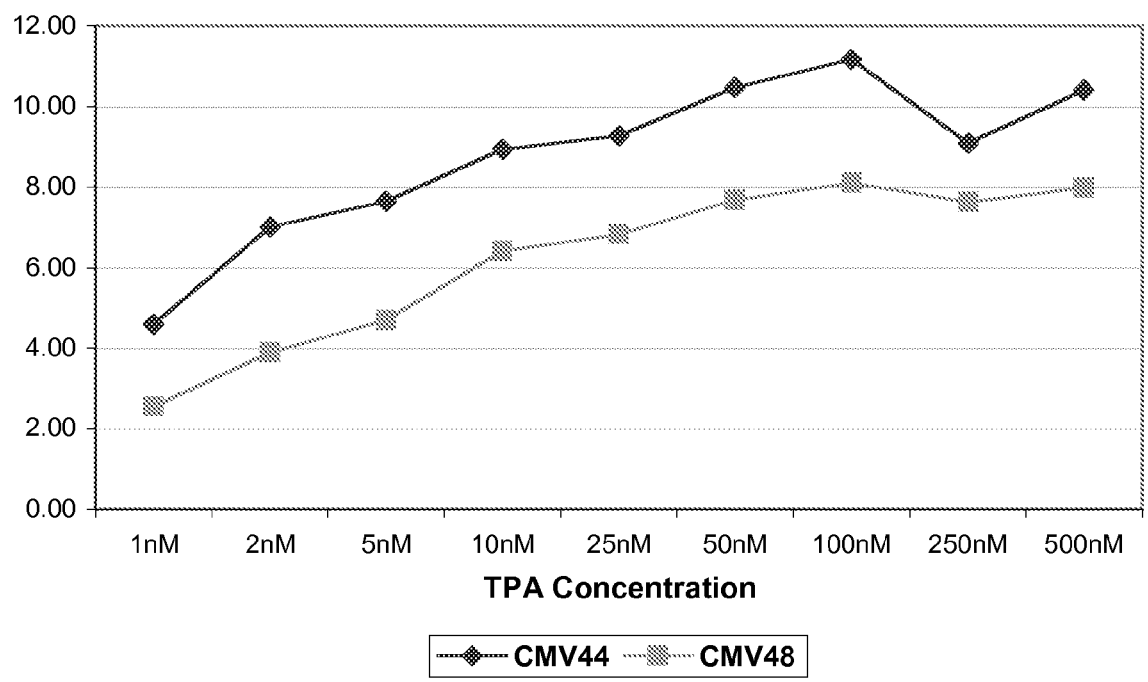

FIG. 27A shows a dose response assay in which triplicate samples of the MCF7 CMV-fLuc subclones #44 and #48 were treated with varying doses of TPA (dose range 1 nM to 500 nM). Following 6 hr exposure to the Single-Toxin TPA assay, cells were lysed and fLuc protein activity measured using a standard microplate reader assay. The raw values were averaged and expressed as the ratio of treated to untreated samples (Fold Induction). Both cell lines displayed a linear increase in fLuc protein synthesis with increasing TPA concentration to a maximal reporter level at the 100 nM TPA dose. This TPA concentration was then used as a control for the Bryostatin 1 and Bryostatin 2 assays shown in FIG. 27B.

Figure 27B:
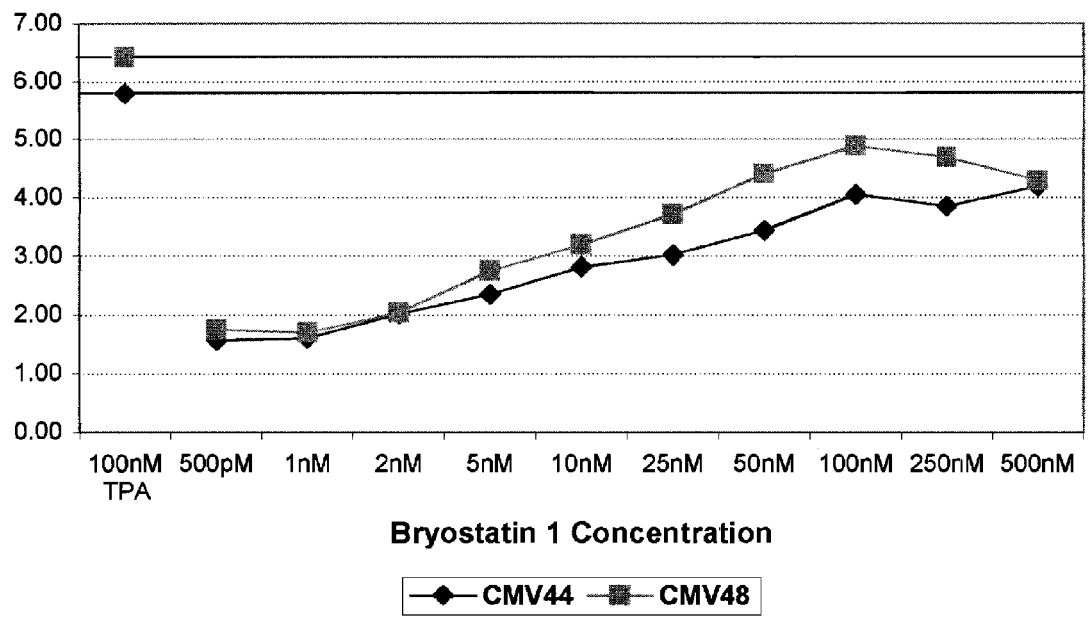
Figure 27B:
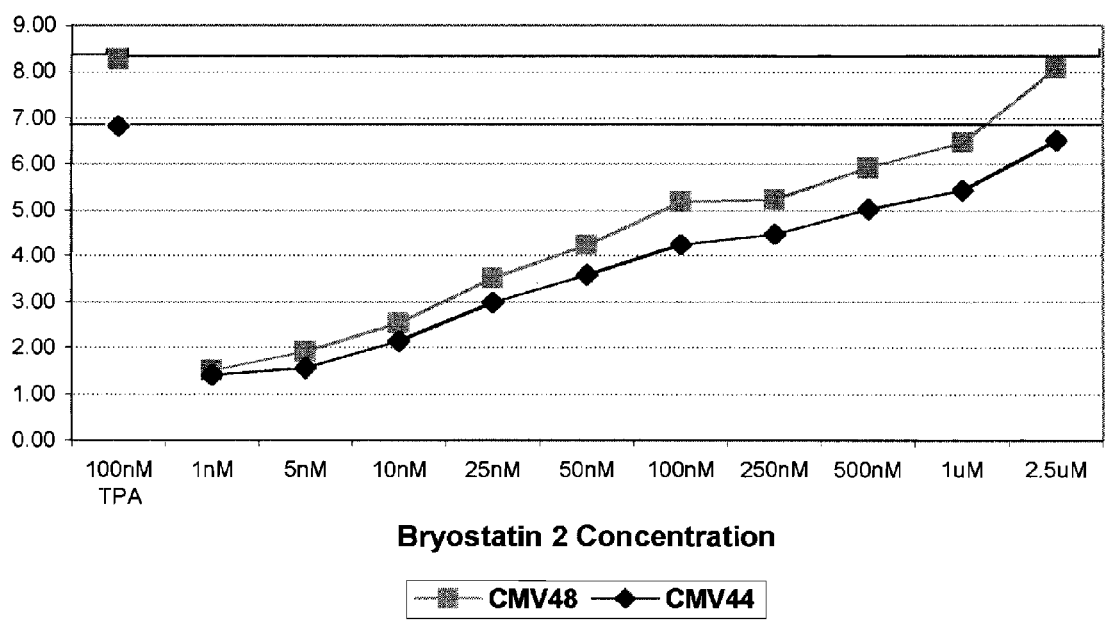

FIG. 27B shows the dose response curves in which triplicate samples of the MCF7 CMV-fLuc subclones #44 and #48 were treated with 100 nM TPA, or varying doses of Bryostatin 1 (dose range of 500 pM to 500 nM) (top panel) or Bryostatin 2 (dose range 1 nM to 2.5 uM) (bottom panel) in Single-Toxin assay. Dashed lines represent translational response levels produced by a 100 nM TPA Single-Toxin assay. The Bryostatin 1 concentrations (top panel) encompassed the TPA concentrations used in FIG. 27A. Although a maximal translational response was observed in the 100 nM Bryostatin 1 assay, the magnitude of the reporter activity never reached the fLuc activity level produced by the 100 nM TPA assay. The Bryostatin 2 dose response curve (bottom panel) employed higher drug concentrations (the maximal tested dose was 5× the largest TPA and Bryostatin 1 amounts). At the highest tested dose (2.5 uM), Bryostatin 2 produced fLuc activity consistent with the level observed with 100 nM TPA.

Figure 27C:
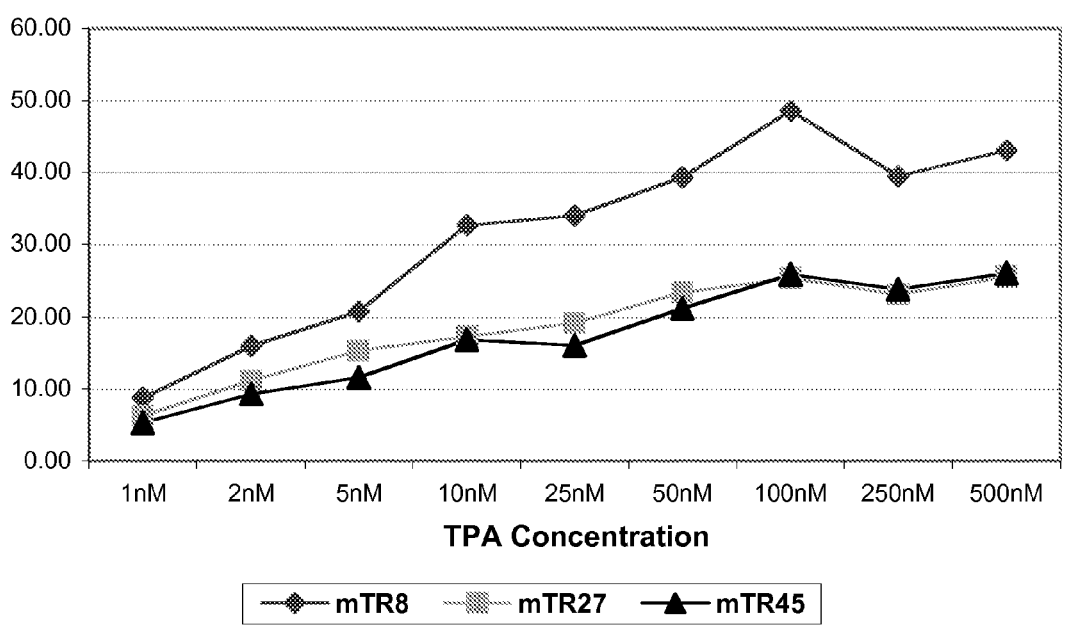

FIG. 27C shows the dose response curve in which triplicate samples of the MCF7 mTRdm-fLuc subclones #8, #27, and #45 were treated with varying doses of TPA (1 nM to 500 nM) to define the TR translational response. Following 6 hr culture with a TPA single-Toxin assay, cells were lysed and fLuc protein activity measured using a standard microplate reader assay. The plate reader values were averaged and expressed as the ratio of treated to untreated samples (Fold Induction). All cell lines displayed a linear increase in fLuc protein activity with increasing TPA concentrations, peaking at a 100 nM TPA dose. This TPA concentration was used as a standard for the Bryostatin 1 and Bryostatin 2 assays shown in FIG. 27D.

Figure 27D:
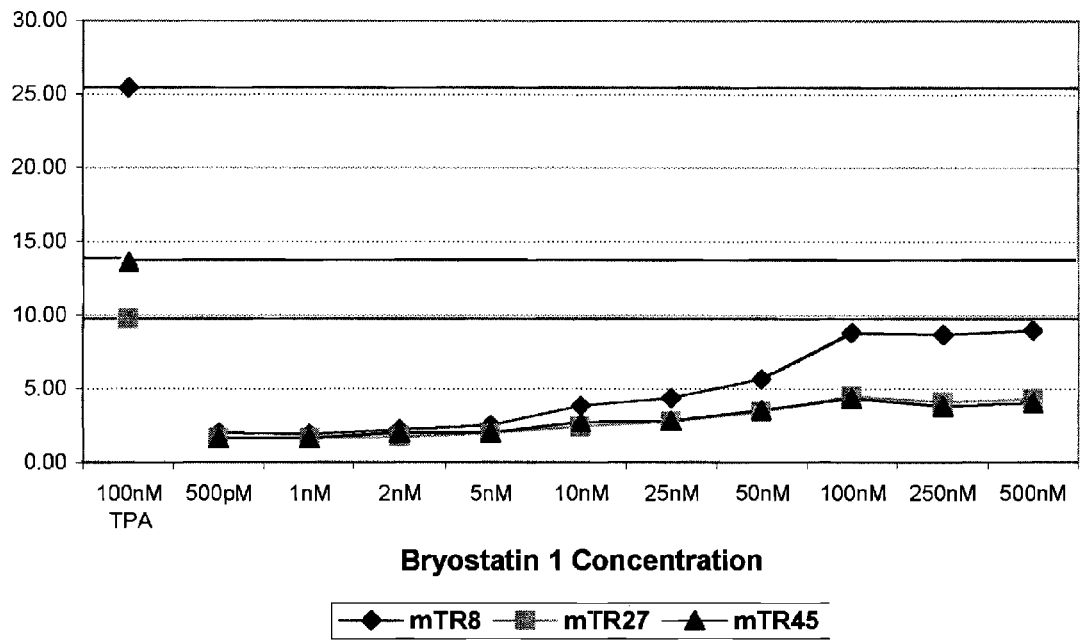
Figure 27D:
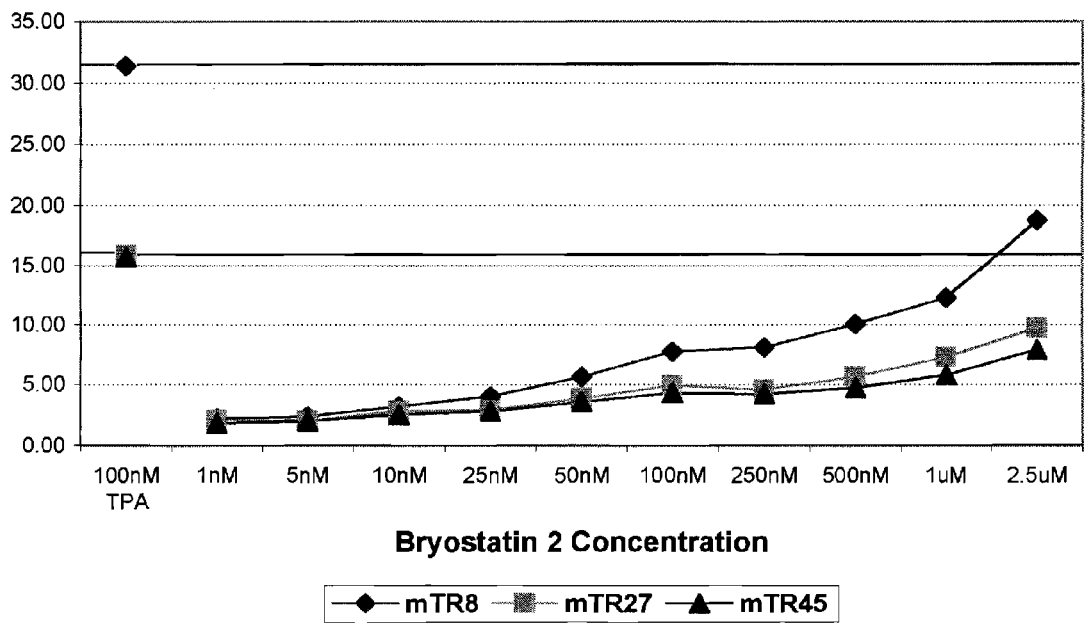

FIG. 27D shows the dose response curves in which triplicate samples of the MCF7 mTRdm-fLuc subclones #8, #27, and #45 were treated with 100 nM TPA or varying doses of either Bryostatin 1 (dose range of 500 pM to 500 nM) (top panel) or Bryostatin 2 (dose range of 1 nM to 2.5 uM) (bottom panel) in single-Toxin assays. As with FIG. 27B, dashed lines represent translational response levels achieved by the 100 nM TPA assay in each cell line. The Bryostatin 1 concentrations (top panel) encompassed the TPA dose response curve shown in FIG. 27C, and exhibited a maximal activity in the 100 nM Bryostatin 1 assay. Although the Bryostatin 2 assays (bottom panel) covered an even larger concentration range, the TR specific expression level did not differ significantly from Bryostatin 1 at similar dosing. The magnitude of the translational response in the Bryostatin 1 and Bryostatin 2 assays never reached the fLuc activity produced in 100 nM TPA tests. In this study and other comparable efforts, the translational differences between the 100 nM TPA, Bryostatin 1 and Bryostatin 2 single-Toxin assays were much greater in the cap-independent assays than the cap-dependent assays in FIG. 27B. A further difference between the cap-dependent and cap-independent assays was the observation that increased Bryostatin 2 concentrations (5× the maximal TPA dose) never produced fLUC activity equivalent to the 100 nM TPA assay. Thus, the Toxin Assay procedure can detect a statistically significant difference in cap-dependent and cap-independent translation in compounds that activate PKC activity.

FIG. 28 illustrates the use of single-Toxin and Combinatorial-Toxin Assays to differentiate toxin-specific translational responses within the Topoisomerase I inhibitor genus (camptothecin drug genus) in MCF7 breast cancer cells. These results also provide an example of a substance with no previously known action on protein translation that selectively reduces translation.

Figure 28A:
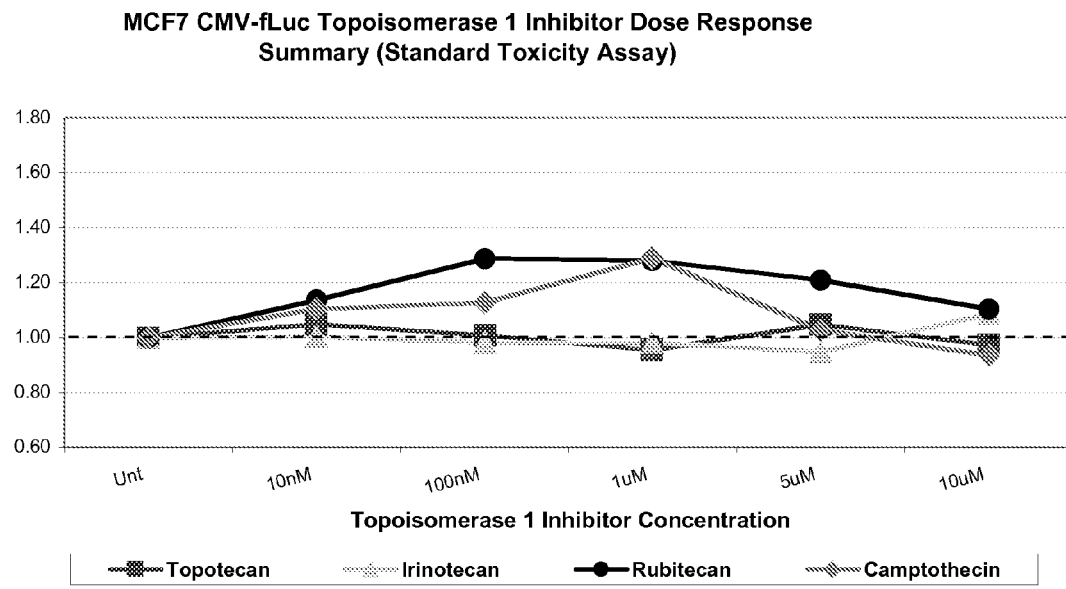

FIG. 28A illustrates a dose response assay of the MCF7 CMV-fLuc subclone #65 treated with varying doses (10 nM to 10 uM range) of the following Topoisomerase 1 inhibitors: camptothecin, topotecan, irinotecan, and rubitecan. Following a 6 hr incubation in a single-Toxin assay, cells were lysed and fLuc protein activity measured using a standard microplate reader assay. The plate reader values were averaged and expressed as the ratio of treated to untreated samples (Fold Induction). The dashed line represents the level of translational response in untreated cell samples. Camptothecin and rubitecan showed similar dose responses with a peak of fLuc protein expression at ~1 uM and a decline to basal levels at higher doses. In contrast, neither topotecan or irinotecan significantly altered cap-dependent translation in the single-Toxin assays.

Figure 28B:
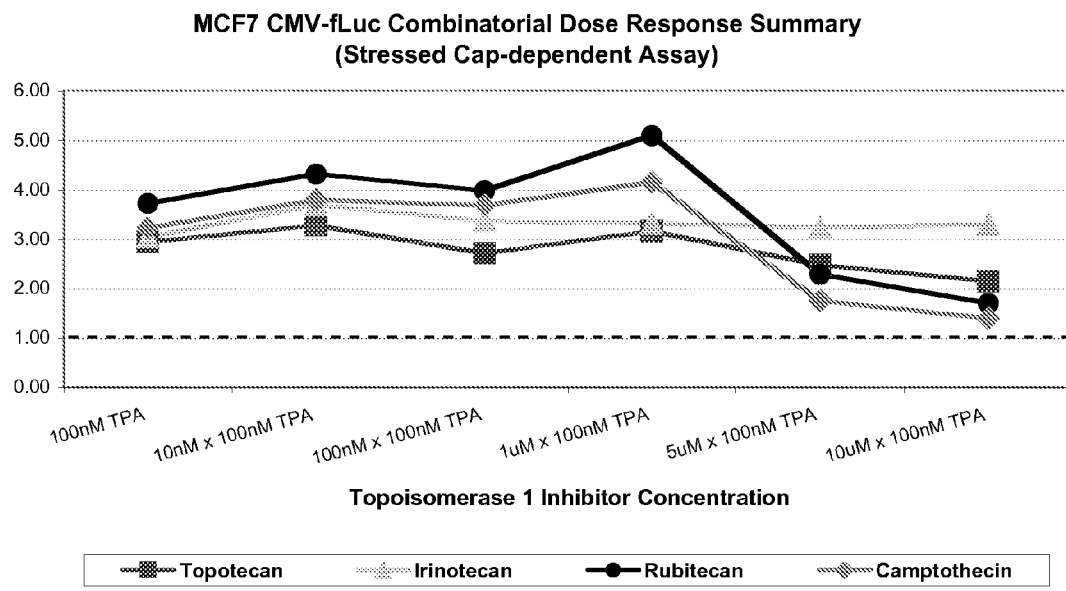

FIG. 28B illustrates the use of a Combinatorial Assay to examine the effects of Topoisomerase 1 inhibitors on cap-dependent translation. A series of dose response assays were performed on the MCF7 CMV-fLuc subclone #65 using varying doses of the Topoisomerase 1 inhibitors (10 nM to 10 uM range) in a Two-Toxin assay with a constant 100 nM TPA dose. The plate reader values were averaged and expressed as the ratio of treated to untreated samples (Fold Induction). The dashed line represents the level of translational response in untreated samples. In a similar manner, camptothecin and rubitecan acted synergistically with TPA to increase fLUC protein activity up to a 1 uM dose but only exhibited a minimal increase in fLUC activity at higher concentrations, whereas irinotecan did not produce any significant change in the TPA-specific translational response, topotecan showed only the TPA inhibitory effect at high doses (i.e. 5 uM and 10 uM).

Figure 28C:
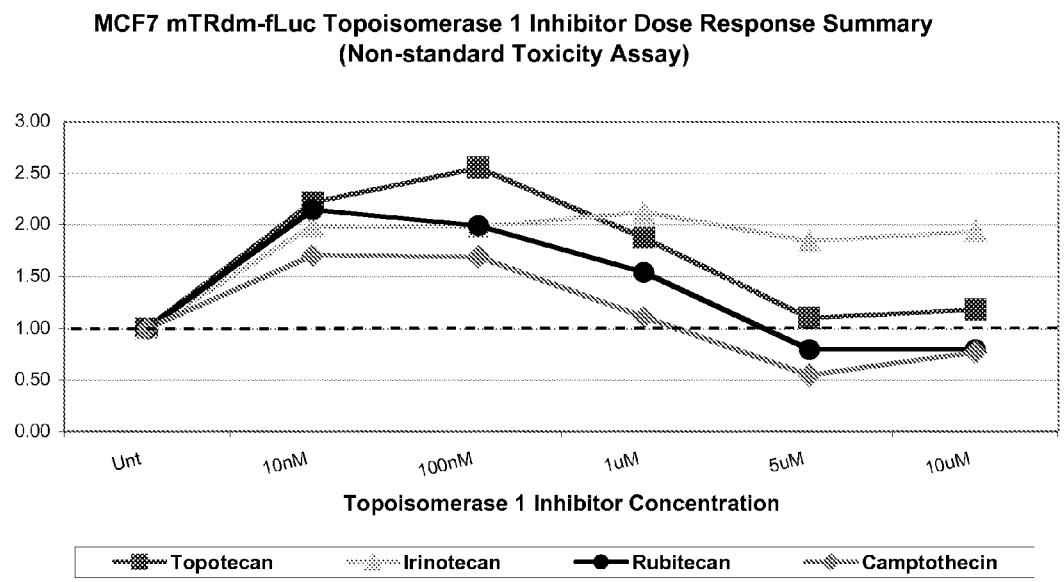

FIG. 28C illustrates the use of single-Toxin Assays to measure the effects of Topoisomerase 1 inhibitors on cap-independent translation in MCF7 cells. Triplicate samples of the MCF7 mTRdm-fLuc subclone #27 were treated with varying concentrations (10 nM to 10 uM range) of the Topoisomerase 1 inhibitors; camptothecin, rubitecan, irinotecan and topotecan. The plate reader values were averaged and expressed as the ratio of treated to untreated samples (Fold Induction). The dashed line represents the level of translational response in untreated controls. All four compounds stimulated cap-independent translation at low doses (10 nM and 100 nM), but only camptothecin, rubitecan, and topotecan exhibited reduced fLUC activity at higher doses (5 uM and 10 uM). In particular, fLUC activity in high concentration camptothecin and rubitecan assays resulted in protein levels below untreated control cells (<100%). These results contrasted with irinotecan which demonstrated a constant amount of fLUC activity at all tested concentrations.

Figure 28D:
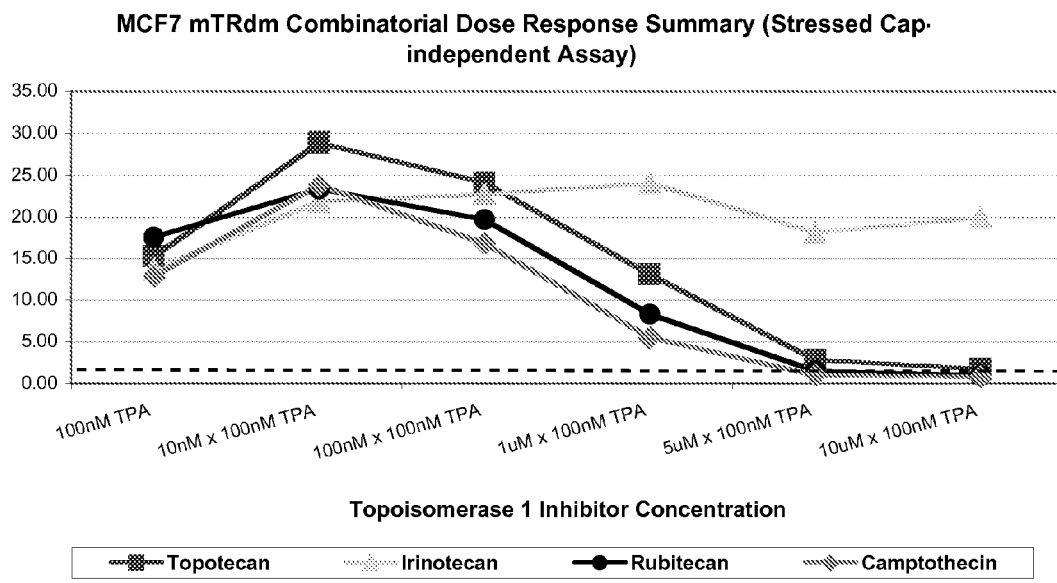

FIG. 28D illustrates the use of a two-Toxin Combinatorial Assay on the MCF7 mTRdm-fLuc subclone #27 treated with 100 nM TPA plus varying doses (10 nM to 10 uM range) of the Topoisomerase 1 inhibitors. The plate reader values were averaged and expressed as the ratio of treated to untreated samples (Fold Induction). The dashed line represents the level of translational response in untreated samples. All four inhibitors acted synergistically with TPA to increase protein activity in the 10 nM two-Toxin assay. However at higher inhibitor concentrations, camptothecin, rubitecan, and topotecan antagonized the TPA activity and exhibited reduced fLUC expression. For camptothecin and rubitecan, this antagonism in the 10 uM two-Toxin assay resulted in fLUC protein levels lower than untreated control cells (<100%). At the highest dose, topotecan exhibited basal level expression. In contrast, the irinotecan two-Toxin assays displayed synergistic action with TPA and enhanced fLUC activity at all tested doses. These results show that in addition to their known action on topoisomerase 1, high doses of these drugs can inhibit protein synthesis with the greatest magnitude changes occurring in toxin-stimulated, TR expressing cell lines.

Figure 29A:
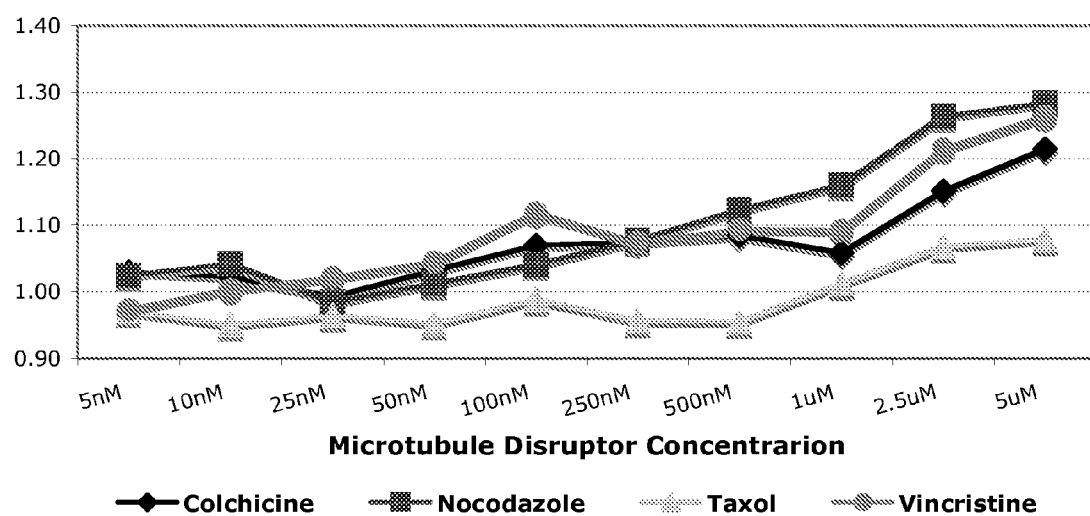
Figure 29B:
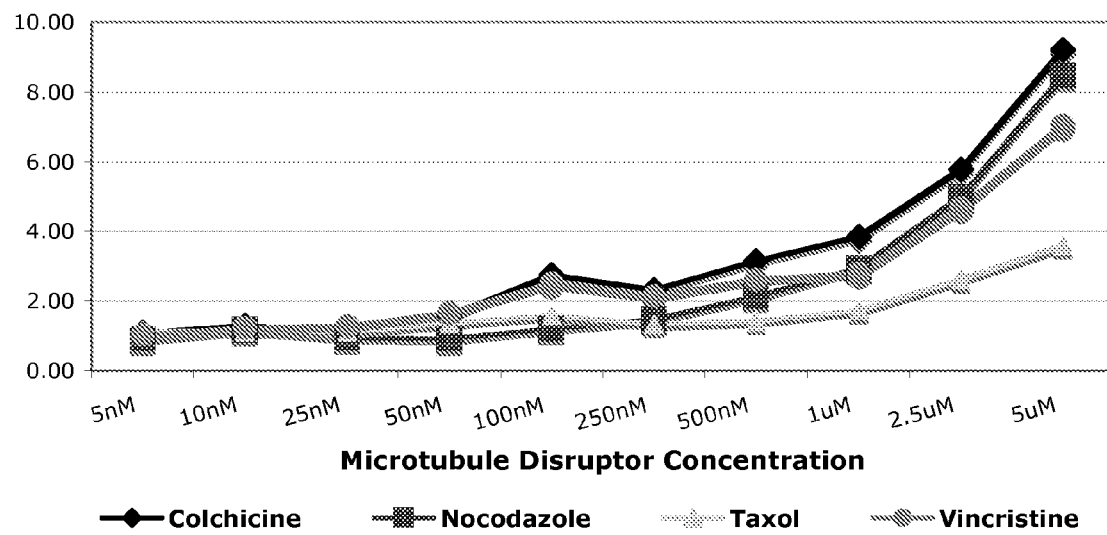
Figure 29B:
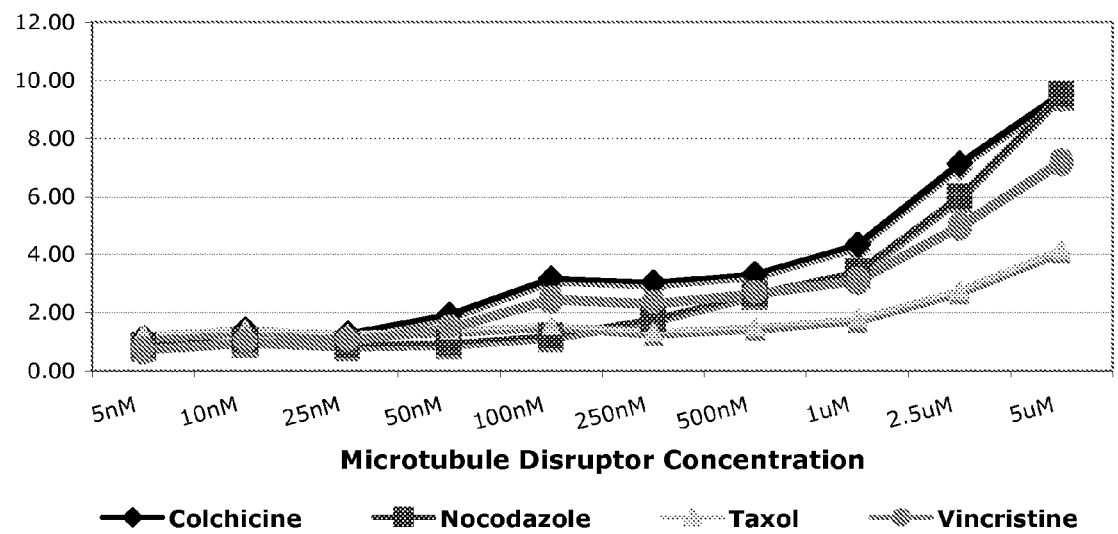

FIG. 29 illustrates the application of the single-Toxin assay to differentiate drug-specific phenotypes within the microtubule disruptor drug genus in HEK293 embryonic kidney cells. Dynamic cytoskeletal structures are important for normal cellular function. In the case of microtubules, interfering with the remodeling of the tubulin subunit protein can produce significant anti-proliferative activity by blocking cell cycle progression. However, drugs that disrupt microtubules exhibit significant biological differences after tubulin binding. For example, nocodazole and colchicine bind microtubules at nonidentical overlapping protein sequences but both compounds block microtubule assembly sites that prevent polymerization and promote depolymerization. Vinca alkaloids, such as vincristine and vinblastine, bind tubulin and induce tubulin protein aggregation into insoluble crystals that prevent microtubule assembly. Finally, taxol binds and stabilizes intact microtubules which interferes with their disassembly during cell division.

FIG. 29A shows the use of single-Toxin assays to measure the effects of microtubule disruptors on the HEK293 CMV-fLuc subclone #3 treated with varying doses (5 nM to 5 uM range) of the following agents: nocodazole, colchicine, vincristine, and taxol. Following 6 hr exposure, cells were lysed and fLuc protein activity measured using a standard microplate reader assay. The plate reader values were averaged and expressed as the ratio of treated to untreated samples (Fold Induction). Nocodazole, colchicine and vincristine exhibited reporter activity increases between 100 nM and 5 uM concentrations. In contrast, significant changes in fLUC expression were only observed at the highest taxol doses (2.5 uM and 5 uM).

FIG. 29B shows the dose response curves for the HEK293 hTRdm-fLuc #53 (top panel) and HEK293 mTRdm-fLuc #12 (bottom panel) subclones treated with varying concentrations (5 nM to 5 uM range) of the microtubule disruptors listed in FIG. 29A. The plate reader values were averaged and expressed as the ratio of treated to untreated samples (Fold Induction). Highly similar TR expression profile were produced by the human (hTRdm, top panel) and the mouse (mTRdm, bottom panel) TR cassettes. As in the cap-dependent assays of FIG. 29A, colchicine and vincristine exhibited increased reporter activity in all doses larger than 100 nM. In contrast, significant increases in reporter activity were only observed at nocodazole concentrations greater than 250 nM. As in the cap-dependent assay, taxol-specific reporter increases were only observed at the 2.5 uM and 5 uM doses. Despite the fact that colchicine and vincristine demonstrated similar translational responses in cap-dependent and cap-independent assays, nocodazole produced a distinct cap-independent response. Even though significant translational increases were observed at high taxol doses in both assays, this drug produced the smallest response profile of all the microtubule disruptor drugs tested, which is consistent with its unique activity.

FIG. 30 shows the TR-specific responses of the human HEK293 cell line to the Updated 15-Assay protocol.

Figure 30A:
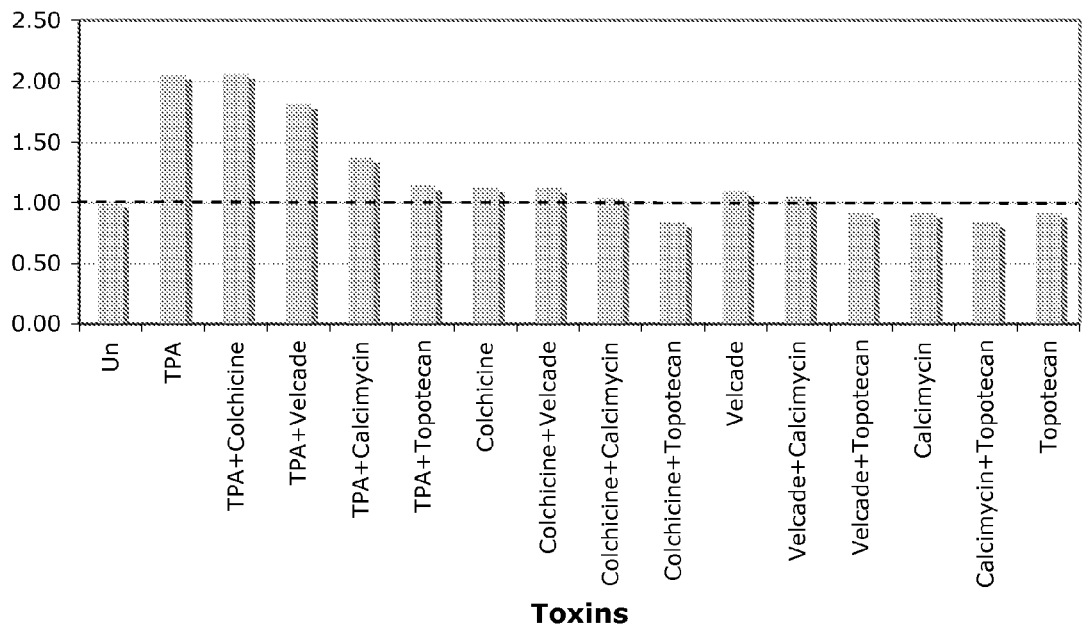

FIG. 30A shows a 15-Assay histogram of cap-dependent translational responses produced by the HEK293 CMV-fLuc subclone #3. The composition and concentration of the toxins used in these studies are shown in Table 3. The dashed line represents the level of translational response in the untreated samples. Significant cap-dependent fLuc production was observed in all TPA combinatorial assays with the exception of the TPA+Topotecan (High Dose or HD) two-Toxin assay.

Figure 30B:
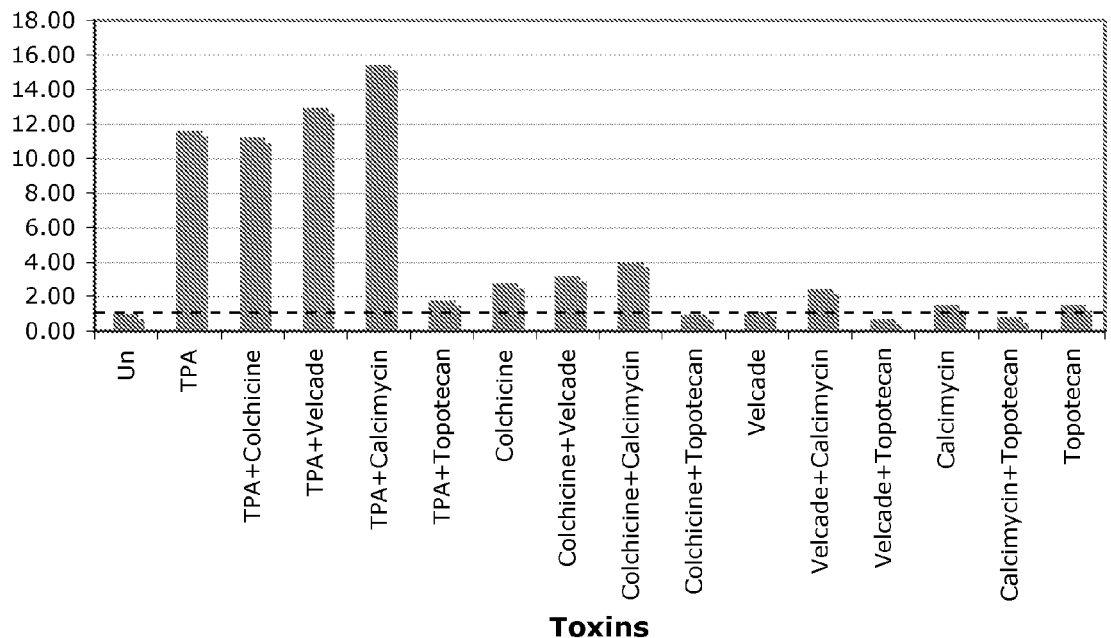

FIG. 30B shows a 15-Assay histogram of the TR translational responses produced by HEK293 mTRdm-fLuc subclone #13. fLUC protein activity was determined using a standard microplate reader assay and is expressed as the ratio of treated to untreated cultures (i.e., Fold Induction). The dashed line represents the level of translational response in the untreated samples. Highly significant increases in the TR-regulated translation were observed in all combinatorial TPA assays with the exception of the TPA+Topotecan (HD) two-Toxin assay.

Figure 30C:
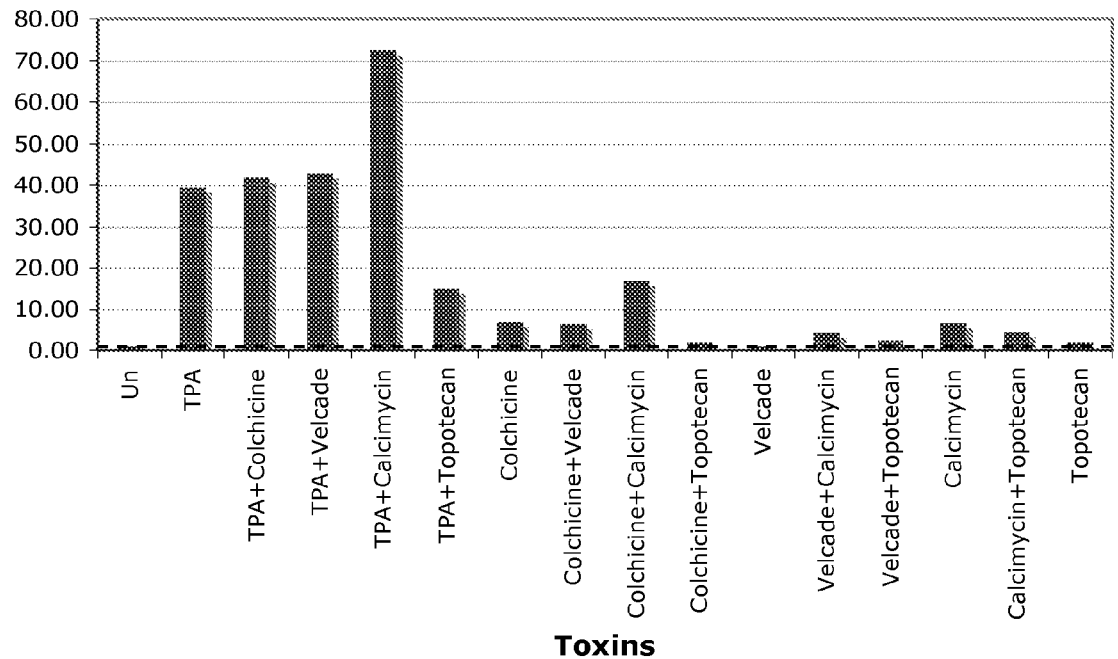

FIG. 30C shows a 15-Assay histogram of the TR translational responses produced by the HEK293 hTRdm-gLuc subclone #79. As before, secreted *Gaussia* Luciferase (gLUC) activity was measured in conditioned media 6 hr after drug application and protein activity expressed as the ratio of treated to untreated samples (Fold Induction). The dashed line represents the translational response in untreated cells. Even though the fLuc protein is a cytosolic protein that is subject to intracellular protein degradation systems and gLuc is a secreted protein that escapes intracellular degradation and accumulates extracellularly, the cap-independent expression profiles in FIG. 30B and FIG. 30C correlate strongly and exhibit similar differences to the cap-dependent assays of FIG. 30A. The cap-independent response in the TPA+Calcimycin two-Toxin assay shows the largest translational increase in the 15-Assay group, which contrasts with the minimal induction observed in the cap-dependent assay of FIG. 30A. Furthermore, the inhibitory effect of Topotecan (HD) was evident in all Single- and two-Toxin assays, with the greatest change observed in the TPA+Topotecan (HD) assay.

FIG. 31 demonstrates the use of a 21-Toxin assay procedure to characterize the effect of an unknown or previously undefined substance on human HEK293 embryonic kidney cells. The 21-Assay setup employs the single and pairwise combinatorial application of 5 toxins, as in a standard 15-Toxin assay, with the addition of a sixth substance. Inclusion of the sixth compound requires the expansion of the assay group to a total of 21 Single- and two-Toxin assays. The composition and concentration of each toxin is described in Table 3. In this example, the previously undefined substance is taxol. Prior to this assay, combinatorial taxol responses had not been measured in the updated 15-Toxin assay protocol in HEK293 cells.

Figure 31A:
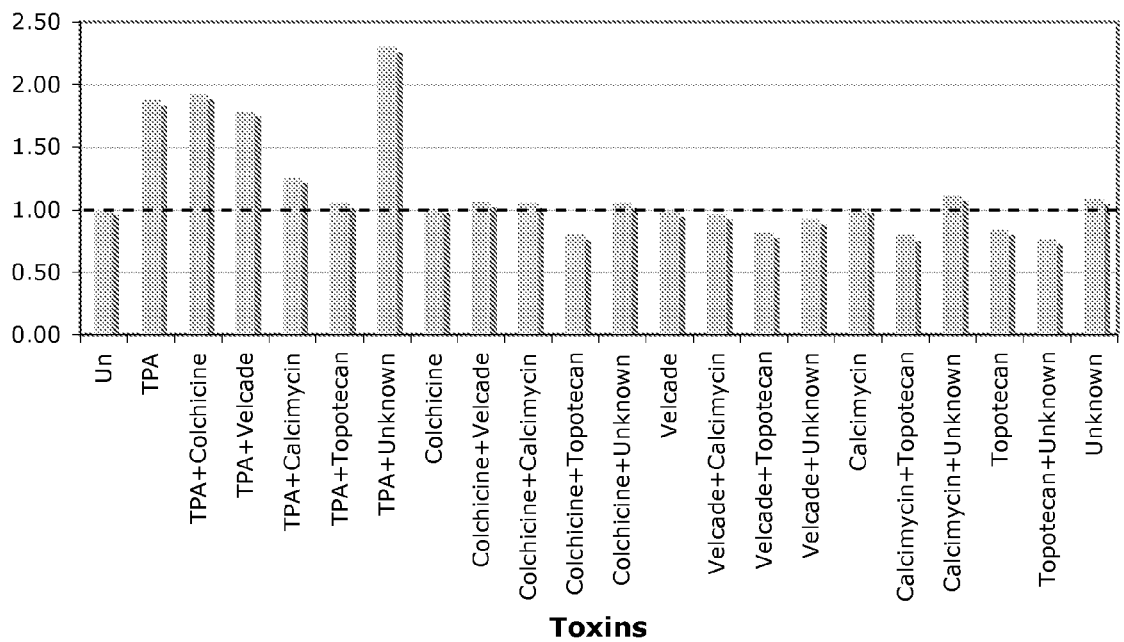

FIG. 31A shows a 21-Toxin histogram of cap-dependent translational responses produced by the HEK293 CMV-fLuc subclone #3. Following 6 hr exposure to the compounds, cells were lysed and fLuc protein activity measured using a standard microplate reader assay. The triplicate plate reader values were averaged and expressed as the ratio of treated to untreated samples (Fold Induction). The dashed line represents the level of translational response in the untreated samples. Although taxol had a minimal effect on cap-dependent fluc protein production in a single-Toxin assay (Unknown), the TPA+taxol two-Toxin assay (TPA+Unknown) exhibited a synergistic interaction and the maximal translational response of this group. No additional significant changes were observed in the two-Toxin assays.

Figure 31B:
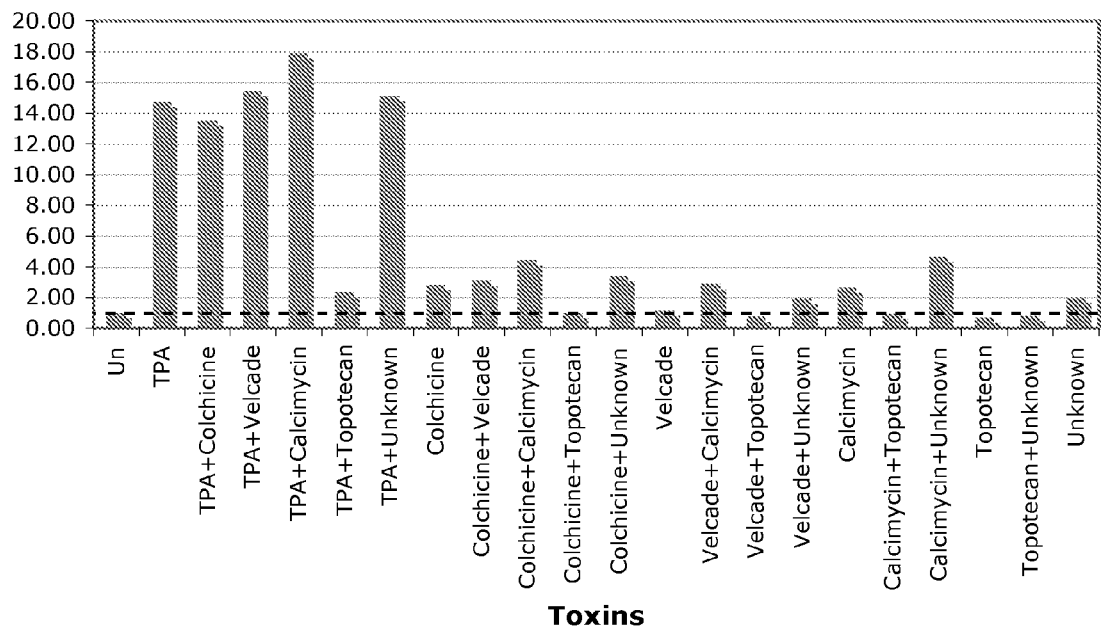

FIG. 31B shows a 21-Toxin histogram of the TR-specific translational responses produced by HEK293 hTRdm-fLuc subclone #13 which expresses the fLUC reporter protein. The dashed line represents the translational response produced by untreated cell samples. In this group, the taxol (Unknown) exhibited small synergistic increases in fLUC activity in the single-Toxin and the colchicine+taxol, calcimycin+taxol, bortezomib+taxol two-Toxin assays, but not in the TPA+taxol or topotecan+taxol assays.

Figure 31C:
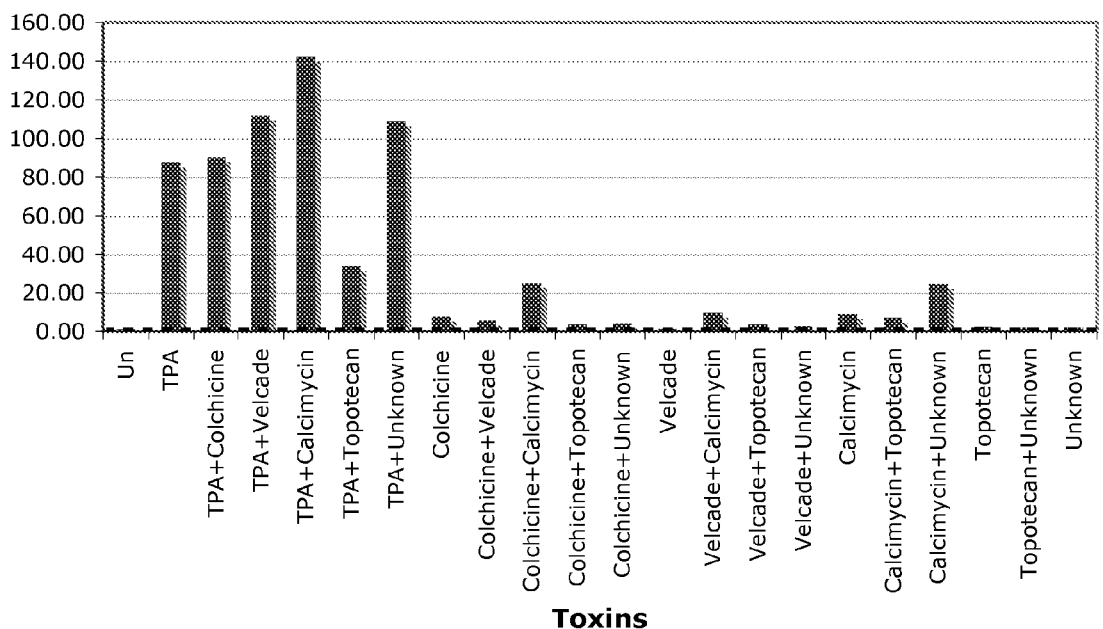

FIG. 31C shows a 21-Assay histogram produced by HEK293 hTRdm-gLuc subclone #79 which expresses the gLUC reporter protein. Following a 6 hr culture time, secreted gLuc activity was measured in conditioned media using a standard microplate reader assay and expressed as the ratio of treated to untreated samples (Fold Induction). The dashed line represents the level of translational response in the untreated samples. Given that the gLuc protein is secreted into the media, it escapes the cytoplasmic protein turnover processes acting on the fLUC protein. Therefore, any difference in the apparent TR response is a likely result of variation in reporter protein synthesis, secretion or reduced protein turnover. However, despite the differences in fLuc and gLuc protein processing, the response profiles generated by HEK293 hTRdm-fLuc subclone #13 and HEK293 hTRdm-gLuc subclone #79 showed a strong correlation. The most significant change was observed in the colchicine+taxol two-Toxin assay which is the likely result of altered protein secretion due to a combinatorial action of the two tubulin protein binding drugs on microtubules.

Figure 32A:
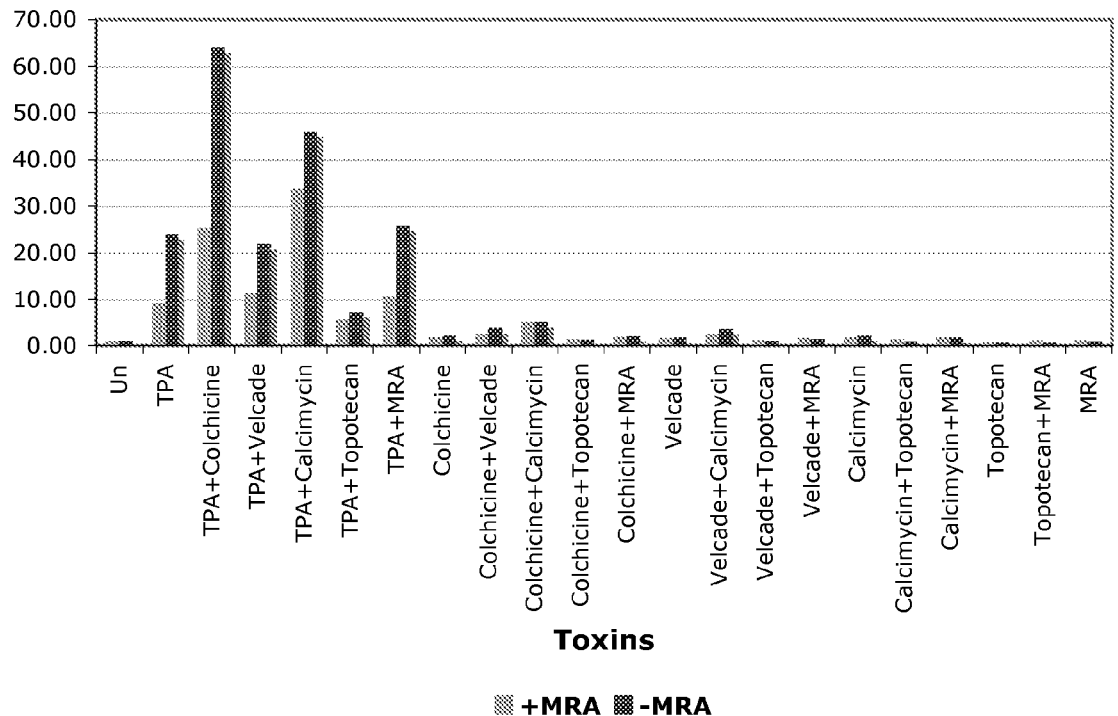
Figure 32A:
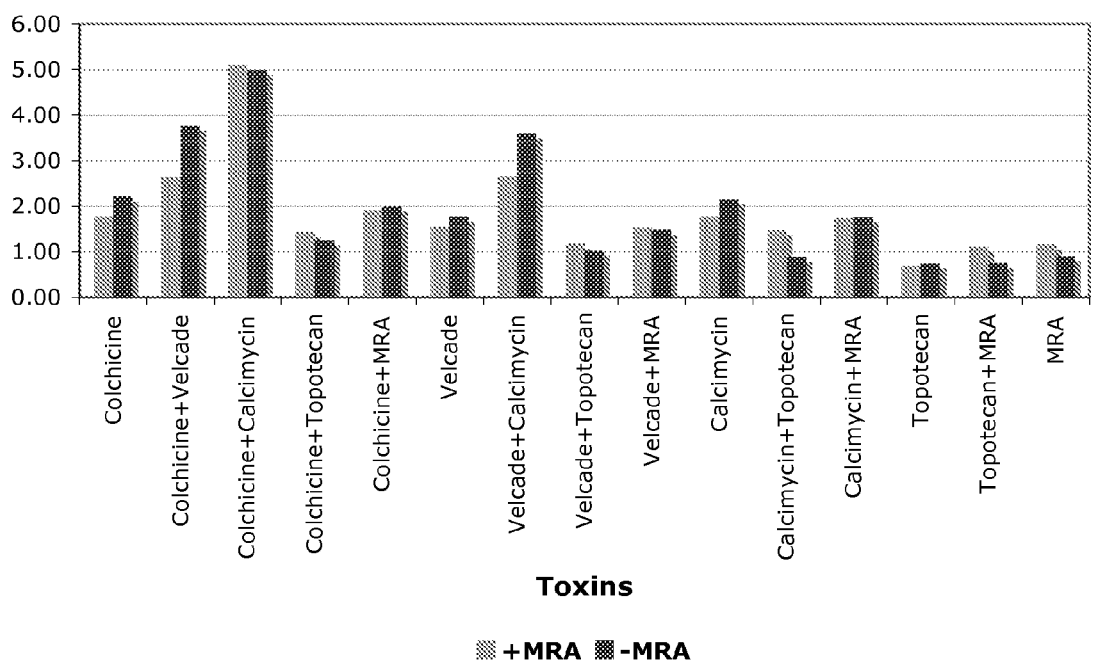
Figure 32B:
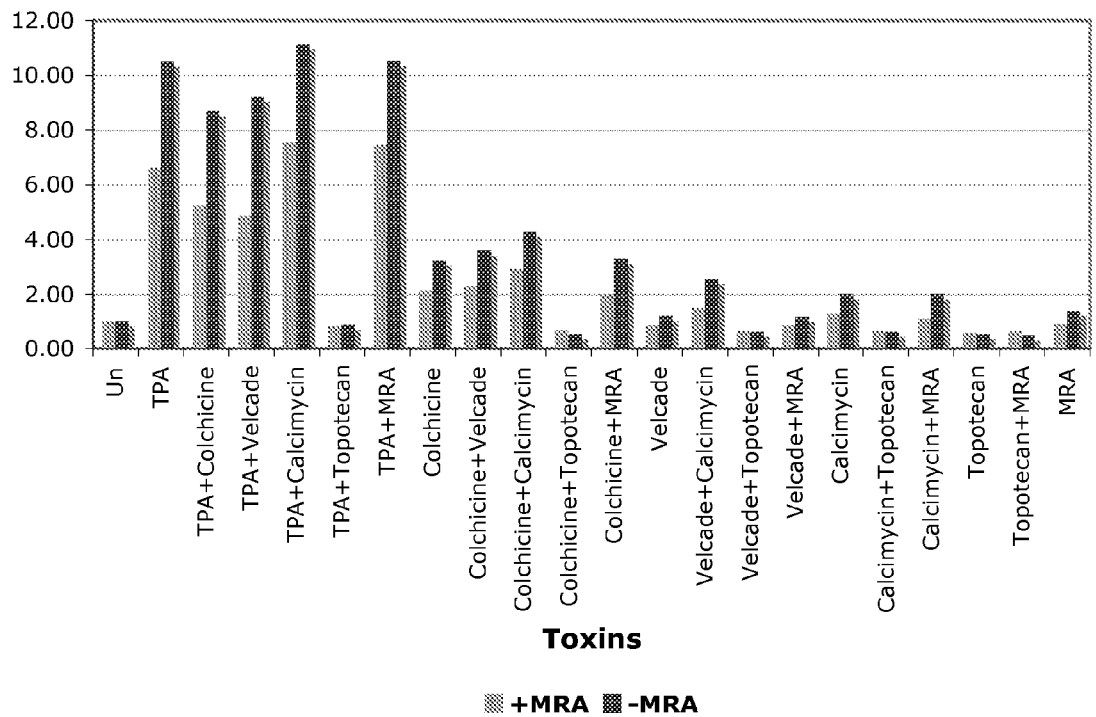

FIG. 32 illustrates the use of the 21-Assay procedure to detect any chronic effects associated with antibiotic treatment of HepG2 hepatocellular carcinoma and HEK293 embryonic kidney cells. Mycoplasma Removal Agent (MRA) or 4-oxoquinoline-3-carboxylic acid derivative is an antibiotic commonly applied to cultured mammalian cells to treat mycoplasma contamination. MRA exhibits minimal toxicity and can be applied for extended culture periods. In this example, the MRA treated cells (+MRA) were incubated with ~150 nM MRA for 7 days prior to the 21-Assay procedure. Although +MRA cells were maintained in antibiotic supplemented media, an additional MRA dose was applied as the Unknown compound. The untreated, –MRA cultures were never exposed to the antibiotic. The names and concentrations of standard toxins are given in Table 3. FIG. 32A shows the effect of prolonged MRA exposure in HepG2 cells, while FIG. 32B illustrates the effect of MRA in HEK 293 cells.

FIG. 32A upper panel shows a 21-Assay histogram of the TR responses produced by HepG2 mTRdm-fLuc subclone #16, which was either treated (light bars) or not treated (dark bars) with ~150 nM MRA for 7 days. Following the 6 hr treatment with standard toxins, cells were lysed and fLuc protein activity measured using a standard microplate reader assay. The plate reader values were averaged and expressed as the ratio of treated to untreated samples (Fold Induction). Lower panel shows the same data set with the TPA assays removed to highlight the responses observed in the other assays. In contrast to the single- and two-Toxin TPA assays, the antibiotic treated HepG2 cells exhibited minimal differences in fLUC activity. For the TPA assays, significant antagonism was observed in each test with a particularly large decrease in fLUC expression observed in the TPA+colchicine two-Toxin assay, where the +MRA culture exhibited a ~2.5-fold decrease in fLUC activity compared to –MRA cells.

FIG. 32B shows a 21-Assay histogram of the cap-independent translational responses produced by the HEK293 mTRdm-fLuc subclone #45, either treated (light bars) or not treated (dark bars) with ~150 nM MRA for 7 days. In contrast to the HepG2 cells in FIG. 32A, chronic MRA exposure of HEK293 cells resulted in a near uniform decrease in fLUC expression in the 21-Assay protocol. However as in FIG. 32A, the greatest magnitude decreases were observed in the TPA single- and two-Toxin assays. These results support the theory that prolonged exposure to fluoroquinolone antibiotics can measurably affect the TR assay, in particular a strong antagonistic toxin-specific phenotype was detected involving the TPA toxin.

FIG. 33 shows the application of the Toxin Assay procedure to identify toxin-specific and cell-specific effects in HEK293 cells associated with translational inhibitors.

Figure 33A:
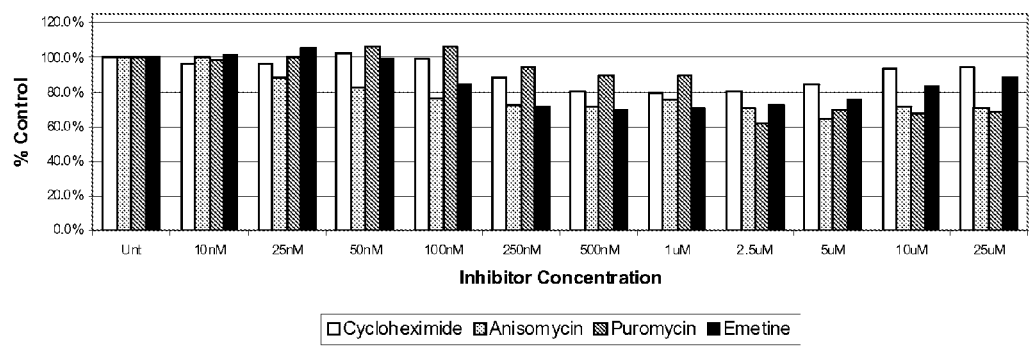
Figure 33A:
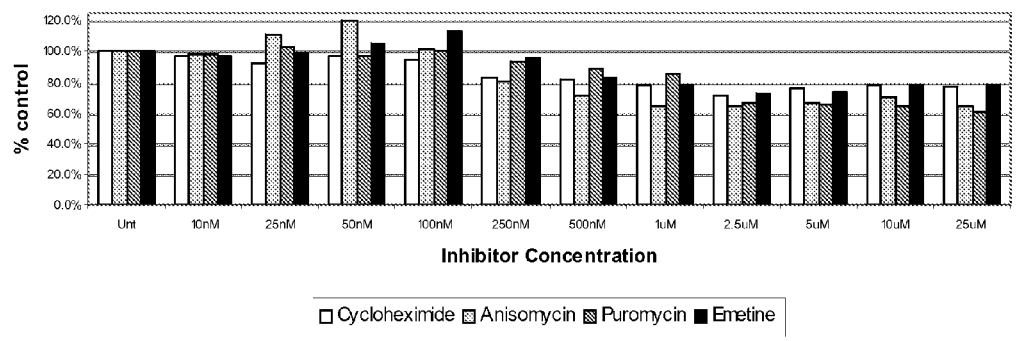
Figure 33A:
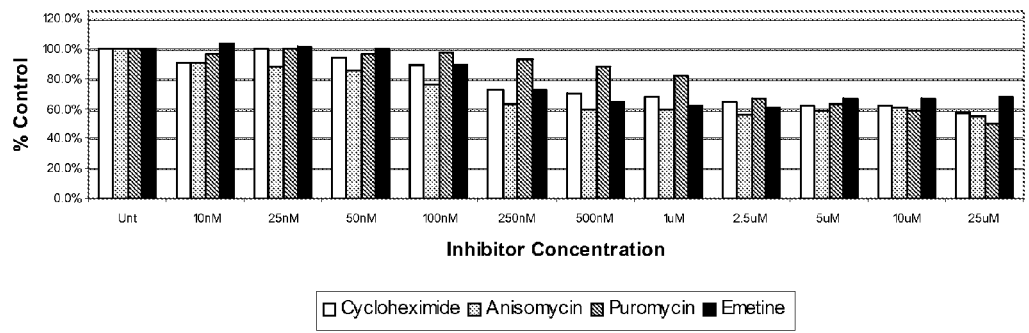

FIG. 33A shows dose response histograms in which the HEK293 CMV-fLUC subclone #3 (top panel), hTRdm-fLUC subclone #13 (middle) and mTRdm-fLUC subclone #45 (bottom) are treated with various concentrations (dose range 10 nM to 25 uM) of the following the translation inhibitors: cycloheximide, anisomycin, puromycin and emetine. At sufficiently large doses, these inhibitors immediately stop protein translation, and the resulting protein turnover reduces reporter protein levels below untreated cell levels (<100% control).

Translation inhibitors exhibited some similar effects on cap-dependent translation (HEK293 CMV-fLUC subclone #3 data, top panel) and cap-independent translation (HEK293 hTRdm-fLUC #13 and mTRdm-fLUC #45 subclones, middle and bottom panels). For example, a 250 nM concentration of each inhibitor was sufficient to reduce protein synthesis below control cell levels. Furthermore, additional increases in inhibitor dose (up to 25 uM, or 100×) produced only minimal additional reductions in reporter protein activity. Also, puromycin required a 2.5 uM concentration to reduce reporter protein levels to levels comparable to the other three inhibitors. In contrast to these similarities, anisomycin and emetine exhibited distinct activities in the HEK293 CMV-fLUC #3 (top panel) and mTRdm-fLUC #45 (bottom panel) subclones. In these cells, low doses of anisomycin (~25 nM) and emetine (100 nM) were sufficient to reduce reporter protein levels below untreated control cells. Lastly, the 30-40% decline in fLUC protein activity in the single-Toxin 25 uM assay suggests that the fLUC protein exhibits a half-life in excess of 6 hr in HEK293 cells.

Figure 33B:
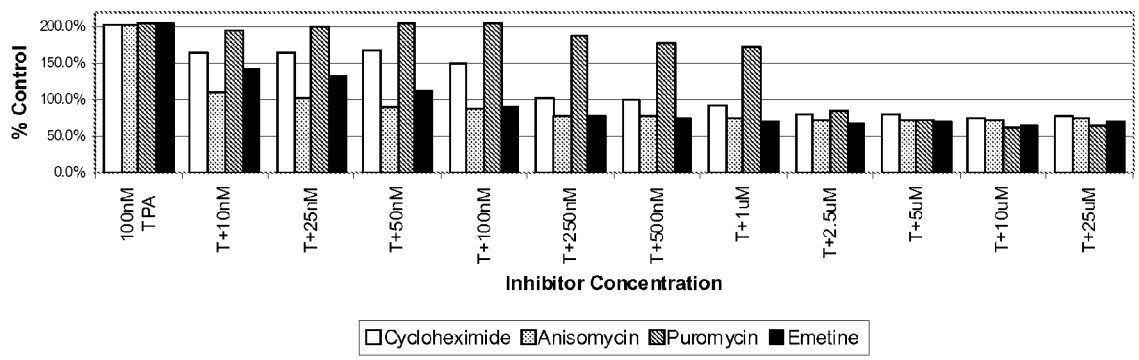
Figure 33B:
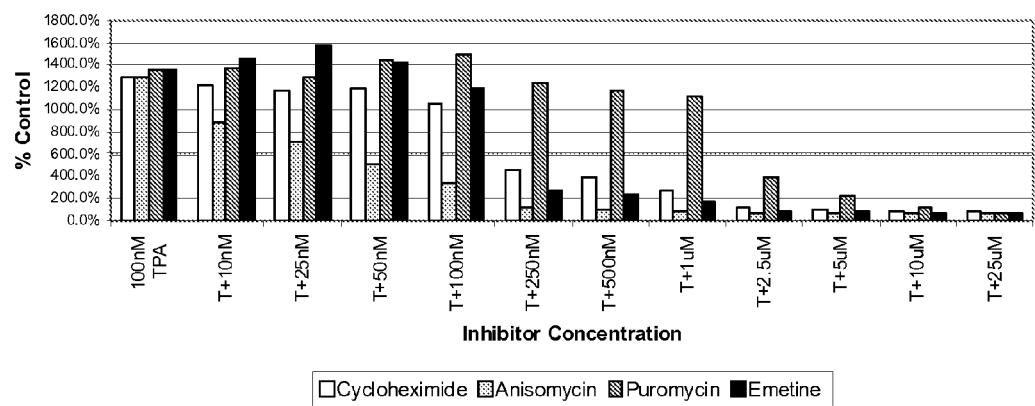
Figure 33B:
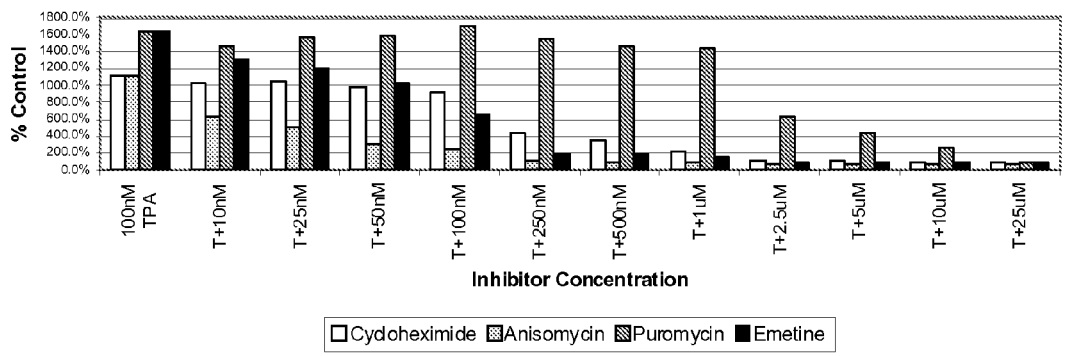

FIG. 33B shows dose response histograms of the HEK293 CMV-fLUC #3 (top panel), hTRdm-fLUC #13 (middle) and mTRdm-fLUC #45 (bottom) subclones treated with a two-Toxin assay of 100 nM TPA in combination with various concentrations (dose range 10 nM to 25 uM) of the translation inhibitors listed in FIG. 33A. For the HEK293 CMV-fLUC #3 (top panel) and mTRdm-fLUC #45 (bottom panel) subclones, anisomycin and emetine antagonized the TPA response at the lowest tested dose (10 nM) and reduced reporter protein levels 50-300% compared to the TPA single-Toxin assay. This contrasted with puromycin, which required a 250 nM concentration (25×) to initially reduce protein synthesis below the TPA Single-Toxin assay level in all three cell lines. Reminiscent of the single-Toxin result, puromycin required a considerably higher dose to reduce reporter protein levels to levels comparable to the other three inhibitors. For example, the CMV-fLUC #3 subclone required a 2.5 uM puromycin dose to correlate with the other inhibitors, which contrasted with hTRdm-fLUC #13 and mTRdm-fLUC #45 subclones which needed a 25 uM puromycin concentration (a 10× increase). As in FIG. 33A, the 40% decline in reporter protein levels in the 25 uM inhibitor concentration in the two-Toxin assays supported the fLUC half-life estimate of about 6 hr.

Figure 33C:
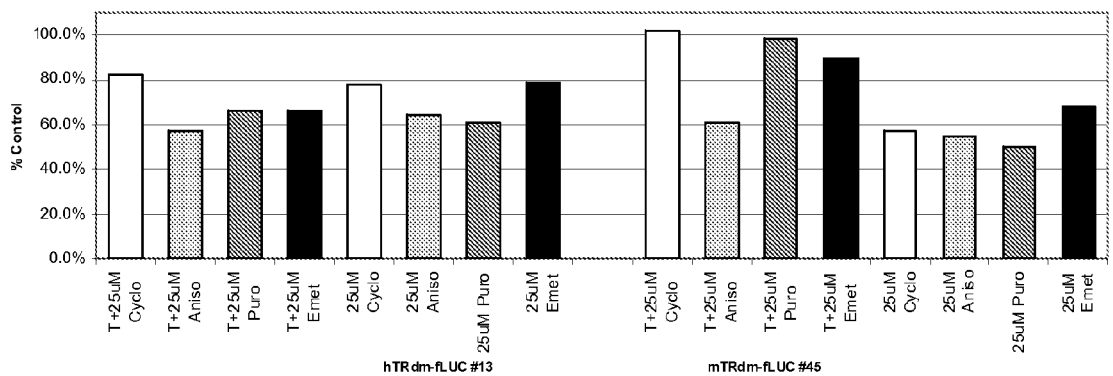

While clear cell-specific differences were observed in FIG. 33B between the HEK293 hTRdm-fLUC #13 and HEK293 mTRdm-fLUC #45 subclones, another significant variation was observed at the highest tested dose (25 uM). To highlight this difference, FIG. 33C shows the response histogram of single- and two-Toxin assays for the HEK293 hTRdm-fLUC #13 and HEK293 mTRdm-fLUC #45 subclones at the 25 uM inhibitor dose only. In contrast to the HEK293 hTRdm-fLUC #13 subclone which displayed equivalent reporter protein levels in both assays, the HEK293 mTRdm-fLUC #45 subclone exhibited little or no reduction below untreated control cell levels for cycloheximide, puromycin and emetine at this dose. Statistical analysis (bottom table) confirms the significance of this variation between the two subclones in the two-Toxin assays. Since the single-Toxin assays for the HEK293 mTRdm-fLUC #45 subclone show that this cell line is sensitive to these three inhibitors at this dose, this result is consistent with altered protein metabolism in these cells following exposure to TPA.

Corresponding reference characters indicate corresponding parts throughout the drawings.

DEFINITIONS

The term "gene" refers to a nucleic acid (e.g., DNA) sequence that comprises coding sequences necessary for the production of a polypeptide or precursor or RNA (e.g., tRNA, siRNA, rRNA, etc.). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends, such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

The term "expression vector" refers to both viral and non-viral vectors comprising a nucleic acid expression cassette.

The term "expression cassette" is used to define a nucleotide sequence containing regulatory elements operably linked to a coding sequence that result in the transcription and translation of the coding sequence in a cell.

A "mammalian promoter" refers to a transcriptional promoter that functions in a mammalian cell that is derived from a mammalian cell, or both.

A "mammalian minimal promoter" refers to a 'core' DNA sequence required to properly initiate transcription via RNA polymerase binding, but which exhibits only token transcriptional activity in the absence of any operably linked transcriptional effector sequences.

The phrase "open reading frame" or "coding sequence" refers to a nucleotide sequence that encodes a polypeptide or protein. The coding region is bounded in eukaryotes, on the 5' side by the nucleotide triplet "ATG" that encodes the initiator methionine and on the 3' side by one of the three triplets which specify stop codons (i.e., TAA, TAG, and TGA).

"Operably linked" is defined to mean that the nucleic acids are placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accord with conventional practice.

"Recombinant" refers to the results of methods, reagents, and laboratory manipulations in which nucleic acids or other biological molecules are enzymatically, chemically or biologically cleaved, synthesized, combined, or otherwise manipulated ex vivo to produce desired products in cells or other biological systems. The term "recombinant DNA" refers to a DNA molecule that is comprised of segments of DNA joined together by means of molecular biology techniques.

"Transfection" is the term used to describe the introduction of foreign material such as foreign DNA into eukaryotic cells. It is used interchangeably with "transformation" and "transduction" although the latter term, in its narrower scope refers to the process of introducing DNA into cells by viruses, which act as carriers. Thus, the cells that undergo transfection are referred to as "transfected," "transformed" or "transduced" cells.

The term "plasmid" as used herein, refers to an independently replicating piece of DNA. It is typically circular and double-stranded.

A "reporter gene" refers to any gene the expression of which can be detected or measured using conventional techniques known to those skilled in the art.

The term "regulatory element" or "effector element" refer to a transcriptional promoter, enhancer, silencer or terminator, as well as to any translational regulatory elements, polyadenylation sites, and the like. Regulatory and effector elements may be arranged so that they allow, enhance or facilitate selective production of a mature coding sequence that is subject to their regulation.

The term "vector" refers to a DNA molecule into which foreign fragments of DNA may be inserted. Generally, they contain regulatory and coding sequences of interest. The term vector includes but is not limited to plasmids, cosmids, phagemids, viral vectors and shuttle vectors.

A "shuttle" vector is a plasmid vector that is capable of prokaryotic replication but contains no eukaryotic replication sequences. Viral DNA sequences contained within this replication-deficient shuttle vector direct recombination within a eukaryotic host cell to produce infective viral particles.

The term "substance" as used herein refers to a matter of defined chemical composition. It is used herein interchangeably with the term "compound."

The term "viral vector" refers to a virus which contains foreign genetic material for delivery into cells it infects.

A "replication-deficient" viral vector is incapable of replication in a "wild-type" or otherwise unmanipulated mammalian cell. Production of significant quantities of such viruses requires that a producer cell line be co-transfected with a helper virus or otherwise modified to supply or complement the missing function(s).

A "replication-competent" viral vectors is one that is capable of infecting cells and undergoing DNA replication, viral packaging and release from the infected cell.

"Conditionally replicating" viral vectors as used herein are replication-competent vectors that are designed to be selectively expressed in particular cell types so that undesired broad spectrum infection is avoided. Conditional replication may be achieved by including in the vector tissue-specific, tumor-specific or cell type-specific or other selectively induced regulatory control sequences that are operably linked to early viral genes.

The terms "stress" and "toxicity" are used to refer to the disturbance of the natural biochemical and biophysical homeostasis of the cell. Whereas stress generally leads to recovery of cellular homeostasis, a toxic response eventually results in cell death.

DESCRIPTION OF THE PREFERRED EMBODIMENTS

The present invention relates to subpopulations of mammalian cells which exhibit distinctive ribosomal profiles, which is evidenced by different translation activities. Once a mammalian cell or cell line is stably transformed with the expression cassette described herein, the desired subpopulations of cells can be identified. Importantly, these subpopulations of cells can be manipulated to exhibit either cap-dependent or cap-independent translation.

Accordingly, in one embodiment, the present invention is directed to a method for identifying a desired subpopulation of mammalian cells. The method includes the following steps. A subset of mammalian cells is treated with at least one toxin to form toxin-treated cells, the mammalian cells being stably transformed with a nucleic acid expression cassette comprising either: (1) a TR element encoding an mRNA molecule that is selectively translated in stressed and/or dying cells, and a nucleotide sequence operably linked to the TR element, which encodes a reporter gene and is translated from the TR element; or (2) a constitutive promoter and a nucleotide sequence operably linked to the promoter, which encodes a reporter gene. A level of a reporter protein encoded by the reporter gene in the toxin-treated cells is measured as compared to a level of the reporter protein expressed by a reference standard to identify whether the subset of mammalian cells exhibit the phenotype of the desired subpopulation of mammalian cells. At least one cell from the mammalian cells is isolated to form a cell culture if the toxin-treated cells of the mammalian cells exhibit the phenotype of the desired subpopulation of the mammalian cells. The cell culture is grown to form a subpopulation of mammalian cells. Optionally, the subpopulation of mammalian cells is treated with the at least one toxin, and the measuring, isolating, and growing steps are repeated until the desired subpopulation of mammalian cells is identified.

The translation regulated (TR) sequence (also referred to as the "TR element") employed in the present invention is the IRES element, which can be distinguished from the 5' UTR IRESs by (a) its nucleic acid sequence context and (b) the cellular activity which regulates translation (US Published Patent Application No. 2006/0173168, which is hereby incorporated by reference). The combination of these two features forms a basis for selective translation of downstream coding sequences in stressed and/or dying mammalian cells that are operably linked to this IRES sequence. Thus, the present invention contemplates the use of any mammalian IRES as the TR element, which is selectively expressed in stressed and/or dying cells.

In some embodiments, the IRES element of this invention has cap-independent translational activity which localizes within the ORF of the mammalian Proteolipid Protein (plp) gene. In its native context, plp IRES activity resides within a multicistronic RNA containing several upstream ORFs ("uORFs") which effectively block ribosome scanning to internal AUG codons in normal cells. However, exposure of cells to toxic agents results in ribosome binding and translation from specific internal RNA sequences so that an internal amino acid sequence is translated from the 3' end of the plp ORF (e.g. the PIRP-M and PIRP-L peptides). In another embodiment, the TR element is derived from the DM20 variant.

In some embodiments, the TR element of the present invention is derived from exons 1-7 of the plp gene. While not being bound to a particular theory, it is believed that the exons 1 through 4 are sufficient to encode a functional IRES activity based on mutational analysis data. Furthermore, it is believed that the TR regulatory system, which plays a role in stress/death-specific translation is located within exons 6 and/or 7.

In some embodiments, the TR element is derived from a mouse. In contrast to the IRES element disclosed in US 2006/0173168, which is expressed in dying cells, a mouse-derived TR element of the present invention derived from PLP/DM20 differs in all of the following features:

1) nucleotide 1 (in SEQ ID Nos. 1 and 2) was mutated from A to T to remove the wild type AUG start codon in the myelin proteolipid protein PLP and DM20 cDNAs that directs the synthesis of the full length PLP and DM20 in order to prevent such synthesis from occurring;

2) nucleotide 4 was mutated from G to A in order to create a stop codon in the second possible reading frame of the PLP and DM20 cDNAs to prevent full length synthesis thereof;

3) nucleotides 6, 7 and 8 were mutated from C to T, T to G and T to A respectively to create a stop codon in the third possible reading frame of the PLP and DM20 cDNAs to prevent synthesis of the full length PLP and DM20;

4) nucleotides 17 and 18 were mutated from G to A and T to G, respectively to create the first stop codon in the main (first) open reading frame of the PLP and DM20 cDNAs to prevent their full length synthesis;

5) nucleotide 21 was mutated from T to A in order to create the second stop codon in the main (first) open reading frame of the PLP and DM20 cDNAs to prevent full length synthesis thereof;

6) nucleotide 27 was mutated from A to T in order to remove the AUG codon from the third possible reading frame of the PLP and DM20 cDNAs to prevent out-of frame translation initiation in the absence of the wild type AUG codon; and 7) the stop codon was deleted from the PLP and DM20 cDNAs to reduce interference with translation of the downstream open reading frame.

As discussed below, the TR elements of the present invention derived from murine PLP/DM20 do not direct translation of either PIRP-M or PIRP-L peptide. In addition to the above changes, the following mutations were introduced into the TR elements from the DM 20 variant of the cDNA:

1) nucleotide 511 was mutated from A to T in order to remove the first in-frame internal AUG start codon in the DM20 variant that directs the synthesis of PIRP-M protein to prevent such synthesis from occurring; and 2) nucleotide 598 was mutated from A to T to remove the second in-frame internal AUG start codon in the DM20 variant that directs the synthesis of PIRP-L protein in order to prevent such synthesis from occurring.

Similarly, the following mutations were introduced into the TR elements from the murine PLP variant of the cDNA:

1) nucleotide 616 was mutated from A to T in order to remove the first in-frame internal AUG start codon in the PLP variant that directs the synthesis of PIRP-M protein to prevent such synthesis from occurring; and 2) nucleotide 703 was mutated from A to T to remove the second in-frame internal AUG start codon in the PLP variant that directs the synthesis of PIRP-L protein in order to prevent such synthesis from occurring.

In a preferred embodiment, a TR element is selected from a human or a mouse TR element. More preferably, the TR element is selected from murine sequences TRdm (SEQ ID NO: 1) and TRplp (SEQ ID NO: 2).

TRdm nucleic sequence (SEQ ID NO: 1) was derived from the DM20 splice variant cDNA of the mouse proteolipid protein gene 1, but has been modified at nucleotide positions 1, 4, 6, 7, 8, 17, 18, 21, 27, 511, and 598. In addition, the last 3 nucleotides encoding the stop codon were removed.

TRplp nucleic sequence (SEQ ID NO: 2) was derived from the PLP splice variant cDNA of the mouse proteolipid protein gene 1, and it contains modifications at nucleotide positions 1, 4, 6, 7, 8, 17, 18, 21, 27, 616, and 703. TRplp differs from TRdm by the presence of nucleotides 349-453. The last 3 nucleotides encoding the stop codon were removed.

In some embodiments, the TR element is derived from a human. By way of example and not of limitation, the IRES element is derived from human PLP/DM20 sequence. More preferably, the TR element from human PLP sequence has a nucleic acid sequence of SEQ ID NO: 3, and the TR element from the human DM20 sequence has a nucleic acid sequence of SEQ ID NO: 4.

In some embodiments, the TR element comprises a nucleotide sequence that is the same as that of a mutated variant of a reference sequence, wherein the reference sequence comprises A) a PLP nucleotide sequence corresponding to at least nts 1-831 of a FIG. 26 PLP sequence and having at least 62% sequence identicality thereto, or B) a DM20 nucleotide sequence corresponding to at least nts 1-726 of a FIG. 26 DM20 sequence and having at least 62% sequence identicality thereto; and the reference sequence comprising C) polypyrimidine tracts at FIG. 26 PLP nucleotide positions 41-48, 50-56, 75-81, 150-156, 200-205, 227-244, 251-257, and 563-570, or at positions corresponding thereto, D) ATG sequences at FIG. 26 PLP nucleotide positions 1-3, 616-618, 703-705, and 811-813, or at positions corresponding thereto, E) GNRA sequences at FIG. 26 PLP nucleotide positions 130-133, 142-145, 190-193, 220-223, and 305-308, or at positions corresponding thereto, and F) an 18S rRNA binding site at FIG. 26 PLP nucleotide positions 503-512, or at positions corresponding thereto; wherein (G) the mutated variant (1) comprises mutations of the reference sequence that
  (a) eliminate ATG1, ATG616, and ATG703, and
  (b) introduce stop codon sequences at FIG. 26 PLP nucleotide positions 2-4, 6-8, 16-18, and 19-21, or at positions corresponding thereto; and (2) retains the polypyrimidine tracts (C), the GNRA sequences (E), and the 18S rRNA binding site (F). In one preferred embodiment, the sequence identicality of (A) or (B) is at least or about 70%, and more preferably it is at least or about 80%. In still another embodiment, the mutations (G1) eliminate ATG1, ATG616, and ATG703 by converting each ATG to TTG. In one embodiment, the reference sequence is a vertebrate PLP consensus nucleotide sequence (SEQ ID NO: 5) or a vertebrate DM20 consensus sequence comprising said vertebrate PLP consensus sequence from which nucleotides 349-453 have been deleted. In another embodiment, the reference sequence is a mammalian PLP consensus nucleotide sequence (SEQ ID NO: 10) or a mammalian DM20 consensus sequence comprising said mammalian PLP consensus sequence from which nucleotides 349-453 have been deleted. In the mammalian sequence, the following standard abbreviations are used for nucleotides: m is a or c, r is a or g, w is a or t, s is c or g, y is c or t, k is g or t, v is a or c or g, h is a or c or t, d is a or g or t, b is c or g or t, x/n is a or c or g or t.

In certain instances, sequence elements operably linked to the TR sequences might disrupt the selective translational activity displayed by the TR expression cassette or exhibit sub-optimal translational activity. To alleviate any effect on TR activity by the linked ORF, the present invention provides for codon-usage variants of the disclosed nucleotide sequences, that employ alternate codons which do not alter the polypeptide sequence (and thereby do not affect the biological activity) of the expressed polypeptides. These variants are based on the degeneracy of the genetic code, whereby several amino acids are encoded by more than one codon triplet. An example would be the codons CGT, CGG, CGC, and CGA, which all encode the amino acid, arginine (R). Thus, a protein can be encoded by a variant nucleic acid sequence that differs in its precise sequence, but still encodes a polypeptide with an identical amino acid sequence. Based on codon utilization/preference, codons can be selected to optimize the translation efficiency of an ORF without affecting regulated translation from the TR expression cassette.

Site directed mutagenesis is one particularly useful method for producing sequence variants by altering a nucleotide sequence at one or more desired positions. Site directed (or site specific) mutagenesis uses oligonucleotide sequences comprising a DNA sequence with the desired mutation, as well as a sufficient number of adjacent nucleotides to provide a sequence of sufficient size and complexity to form a stable duplex on both sides of the proposed mutation. Typically, a synthetic primer of about 20 to 25 nucleotides in length is preferred, with about 5 to 10 residues on both sides of the proposed mutation of the sequence being altered. Typical vectors useful in site directed mutagenesis include the disclosed vectors, as well as any commercially or academically available plasmid vector. In general, nucleotide substitutions are introduced by annealing the appropriate DNA oligonucleotide sequence with the target DNA and amplifying the target sequence by PCR procedures known in the art. The present invention contemplates the use of every possible codon in a coding sequence for producing the desired ORF sequence for use in accordance with this invention.

Directed evolution techniques can be used to prepare sequence variants having improved TR function. In a directed evolution technique, at least one round of nucleic acid mutation or nucleic acid splicing or homologous recombination can be performed, starting from a TR-containing polynucleotide. Mutation, splicing, and homologous recombination can be performed in a directed or random manner. For example, one or more oligonucleotides can be designed for site-directed mutagenesis of the TR element, as described above, or one or more randomly generated oligonucleotides can be contacted with the initial TR-containing polynucleotide template. Alternatively, or in addition, PCR amplification of the initial template can be performed under error-permissive conditions and/or an error-prone polymerase to permit introduction of mutations, a technique referred to as "sloppy" PCR.

Similarly, a set of homologous, TR-element-containing polynucleotides can be spliced or recombined in a directed or random manner. For example, one or more restriction endonucleases can be used to digest the homologous polynucleotide templates, randomly or in a predetermined manner, and the resulting fragments can then be ligated together. Alternatively or in addition, the set of TR-element-containing polynucleotides can be pooled and treated under conditions favoring homologous recombination among them, either in vitro or in cyto. In particular, regulatory sequences important for TR-specific translational efficiency could be combined or amplified in number so that sequences containing multiple copies are produced. For this effort, any combination of mutation and splicing or recombination techniques can be employed. One or more than one rounds of any of these can be performed.

After one or more rounds of mutation, splicing, and/or recombination, the resulting polynucleotides are then tested to screen for TR activity. Typically, this can be done by placing a reporter molecule coding sequence under the operative control of one or more of the TR variants that have been produced. The resulting construct(s) are then expressed in a cell that is placed under conditions, such as a condition of stress, for which TR translation can take place. The testing can be used to detect a desired improvement in TR element function. For example, any one of improvement in specificity of TR element translation to a stress condition, sensitivity of TR element activation to a cellular stress response (e.g., a biochemical change antecedent to cell stress and/or death), or efficiency (i.e. magnitude) of translation initiation upon TR element activation can be the focus of the assay).

Based on the assay result, one or more improved TR elements can be selected for use, or for further development; in some embodiments, the selected improved TR element nucleic acids can be used as a starting polynucleotide or as a starting set of polynucleotides for another round, or course of rounds, of directed evolution.

In various embodiments herein, a TR element can comprise, or can be made by mutation of a PLP/DM20 polynucleotide comprising bases of, or corresponding to, bases from about 27 to about 615/510 of a murine or human PLP/DM20 DNA sequences of FIG. 26; and this can comprise further bases of, or corresponding to, bases from about 616/511 to about 702/597, bases from about 703/598 to about 772/666, and/or bases from about 773/667 to about 810/705. For example, a TR element can comprise, or can be made by mutation of a PLP/DM20 polynucleotide comprising bases of, or corresponding to, bases from about 27 to about 810/705, with or without omission of bases from about 616/511 to about 702/597, numbered with reference to FIG. 26.

In PLP/DM20 coding sequences, and TR elements thereof or constructed therefrom, mutations can be made, without adverse effect on TR-element function, at one or more positions corresponding to the following PLP/DM20 positions stated with reference to FIG. 26, i.e. positions: 01, 02, 03, 04 to 21 (including deletion of all of part of this segment), 25, 26, 314, 332, 560/455, 614/509, 622/518 to 696/591 (including deletion of all or part of this segment, which removes exon 5), 616/511, 703/598, 806/701, 811/706, 817/712, 818/713, and 827/722. In various embodiments, other nucleobases than the foregoing can be conserved in PLP/DM20 coding sequences. For example, in various embodiments, a nucleobase sequence of a PLP/DM20 coding sequence hereof can comprise polypyrimidine motifs at nucleotide positions corresponding to PLP nucleotide positions 41-48, 50-56, 75-81, 150-156, 200-205, 227-244, 251-257, and 563-570. In some embodiments, such a sequence can further comprise polypyrimidine motifs at one or more of PLP positions 270-274, 299-303, 490-494, 578-582, 597-601; and in some embodiments, also at one or more of PLP positions 626-632, 642-648, 669-674, 707-712, 755-761, 767-771, and 800-804.

Similarly, in various embodiments, a nucleobase sequence of a PLP/DM20 coding sequence hereof can comprise GNRA motifs at nucleotide positions corresponding to PLP nucleotide positions: 130-133, 142-145, 190-193, 220-223, 305-308; and in some embodiments further at 635-638; and in other embodiments further at one or more of positions 329-332, 343-346, and 572-575; and in some, still further at one or more of positions 650-653 and 683-686.

However, as mentioned above, mutation of the following positions can be undertaken with no adverse effect, and in some cases with an enhancing effect: 01, 04, 06, 07, 08, 17, 18, 21, 27. In some embodiments, these mutations can be one or more of: 01t, 04a, 06t, 07g, 08a, 17a, 18g, 21a, and 27t. Other positions that can be mutated with no adverse effect on function include mutations at one or more of PLP positions: 25, 26, 314, 332, 560/455, 616/511, 703/598, 806/701, 811/706, 817/712, 818/713, and 827/722. In some embodiments, these can be one or more of: 25g, 26c, 314g, 332g, 560/455c, 616/511t, 703/598t, 806/701g, 811/706t, 817/712a, 818/713a, and 827/722g. In addition, insertions, e.g., insertions of up to or about 5 nucleotides, can be made at PLP position 614/509, with no adverse effect on function. In addition, fusions to position 831/726, e.g., in-frame fusions thereto of reporter or other target gene coding sequences, do not exhibit any adverse effect on TR element function.

In another embodiment, the TR element of the present invention is derived from a vertebrate PLP or DM20 sequence other than a human or a mouse. In some embodiments, this can be a primate, rod equine, bovine, ovine, porcine, canine, feline, lapine, marsupial, avian, piscine, amphibian, or reptilian sequence. In various embodiments, a vertebrate sequence can be a native sequence, whether wild-type or variant; in some embodiments, a vertebrate sequence can be a wild-type sequence.

As used herein in regard to PLP/DM20 sequences, "vertebrate consensus sequence" refers to the DNA sequence SEQ ID NO: 5. The "vertebrate specific sequence" refers to the PLP or DM20 sequences of the species *Homo sapiens, Pongo pygmaeus* (orangutan), *Pan troglodytes* (chimpanzee), *Macaca mulatta* (rhesus monkey), *Macaca fascicularis* (crab-eating macaque), *Sus scrofa* (pig), *Mus musculus* (mouse), *Rattus norvegicus* (rat), *Monodelphis domestica* (opossum), *Oryctolagus cuniculus* (rabbit), *Bos taurus* (cattle), *Canis familiaris* (dog), *Gallus gallus* (chicken), *Taeniopygia guttata* (zebra finch), *Gekko japonicus* (gecko lizard), *Xenopus laevis* (frog), and *Latimeria chalumnae* (coelacanth). In some embodiments, the vertebrate specific sequence can comprise, or encode, any one of the amino acid sequences having Genbank numbers: P60201 (human), Q5R6E6 (orangutan), XP_001140782 (chimpanzee), XP_001088537 (rhesus monkey), Q8HXW7 (crab-eating macaque), NP_999139 (pig), NP_035253 (mouse), NP_112252 (rat), XP_001374483 (opossum), P47789 (rabbit), CAA08909 (cattle), 39025 (dog), CAA43839 (chicken), P47790 (zebra finch), AAW79015 (gecko lizard), CAA79582 (frog), or BAA84207 (coelacanth).

DNA sequences encoding these are readily available to one of ordinary skill in the art by searching NCBI Genbank in the Nucleotide menu at the http World Wide Web ncbi.nlm.nih.gov/sites/entrez website. For example, useful DNA sequences include those listed under Genbank accession numbers: AJ006976 (human), CR860432 (orangutan), XM_001140782 (chimpanzee), XM_001088537 (rhesus monkey), AB083324 (crab-eating macaque), NM_213974 (pig), NM_011123 (mouse), NM_030990 (rat), XM_001374446 (opossum), NM_001082328 (rabbit), AJ009913 (cattle), X55317 (dog), X61661 (chicken), NM_001076703 (residues 113-946, zebra finch), AY880400 (gecko lizard), 219522 (frog), and AB025938 (coelacanth).

The TR element of the present invention exhibits selective translation in stressed and/or dying cells. The term "selectively translated" or "selective translation" in stressed and/or dying cells means that the mRNA translation activity is observed in more than 95% of any cell line transformed with the TR expression cassette of the present invention at the peak of the translation activity, e.g., within about 6 to about 18 hours following treatment with an acute toxic agent that induces cell stress and/or death, and that the translational levels of the first ORF of the inventive expression cassette rise to at least 50% of the expression levels of the same ORF when transcribed and translated from the same expression cassette lacking an operably linked TR element following treatment with the acute toxic agent. For example, a TR element within an expression cassette of the invention exhibits selective translation in stressed and/or dying cells within about 9 hours following treatment with calcium ionophore A23187 at a concentration of 5 µM, with mRNA translation being observed in more than 95% of a HEK293 cell line transformed with the expression cassette, and translation levels of the first ORF of the expression cassette being at least 50% of the translation levels of the same ORF when transcribed and translated from the same expression cassette lacking an operably linked TR element following the treatment. In some instances, a TR element within an expression cassette of the invention exhibits selective translation in stressed and/or dying cells within about 6 to about 9 hours following treatment with calcium ionophore A23187 at a concentration of 5 µM, with mRNA translation being observed in about 96, 97, 98, 99, 99.5 or 99.9% of a HEK293 cell line transformed with the expression cassette, and translation levels of the first ORF of the expression cassette being about 55, 60, 65, 70, 75, 80, 85, 90, or 95% of the translation levels of the same ORF when transcribed and translated from the same expression cassette lacking an operably linked TR element following the treatment.

In some embodiments of the present invention, the TR element is a plp IRES element, which does not direct translation of PIRP-M or PIRP-L. In other embodiments, the TR element is not derived from the plp IRES.

In some embodiments, the mammalian cells are stably transformed with a nucleic acid expression cassette comprising a constitutive promoter and a nucleotide sequence operably linked to the promoter, which encodes a reporter gene. Transformation with such expression cassette allows for identification of desired subpopulations of mammalian cells exhibiting different translational profiles. In one preferred embodiment, such cell subpopulations exhibit different cap-dependent translational profiles. Any constitutive promoter operable in mammalian cells can be used. In some embodiments, the constitutive promoter is selected from the group consisting of Rous sarcoma virus (RSV) long terminal repeat (LTR) promoter, cytomegalovirus immediate early gene (CMV) promoter, simian virus 40 early (SV40E) promoter, cytoplasmic beta-actin promoter, adenovirus major late promoter, and the phosphoglycerol kinase (PGK) promoter. In some preferred embodiments, the constitutive promoter is selected from the group consisting of SV40E promoter, CMV promoter, and cytoplasmic beta-actin promoter. In even more preferred embodiments, the constitutive promoter is the cytoplasmic beta-actin promoter. In still another preferred embodiment, the constitutive promoter is the CMV promoter.

The nucleic acid expression cassette of the present invention has the following elements in a 5' to 3' direction: a TR element encoding an mRNA molecule that is selectively translated in stressed and/or dying cells, and a nucleotide sequence operably linked to the TR element, which encodes a reporter gene and is translated from the TR element; or (2) a constitutive promoter and a nucleotide sequence operably linked to the promoter, which encodes a reporter gene. Additionally, the expression cassette can also include the following elements: at least one transcriptional effector sequence 5' to the TR element; a 3' sequence flanking the TR element that contains restriction enzyme sites common in the art; and/or a polyadenylation sequence.

In some of the embodiments, the expression cassette of the present invention comprises an upstream transcriptional effector sequence which regulates gene expression. In one embodiment, the transcriptional effector sequence is a mammalian promoter. In addition, the transcriptional effector can also include additional promoter sequences and/or transcriptional regulators, such as enhancer and silencers or combinations thereof. These transcriptional effector sequences can include portions known to bind to cellular components which regulate the transcription of any operably linked coding sequence. For example, an enhancer or silencer sequence can include sequences that bind known cellular components, such as transcriptional regulatory proteins. The transcriptional effector sequence can be selected from any suitable nucleic acid, such as genomic DNA, plasmid DNA, viral DNA, mRNA or cDNA, or any suitable organism (e.g., a virus, bacterium, yeast, fungus, plant, insect or mammal). It is within the skill of the art to select appropriate transcriptional effector sequences based upon the transcription and/or translation system being utilized. Any individual regulatory sequence can be arranged within the transcriptional effector element in a wild-type arrangement (as present in the native genomic order), or in an artificial arrangement. For example, a modified enhancer or promoter sequence may include repeating units of a regulatory sequence so that transcriptional activity from the vector is modified by these changes.

In one embodiment, the promoters used in the TR-containing expression cassette are selected from constitutive, tissue specific, and tumor specific promoters. Constitutive promoters can be selected, e.g., from Rous sarcoma virus (RSV) long terminal repeat (LTR) promoter, cytomegalovirus immediate early gene (CMV) promoter, simian virus 40 early (SV40E) promoter, cytoplasmic beta-actin promoter, adenovirus major late promoter, and the phosphoglycerol kinase (PGK) promoter. In a preferred embodiment, a constitutive promoter is a CMV promoter. In another preferred embodiment, a constitutive promoter is an SV40E promoter.

Tissue specific promoters can be selected, e.g., from the transferrin (TF), tyrosinase (TYR), albumin (ALB), muscle creatine kinase (CKM), myelin basic protein (MBP), glial fibrillary acidic protein (GFAP), neuron-specific enolase (NSE), and synapsin I (SYN1) promoters. In a preferred embodiment, the tissue specific promoter is a synapsin I (SYN1) promoter. In another preferred embodiment, the tissue specific promoter is the ALB promoter.

Tumor specific promoters include but are not limited to promoters for vascular endothelial growth factor (VEGF), a VEGF receptor (i.e. KDR, E-selectin, or endoglin), alpha-fetoprotein (AFP), carcinoembryonic antigen (CEA), erbB2 (v-erbb2 erythroblastic leukemia viral oncogene homolog 2), osteocalcin (bone gamma-carboxyglutamate protein, BGLAP), SLP1 (secretory leukoproteinase inhibitor or anti-leukoproteinase 1), hypoxia-response element (HRE), L-plastin (lymphocyte cytosolic protein 1) and hexokinase II (HK2). In a preferred embodiment, the tumor specific promoter is an alpha fetoprotein (AFP) promoter. In another preferred embodiment, the tumor specific promoter is a SLP1 promoter.

In some embodiments, a specific transcriptional effector element is isolated and then operatively linked to a minimal promoter to produce an expression cassette whose transcriptional activity is dependent upon a single or limited type of cellular response (e.g., a heat shock response or metal-regulated element).

In additional embodiments, the expression cassette can include species-specific transcriptional regulatory sequences. Such DNA regulatory sequences can be selected on the basis of the cell type into which the expression cassette will be inserted and can be isolated from prokaryotic or eukaryotic cells, including but not limited to bacteria, yeast, plant, insect, mammalian cells or from viruses. In such example, a mammalian promoter would be selected to express a nucleic acid of choice in a mammalian cell.

The open reading frame sequence for a reporter protein is placed 3' from the TR element or the constitutive promoter in the expression cassette. The nucleic acid sequence for a reporter protein can be either a full genomic sequence (e.g., including introns), synthetic nucleic acid or a cDNA copy of a gene encoding the reporter protein. In a preferred embodiment, cDNA sequences of reporter proteins are used for the purposes of the present invention due to the reduction in genomic complexity provided by removal of mRNA splice sites.

As described herein, a reporter gene encodes a product that confers on the cell a detectable biochemical or visually observable (e.g., fluorescent) phenotype. The reporter protein can also include a fused or hybrid polypeptide in which another polypeptide is fused at the N-terminus or the C-terminus of the polypeptide or fragment thereof. A fused polypeptide is produced by cloning a nucleic acid sequence (or a portion thereof) encoding one polypeptide in-frame with a nucleic acid sequence (or a portion thereof) encoding another polypeptide. Techniques for producing fusion polypeptides are known in the art, and include, ligating the coding sequences encoding the polypeptides so that they are in-frame and translation of the fused polypeptide is under the control of the TR cassette or its transcription is under the control of a constitutive promoter. For example, cloning the plp ORF in-frame with the enhanced green fluorescent protein (EGFP) ORF produced a fusion protein that was used to monitor the expression, subcellular localization and biological effect of the fusion protein in cultured cells (Ghandour S et al. Glia (2002) 40(3):300-11; Boucher S et al. J Neurosci (2002) 22(5): 1772-83).

One commonly used class of reporter genes encodes an enzyme or other biochemical marker, which, when expressed in a mammalian cell, cause a visible change in the cell or the cell environment. Such a change can be observed directly, can involve the addition of an appropriate substrate that is converted into a detectable product or the addition and binding of a metabolic tracer. Examples of these reporter genes are the bacterial lacZ gene which encodes the β-galactosidase (β-gal) enzyme, the Chloramphenicol acetyltransferase (CAT) enzyme, Firefly luciferase (Coleoptera beetle), *Renilla* luciferase (sea pansy), *Gaussia* luciferase, Herpes Simplex 1 thymidine kinase (HSV1-TK) and the mutant Herpes Simplex 1 thymidine kinase (HSV1-sr39tk) genes. In the case of β-gal, incubation of expressing cells with halogen-derivatized galactose results in a colored or fluorescent product that can be detected and quantitated histochemically or fluorimetrically. In the case of CAT, a cell lysate is incubated with radiolabeled chloramphenicol or another acetyl donor molecule such as acetyl-CoA, and the acetylated chloramphenicol product is assayed chromatographically. Other useful reporter genes encode proteins that are naturally fluorescent, including the (green fluorescent protein (GFP), enhanced yellow fluorescent protein (EYFP), or monomeric red fluorescent protein (mRFP1).

As can be seen from above, exemplary reporter genes can be selected from luciferase, GFP, EYFP, mRFP1, β-Gal, and CAT but any other reporter gene known in the art can be used. In a preferred embodiment, the reporter gene is Firefly Luciferase. In another preferred embodiment, the reporter gene is *Renilla* Luciferase. In still another preferred embodiment, the reporter gene is *Gaussia* Luciferase.

Another reporter that can be used in the present invention is a G-protein coupled receptor (GPCR), which is an integral membrane protein that translates hormone or ligand binding into intracellular signal. GPCRs are found in all animals, insects, and plants. GPCR signaling plays a role in regulating various physiological functions including phototransduction, olfaction, neurotransmission, vascular tone, cardiac output, digestion, pain, and fluid and electrolyte balance. Although they are involved in various physiological functions, GPCRs share a number of common structural features. They contain seven membrane domains bridged by alternating intracellular and extracellular loops and an intracellular carboxyl-terminal tail of variable length. The carboxyl-terminal tail of a GPCR starts following the membrane span 7, and in many GPCRs, it begins shortly after the conserved NPXXY motif that marks the end of the seventh transmembrane domain. The carboxyl-terminal tail can be relatively long (approximately tens to hundreds of amino acids), relatively short (approximately tens of amino acids), or virtually non-existent (less than approximately ten amino acids). It can also contain palmitoylated cysteine residue(s).

Any G-protein coupled receptor (GPCR) can be used in the methods of the present invention such as a known GPCR, unknown or orphan GPCR, and chimeric or modified GPCR, but is preferably a GPCR for which there is a known ligand or an antibody against the receptor.

A non-limiting list of known GPCRs that may be used with the present invention is shown in Table 1.

TABLE 1

| Class | Ligand | Number | Tissue | Physiology |
|---|---|---|---|---|
| I | Acetylcholine (muscarinic and nicotinic) | 5 | Brain, nerves, heart | neurotransmitter |
| I | Alpha adrenoreceptors | 6 | Brain, kidney, lung | Gluconeogenesis |
| I | Beta adrenoreceptors | 3 | Kidney, heart | Muscle contraction |
| I | Dopamine | 5 | Brain, kidney, GI | Neurotransmitter |
| I | Histamine | 2 | Vascular, heart, brain | Vascular permeability |
| I | Serotonin (5-HT) | 16 | Most tissues | neurotransmitter |
| I | Angiotensin | 2 | Vascular, liver, kidney | Vasoconstiction |
| I | Bradykinin | 1 | Liver, blood | vasodilation |
| I | C5a anaphylatoxin | 1 | Blood | Immune system |
| I | Fmet-leu-phe | 3 | Blood | Chemoattractant |
| I | Interleukin-8 | 1 | Blood | Chemoattractant |
| I | Chemokine | 6 | Blood | Chemoattractant |
| I | Orexin | 2 | Brain | Fat metabolism |
| I | Norciceptin | 1 | Brain | Bronchodilator, pain |
| I | CCK (gastrin) | 2 | GI | Motility, fat absorption |
| I | Endothelin | 2 | Heart, bronchus, brain | Muscle contraction |
| I | Melanocortin | 5 | Kidney, brain | Metabolic regulation |
| I | Neuropeptide Y | 5 | Nerves, intestine, blood | neurotransmitter |
| I | Neurotensin | 1 | Brain | CNS |
| I | Opioid | 3 | Brain | CNS |
| I | Somatostatin | 5 | Brain, GI | Neurotransmitter |
| I | Tachykinin (substance P, NKA[1]) | 3 | Brain nerves | Neurohormone |
| I | Thrombin | 3 | Platelets, blood vessels | Coagulation |
| I | Vasopressin-like | 4 | Arteries, heart, bladder | Water balance |
| I | Galanin | 1 | Brain, pancreas | Neurotransmitter |
| I | Follicle stimulating hormone | 1 | Ovary, testis | Endocrine |
| I | Lutropin-choriogonado-tropic | 1 | Ovary, testis | Endocrine |
| I | Thyrotropin | 1 | Thyroid | Endocrine |
| I | Opsin | 5 | Eye | Photoreception |
| I | Olfactory | 4(~1000) | Nose | Smell |
| I | Prostaglandin | 5 | Arterial, GI | Vasodilation, pain |
| I | Lysophosphat-idic acid | 2 | Vessels, heart, lung | Inflammation |
| I | Sphingosine-1-phosphate | 2 | Most cells | Cell proliferation |
| I | Leukotriene | 1 | White blood cells, bronchus | Inflammation |
| I | Prostacyclin | 1 | Arterial, GI | Platelet regulation |
| I | Thromoxane | 1 | Arterial, bronchus | Vasoconstriction |
| I | Adenosine | 4 | Vascular, bronchus | Multiple effects |
| I | Purinoceptors | 4 | Vascular, platelets | Relaxes muscle |
| I | Cannabis | 2 | Brain | Sensory perception |
| I | Platelet activating factor | 1 | Most peripheral tissues | Inflammation |
| I | Gonadotropin-releasing hormone | 1 | Reproductive organs, pituitary | Reproduction |
| I | Thyrotropin-releasing hormone | 1 | Pituitary, brain | Thyroid regulation |
| I | Growth hormone-inhibiting factor | 1 | GI | Neuroendocrine |
| I | Melatonin | 1 | Brain, eye, pituitary | Neuroendocrine |
| II | Secretin | 1 | GI, heart | Digestion |
| II | Calcitonin | 1 | Bone, brain | Bone resorpion |
| II | Corticotropin releasing factor/urocortin | 1 | Adrenal, vascular, brain | Neuroendocrine |
| II | Gastric inhibitory peptide (GIP) | 1 | Adrenals, fat cells | Sugar/fat metabolism |
| II | Glucagon | 1 | Liver, fat cells, heart | Gluconeogenesis |
| II | Glucagon-like peptide 1 (GLP-1) | 1 | Pancreas, stomach, lung | Gluconeogenesis |
| II | Growth hormone-releasing hormone | 1 | Brain | Neuroendocrine |
| II | Parathyroid hormone | 1 | Bone, kidney | Calcium regulation |
| II | PACAP | 1 | Brain, pancreas, adrenals | Metabolism |
| II | Vasoactive intestinal polypeptide (VIP) | 1 | GI | Motility |
| III | Metabotropic glutamate | 7 | Brain | Sensory perception |
| III | GABA$_B$ | 1 | Brain | Neurotransmitter |
| III | Extracellular calcium sensing | 1 | Parathyroid, kidney, GI tract | Calcium regulation |

Modified GPCRs include GPCRs that have one or more modifications in the carboxyl-terminal tail, modifications in the intracellular loop(s), and/or in the cytoplasmic end of the transmembrane region.

The GPCR receptors can be grouped according to classical divisions based on structural similarities and ligands. By way of example, three major classes of GPCRs for known receptors have been identified: Class A receptors, Class B receptors, and receptors with virtually non-existent carboxyl-terminal tails. The receptors are classified based on their interactions with an affinity for rat beta-arrestin-2 in HEK-293 cells and may be predicted based on the amino acid residues in their carboxyl-terminal tail and the length of their carboxyl-terminal tail. A Class B receptor is a GPCR that has one or more sites of phosphorylation (e.g., clusters of phosphorylation sites) properly positioned in its carboxyl-terminal tail such that it recruits rat beta-arrestin-2 to endosomes in HEK-293 cells under conditions as described in U.S. Pat. No. 5,891,646, Oakley, et al. (Journal of Biological Chemistry, Vol 275, No. 22, pp 17201 17210, Jun. 2, 2000), and Oakley et al., (Journal of Biological Chemistry, Vol. 276, No. 22, pp 19452 19460, 2001). A Class A receptor is a GPCR that does not have one or more sites of phosphorylation (e.g., clusters of phosphorylation sites) properly positioned in its carboxyl-terminal tail such that it does not recruit rat beta-arrestin-2 to endosomes in HEK-293 cells under conditions as described above for Class B receptors. Receptors with virtually non-existent carboxyl-terminal tails include, for example, olfactory and taste receptors.

An illustrative, non-limiting list of known GPCRs with which the methods of the present invention can be performed is shown below. Class A G-protein coupled receptors include but are not limited to: A1 adenosine receptor (accession no. AAB25533), adrenergic receptor alpha 1B (accession no. NP_000670), adrenergic receptor alpha 2A (accession no. AAG00447), adrenergic receptor alpha 2B (accession no. A37223), adrenergic receptor alpha 2C (accession no. A31237), adrenergic receptor beta 1 (accession no. NP_000675), adrenergic receptor beta 2 (accession no. P07550), dopamine receptor D1 (accession no. NP_000785), dopamine receptor D2 (accession no. P14416), dopamine receptor D3 (accession no. G01977), dopamine receptor D4 (accession no. DYHUD4), dopamine receptor D5 (accession no. DYHUD5), muscarinic acetylcholine receptor M1 (accession no. NP_000729), muscarinic acetylcholine receptor M2 (accession no. NP_000730), muscarinic acetylcholine receptor M3 (accession no. NP_000731), muscarinic acetylcholine receptor M4 (accession no. NP_000732), muscarinic receptor M5 (accession no. AAA51569), 5-hydroxytryptamine (serotonin) receptor 1A (accession no. BAA90449), 5-hydroxytryptamine (serotonin) receptor 1B (accession no. BAA94455), 5-hydroxytryptamine (serotonin) receptor 1E (accession no. BAA94458), olfactory receptor 6A1 (accession no. O9522), olfactory receptor 2C1 (accession no. O95371), galanin receptor 3 (accession no. 10879541), edg-1 (accession no. A35300), central cannabinoid receptor (accession no. NP-057167), delta opioid receptor (accession no. I38532) and proteinase activated receptor 2 [PAR-2] (accession no. P55085). Class B G-protein coupled receptors include but are not limited to: angiotensin receptor 1 (accession no. NP_033611), angiotensin receptor 2 (accession no. NP_000677), interleukin 8 receptor beta [CXCR2] (accession no. NM_001557), CX3C chemokine receptor 1 [CX3CR1] (accession no. P49238), neurotensin receptor (accession no. S29506), substance P receptor [SPR, NK-1 receptor] (accession no. P25103), vasopressin receptor type 2 (accession no. AAD16444), thyrotropin-releasing hormone receptor (accession no. JN0708), oxytocin receptor (accession no. A55493), neuromedin U receptor (accession no. AAG24793), gastrin receptor (accession no. AAC37528) and vasopressive intestinal peptide receptor [VIPR] (accession no. NM_012685).

The modified GPCRs of the present invention include GPCRs that have been modified in the DRY motif to localize to endocytic vesicles or endosomes in an agonist-independent manner. The polypeptide sequences of the modified GPCRs of the present invention include sequences having one or more additions, deletions, substitutions, or mutations. These mutations may be substitution mutations made in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The present invention includes sequences containing conservative changes that do not significantly alter the activity or binding characteristics of the resulting protein. It also includes sequences containing non-conservative changes that do not significantly alter the activity or binding characteristics of the resulting protein.

GPCRs can be modified to comprise one or more sites of phosphorylation (e.g., clusters of phosphorylation sites) properly positioned in their carboxyl-terminal tail or properly positioned at other positions in the amino acid sequence (e.g., in the third intracellular loop). This modification allows the altered GPCR to form a stable complex with an arrestin that will internalize into endosomes.

The modified GPCRs of the present invention can also include GPCRs comprising one or more modifications in their carboxyl-terminal tail. The carboxyl-terminal tail of many GPCRs begins shortly after a conserved NPXXY motif that marks the end of the seventh transmembrane domain. The carboxyl-terminal tail of many GPCRs comprises a putative site of palmitoylation approximately 10 to 25 amino acid residues (e.g., 15 to 20 amino acid residues) downstream of the NPXXY motif.

One skilled in the art will readily recognize that any polyadenylation (polyA) signal can be incorporated into the 3' untranslated (3'UTR) of the TR-containing or constitutive promoter-containing expression cassettes described herein. Examples of polyA sequences useful for the present invention include the SV40 early and late gene, the HSV-TK, and human growth hormone (hGH) sequences. In a preferred embodiment, the polyA sequence is the SV40 early gene sequence.

In other embodiments, the 3'UTR of the expression cassette of the present invention can include one or more elements which regulate gene expression by altering mRNA stability. Typically, mRNA decay is exemplified by the loss of the mRNA polyA tail, recruitment of the deadenylated RNA to the exosome, and ribonuclease (RNAse) degradation. In select mRNAs, this process is accelerated by specific RNA instability elements that promote the selective recognition of a mRNA by cellular degradation systems. In this invention, the expression cassette mRNA can contain elements such as the 3'UTR AU-rich element ("ARE") sequences derived from mRNA species encoding cellular response/recovery genes.

Examples of ARE sequences available to this invention include 3'UTR sequences from the c-fos, the granulocyte-macrophage colony stimulating factor (GM-CSF), c-jun, tumor necrosis factor alpha (TNF-α), and IL-8 mRNAs. In a preferred embodiment, the ARE sequences from the c-fos gene are used.

The nucleic acid expression cassettes of the present invention can also include a 5' untranslated region (5'UTR), which is located 3' to the promoter and 5' to the TR element. In some embodiments, such a region comprises a mRNA transcription initiation site. In other embodiments, the 5' untranslated region comprises an intron sequence, which directs mRNA splicing and is required for the efficient processing of some mRNA species in vivo. A general mechanism for mRNA splicing in eukaryotic cells is defined and summarized in Sharp (Science 235: 736-771 (1987)). There are four nucleic acid sequences which are necessary for mRNA splicing: a 5' splice donor, a branch point, a polypyrimidine tract and a 3' splice acceptor. Consensus 5' and 3' splice junctions (Mount, Nucl. Acids. Res. 10:459-472 (1992)) and branch site sequences (Zhuang et al., PNAS 86:2752-2756 (1989)) are known in the art.

In some embodiments, the 5' UTR sequences comprise natural introns which exist in a native gene sequence or an artificial intron, such as the human beta-globin-immunoglobulin sequence present in the pAAV-MCS vector (Stratagene).

Additionally, the expression cassettes of the present invention can include one or more of the following:

a sequence of between about 15-50 nucleotides located 5' to the promoter, that includes one or more restriction sites for insertion of the expression cassette into a plasmid, shuttle vector or viral vector;

a sequence of between about 15-50 nucleotides located 3' to the TR element or constitutive promoter and 5' to the reporter sequence, that includes one or more restriction sites for insertion and operative linkage of the TR element or constitutive promoter and the reporter sequence;

a sequence of between about 15-50 nucleotides located 3' to the reporter sequence and 5' to the polyadenylation signal, that includes one or more restriction sites for insertion and operative linkage of the ORF sequence and the polyadenylation sequence; and a sequence of between about 15-50 nucleotides located 3' to the polyadenylation sequence, that includes one or more restriction sites for insertion of the nucleic acid expression cassette into a plasmid, shuttle vector or viral vector.

The nucleic acid expression cassettes described herein can be inserted into plasmid or viral ("shuttle") vectors depending upon the host cell which is used to replicate the expression cassette. In general, the DNA expression cassette of the present invention is inserted into the appropriate restriction endonuclease site(s) in the disclosed vectors using techniques known in the art. Numerous vectors useful for this purpose are generally known (Miller, Human Gene Therapy 15-14, 1990; Friedman, Science 244:1275-1281, 1989; Eglitis and Anderson, BioTechniques 6:608-614, 1988; Tolstoshev and Anderson, Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechniques 7:980-990, 1989; Le Gal La Salle et al., Science 259:988-990, 1993; and Johnson, Chest 107:77 S-83S, 1995).

A plasmid vector is selected in part based upon the host cell that is to be transformed with the plasmid. For example, the presence of bacterial or mammalian selectable markers present in the plasmid, the origin of replication, plasmid copy number, an ability to direct random or site specific recombination with chromosomal DNA, etc. can influence the choice of an appropriate vector. In some embodiments, bacterial plasmids such as pBluescript II, pET14, pUC19, pCMV-MCS and pCMVneo are employed for propagating an expression cassette of the present invention in bacterial cells. In a preferred embodiment, a plasmid is the pCMVneo vector. In another preferred embodiment, the plasmid is the pBluescript II vector.

In another embodiment, an expression cassette of the present invention is inserted into a mammalian or viral shuttle vector. Whereas mammalian shuttle vectors contain mammalian selectable markers and provide for the isolation of cells containing stable genomic integrants, viral shuttle vectors provide for the reconstitution of a viral genome using recombination or genetic complementation. In some embodiments, a mammalian shuttle vector is selected from the pCMV, pEYFP-N1, pEGFP-N1, or pEGFP-C1 plasmids. In a preferred embodiment, the mammalian shuttle vector is pEYFP-N1. In some embodiments, a viral shuttle vector is selected from the pAAV-MCS (Adeno-associated Virus serotype 2 or AAV2 genome) or pBac-1, pBacPAK8/9 (*Autographa californica* baculovirus genome) plasmids. In one preferred embodiment, the viral shuttle vector is pAAV-MCS. In another preferred embodiment, the viral shuttle vector is the pBac-1 plasmid.

To insure efficient delivery of the expression cassette to a particular cell, tissue or organ, it can be incorporated into a non-viral delivery system, which facilitates cellular targeting. For example, a mammalian shuttle plasmid that includes the expression cassette of the present invention may be encapsulated into liposomes. Liposomes include emulsions, foams, micelles, insoluble monolayers, liquid crystals, phospholipid dispersions, lamellar layers and the like. The delivery of DNA sequences to target cells using liposome carriers is well known in the art as are methods for preparing such liposomes.

The viruses useful in the practice of the present invention include recombinantly modified enveloped or non-enveloped DNA and RNA viruses, preferably selected from the baculoviridiae, parvoviridiae, picornoviridiae, herpesviridiae, poxyiridiae, and adenoviridiae viruses. In some embodiments, the recombinant virus is a baculoviridiae virus. In a preferred embodiment, the baculovirus is an *Autographa californica* derivative virus. In other embodiments, the virus is a parvoviridiae virus. In a preferred embodiment, the adeno-associated virus ("AAV") is an AAV serotype 2. In another embodiment, the AAV is an AAV serotype 1.

The viral genomes are preferably modified by recombinant DNA techniques to include the expression cassette of the present invention and may be engineered to be replication deficient, conditionally replicating or replication competent. For example, it may prove useful to use a conditionally replicating virus to limit viral replication to specific, regulated cell culture conditions.

Chimeric viral vectors which exploit advantageous elements of more than one "parent" virus properties are included herein. Minimal vector systems in which the viral backbone contains only the sequences needed for packaging of the viral vector and optionally includes the expression cassette may also be produced and used in the present invention. It is generally preferred to employ a virus from the species to be treated, such as a human herpes virus when a human cell or a human cell line is transduced with it. In some instances, viruses which originated from species other than the one which is to be transduced therewith can be used. For example, adeno-associated viruses (AAV) of serotypes derived from non-human sources may be useful for treating humans because the non-human serotypes should not be immediately recognized by natural or pre-existing human antibodies. By minimizing immune responses to the vectors, rapid systemic clearance of the vector is avoided and the duration of the vector's effectiveness in vivo is increased.

A TR-containing or a constitutive promoter-containing expression cassette in any of the mammalian shuttle vectors described above can be transformed into a mammalian cell. A shuttle vector can be introduced into the host cell by any technique available to those of skill in the art. These include, but are not limited to, chemical transfection (e.g., calcium chloride method, calcium phosphate method), lipofection, electroporation, cell fusion, microinjection, and infection with virus (Ridgway, A. "Mammalian Expression Vectors" Ch 24, pg 470-472, Rodriguez and Denhardt, Eds., Butterworhs, Boston Mass. 1988).

A mammalian cell can be a mammalian cell that is isolated from an animal (i.e., a primary cell) or a mammalian cell line.

Methods for cell isolation from animals are well known in the art. In some embodiments, a primary cell is isolated from a mouse. In other embodiments, a primary cell is isolated from a human. In still other embodiments, a mammalian cell line can be used. Exemplary cell lines include HEK293 (human embryonic kidney), HT1080 (human fibrosarcoma), NTera2D (human embryonic teratoma), HeLa (human cervical adenocarcinoma), Caco2 (human colon adenocarcinoma), HepG2 (human liver hepatocellular carcinoma), HCT116 (human colon tumor), MDA231 (human breast cancer), U2 OS (human bone osteosarcoma), DU145 (human prostate carcinoma), LNCaP (human prostate adenocarcinoma), LoVo (human colon cancer), MiaPaCa2 (human pancreatic carcinoma), AsPC1 (human pancreatic adenocarcinoma), MCF-7 (human breast cancer), PC3, Capan-2 (human pancreas adenocarcinoma), COLO201 (human colon cancer), COLO205 (human colon tumor), H4 (human brain neuroglioma), HuTu80 (human duodenum adenocarcinoma), HT1080 (human connective tissue fibrosarcoma), and SK-N-MC (human brain neuroepithelioma).

Host cell lines are typically available from, for example, the American Tissue Culture Collection (ATCC), any approved Budapest treaty site or other biological depository.

In still other embodiments, a mammalian embryonic stem (ES) cell can be used, such as a mouse ES cell mES-D3 or a human ES cell hES H1.

Stem cells also find application in the methods of the present invention. Pluripotent, adult, blastocyst-derived, gonadal, teratoma-derived, totipotent, multipotent, embryonic (ES), embryonic germ (EG), induced pluripotent stem cells (iPS), umbilical cord blood and embryonic carcinoma (EC) cells are all examples of stem cells for use in these methods. Cancer stem cells, such as tumor derived stem cells can also be used in the methods of the present invention.

Pluripotent stem cells can be produced from the fetal material of any animal, such as any mammal. However, in one embodiment, the mammal is a rodent, such as a mouse, guinea pig or rat. In a preferred embodiment, the mouse ES cell is mES-D3. The fetal material can be from livestock, such as cattle, horses, pigs, sheep, goats, etc. The fetal material can also be from primates, including humans. Pluripotent stem cell lines have been reported, for example but not limited to, in chicken (Pain, B. et al., (1996) Development (Cambridge, U.K.) 122, 2339-2348), mink (Sukoyan, M. A. et al., (1993) Mol. Reprod. Dev. 36, 148-158), hamster (Doetschman, T. et al., (1988) Dev. Biol. 127, 224-227), pig (Wheeler, M. B. (1994) Reprod. Fertil. Dev. 6, 563-568; Shim, H. et al., (1997) Biol. Reprod. 57, 1089-1095), rhesus monkey (Thomson, J. A. et al., (1995) Proc. Natl. Acad. Sci. USA 92, 7844-7848), and common marmoset (Thomson, J. A. et al., (1996) Biol. Reprod. 55, 254-259). The derivation of stem cell lines is described in the references cited in the above paragraph.

Stem cells exhibit a variety of distinct properties and categories of properties. For example, in some forms, stem cell lines are capable of prolonged proliferation ex vivo (>1 year) in an undifferentiated state. Stem cells can also maintain a normal karyotype while proliferating and/or differentiating. Stem cells can also exhibit the ability to form every cell type in an organism (i.e. totipotent trait). Other stem cells retain the ability to differentiate into mesoderm, endoderm and ectoderm tissues, including germ cells, eggs and sperm. Some stem cells can form embryoid bodies (EBs) under certain growth conditions, such as culture conditions which do not maintain an undifferentiated state. Moreover, stem cells can often form chimeras through fusion with blastocysts, which is required for producing transgenic animals.

In addition to being kept in an undifferentiated state, the ES cells can be manipulated through changing growth conditions to induce differentiation into a particular cell type (referred to as "directed differentiation"). For example, pluripotent stem cells can be directed towards a specific lineage by molecules such as drugs, prodrugs, peptides and nucleic acids that 1) activate endogenous transcription programs which regulate differentiation; 2) introduce exogenous nucleic acids that ubiquitously express differentiation-specific transcription factors; 3) provide cell cultures with medium containing growth factors/regulatory molecules that induce differentiation; or 4) allow cocultures of stem cells and cell types capable of lineage induction. A number of ectodermal derivatives (ED) directed differentiation methods are described below, and can be used in the methods of the present invention.

Genetic manipulation can be used to alter the properties of the stem cells. A modified stem cell is a stem cell that has a genetic background different than the original genotype of the cell. For example, a modified stem cell can be a stem cell that expresses protein sequences from an extra-chromosomal or integrated DNA sequence. Stem cell properties can be modified using selection for dominant selectable markers. For example, transformation/transduction with a vector encoding an antibiotic resistance gene can be used to select for a cell population that can survive antibiotic application. Cells that express the marker gene can also integrate cis-linked transgenes such as the TR cassette so that these transgenes are stably incorporated into the genome. Various methods exist in the art to prepare cell lines of genetically modified stem cells. One application of this invention is a method to employ genetically modified stem cell lines, capable of expressing the TR cassette, for cell based toxicology assays. In one embodiment, the TR cassette encodes a reporter gene such as firefly luciferase, from the CMV promoter, providing a method for constitutive measurement of cell stress and death. In another embodiment, the TR cassette encodes a reporter gene such as firefly luciferase, from the EGR-1 promoter, providing a method for detecting cell death as a function of early stress responses. It is anticipated that a skilled artisan could design similar methods of measuring cell death in transgenic stem cells based upon a particular need or process of measuring and/or inducing cell death. By way of example, a number of methods are described in the art for producing the directed differentiation of stem cells ex vivo. Some of these are summarized in the subsequent sections. The formation of ectodermal derivative cells is common in spontaneously differentiating stem cells and is generally considered a default developmental pathway. The neuroectoderm cell fate can be selectively promoted to generate neural progenitors and differentiated neural cell types (e.g. neurons, astroglia and oligodendroglia) (Carpenter M K, et al. 2001). Oligodendrocytes can be produced from stem cell lines using FGF (e.g. FGF2) and epidermal growth factor (EGF), followed by supplementation with retinoic acid (RA). These oligodendrocyte precursors are able to mature and remyelinate neurons (Nistor G I, et al. 2005). Alternative multistep methods can produce dopaminergic neurons (Park S, et al. 2004; Perrier A L, et al. 2004) and motor neurons by culturing stem cells in RA and FGF-2, then RA and sonic hedgehog (SHH), and finally brain-derived neurotrophic factor (BDNF), glial-derived neurotrophic factor (GDNF), insulin-like growth factor-1 (IGF1) and low levels of SHH.

In contrast, treating stem cell cultures with bone morphogenetic protein (BMP), an antagonist of Noggin, generates stem cells with a flattened epithelial morphology and a gene expression pattern characteristic of extra-embryonic endoderm, a cell type commonly associated with the yolk sac and placenta in developing embryos. Thus, prolonged culture of stem cells in serum-free medium with BMP4 will produce flat epithelial cells that express genes (e.g., MSX2), and proteins (e.g., human chorionic gonadotrophin) associated with trophoblast or placental development.

Similarly, coculture of stem cells with the mouse bone marrow mesenchymal PA6 cell line, which expresses stromal cell derived inducing activity (SDIA), will produce a mixture of midbrain neurons that are tyrosine hydrolase positive (TH+) and express the nurr1 and LMX1b genes (Kawasaki H, et al. 2002; Mizuseki K, et al. 2003), as well as pigmented retinal epithelium cells. Further manipulation of culture conditions with BMP4 induces the formation of neural crest cells and dorsal-most central nervous system cells. Suppression of SHH promotes the formation of motor neurons (Trounson A. 2004). Stem cells can also be directed into midbrain dopamine neurons when grown with mouse bone marrow mesenchyme cell lines (e.g. MS5 and S2 cells), where there is sequential expression of the Pax2, Pax5 and engrailed-1 transcription factors in response to FGF-8, SHH, ascorbic acid/vitamin C and BDNF (Perrier A L, et al. 2004).

Exposure of partially differentiated neuroepithelial derivatives to FGF-8 and SHH promotes the production of dopaminergic neurons with a forebrain phenotype; however, early exposure to FGF-8 during neuroepithelial specification promotes a midbrain phenotype and a differentiation pathway leading to midbrain dopaminergic neurons. Hence, the order of administering FGF-8 and SHH can determine neuronal fate.

Coculture methodologies have also been used to produce differentiated cardiomyocytes from stem cells. 15-20% of cultures of stem cells grown with the mouse visceral endoderm cell type END-2, form beating heart muscle colonies (e.g. cardiomyocytes) (Mummery C, et al. 2002; Mummery C, et al. 2003). Beating heart muscle cells derived from stem cells express cardiomyocyte markers including alpha-myosin heavy chain, cardiac troponins and atrial natriuretic factor as well as transcription factors typical of cardiomyocytes, (e.g. GATA4 and MEF3) (Kehat I, et al. 2001; Xu C, et al. 2002). These cells respond to pharmacological drugs and exhibit cardiomyocyte action potentials most commonly observed in human fetal left ventricular cardiomyocytes, which can be easily distinguished from mouse cardiomyocytes (Mummery C, et al. 2003; He J Q, et al. 2003). Atrial- and pacemaker-like cells can also be formed in the differentiating stem cell cultures. These stem cell derived cardiomyocytes integrate normally into transplanted rodent and porcine heart muscle, form normal gap junction connections between stem cell myocytes and the recipient mouse adult cardiomyocytes (Xue T, et al. 2005; Kehat I, et al. 2004; Hassink R J, et al. 2003).

Type II pneumocytes that express Surfactant Protein C (SPC), a respiratory specific marker, can be generated by coculture of stem cells with mouse embryonic foregut mesenchyme (Denham M, et al. 2002). Stem cells can also be induced to form airway epithelial tissue when differentiated as embryoid bodies or grown on type 1 collagen, and then the resulting Clara cells grown in an air-fluid interface to form a pseudostratified surface epithelium (Coraux C, et al. 2005).

Keratinocytes can be derived from stem cells by replating embryoid bodies (Green H, et al. 2003). Cells expressing the transcription factor p63 in the periphery of the secondary cultures identify the keratinocyte progenitors that produce more mature cell types in which cytokeratin 14 and basonuclin are detected. These cells can form terminally differentiated stratifying epithelium but are not the same as keratinocyte epithelium isolated from neonatal or adult skin.

Embryoid bodies (EBs) can also be used to produce hematopoietic progenitors using a cocktail of hematopoietic cytokines and BMP-4 (Kaufman D S, 2001, Chadwick K, et al. 2003). EBs are formed by withdrawal of leukemia inhibitory factor (LIF) from the ES cell culture and manifest as cell clusters or spherical multicellular aggregates. Growth factors such as stem cell factor (SCF), interleukins-3 and -6 (IL-3, IL-6), granulocyte colony-stimulating factor (GCSF), Flt-3 ligand, as well as vascular endothelial growth factor-A (VEGF-A) (Cerdan C, et al. 2004) augment hematopoietic cell fate and lineage commitment during EB development. These progenitors are immunologically similar to hematopoietic progenitors of the dorsal aorta.

Endodermal cells can be detected in stem cells cultures following exposure to Activin A (Kubo A, et al. 2004). Insulin producing cells can be formed by differentiating neuroectodermal cells using the method of Lumelsky et al. (Lumelsky N, et al. 2001). Similarly, Segev et al. (Segev H, et al. 2004) produced islet-like clusters by culturing embryoid bodies in medium containing insulin, transferrin, selenium and fibronectin. Disaggregated cultures were allowed to form clusters in medium containing FGF-2 and then exposed to nicotinamide with low glucose in suspension culture. A high percentage of cell clusters expressed insulin, glucagon and somatostatin similar to immature pancreatic cells. Responsiveness to glucose and other antagonists suggested that these cells were immature, fetal-like pancreatic beta-islet cells.

Rambhatla et al. (2003) reported differentiation of stem cells into cells that expressed markers of hepatocytes (albumin, alpha-1-antitrypsin, cytokeratin 8 and 18) and accumulate glycogen. Treating embryoid bodies with sodium butyrate or adherent stem cell cultures with dimethyl sulfoxide followed by sodium butyrate resulted in hepatic-like endodermal cells (Lavon N, et al. 2004). Cellular morphology in differentiated adherent stem cell cultures can be used to select for endodermal populations that express markers of fetal liver (Stamp L A, et al. 2003).

As mentioned above, the present invention utilizes the expression cassettes described herein to identify subpopulations of mammalian cells with distinct ribosomal profiles. One aspect of the invention is the surprising discovery that mammalian cells stably transformed with the expression cassette of the present invention can be divided into three classes based on the level of protein translation. The three classes of cells were arbitrarily named class I, class II and class III cells, and can be classified as follows. Upon treatment with at least one toxin, class I cells are characterized by the level of a reporter protein being up to 500% greater than the level of the reporter protein in the reference standard, wherein the reference standard represents the level of the reporter protein in mammalian cells stably transformed with the nucleic expression cassette and not treated with the toxin(s). Similarly, class II cells are characterized by the level of a reporter protein being more than 500% and not more than 1400% greater than the level of the reporter protein in the reference standard, and class III are characterized by the level of a reporter protein being more than 1400% greater than the level of the reporter protein in the reference standard. In one preferred embodiment, the class III cells are characterized by the level of a reporter protein being more than 1400% and not more than 75000% greater than the level of the reporter protein in the reference standard.

Two methods are typically employed in the art to establish, characterize and store an expressing cell. The first involves the establishment, collection and storage of the entire population of transformed and drug resistant cells, in which each cell comprises at least one integration event of the transgene conferring drug resistance, termed a "cell pool." The second involves the isolation of individual cell colonies/clones derived from a single drug resistant cell, screening for a desired trait and storage as a cellular stock termed a "cell line."

In contrast to the first approach, which provides a mixed population of resistant cells with a wide array of gene expression levels, the second approach requires the selection of distinct clones from hundreds of isolated cell colonies to identify a select group of colonies which express the desired gene product at a desired level. Once these cells are identified, they are amplified, and either maintained in cell culture or frozen for future use.

Accordingly, in the method for identifying a desired subpopulation of mammalian cells, the cells stably transformed with a nucleic acid expression cassette can be comprised of cell pools or cell lines, wherein the cell lines are obtained by subcloning of individual cells from cell pools. The cells are next treated with at least one toxin. Since the toxins are damaging and/or deadly to the cells, a subset of stably transformed cells is used for toxin testing, whereas the remaining cells are either kept in culture or frozen for future use. Thus, the subset of cells can generally be treated with one, two, three, four, five, six, seven, eight, nine, ten, eleven, twelve, thirteen, fourteen or fifteen individual toxins or any combination of toxins. In some embodiments, the cells are treated with one toxin. In other embodiments, the cells are treated with two toxins. In still other embodiments, the cells are treated with three toxins or with five toxins. Any toxin, such as a plant toxin, animal toxin, or synthetic toxin can be used for the purposes of the present invention. By way of example and not of limitation, the toxin is selected from the group consisting of cAMP, TPA, paclitaxel (Taxol), MG132, thapsigargin, nocodazole, vinblastin, Calcium Ionophore A23167, bortezomib (Velcade), hycamtin (Topotecan), colchicine, 4-oxoquinoline-3-carboxylic acid derivative antibiotic, ethanol and methanol. In some embodiments, the toxin is selected from the group consisting of cAMP, TPA, Taxol, MG132, thapsigargin, nocodazole, vinblastin, Calcium Ionophore A23167, bortezomib, hycamtin, colchicine, and 4-oxoquinoline-3-carboxylic acid derivative antibiotic.

When using at least two toxins, any combination of toxins can be used. One skilled in the art can readily determine which toxin combinations may be particularly useful based on their mechanism of action. Exemplary combinations of two toxins, three toxins, and five toxins are detailed below. By way of example, two toxin combinations include but are not limited to cAMP and TPA; cAMP and paclitaxel, cAMP and thapsigargin, cAMP and nocodazole, cAMP and vinblastin, cAMP and colchicine, cAMP and MG132, cAMP and bortezomib (Velcade), cAMP and Calcium Ionophore A23167, cAMP and 4-oxoquinoline-3-carboxylic acid derivative antibiotic, cAMP and hycamtin; TPA and paclitaxel, TPA and thapsigargin, TPA and nocodazole, TPA and vinblastin; TPA and colchicine, TPA and MG132, TPA and bortezomib, TPA and Calcium Ionophore A23167, TPA and 4-oxoquinoline-3-carboxylic acid derivative antibiotic, TPA and hycamtin; paclitaxel and thapsigargin; paclitaxel and nocodazole; paclitaxel and vinblastin; paclitaxel and colchicine, paclitaxel and MG132, paclitaxel and bortezomib, paclitaxel and Calcium Ionophore A23167, paclitaxel and 4-oxoquinoline-3-carboxylic acid derivative antibiotic, paclitaxel and hycamtin; MG132 and thapsigargin; MG132 and nocodazole; MG132 and vinblastin; MG132 and colchicine; MG132 and bortezomib, MG132 and Calcium Ionophore A23167, MG132 and 4-oxoquinoline-3-carboxylic acid derivative antibiotic, MG132 and hycamtin; thapsigargin and nocodazole, thapsigargin and vinblastin; thapsigargin and colchicine, thapsigargin and bortezomib, thapsigargin and Calcium Ionophore A23167, thapsigargin and 4-oxoquinoline-3-carboxylic acid derivative antibiotic, thapsigargin and hycamtin; nocodazole and vinblastin; nocodazole and colchicine, nocodazole and Calcium ionophore A23167, nocodazole and 4-oxoquinoline-3-carboxylic acid derivative antibiotic, nocodazole and hycamtin; vinblastin and colchicine, vinblastin and bortezomib, vinblastin and Calcium Ionophore A23167, viblastin and 4-oxoquinoline-3-carboxylic acid derivative antibiotic, vinblastin and hycamtin; colchicine and bortezomib, colchicine and Calcium Ionophore A23167; colchicine and 4-oxoquinoline-3-carboxylic acid derivative antibiotic, colchicine and hycamtin; bortezomib and Calcium Ionophore A23167; bortezomib and 4-oxoquinoline-3-carboxylic acid derivative antibiotic, bortezomib and hycamtin; Calcium Ionophore A23167 and 4-oxoquinoline-3-carboxylic acid derivative antibiotic, Calcium Ionophore A23167 and hycamtin; and 4-oxoquinoline-3-carboxylic acid derivative antibiotic and hycamtin.

Exemplary three toxin combinations include but are not limited to cAMP, TPA and paclitaxel; cAMP, TPA and MG132; cAMP, TPA and bortezomib; cAMP, TPA and thapsigargin; cAMP, TPA and nocodazole; cAMP, TPA and vinblastin; cAMP, TPA and colchicine; cAMP, TPA and Calcium Ionophore A23167; cAMP, TPA, and 4-oxoquinoline-3-carboxylic acid derivative antibiotic; cAMP, TPA, and hycamtin; cAMP, paclitaxel and MG132; cAMP, paclitaxel and bortezomib; cAMP, paclitaxel and thapsigargin; cAMP, paclitaxel and nocodazole; cAMP, paclitaxel and vinblastin; cAMP, paclitaxel and colchicine; cAMP, paclitaxel and Calcium Ionophore A23167; cAMP, paclitaxel, and 4-oxoquinoline-3-carboxylic acid derivative antibiotic; cAMP, paclitaxel, and hycamtin; cAMP, MG132 and bortezomib; cAMP, MG132 and thapsigargin; cAMP, MG132 and nocodazole; cAMP, MG132 and vinblastin; cAMP, MG132 and colchicine; cAMP, MG132 and Calcium Ionophore A23167; cAMP, MG132, and 4-oxoquinoline-3-carboxylic acid derivative antibiotic; cAMP, MG132, and hycamtin; cAMP, thapsigargin and bortezomib; cAMP, thapsigargin, and nocodazole; cAMP, thapsigargin, vinblastin; cAMP, thapsigargin and colchicine; cAMP, thapsigargin and Calcium Ionophore A23167; cAMP, thapsigargin, and 4-oxoquinoline-3-carboxylic acid derivative antibiotic; cAMP, thapsigargin, and hycamtin; cAMP, bortezomib, and nocodazole; cAMP, bortezomib, and vinblastin; cAMP, bortezomib, and colchicine; cAMP, bortezomib and Calcium Ionophore A23167; cAMP, bortezomib, and 4-oxoquinoline-3-carboxylic acid derivative antibiotic; cAMP, bortezomib, and hycamtin; cAMP, nocodazole, and vinblastin; cAMP, nocodazole, and colchicine; cAMP, nocodazole and Calcium Ionophore A23167; cAMP, nocodazole, and 4-oxoquinoline-3-carboxylic acid derivative antibiotic; cAMP, nocodazole, and hycamtin; cAMP, vinblastin and colchicine; cAMP, vinblastin and Calcium Ionophore A23167; cAMP, vinblastin, and 4-oxoquinoline-3-carboxylic acid derivative antibiotic; cAMP, vinblastin, and hycamtin; cAMP, colchicine and Calcium Ionophore A23167; cAMP, colchicine, and 4-oxoquinoline-3-carboxylic acid derivative antibiotic; cAMP, colchicine, and hycamtin; cAMP, Calcium Ionophore A23167, and 4-oxoquinoline-3-carboxylic acid derivative antibiotic; cAMP, Calcium Ionophore A23167, and hycamtin; cAMP, calcimycin, and hycamtin; and cAMP, 4-oxoquinoline-3-carboxylic acid derivative antibiotic and hycamtin.

Examples of five toxin combinations include but are not limited to cAMP, TPA, paclitaxel, MG 132, and thapsigargin; cAMP, TPA, paclitaxel, MG 132, and nocodazole; cAMP, TPA, paclitaxel, MG 132, and vinblastin; cAMP, TPA, paclitaxel, MG 132, and Calcium ionophore A23167; TPA, paclitaxel, MG132, thapsigargin and nocodazole; TPA, paclitaxel, MG132, thapsigargin and vinblastin; TPA, paclitaxel, MG132, thapsigargin and Calcium Ionophore A23167; paclitaxel, MG132, thapsigargin, nocodazole, and vinblastin; paclitaxel, MG132, thapsigargin, nocodazole, and Calcium Ionophore A23167; and MG132, thapsigargin, nocodazole, vinblastin and Calcium Ionophore A23167; TPA, paclitaxel, MG132, Calcium ionophore A23167, hycamtin; TPA, nocodazole, MG132, Calcium ionophore A23167, hycamtin; TPA, vinblastin, MG132, Calcium ionophore A23167, hycamtin; TPA, Colchicine, MG132, Calcium ionophore A23167, hycamtin; TPA, paclitaxel, bortezomib, Calcium ionophore A23167, hycamtin; TPA, nocodazole, bortezomib, Calcium ionophore A23167, hycamtin; TPA, vinblastin, bortezomib, Calcium ionophore A23167, hycamtin; TPA, Colchicine, bortezomib, Calcium ionophore A23167, hycamtin; TPA, paclitaxel, MG132, calcimycin, hycamtin; and TPA, vinblastin, MG132, calcimycin, hycamtin.

The cells are treated with at least one toxin as is standard in the art. Depending on the amount of time that the cells are incubated with the toxin(s), the toxin assays can generally be divided into acute and chronic toxin assays. Acute toxin assays generally refer to cell incubation with toxin(s) for a shorter amount of time, e.g., up to 24 hours, whereas chronic toxin assays generally refer to cell incubation with toxin(s) for a longer period of time, e.g., from greater than 24 hours to about 15 days. For example, in an acute toxin assay one or more toxins are added to the media in which the cells are cultured, and one or more toxins are kept in the media for at least 5 minutes, 15 minutes, 30 minutes, 45 minutes, 1 hour, 1.5 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 10.5 hours, 11 hours, 11.5 hours, or 12 hours. In one preferred embodiment, one or more toxins are incubated with the cells for 4 hours. In another preferred embodiment, one or more toxins are incubated with the cells for 6 hours. In still another preferred embodiment, one or more toxins are incubated with the cells for 24 hours.

In an example of a chronic toxin assay, the cells are treated with at least one toxin as is standard in the art. For example, one or more toxins are added to the media in which the cells are cultured, and one or more toxins are kept in the media for at least 1 day, 2 days, 3 days, 4 days, 5 days, 6 days, 7 days, 8 days, 9 days, 10 days, 11 days, 12 days, 13 days, or 14 days. In one preferred embodiment, one or more toxins are incubated with the cells for 3 days. In another preferred embodiment, one or more toxins are incubated with the cells for 7 days. In still another preferred embodiment, one or more toxins are incubated with the cells for 14 days. Similarly, a chronic toxin assay can be performed such that cells are first incubated with a toxin or a compound whose effect on translation is evaluated, followed by 5-, 15- or 21-assay procedures, which will show the magnitude of the translational response. By way of example, cells can be incubated with ciprofloxacin for 7 days, followed by performance of a 15-assay procedure in order to determine the effect of ciprofloxacin on cells' translational response.

Following the toxin treatment, the level of a reporter protein encoded by the reporter gene in the toxin-treated cells is measured and compared to a level of the reporter protein expressed by a reference standard to identify whether the subset of mammalian cells exhibit the phenotype of the desired subpopulation of mammalian cells. The appropriate reference standard can be readily determined by one skilled in the art. In one embodiment, the reference standard is the level of reporter protein expressed by the same stably transformed mammalian cells that have not been treated with the toxin(s). In some embodiments, the level of the reporter protein is measured when mRNA translational activity is at its peak. One of ordinary skill in the art can readily determine the peak of translational activity by performing assays which follow the accumulation of the reporter protein over time. In one embodiment, the level of the reporter protein is measured at least 6 hours after the mammalian cells are treated with at least one toxin. In another embodiment, the level of the reporter protein in the subpopulation of mammalian cells is measured at a time from 6 hours to about 30 hours after the mammalian cells are treated with at least one toxin.

One of ordinary skill in the art will readily recognize that different toxins or combinations of different toxins will produce optimal results for a particular cell line, i.e. the highest reporter expression. The optimal toxin to be used can readily be determined by testing the cells with varying amounts of different toxins. As shown in FIGS. 1, 2 and 10, 5-toxin assays and 15-toxin assays are useful for determining the optimal toxin(s). The toxins used in these screens are listed in the Figures as well; however, it should be noted that different 5-toxin and 15-toxin assays can readily be designed by including different toxins in the screens. One skilled in the art can readily determine the most appropriate toxins that should be screened for a particular cell line. For example, if the cell line being tested is a breast cancer cell line, paclitaxel should preferably be included as a single-Toxin assay.

Methods for measuring the level of a reporter protein are well known. A variety of ex vivo protein detection methods are known in the art. For example, the polypeptides may be detected using methods known in the art that are specific for the polypeptides. These detection methods may include use of specific antibodies, formation of an enzyme product or disappearance of an enzyme substrate. Thus, the detection of reporter proteins can be achieved using any of the standard methods known in the art, such as luminescence readout, fluorescence microscopy, immunohistochemistry, microplate reader analysis, ELISA assays, FACS (Fluorescence Activated Cell Sorting), or spectrophotometry. For example, fluorescence microscopy can be used to detect EYFP and mRFP1. Similarly, antibodies against Firefly Luciferase or β-Galactosidase can be used to detect presence thereof following immunofluorescence staining. By way of another example, luminescence microplate readers can be used to determine the levels of reporter proteins when a reporter is, e.g., Firefly luciferase or *Gaussia* luciferase.

Additionally, a number of noninvasive methods are available in the art to detect protein synthesis in vivo. By way of example, Herpes simplex virus type 1 thymidine kinase (HSV1-TK) ORF placed downstream of the TR element can be used to detect in vivo cell death using metabolic tracers. Unlike mammalian thymidine kinase, this enzyme can efficiently phosphorylate nucleoside analogues (e.g., ganciclovir, penciclovir), as well as various radioactive derivatives such as (9-(4-[18F]-fluoro-3-hydroxymethylbutyl)guanine; [18F]FHBG), which is then retained and accumulates within expressing cells. Thus if a cell is undergoing stress/death, the HSV1-TK will be translated from the TR cassette, resulting in accumulation of a radioactive tracer. The radioactivity can be detected using positron emission tomography (PET), which allows for monitoring of the detailed location, magnitude, and persistence of reporter gene expression. Methods are also provided for mutant HSV1-TK enzymes (e.g., TKsr39) that exhibit enhanced enzymatic activity and/or binding constants that improve the sensitivity of PET imaging by enhancing the cellular accumulation of a radioactive tracer.

When a reporter ORF is a G-protein coupled receptor, GPCR binding assays can be used to detect and measure reporter levels. These assays are well known in the art, and are briefly described below.

By way of example, a known ligand of a specific GPCR is labeled, and then the labeled ligand is incubated with mammalian cells (or cellular components such as membrane lysates) containing the expression cassette of the present invention such that the labeled ligand is added in excess. Any suitable label may be used such as for example, radioactive labels such as $^3$H, $^{32}$P, $^{125}$I, etc., and nonradioactive labels. The label can also comprise any marker molecules such as epitope tags, fluorescent groups, and chemiluminescent groups. Following incubation of the labeled ligand (e.g., radiolabeled ligand) and the mammalian cells (or cellular components such as membrane lysates) containing the expression cassette, the excess ligand is removed (e.g., by washing) and the cells are assayed to determine the amount of the labeled ligand bound to the GPCR, thereby indicating the level of GPCRs in the cells. The binding assay can be conducted using cells comprising the specific GPCR or can be conducted using a cell-free format (e.g., using membrane preparations containing the specific GPCR). After the GPCR-transformed cells and the labeled ligand are allowed to compete for binding with the specific GPCR, the amount of labeled ligand bound to the GPCR is measured. Any methods which allow the measurement of the labeled ligand can be used, such as radioactive binding assays, FACS analysis, ELISA, and the like. When the ligand labels are fluorescence and bioluminescence molecules, bioluminescence-(BRET) and fluorescence resonance energy transfer (FRET) techniques can also be used to detect the binding.

For this invention, luciferase is particularly useful as a reporter for low-light imaging of bioluminescence in living cells and organisms. Although resolution is less than with MRI or PET, bioluminescence imaging, typically with a sensitive charged coupled device (CCD) camera, allows rapid, high throughput (simple data collection from multiple animals simultaneously), progressive (repeated analysis of the same animal), noninvasive, and nondestructive data collection in vivo. A variety of detection devices, image processors and image analysis systems are available in the art.

Once the reporter protein expression is measured, the level thereof indicates the Class phenotype of the subset of treated cells when compared to the reference standard. Based on the assays performed with cell lines as described in the Examples, the responsive cells (i.e. produce mRNA from an intact TR cassette) within a cell pool can exhibit different divisions into Class I, Class II, and Class III categories. As seen in FIG. 2, approximately 60-90% of responsive cells within the HEK293 mTdm-fLUC transformed cell pool fell into Class I, approximately 10-30% fell into Class II, and approximately 1-10% fell into Class III. By way of another example, approximately 50-90% of cells can fall into Class I, 5-40% can fall into Class II, and 0-15% can fall into Class III. Figures with ranking plots show a number of different Class I, II, and III distributions. One skilled in the art would recognize that the most accurate Class distributions can be obtained if the number of cell samples that are analyzed are statistically relevant. Preferably, analyzing at least about 40, more preferably at least about 50, and even more preferably at least about 60 responding clones with an optimal toxin assay produces a random distribution of the Class phenotype, and adding additional subclones to the pool data does not significantly alter the Class ranking.

A subset of cells exhibiting desired Class characteristics indicates that the cell pool from which it is derived will generally fall into the same category. However, as is well known in the art, the initial cell pool contains a number of different cell clones, and it is generally desirable to further subclone the cells from the cell pool in order to obtain a pure cell culture. Subcloning is performed as is standard in the art, and is generally done to obtain a pure population of cells exhibiting the preferred characteristics not optimally exhibited by the parental cell. Thus, one skilled in the art would recognize that another factor playing a role in obtaining the most accurate Class distributions includes having a large enough number of subclones in a cell pool. In one preferred embodiment, it may be useful to screen a primary cell pool containing greater than about 500 primary transformants, and further screening a subclone group of at least about 30 independent subclones, more preferably of at least about 40 independent subclones, still more preferably of at least about 50 independent subclones, and even more preferably of at least about 60 independent subclones.

Accordingly, the present method further includes isolating at least one cell from a desired cell pool, and growing it in culture in order to obtain a subpopulation of cells with the desired Class phenotype. It should be noted that subcloning can be performed more than once in order to increase the purity of the cell population and/or improve any associated characteristic or trait. After each subcloning step, it is desirable to again test a subset of subcloned cells with at least one toxin, and repeat the measuring, isolating, and growing steps as described above in order to insure that the subcloned cells exhibit the characteristics of the desired Class. In some embodiments, subcloning is repeated at least two, three, four, five, six seven, eight, nine, ten, eleven, twelve, thirteen, fourteen or fifteen times. The methods for isolation of desired subpopulations of mammalian cells including multiple rounds of subcloning are described in detail in the Examples.

In addition to the method described above, the present invention also relates to subpopulations of mammalian cells identified and/or isolated according to the foregoing method. In one embodiment, the present invention relates to a Class I mammalian cell. In another embodiment, the invention relates to a Class II mammalian cell. It is still another embodiment to provide a class III mammalian cell as described herein. Any of the above mentioned mammalian cells, including primary cells, cell lines and stem cells can be manipulated to obtain Class I, Class II, and Class III subpopulations thereof. In some embodiments, the mammalian cells lines are selected from human cancer cell lines; the primary cells are human or murine and stem cells are cancer stem cells, human embryonic stem cells or murine embryonic stem cells.

The subpopulations of mammalian cells as described herein find uses in a number of different methods. In one embodiment, the present invention relates to a method for identifying whether or not mammalian cell translation is resistant to a substance or for determining whether or not a substance is toxic to mammalian cells. In another embodiment, the present invention relates to a method for determining toxicity of a substance to mammalian cells. In both methods, a cell line or a primary cell that is to be tested is first transformed with a nucleic acid expression cassette described herein comprising either the TR element or a constitutive promoter and a nucleotide sequence operably linked thereto, which encodes a reporter gene. Introduction of the nucleic acid expression cassette can be done by any methods described above, such as lipofection or electroporation. In one embodiment, the TR element in the expression cassette is selected from SEQ ID NO: 1, SEQ ID NO: 2, SEQ ID NO: 3, and SEQ ID NO: 4. In another embodiment, the expression cassette comprises a CMV constitutive promoter. In still another embodiment, the reporter is a luciferase, and more preferably, it is a *Renilla* luciferase, firefly luciferase or *Gaussia* luciferase.

Once the desired cells are transformed, the cells are manipulated in the same manner as described above in the method for identifying a desired subpopulation of mammalian cells. Briefly, a subset of transformed cells is treated with at least one toxin, the level of a reporter protein encoded by the reporter gene in the toxin-treated cells is measured, and a subset of cells exhibiting the phenotype of the desired cell subpopulation is further subcloned. Once the desired subpopulation of cells is obtained, it is contacted with a substance to be tested, and the levels of the reporter protein are tested following exposure to the substance. In one embodiment, the substance is added to the culture in which the cells are maintained. In another embodiment, the substance is incubated with the cells for at least 5 minutes, 15 minutes, 30 minutes, 45 minutes, 1 hour, 1.5 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 10.5 hours, 11 hours, 11.5 hours, or 12 hours. In one preferred embodiment, the substance is incubated with the cells for 4 hours. In another preferred embodiment, the substance is incubated with the cells for 6 hours. In still another preferred embodiment, the substance is incubated with the cells for 24 hours. Any substance can be tested for purposes of the above two methods. Preferably, the substance is a compound being tested for therapeutic or research purposes, such as a new small molecule drug.

The toxicity of the substance correlates to the presence or the increase in the level of the reporter protein as compared to control mammalian cells that are not exposed to the substance. Similarly, the absence or the decrease in the level of the reporter protein as compared to control mammalian cells that are not exposed to the substance correlates with the lack of resistance of the mammalian cell translation to the substance. Moreover, the presence or the increase in the level of the reporter protein as compared to control mammalian cells that are not exposed to the substance correlates with the resistance of the mammalian cell translation to the substance.

It will be apparent to one of ordinary skill in the art that any of the Class I, II or III cells can be used in the methods for identifying whether or not mammalian cell translation is resistant to a substance or for determining whether or not a substance is toxic to mammalian cells. However, due to a higher translation and subsequent reporter expression in Class II and Class III cells when compared to Class I cells, it is preferable to use the former cells in the foregoing methods. As mentioned above, Class III cells are characterized by the level of a reporter protein being more than 1400% (14 Fold Induction) greater than the level of the reporter protein in the reference standard, wherein the reference standard represents the level of the reporter protein in mammalian cells stably transformed with the nucleic expression cassette and not treated with the toxin(s). Accordingly, Class III cells can be used as "cell factories" to produce large quantities of any polypeptide of interest. In order to be used as cell factories, Class III cells are transformed with a second nucleic acid expression cassette comprising either (1) a TR element encoding an mRNA molecule that is selectively translated in stressed and/or dying cells, and a nucleotide sequence operably linked to the TR element, which encodes a reporter gene and is translated from the TR element; or (2) a constitutive promoter and a nucleotide sequence operably linked to the promoter, which encodes a reporter gene. Thus, the first nucleic acid expression cassette can be used to monitor translation efficiency of the cell line, whereas the second expression cassette is used to provide a nucleic acid sequence for a polypeptide of interest that is to be expressed. Introduction of the second nucleic acid expression cassette into Class III cells can be performed by any of the standard transformation techniques mentioned above, such as, e.g., chemical transfection, lipofection and electroporation. In one embodiment, the second expression cassette is transiently transformed. In another embodiment, the second expression cassette is stably transformed into Class III cells. The first expression cassette can be any of the expression cassettes described above comprising either a TR element or a constitutive promoter and a nucleic acid operably linked thereto, which encodes a reporter. In one embodiment, the first expression cassette comprises a TR element selected from SEQ ID NO: 1, SEQ ID NO: 2, SEQ ID NO: 3, and SEQ ID NO: 4, and a luciferase reporter, such as *Renilla* luciferase, firefly luciferase or *Gaussia* luciferase. In another embodiment, the first expression cassette comprises a CMV constitutive promoter and a luciferase reporter. The second expression cassette can contain either the same or different TR element or constitutive promoter as the first expression cassette. Exemplary combinations of first and second expression cassettes are listed below in Table 2, wherein n.a. denotes nucleic acid for the polypeptide of interest and CMVp is CMV promoter.

TABLE 2

| First Expression Cassette | | Second Expression Cassette | |
|---|---|---|---|
| Mouse plp TR | luciferase | mouse plp TR | n.a. |
| Mouse plp TR | luciferase | Mouse dm TR | n.a. |
| Mouse plp TR | luciferase | Human plp TR | n.a. |
| Mouse plp TR | luciferase | Human dm TR | n.a. |
| Mouse plp TR | GFP | mouse plp TR | n.a. |
| Mouse plp TR | GFP | Mouse dm TR | n.a. |
| Mouse plp TR | GFP | Human plp TR | n.a. |
| Mouse plp TR | GFP | Human dm TR | n.a. |
| Mouse plp TR | luciferase | CMVp | n.a. |
| Mouse plp TR | luciferase | PGK promoter | n.a. |
| Mouse plp TR | luciferase | Beta-actin promoter | n.a. |
| Mouse dm TR | luciferase | mouse plp TR | n.a. |
| Mouse dm TR | luciferase | Mouse dm TR | n.a. |
| Mouse dm TR | luciferase | Human plp TR | n.a. |
| Mouse dm TR | luciferase | Human dm TR | n.a. |
| Mouse dm TR | GFP | mouse plp TR | n.a. |
| Mouse dm TR | GFP | Mouse dm TR | n.a. |
| Mouse dm TR | GFP | Human plp TR | n.a. |
| Mouse dm TR | GFP | Human dm TR | n.a. |
| Mouse dm TR | luciferase | CMVp | n.a. |
| Mouse dm TR | luciferase | PGK promoter | n.a. |
| Mouse dm TR | luciferase | Beta-actin promoter | n.a. |
| Human plp TR | luciferase | mouse plp TR | n.a. |
| Human plp TR | luciferase | Mouse dm TR | n.a. |
| Human plp TR | luciferase | Human plp TR | n.a. |
| Human plp TR | luciferase | Human dm TR | n.a. |
| Human plp TR | GFP | mouse plp TR | n.a. |
| Human plp TR | GFP | Mouse dm TR | n.a. |
| Human plp TR | GFP | Human plp TR | n.a. |
| Human plp TR | GFP | Human dm TR | n.a. |
| Human plp TR | luciferase | CMVp | n.a. |
| Human plp TR | luciferase | PGK promoter | n.a. |
| Human plp TR | luciferase | Beta-actin promoter | n.a. |
| Human dm TR | luciferase | mouse plp TR | n.a. |
| Human dm TR | luciferase | Mouse dm TR | n.a. |
| Human dm TR | luciferase | Human plp TR | n.a. |
| Human dm TR | luciferase | Human dm TR | n.a. |
| Human dm TR | GFP | mouse plp TR | n.a. |
| Human dm TR | GFP | Mouse dm TR | n.a. |
| Human dm TR | GFP | Human plp TR | n.a. |
| Human dm TR | GFP | Human dm TR | n.a. |
| Human dm TR | luciferase | CMVp | n.a. |
| Human dm TR | luciferase | PGK promoter | n.a. |
| Human dm TR | luciferase | Beta-actin promoter | n.a. |

TABLE 2-continued

| First Expression Cassette | | Second Expression Cassette | |
|---|---|---|---|
| CMVp | luciferase | mouse plp TR | n.a. |
| CMVp | luciferase | Mouse dm TR | n.a. |
| CMVp | luciferase | Human plp TR | n.a. |
| CMVp | luciferase | Human dm TR | n.a. |
| CMVp | GFP | mouse plp TR | n.a. |
| CMVp | GFP | Mouse dm TR | n.a. |
| CMVp | GFP | Human plp TR | n.a. |
| CMVp | GFP | Human dm TR | n.a. |
| CMVp | luciferase | CMVp | n.a. |
| CMVp | luciferase | PGK promoter | n.a. |
| CMVp | luciferase | Beta-actin promoter | n.a. |
| PGK promoter | luciferase | mouse plp TR | n.a. |
| PGK promoter | luciferase | Mouse dm TR | n.a. |
| PGK promoter | luciferase | Human plp TR | n.a. |
| PGK promoter | luciferase | Human dm TR | n.a. |
| PGK promoter | GFP | mouse plp TR | n.a. |
| PGK promoter | GFP | Mouse dm TR | n.a. |
| PGK promoter | GFP | Human plp TR | n.a. |
| PGK promoter | GFP | Human dm TR | n.a. |
| PGK promoter | luciferase | CMVp | n.a. |
| PGK promoter | luciferase | PGK promoter | n.a. |
| PGK promoter | luciferase | Beta-actin promoter | n.a. |
| Beta-actin promoter | luciferase | mouse plp TR | n.a. |
| Beta-actin promoter | luciferase | Mouse dm TR | n.a. |
| Beta-actin promoter | luciferase | Human plp TR | n.a. |
| Beta-actin promoter | luciferase | Human dm TR | n.a. |
| Beta-actin promoter | GFP | mouse plp TR | n.a. |
| Beta-actin promoter | GFP | Mouse dm TR | n.a. |
| Beta-actin promoter | GFP | Human plp TR | n.a. |
| Beta-actin promoter | GFP | Human dm TR | n.a. |
| Beta-actin promoter | luciferase | CMVp | n.a. |
| Beta-actin promoter | luciferase | PGK promoter | n.a. |
| Beta-actin promoter | luciferase | Beta-actin promoter | n.a. |

One skilled in the art can readily determine which Class III cell line should be used to express a polypeptide of interest. The selection of the cell type will depend on many different factors, such as a polypeptide of interest, toxin(s) to be used for screening, post-translational modification of the expressed protein, cell type-specific protein processing, etc. A skilled artisan can prepare Class III cells from any cell line as discussed above or can use Class III cells available in kits. By way of example and not of limitation, Class III HEK293 and HCT116 cells can be used to express a number of different polypeptides of interest.

Any polypeptide can be expressed in Class III cells as described above. In one embodiment, the polypeptide to be expressed is a polypeptide that can be used therapeutically, such as an antibody, antibody fragment, receptor, receptor fragment, enzyme, etc. Preferably, cDNA sequences of the polypeptides of interest are used for expression. Thus, Class III cells containing a second expression cassette with a nucleic acid sequence for a polypeptide of interest are grown in media under conditions which allow for expression of the polypeptide of interest. One of ordinary skill in the art can determine the most suitable conditions for each Class III cell line and particular polypeptide of interest without undue experimentation by altering factors such as incubation time, media components, exposure to different toxins, duration of the exposure, and the like. The expressed polypeptide is next purified according to the standard protocols used in the art. Depending on whether the polypeptide is intracellular or secreted, different purification methods are used to purify the polypeptide. Such methods include affinity chromatography, ultracentrifugation, size exclusion chromatography, ion exchange chromatography and electrophoresis techniques.

The TR-containing expression cassettes and cells containing the same also find use in methods for identifying proteins involved in regulation of cap-independent translation. As already discussed, the TR element encodes an mRNA molecule that is selectively translated in stressed and/or dying cells. Thus, the nucleic acid encoding a reporter protein that is operably linked to the TR element is translated under cell stress/death conditions, such as the exposure to at least one toxin. This property of the TR-reporter cassette is used to identify proteins involved in cap-independent translation. Briefly, the cells to be studied are stably transformed with a nucleic acid expression cassette comprising a TR element and a nucleotide sequence operably linked to the TR element, which encodes a reporter gene and is translated from the TR element. Alternatively, any cells already transformed with such expression cassette can be used. The transformed cells are next treated with at least one toxin in order to induce TR-reporter sequence translation, and the cell lysate from the toxin-treated cells is obtained. The cell lysate can be isolated by any methods known in the art for undenatured or denatured protein extracts, such as chemical lysis (e.g., using a detergent-based lysis buffer), sonication or repeated freeze and thaw cycles. In one embodiment, the cell lysis is performed by incubating the cells with a cell lysis buffer. Next, the mRNA encoding the TR element and the nucleotide sequence operably linked to the TR element is isolated and contacted with the cell lysate in order to allow for binding of any proteins from the lysate to the TR-reporter mRNA, as proteins that bind to this mRNA will likely play a role in cap-independent translation. The contacting step can generally be performed by incubating the mRNA with the cell lysate. A skilled artisan can readily determine the most suitable conditions for such incubation by varying factors such as mRNA concentration, amount of the cell lysate used, temperature, prior cell exposure to toxin(s) and the like. Any proteins bound to the mRNA are next isolated and identified as is known in the art. By way of example and not of limitation, proteins can be isolated using sepharose beads and columns, magnetic bead-based separation, Western blots, immunoaffinity, etc., and can be identified using, e.g., protein sequencing, mass spectrometry (MS), etc.

Related to this method, one of ordinary skill in the art will recognize that the expression cassettes of the present invention can further be used to identify substances which inhibit protein translation (for example FIG. 28 and FIG. 33). Of note, a nucleic acid expression cassette comprising a TR element encoding an mRNA molecule that is selectively translated in stressed and/or dying cells, and a nucleotide sequence operably linked to the TR element, which encodes a reporter gene and is translated from the TR element is used to determine the ability of the substance to inhibit cap-independent translation, whereas a nucleic acid expression cassette comprising a constitutive promoter and a nucleotide sequence operably linked to the promoter, which encodes a reporter gene is used to determine the ability of the substance to inhibit cap-dependent translation. Any of the foregoing TR elements, constitutive promoters and reporter sequences can be used.

Accordingly, the present invention provides a method for determining the ability of a substance to inhibit protein translation in mammalian cells (for example FIG. 28 and FIG. 33). In one embodiment, the method can include the following steps if Class, I, II or III mammalian cells are not readily available and need to be isolated first. A subset of mammalian cells is treated with at least one toxin to form toxin-treated cells, the mammalian cells being stably transformed with a nucleic acid expression cassette comprising either: (1) a TR element encoding an mRNA molecule that is selectively translated in stressed and/or dying cells, and a nucleotide sequence operably linked to the TR element, which encodes a reporter gene and is translated from the TR element; or (2) a constitutive promoter and a nucleotide sequence operably linked to the promoter, which encodes a reporter gene. A level of a reporter protein encoded by the reporter gene in the toxin-treated cells is measured as compared to a level of the reporter protein expressed by a reference standard to identify whether the subset of mammalian cells exhibit the phenotype of the desired subpopulation of mammalian cells. At least one cell from the mammalian cells is isolated to form a cell culture if the toxin-treated cells of the mammalian cells exhibit the phenotype of the desired subpopulation of the mammalian cells. The cell culture is grown to form a subpopulation of mammalian cells. Optionally, the subpopulation of mammalian cells is treated with the at least one toxin, and the measuring, isolating, and growing steps are repeated until the desired subpopulation of mammalian cells is identified. The desired subpopulation of the mammalian cells is contacted with the substance. The expression of the reporter protein produced by the desired subpopulation of mammalian cells is determined after contact with the substance as compared to the expression of the reporter protein by the cells which have not been treated with the substance. The reduction in the expression of the reporter protein produced by the substance-treated cells as compared to the expression of the reporter protein produced by the cells which have not been treated with the substance indicates that the substance inhibits protein translation. The steps of treating cell with a toxin, measuring reporter protein levels, isolating a desired subpopulation of cells, and contacting the cells with a substance have been addressed in the foregoing sections.

Alternatively, the method for determining the ability of a substance to inhibit protein translation in mammalian cells can utilize any of the Class I, II or III cells without having to isolate a desired subpopulation of cells first. Thus, the method includes contacting Class I, II or III mammalian cells with the substance; and determining the expression of the reporter protein produced by the mammalian cells after contact with the substance as compared to the expression of the reporter protein by the cells which have not been treated with the substance, wherein reduction in the expression of the reporter protein produced by the substance-treated cells as compared to the expression of the reporter protein produced by the cells which have not been treated with the substance indicates that the substance inhibits protein translation.

It is preferable to use either Class II or Class III cells when their increased translational activity is required for enhanced detection and sensitivity or biological correlation. In another example, determining the ability of a substance to inhibit protein translation would use Class I cells to examine substance responses in cells generally resistant to toxin exposure. Thus, while not being bound to a particular theory, it is believed that it will be easier to detect the effect of a tested substance on protein translation by using Class II or III cells compared to Class I cells.

One of ordinary skill in the art will realize that it is possible for Class I, II, and III cells to change classes or lose reporter expression completely. For example, extended passage in culture (e.g., increasing passage number by 10-20 passages) may result in Class III cells converting into Class II cells, Class II cells converting into Class I cells and Class I cells converting into nonresponsive cells. Thus, the present invention also relates to a method for verifying that Class I, Class II, or Class III mammalian cells retain their phenotype. Briefly, this rescreening method includes the following steps. A subset of the Class I, Class II and/or Class III mammalian cells is treated with at least one or two toxins. A level of a reporter protein encoded by the reporter gene in the subset of mammalian cells is measured as compared to a level of the reporter protein expressed by a reference standard. The mammalian cells are then verified with regard to whether the cells retain their phenotype wherein the class I cells are characterized by the expression of the reporter protein that is up to 500% greater than the expression of the reporter protein in the mammalian cells which have not been treated with the toxins, the class II cells are characterized by the expression of the reporter protein that is more than 500% to 1400% greater than the expression of the reporter protein in the mammalian cells which have not been treated with the toxins, and the class III cells are characterized by the expression of the reporter protein that is more than 1400% to about 75000% greater than the expression of the reporter protein in the mammalian cells which have not been treated with the toxins.

In one embodiment, the cells are treated with at least two toxins. In another embodiment, the cells are treated with at least three toxins. In still another embodiment, the cells are treated with at least five toxins. By way of example and not of limitation, the toxin is selected from the group consisting of cAMP, TPA, paclitaxel, MG132, thapsigargin, nocodazole, vinblastin, Calcium Ionophore A23167, bortezomib, hycamtin, colchicine, 4-oxoquinoline-3-carboxylic acid derivative antibiotic, methanol and ethanol. In some embodiments, the toxin is selected from the group consisting of cAMP, TPA, paclitaxel, MG132, thapsigargin, nocodazole, vinblastin, and Calcium Ionophore A23167. Exemplary toxin combinations are described in the foregoing sections.

In addition to verifying the phenotype of Class I, II an III cells, the present invention also provides a method for restoring the phenotype of Class I, II and III cells in cases of apparent loss of a Class designation. Briefly, the method is based on the fact that the cells which have apparently lost their phenotype have most likely done so because of segregation or disruption of the TR-responsive plasmid or the promoter-TR expression cassette. The method comprises culturing at least a subset of the mammalian cells, which have lost their Class phenotype to form cultured cells, wherein the mammalian cells are stably transformed with a nucleic acid expression cassette of the present invention, namely the expression cassette comprising a nucleotide sequence for (1) a TR element encoding an mRNA molecule that is selectively translated in stressed and/or dying cells, and a nucleotide sequence operably linked to the TR element, which encodes a reporter gene and is translated from the TR element; or (2) a constitutive promoter and a nucleotide sequence operably linked to the promoter, which encodes a reporter gene. The expression cassettes also contain a nucleotide sequence for a selection marker gene, which confers a trait suitable for cell selection.

The expression cassette can contain a positive selection marker and/or a negative selection marker. In various embodiments, the construct contains both positive and negative selection markers. In one aspect, methods which rely on expression of the selection marker are used, for example, by adding the appropriate substrate to select only those cells which express the product of the positive selection marker or to eliminate those cells expressing the negative selection marker. For example, where the positive selection marker encodes neomycin resistance, G418 is added at increasing dosages to the media containing mammalian cells with the expression cassette of the present invention. Similarly, where the negative selection marker is used, a suitable substrate (e.g., gancyclovir if the negative selection marker encodes HSV-TK) is added to the cell culture. Either before or after selection using the appropriate substrate, the presence of the positive and/or negative selection markers in a recipient cell can also be determined by others methods, for example, hybridization, detection of radiolabelled nucleotides, PCR and the like. In a preferred embodiment, the selection marker gene is a positive selection marker, and more preferably it is an antibiotic resistance gene. In still other preferred embodiments, the antibiotic resistance gene is selected from the group consisting of neomycin, ampicillin, kanamycin, tetracycline, chloramphenicol, hygromycin B, blasticidin and G418.

The cultured cells are next treated with a substance to which the selection marker provides resistance, such that the cultured cells which have segregated the nucleic acid expression cassette die. By way of example, if the selection marker is the neomycin resistance gene, adding G418 to the cellular medium results in the death of cells which have lost the expression cassette and proliferation (growth) of cells which still contain the expression cassette. The cells which remain following the treatment with an antibiotic (or any other substance to which the selection marker provides resistance) are a subpopulation of cells that may have their Class phenotype restored. Optionally, the steps of culturing, treating and growing the cells can be repeated until the restored phenotype is highly similar to the one of the original parent line prior to the Class phenotype loss. For example, if a Class III cell line is characterized by the level of a reporter protein being 50 fold higher than that of a reference standard prior to losing the reporter expression, and its reporter expression is 25 fold higher than the reference standard following restoration of its phenotype, it may be desirable to repeat the steps of the restoration method until the reporter expression is closer to the parent's reporter expression (i.e. 50 fold). As shown in FIG. 12, a comparison of the Sub#30 and Sub#38 subclones to all secondary 12-16 subclones treated with TPA+Taxol two-Toxin assay found significant increase in reporter expression in subclones Sub#30 and Sub#38, suggesting that culture reselection can improve the TR-specific response.

In situations where reselection with the selectable marker gene on the TR plasmid does not provide Class restoration (i.e the TR cassette has been inactivated by a disruptive mutation), the cells can be resubcloned and rescreened according to the method for identifying a desired subpopulation of mammalian cells as described above.

Also provided herein are kits comprising one or more of the components described herein in any number of separate containers, packets, tubes, vials and the like, or the components may be combined in any combination in such containers. In one embodiment, the kit contains Class II mammalian cells or a cell lysate thereof, and instructions for use of the kit. In another embodiment, the kit contains Class III mammalian cells or a cell lysate thereof, and instructions for use of the kit. Preferably, the plurality of cells in this kit are derived from a single cell line. When the Class II or Class III cells contain a TR-reporter expression cassette, a kit of this invention may also optionally contain one or more reagents useful for detecting transcription of the TR cassette (such as cassette-specific oligonucleotides useful for PCR amplification), translation from the TR cassette (such as an antibody or enzyme substrate), one or more control compounds known to induce or inhibit promoter activity (and thereby expression of the TR cassette), one or more control compounds that produce a defined toxic response (and thereby promotes stress/death-specific translation of the TR cassette), one or more molecules or other compounds that inhibit, influence or activate a drug target or drug metabolizing enzyme expressed from the TR cassette and/or written information on the use of the vectors, cells or other components of the kit for drug screening or validation. The oligonucleotides employed in the above kits and methods of this invention are chosen based upon their ability to specifically hybridize under high stringency conditions to the transcription product synthesized from the TR cassette. Various methods of selecting the oligonucleotide sequences are known in the art.

The Class II and Class III cells provided in the kit of the present invention can be used to practice methods described herein. Furthermore, cell lysates from Class II and Class III cells find use in a number of different assays.

The cell lysates of Class II and Class III cells as described herein can be used to characterize protein products from RNA transcripts, investigate transcriptional and translational control, and identify mRNA species. The cell lysates are obtained by lysing the cells by any of the standard lysis methods, such as chemical lysis (e.g., using a detergent-based lysis buffer), sonication or repeated freeze and thaw cycles. In one embodiment, the cell lysis is performed by incubating the cells with a cell lysis buffer. The cell lysates can either be nuclease treated or nuclease untreated.

The nuclease treated lysate can be treated with micrococcal nuclease to destroy endogenous mRNA, and contains the cellular components necessary for protein synthesis (tRNA, ribosomes, amino acids, and initiation, elongation and termination factors).

The nuclease treated cell lysate can further be optimized for mRNA translation by the addition of one or more of the following:

1) an energy-generating system consisting of prequalified phosphocreatine and phosphocreatine kinase;

2) a mixture of tRNAs to expand the range of mRNAs that can be translated;

3) hemin (to prevent inhibition of translation initiation); and 4) potassium acetate and magnesium acetate.

The nuclease treated cell lysate of Class II and III cells can also contain a number of other elements, such as enzymes, which are involved in a variety of post-translational processing activities, including acetylation, isoprenylation and some phosphorylation activity. Processing events such as signal peptide cleavage and core glycosylation can be examined by adding Canine Pancreatic Microsomal Membranes (e.g., available from Promega) to a standard translation reaction. The untreated cell lysate contains the cellular components necessary for protein synthesis (tRNA, ribosomes, amino acids, and initiation, elongation and termination factors) but has not been treated with micrococcal nuclease. Untreated lysate can be used primarily for the isolation of these components and as an abundant source of endogenous globin mRNA.

In one embodiment, the untreated lysate is not supplemented with tRNA, creatine phosphate, creatine phosphokinase, DTT, potassium acetate, magnesium chloride or hemin. In another embodiment, the untreated lysate is supplemented with tRNA, creatine phosphate, creatine phosphokinase, DTT, potassium acetate, magnesium chloride or hemin. A skilled artisan will recognize that unsupplemented lysate is not recommended for in vitro translation without adding supplements first.

In another embodiment, the cell lysate can be used to direct cap-independent translation via a coupled transcription-translation protocol. An expression vector containing a TR-ORF RNA sequence operatively linked to a bacterial or viral promoter (i.e. SP6, T7, etc promoters) can be used as a template for in vitro RNA synthesis. Since toxin-treated lysates should contain an impaired cap-dependent translation system, translation of the cap-independent TR RNA would be enhanced. In another embodiment, cell lysates could be supplemented with a natural or artificially synthesized cap-independent TR RNA which would direct the selective synthesis of any operatively linked ORF as above.

The cell lysates of both Class II and Class III mammalian cells can be used for the following exemplary applications:
1) drug screening (for drugs affecting translation rates)
2) mutation and detection analysis (i.e., enzyme kinetics)
3) protein:protein interactions (e.g., using GST fusion proteins)
4) immunoprecipitation of protein complexes
5) ligand-binding region determination/confirmation/competition assays
6) protein structure analysis
7) electrophoretic mobility shift assays (EMSAs) for protein-DNA interactions
8) DNA footprinting and protein cross-linking studies
9) protein-RNA binding assays
10) post-translational modification tests
11) verification/characterization of cloned gene products, and
12) protein dimerization assays.

The above procedures are known in the art, and can be easily adapted for Class II and Class III cell lysates. By way of example, a skilled artisan can replace the rabbit reticulocyte lysate system (e.g., available from Promega) used for any of the above applications with the cell lysates of the present invention without undue experimentation.

Molecular biological techniques, biochemical techniques, and microorganism techniques as used herein are well known in the art and commonly used, and are described in, for example, Sambrook J. et al. (1989), Molecular Cloning: A Laboratory Manual, Cold Spring Harbor and its 3rd Ed. (2001); Ausubel, F. M. (1987), Current Protocols in Molecular Biology, Greene Pub. Associates and Wiley-interscience; Ausubel, F. M. (1989), Short Protocols in Molecular Biology: A Compendium of Methods from Current Protocols in Molecular Biology, Greene Pub. Associates and Wiley-interscience; Innis, M. A. (1990), PCR Protocols: A Guide to Methods and Applications, Academic Press; Ausubel, F. M. (1992), Short Protocols in Molecular Biology: A Compendium of Methods from Current Protocols in Molecular Biology, Greene Pub. Associates; Ausubel, F. M. (1995), Short Protocols in Molecular Biology: A Compendium of Methods from Current Protocols in Molecular Biology, Greene Pub. Associates; Innis, M. A. et al. (1995), PCR Strategies, Academic Press; Ausubel, F. M. (1999), Short Protocols in Molecular Biology: A Compendium of Methods from Current Protocols in Molecular Biology, Wiley, and annual updates; Sninsky, J. J. et al. (1999), PCR Applications: Protocols for Functional Genomics, Academic Press; Special issue, Jikken Igaku [Experimental Medicine] "Idenshi Donyu & Hatsugenkaiseki Jikkenho [Experimental Method for Gene introduction & Expression Analysis]", Yodo-sha, 1997; and the like. Relevant portions (or possibly the entirety) of each of these publications are herein incorporated by reference.

Any technique may be used herein for introduction of a nucleic acid molecule into cells, including, for example, transformation, transduction, transfection, and the like. Such a nucleic acid molecule introduction technique is well known in the art and commonly used, and is described in, for example, Ausubel F. A. et al., editors, (1988), Current Protocols in Molecular Biology, Wiley, New York, N.Y.; Sambrook J. et al. (1987) Molecular Cloning: A Laboratory Manual, 2nd Ed. and its 3rd Ed., Cold Spring Harbor Laboratory Press, Cold Spring Harbor, N.Y.; Special issue, Jikken Igaku [Experimental Medicine] Experimental Method for Gene introduction & Expression Analysis", Yodo-sha, 1997; and the like. Gene introduction can be confirmed by method as described herein, such as Northern blotting analysis and Western blotting analysis, or other well-known, common techniques.

Amino acid deletion, substitution or addition of the polypeptide of the present invention can be carried out by a site-specific mutagenesis method which is a well known technique. One or several amino acid deletions, substitutions or additions can be carried out in accordance with methods described in Molecular Cloning, A Laboratory Manual, Second Edition, Cold Spring Harbor Laboratory Press (1989); Current Protocols in Molecular Biology, Supplement 1 to 38, John Wiley & Sons (1987-1997); Nucleic Acids Research, 10, 6487 (1982); Proc. Natl. Acad. Sci., USA, 79, 6409 (1982); Gene, 34, 315 (1985); Nucleic Acids Research, 13, 4431 (1985); Proc. Natl. Acad. Sci. USA, 82, 488 (1985); Proc. Natl. Acad. Sci., USA, 81, 5662 (1984); Science, 224, 1431 (1984); PCT WO85/00817 (1985); Nature, 316, 601 (1985); and the like.

Having described the invention in detail, it will be apparent that modifications and variations are possible without departing the scope of the invention defined in the appended claims. Furthermore, it should be appreciated that all examples in the present disclosure, while illustrating the invention, are provided as non-limiting examples and are, therefore, not to be taken as limiting the various aspects of the invention so illustrated.

EXAMPLES

The following non-limiting examples are provided to further illustrate the present invention.
Materials and Methods
A. Cell Culture All mammalian cells were maintained at 37° C., 5% $CO_2$ in appropriate complete growth medium (specified below for each cell line), supplemented with 10% fetal bovine serum (Hyclone) and 30-50 mg/L gentamicin sulfate (Invitrogen Life Technologies).
Media Formulations:
DMEM:
1 packet/L DMEM powder (Invitrogen Life Technologies)
3.7 g/L sodium bicarbonate
30-50 mg/L gentamicin sulfate
10% FBS
MEM:
1 packet/L MEM powder with Earle's salts (Invitrogen Life Technologies)
1.5 g/L sodium bicarbonate
10 mL/L 100 mM sodium pyruvate solution (Invitrogen Life Technologies)
10 mL/L 10 mM MEM nonessential amino acid solution (Invitrogen Life Technologies)
30-50 mg/L gentamicin sulfate
10% FBS
RPMI:
1 packet/L RPMI 1640 powder (Invitrogen Life Technologies)
10 mL/L 100 mM sodium pyruvate solution (Invitrogen Life Technologies)
30-50 mg/L gentamicin sulfate
10% FBS
McCoy's 5A:
1 L McCoy's 5A liquid (Invitrogen Life Technologies)
30-50 mg/L gentamicin sulfate
10% FBS
Ham's F12K:

1 L F12K, Kaighn's modification liquid (Invitrogen Life Technologies)
30-50 mg/L gentamicin sulfate
10% FBS
Media Requirements by Cell Line:
DMEM: HEK293, MCF7, H4, Hs 683, NTERA-2 cl.D, HeLa, MIA PaCa-2, PC3
MEM: HepG2, CaCo-2, HeLa, A-498, RPMI 2650, HT-1080, SK-N-MC, HuTu 80, IMR32
RPMI: SupT 1, A3.01, CCF-STTG1, Colo201, Colo205, DU145, LNCaP clone FGS, PC3, HCT116, AsPC-1, H1299, MDA231
McCoy's 5A: A-204, Capan-2, U2 Os, HT29
Ham's F12K: AGS, A549, BeWo, LoVo B. Transfection and Isolation of Stably Transformed Mammalian Cell Pools Mammalian transfections were performed using the non-lipidic Transfectol transfection reagent (Continental Lab Products) or FuGENE6 lipid-based transfection reagent (Roche Applied Science) as suggested by the vendor.

Plasmid DNAs:

The following plasmids were used to transfect mammalian cells: pCMV-fLuc, pCMV-gLuc, pmTRplp-fLuc, pmTRplp-GLuc, pmTRdm-fLuc, pmTRdm-GLuc, phTRdm-fLuc, phTRdm-GLuc.

Transfectol Procedure Summary:

Prior to transfection, mammalian cells were grown in 100 mm dishes to 50% confluence and fed with the appropriate growth medium supplemented with 2.5-5% FBS 1-3 hrs prior to addition of the DNA/transfection reagent mixture. The mixtures were prepared by first combining 1 mL Diluent with 15 µg plasmid DNA and vortexing, then adding 60 µL Transfectol and vortexing for 5 sec. Each DNA/transfection reagent mixture was incubated at RT for 15 min, then added dropwise to cells. Cells were grown in the presence of the DNA/Transfectol mixtures for 2-16 hr. At this time, the culture medium was replaced with complete growth medium, 10% FBS and cells were grown for additional 24 hr prior to addition of G418 selective medium.

FuGENE6 Procedure Summary:

Prior to transfection, mammalian cells were grown in T-25 flasks to 50% confluence and fed with the appropriate complete growth medium, 10% FBS 1-3 hrs prior to addition of the DNA/transfection reagent mixture. Three DNA/transfection reagent mixtures were prepared for each plasmid DNA using 1:3, 2:3, and 1:6 DNA:FuGENE6 ratios. To set up the DNA/FuGENE6 mixtures, FuGENE6 was diluted in the appropriate serum free growth medium as follows:
1:3 Ratio Mix: 242.5 µL SFM+7.5 µL FuGENE6
2:3 Ratio Mix: 242.5 µL SFM+7.5 µL FuGENE6
1:6 Ratio Mix: 235 µL SFM+15 µL FuGENE6

FuGENE6 dilutions were vortexed and incubated for 5 min at RT. Then the plasmid DNA was added as follows:
1:3 Ratio Mix: 2.5 µg
2:3 Ratio Mix: 5 µg
1:6 Ratio Mix: 2.5 µg The DNA/FuGENE6 mixtures were vortexed and incubated at RT for 15 min prior to their addition to cells. Cells were grown in the presence of the DNA/FuGENE6 mixtures overnight. At this time, the culture medium was replaced with complete growth medium, 10% FBS and cells were grown for additional 24 hr prior to addition of G418 selective medium.

G418 Selection Summary:

The G418 selective medium (complete growth medium supplemented with 500 µg/mL G418) was applied about 48 hrs post transfection. Then, the selection medium was changed every second day for 2-3 weeks, during which the majority of cells detached and G418 resistant "primary" colonies emerged. Depending upon the number and density of colonies, surviving cells were grown for several days in G418-free medium until the plate was 50-60% confluent. At this point, all of the "primary" colonies on a selection plate were collected together in one sample, transferred to 100 mm dish, fed 24 hrs after plating, and grown until ~80% confluent. This collection of colonies was termed a stable cellular "pool", passage 1 (P1). This pooled population of stably transformed mammalian cells was tested for a translational response to toxins using the 5-Toxin and 15-Toxin assays. Responsive pools were used to isolate clonal cell lines with distinct ribosomal phenotypes by infinite dilution or manual colony subcloning and then cryopreserved in liquid nitrogen.

C. Measuring TR-Mediated Ribosome Responses in Stably Transformed Mammalian Cell Pools Firefly Luciferase (fLuc) Pools:

The 5-Assay and 15-Assay procedures were applied to cellular pools using either of two growth procedures (e.g. a Cell Count or Confluence growth assay). For a Cell Count assay, cells from the P1 pool dish were counted and passed into a white clear bottom 96-well microtiter tray at a density of 25,000 cells per well; the leftover cells were passed into a passage 2 (P2) dish. Cells in the microtiter plate were allowed to grow for about 40 hr to achieve a ~75% cell confluence prior to incubation with a toxic agent. Then cells in a microtiter plate were treated with complete growth medium containing either no toxin or an optimal toxin, defined as a single or multiple toxin assay that produces a maximal translational response (taken from Table 3) and incubated for 6 hours at 37° C. Each treatment was performed on triplicate wells.

For the Confluence assay, a confluent P1 culture is processed for passage and a fixed volume of the cell suspension (approximately 1% of the total or 60,000 cells per well) is passed into a white clear bottom 96-well microtiter tray. Cells in the microtiter plate were allowed to grow for 40 hr until all sample wells had reached confluence (i.e. the maximum number of cells per square centimeter). Toxin treatment and sample analyses are as described above for the cell count assay.

TABLE 3

| | Toxin(s) Name | Concentration(s) |
|---|---|---|
| | 5-Assay Reagents | |
| 1 | dbcAMP[1] | 5 mM |
| 2 | TPA[2] | 100 nM |
| 3 | Paclitaxel | 500 nM |
| 4 | MG132[3] | 50 uM |
| 5 | High dose (HD) CaIon[4] | 10 uM |
| 6 | Low dose (LD) CaIon[4] | 1 uM |
| 7 | Low Dose (LD) Hycamtin[5] | 100 nM |
| 8 | High Dose (HD) Hycamtin (Topotecan)[5] | 10 uM |
| 9 | Colchicine[6] | 1 uM |
| 10 | MRA[7] | 150 nM |
| 11 | Bortezomib (Velcade)[8] | 50 nM |
| | 15-Assay Reagents | |
| 1 | dbcAMP[1] | 5 mM |
| 2 | TPA[2] | 100 nM |
| 3 | Paclitaxel (Taxol) | 500 nM |
| 4 | MG132[3] | 50 uM |
| 5 | High dose (HD) CaIon[4] | 10 uM |
| 6 | dbcAMP[1] + TPA[2] | 5 mM + 100 nM |
| 7 | dbcAMP[1] + Paclitaxel (Taxol) | 5 mM + 500 nM |
| 8 | dbcAMP[1] + MG132[3] | 5 mM + 50 uM |
| 9 | dbcAMP[1] + High dose (HD) CaIon[4] | 5 mM + 10 uM |
| 10 | TPA[2] + Paclitaxel (Taxol) | 100 nM + 500 nM |
| 11 | TPA[2] + MG132[3] | 100 nM + 50 uM |
| 12 | TPA[2] + High dose (HD) CaIon[4] | 100 nM + 10 uM |

TABLE 3-continued

| | Toxin(s) Name | Concentration(s) |
|---|---|---|
| 13 | Paclitaxel (Taxol) + MG132[3] | 500 nM + 50 uM |
| 14 | Paclitaxel (Taxol) + High dose (HD) CaIon[4] | 500 nM + 10 uM |
| 15 | MG132[3] + High dose (HD) CaIon[4] | 50 uM + 10 uM |
| | Updated 15-Assay Reagents | |
| 1 | TPA[2] | 100 nM |
| 2 | Colchicine[6] | 1 uM |
| 3 | Bortezomib[8] | 50 nM |
| 4 | Low dose (LD) CaIon[4] | 1 uM |
| 5 | High Dose (HD) Hycamtin[5] | 10 uM |
| 6 | TPA[2] + Colchicine[6] | 100 nM + 1 uM |
| 7 | TPA[2] + Bortezomib[8] | 100 nM + 50 nM |
| 8 | TPA[2] + Low dose (LD) CaIon[4] | 100 nM + 1 uM |
| 9 | TPA[2] High Dose (HD) Hycamtin[5] | 100 nM + 10 uM |
| 10 | Colchicine[6] + Bortezomib[8] | 1 uM + 50 nM |
| 11 | Colchicine[6] + Low dose (LD) CaIon[4] | 1 uM + 1 uM |
| 12 | Colchicine[6] + High Dose (HD) Hycamtin[5] | 1 uM + 10 uM |
| 13 | Bortezomib[8] + Low dose (LD) CaIon[4] | 50 nM + 1 uM |
| 14 | Bortezomib (Velcade)[8] High Dose (HD) Hycamtin[5] | 50 nM + 10 uM |
| 15 | Low dose (LD) CaIon[4] + H High Dose (HD) Hycamtin[5] | 1 uM + 10 uM |

[1]Dibutyryl-cyclic AMP
[2]12-O-tetradecanoylphorbol-13-acetate
[3]Z-Leu-Leu-Leu-aldehyde
[4]Calcium Ionophore A23187, Calcimycin
[5](S)-10-[(dimethylamino)methyl]-4-ethyl-4,9-dihydroxy-1H-pyrano[3',4':6,7]indolizino [1,2-b]quinoline-3,14(4H,12H)-dione monohydrochloride; Topetecan
[6]N-[(7S)-1,2,3,10-tetramethoxy-9-oxo-5,6,7,9-tetrahydrobenzo[a]heptalen-7-yl]acetamide
[7]Mycoplasma Removal Agent, 4-oxoquinoline-3-carboxylic acid derivative
[8][(1R)-3-methyl-1-[[(2S)-1-oxo-3-phenyl-2-[(pyrazinylcarbonyl) amino]propyl]amino] butyl] boronic acid; Velcade The 21-Assay procedure employs the same standard toxins as the Updated 15-Assay protocol. The extra 6 assays involve an unknown or an uncharacterized compound and its pairwise combinations with the five toxins: Unknown, Unknown+TPA, Unknown+Colchicine, Unknown+Bortezomib (Velcade), Unknown+Low dose CaIon, and Unknown+Hycamtin (Topotecan).

After toxin incubation, cells were examined by phase contrast microscopy for signs of detachment. If more than ~10% of cells were detached, the 96-well plates were centrifuged at 1200 rpm for 3 min to pellet the detached cells. The media were removed and replaced with 50 μL of Cell Lysis Buffer (25 mM Tris-phosphate (pH7.8), 10% glycerol, 1% Triton X-100, 1 mg/ml BSA, 2 mM EGTA and 2 mM DTT). Cells were incubated with the Cell Lysis Buffer for 10 min at RT and cell lysis was verified using a phase contrast microscope. To ensure complete lysis, the lysates were vigorously agitated using the multichannel pipettor. Any air bubbles formed as a result of agitation were manually removed with a syringe needle. Luminescence was measured using the FLUOstar Optima (BMG Labtech) microplate reader. To develop luminescence, wells were injected with 5 μL of the D-luciferin solution dissolved in Reaction Buffer (25 mM Glycylglycine (pH 7.8), 15 mM MgSO4, 4 mM EDTA, 15 mM Potassium phosphate, 1 mM DTT, 1 mM Coenzyme A, 6.7 mM ATP and 3.35 mM D-luciferin). After 4 sec with shaking, luminescence values were measured using the lens filter at gains of 2500-4000.

Light values were converted to Fold Induction using the ratio of values produced by treated and untreated cells. The maximal TR-specific translational response produced by the 5-Toxin or 15-Toxin assay was used to assign an optimal toxin assay (maximal translational response) which was subsequently used to screen subclones derived from this pool and to assign a Class designation.

Although dependent upon the cell line, the constitutive CMV-fLuc pools were judged to be responsive when the total relative light units (RLU) at a gain of 3500 were no lower than a value of 50,000 in the toxin untreated wells and the induction in the treated cells was 1.5 to 2.5 fold. Similarly, the TRplp-fLuc and TRdm-fLuc pools were judged to be responsive when the total relative light units (RLU) at a gain of 3500 were no lower than a value of 1000 in the toxin untreated and treated wells and the induction in the treated cells was 3 to 100 fold.

*Gaussia* Luciferase (gLuc) Pools:

Cells were grown as described for the firefly luciferase pools, except that the CMV-gLuc cells were not routinely screened with toxins but tested directly from the 100 mm dishes when the cells reached confluence. mTRplp-gLuc, mTRdm-gLuc hTRdm-gLuc cells were processed and treated with toxins as described for the firefly luciferase pools, but the cells were not lysed after the toxin incubation period. At that time, 50 μL of conditioned media was removed, transferred to a new white bottom plate and luminescence was measured in the FLUOstar Optima (BMG Labtech) microplate reader by adding 5.5 μL of Coelenterazine (2.5 mM solution in HCL/MeOH diluted in 10 mM Tris, pH7.8 containing 1 mM EDTA and 0.60M NaCl) directly to the conditioned media.

Although cell line dependent, the constitutive CMV-gLuc pools were judged to be responsive when the total relative light units (RLU) at a gain of 3500 were no lower than a value of 5,000,000 in the toxin untreated wells. Similarly, the mTRplp-gLuc, mTRdm-gLuc and hTRdm-gLuc pools were judged to be responsive when the total relative light units (RLU) at gain 3500 were no lower than a value of 1000 in the toxin untreated and treated wells and the induction in the treated cells was consistent with the Class definition.

D. Isolation of Clonal Cell Lines with Distinct Ribosomal Phenotypes.

To prepare stable colonies from responsive pooled samples, cells from P3-P4 plates were diluted and replated prior to colony subcloning. Plating densities ranged from 500 to 10,000 cells per 100 mm dish, depending on cell type. Slow growing, low density sensitive cell types were plated at higher cell numbers, while the faster growing, density insensitive cells were plated at lower cell numbers. Cells were allowed to grow into colonies (1-4 weeks, depending on cell type). Once colonies reached an appropriate size (visible with the naked eye), colony plates were marked for subcloning. Flame sterilized cloning rings were treated with a light coating of high vacuum grease and placed around the colonies. The cells were removed by treatment with 1× trypsin-EDTA (Invitrogen) and passed into 24-well trays and marked passage 1, or P1. Sufficient colonies per pool (~150-400 independent isolates) were processed to recover ~50-75 translationally responsive subclones. As each subclone reached confluence, each isolate was passed into a T-25 flask (marked as P2), grown to confluence, and analyzed using the optimal toxin treatment.

E. Rapid Subclone Screening Using a Confluence Assay

Firefly Luciferase (fLuc) Subclones:

Confluent P2 subclones growing in T-25 flasks were assayed in 96-well trays using the Confluence Assay protocol. After passage (about 1% of the total cell population or ~60,000 cells) were placed in a well and grown to confluence, cells were treated with complete growth medium containing either no toxin or one or more toxins (i.e. an optimal toxin assay) and incubated for 6 hours at 37° C. Each treatment was performed on triplicate wells.

After toxin incubation, cells were examined by phase contrast microscopy for signs of detachment. If more than ~10% of cells were detached, the 96-well plates were centrifuged at 1200 rpm for 3 min to pellet the detached cells. The media were removed and replaced with 50 µL of Cell Lysis Buffer (25 mM Tris-phosphate (pH7.8), 10% glycerol, 1% Triton X-100, 1 mg/ml BSA, 2 mM EGTA and 2 mM DTT). Cells were incubated with the Cell Lysis Buffer for 10 min at RT and cell lysis was verified using a phase contrast microscope. To ensure complete lysis, the lysates were vigorously agitated using a multichannel pipettor. Any air bubbles formed as a result of agitation were manually removed with a syringe needle. Luminescence was measured using the FLUOstar Optima (BMG Labtech) microplate reader following injection of 5 µL of the D-luciferin solution dissolved in Reaction Buffer (25 mM Glycylglycine (pH 7.8), 15 mM MgSO4, 4 mM EDTA, 15 mM Potassium phosphate, 1 mM DTT, 1 mM Coenzyme A, 6.7 mM ATP and 3.35 mM D-luciferin). After 4 sec with shaking, luminescence values were measured using the lens filter at gains of 2500-4000.

Based upon the luminescence readout, a Fold Induction was calculated for each subclone. These values were ordered into a rank from lowest to highest values and plotted as a function of rank order versus Fold Induction value (i.e. a Ranking Plot). To assign a Class designation, geometric and linear trends identified on these plots were used to define Class designations for each sample. Based upon the lowest ranking series (lowest translational response), cell subclones were classified as a Class I. Using an analogous procedure, Class II and III cell subclones were also identified. The compilation of all available Class designations was used to establish the Class I, II and III definitions.

Representatives of each Class were selected for cryo-preservation and quantitative testing by the Cell Counting protocol as follows: Class I: no fewer than 2 to 3 representatives plus all boundary clones (Class designations that border Class I and II); Class II: no fewer than 3 to 4 representatives including all boundary clones; Class III: all subclones were selected. Each selected subclone (P3-P4) was passaged into multiple 100 mm dishes which were used to prepare two cryogenic stocks. Most cell lines were maintained as an active culture for continued testing and secondary subcloning.

*Gaussia* Luciferase (GLuc) Subclones:

Subcloned cells were prepared as described for the firefly luciferase subclones, except that CMV-gLuc cells were plated in 24 well trays, grown to confluence (>5 days) and assayed without toxin treatment. The accumulation of secreted gLUC protein in the culture medium allowed for the direct testing of gLUC activity from the 24 well trays. In this case, 50 µL of media was taken, transferred to a new white bottom plate and luminescence was measured in the FLU-Ostar Optima (BMG Labtech) microplate reader by adding 5.5 µL of Coelenterazine (2.5 mM solution in HCL/MeOH diluted in 10 mM Tris, pH7.8 containing 1 mM EDTA and 0.60M NaCl) directly to the media. In contrast, confluent TRplp-gLuc and TRdm-gLuc subclones were processed and treated with toxins as described for the firefly luciferase subclones; however, the cells were not lysed after toxin incubation. As for the CMV-gLUC expressing cells, 50 µL of media was transferred to a fresh 96-well microtiter plate and luminescence measured as above.

F. Quantitative 5-Assay Procedure

After the optimal Toxin assay had been defined by the 5-Assay procedure, quantitative analysis of TR-specific translational responses was examined by application of the 5-Assay procedure to cultures prepared using the Cell Count procedure. The 5-Assay procedure was performed essentially as described above. Cell cultures were routinely in their P5-P6 passage. Based upon the luminescence values produced by triplicate samples in three independent assays, the Fold Induction values were used to place subclones into Classes.

G. Quantitative 15-Toxin Assays

Class assignment using the 15-Assay method was performed in the same manner as with the 5-Assay procedure. These tests were routinely performed on P7-P8 cells that were maintained in continuous culture or P5-P6 cells that were recovered from frozen P4 stocks. Based upon the luminescence values produced by triplicate samples in three independent assays, the Fold Induction values were used to place subclones into Classes and verify the best toxin assay for subsequent applications.

H. Resubcloning and Purification of Class Defined Subclones

Occasionally, Class defined cell lines will need to be repurified and retested. To further purify Class defined cells, subclones are subjected to infinite dilutions or manual plating as previously described, subcloning, propagation and re-testing as described above. Generally this procedure can result in enhanced TR-specific responses (e.g., 3-5 fold improvement in protein expression over the parental subclones).

I. Western Blot Analysis of Select Subclones and Protein Concentration Estimate Using Recombinant Firefly Luciferase Protein as a Standard Firefly Luciferase (fLuc) Subclones:

In some cases, it may be necessary to correlate the plate reader luminescence readout (i.e. luciferase activity) with the amount of luciferase protein produced in response to a toxin treatment. To that end, the amount of luciferase was determined by correlating the specific activity of a TR-regulated protein in an optimal Toxin treatment with a standard dose response curve generated using purified recombinant firefly luciferase (Sigma). In this situation, fLUC specific activity was expressed as relative light units (RLU)/µg protein/cell after 6 hours of a defined Toxin treatment.

To produce a dose response curve, recombinant firefly luciferase protein (Sigma) of known protein concentration (as determined by Lowry assay) was subjected to serial dilutions and assayed using a standard plate reader assay. Serial dilutions were prepared in 40 µL Reaction Buffer without ATP and Luciferin (25 mM Glycylglycine (pH 7.8), 15 mM MgSO4, 4 mM EDTA, 15 mM Potassium phosphate, 1 mM DTT, 1 mM Coenzyme A,) and assayed for activity in the FLUOstar Optima (BMG Labtech) microplate reader using 5 µL of the D-luciferin solution dissolved in Reaction Buffer (25 mM Glycylglycine (pH 7.8), 15 mM MgSO4, 4 mM EDTA, 15 mM Potassium phosphate, 1 mM DTT, 1 mM Coenzyme A, 6.7 mM ATP and 3.35 mM D-luciferin). This provided a value of relative light units per microgram of protein.

To determine the purity of the recombinant firefly luciferase protein, defined protein amounts were resolved by SDS PAGE, fixed overnight in Preblot gel fixer (25% isopropanol, 10% acetic acid), and stained in 0.05% Coomassie blue (0.05% brilliant blue R, 50% methanol, 10% acetic acid) for 20 min, RT. Gels were destained in 10% acetic acid and dried under vacuum. The dried gels were used to assess the protein's purity which was judged to be >98% pure. This negligible contamination was too insignificant to affect the serial dilution calculations. A plot was made of relative light units per protein standard concentration using the serial dilutions that produced a linear dose response (FIG. 15A).

The amount of luciferase produced by a defined cell number cultured in a 15-Toxin assay was determined by assaying the number of relative light units in a standard plate reader analysis. For this test, the Class III HCT116 mTRdm-fLUC 12-16 cell line was counted, passed into 12-well trays at a density of 200,000 cells per well, and cultured for about 24 hr prior to incubation with toxic agents. Cells were treated with complete growth medium containing either no toxin or a standard Single- or Dual-Toxin assay listed in Table 3 and incubated for 6 hours at 37° C. Each treatment was performed in triplicate wells. At the end of the incubation period, cells from each of the triplicate wells were collected in 1 mL of ice-cold 1×PBS, and each well was washed with an additional 200 μL of 1×PBS (1200 μL total). Then, 60 μL of each cell suspension (5%) was removed and centrifuged at 10,000 rpm, for 1 min. The cell pellet was resuspended in 40 μL of Cell Lysis Buffer (25 mM Tris-phosphate (pH7.8), 10% glycerol, 1% TritonX-100, 1 mg/ml BSA, 2 mM EGTA and 2 mM DTT), incubated at RT for 10 min, and assayed for luciferase activity in the FLUOstar Optima (BMG Labtech) microplate reader using the standard procedure described previously. These values were positioned on the linear dose response graph prepared from the recombinant protein (FIG. 15A) which provided a correlation of relative light units produced by the recombinant protein to the relative light units produced by toxin treated HCT116 cells. This provided a correlation between amount of recombinant protein and the amount of protein in toxin treated cells. Knowing the number of cells used to produce the cell pellet allowed the calculation of relative light units/microgram of fLUC protein/cell after 6 hr in a defined toxin assay.

The remaining cell suspension was centrifuged as described above and the pellets stored at −70/−80° C. for subsequent protein extraction and Western blot analysis. For protein extraction, cells were thawed on ice and resuspended in equal volumes of the Suspension Buffer (100 mM NaCl, 10 mM TrisHCl [pH 7.6], 1 mM EDTA, 1 mg/mL aprotinin, 100 μg/mL PMSF) and the 2×SDS Buffer (100 mM TrisHCl (pH6.8), 4% SDS, 20% glycerol, 20 mM DTT, 10 mM EDTA, 2× Roche Protease Inhibitor Cocktail). The extracts were homogenized by vigorous mixing and boiling for 3 min. Additional homogenization (when needed) was achieved by passing samples through a syringe fitted with a 26 G needle. At this point, the extracts were either analyzed by SDS-PAGE gel or stored at −80° C.

To produce a near quantitative Western blot analysis, equal protein concentrations are loaded on Western blots. To establish total protein amounts, a preliminary SDS-PAGE gel was used to resolve 10 μL of each protein extract. The gel was fixed overnight in Preblot gel fixer (25% isopropanol, 10% acetic acid), and stained in 0.05% Coomassie blue (0.05% brilliant blue R, 50% methanol, 10% acetic acid) for 20 min, RT. Gels were destained in 10% acetic acid and dried under vacuum. Using the dried gels, any necessary volume adjustment was made to samples prior to Western blotting. 12% SDS-PAGE gels were used to resolve the volume-adjusted samples. Protein transfer to a solid membrane support by electrophoresis was accomplished using standard methodology. The membranes were dried overnight and Western blot analysis involved membrane rehydration in 1×PBS-T, washing with a protein solution (5% powdered milk or 3% BSA) to block stray protein binding sites on the filter, incubation with an antibody that recognizes the TR regulated ORF, and chemiluminescent detection using a labeled secondary antibody. The fLUC protein was detected using an anti-fLUC primary antibody (Sigma; 1:1000 dilution). After incubation with a primary antibody and extensive washing with 1×PBS-T, proteins binding the primary antibody were detected by incubation with a horseradish peroxidase (HRP) conjugated anti-rabbit secondary antibody (Amersham; 1:10000 dilution). Following incubation with the secondary antibody and extensive washing, reactive proteins were detected with the ECL reagent system (Amersham) as described by the vendor. Densitometric analysis was performed using Gene Tools Analysis Software from SYNGENE.

J. Cryopreservation of Pools and Subclones

Cryopreserved stocks were generally prepared using passage 2 or 3 (P2-P3) pool stocks and P4 subclone stocks. These stocks were grown to confluence, washed at least twice with 1× trypsin-EDTA (1 min, RT), collected in 2 mL freezing medium (90% fetal bovine serum, 10% DMSO) per 100 mm dish, and transferred to cryovials (1 ml cells per vial; ~1Exp7 cells per vial). Cryovials were placed in a −70/−80 C freezer in a slow freeze container for 16-24 hr, then transferred to liquid nitrogen for long-term storage.

Example I

Procedure for Combinatorial Toxin Screening

This example describes the application of toxins to mammalian cells expressing a Translational Regulator (TR) cassette so that a TR-ORF mRNA is selectively translated during cap-independent translational processes. Although cap-independent translation is a widely accepted biological process, the quantitative response of ribosomes to toxins and toxic environments remained largely undefined prior to the present invention. In order to demonstrate the feasibility and efficacy of a TR-based toxin screening process as an indicator of cell stress and death, the initial studies described herein employ a variety of toxin screening procedures. These studies included the use of toxins that affect defined biological processes (i.e. signal transduction activators, microtubule disruptor agents, proteasome inhibitors, intracellular calcium ion regulators, etc.) which provide information about the affected biological systems that regulate cell death.

For this example, a set of such toxins were applied individually (a single-Toxin assay) and in combinations (a two-Toxin assay) to cells so that the responsive cellular pathway could provide correlative information about ribosome activity and defined cell death responses (Table 3). The human colorectal carcinoma HCT116 cell line was stably transformed with the mTRdm-fLUC expression cassette and subcloned using procedures described above. This expression vector consists of the mouse dm20 derivatized TR sequence (SEQ ID NO: 1) coupled to the firefly luciferase coding sequence (fLUC).

Figure 1A:
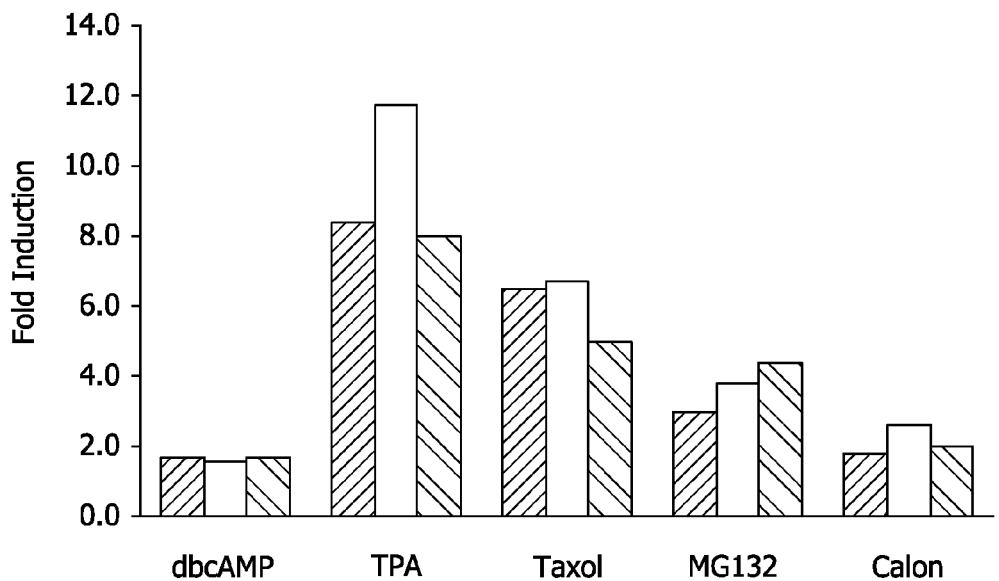
FIG. 1A displays a 5-Assay histogram in which cells were tested with five single-Toxin Assays. The composition and concentration of the toxins used in these studies are shown in Table 3. In this histogram, the TR-specific responses are shown as three independent assays (three bars) performed in triplicate (three samples per bar) on the HCT116 mTRdm-fLUC 12-16 subclone #30 cell line. Firefly luciferase (fLUC) protein activity was determined using a standard microplate reader assay and is expressed as the ratio of treated to untreated cultures (i.e., Fold Induction). Each bar represents Ratios in excess of 1.0 and is indicative of cells exhibiting TR-dependent translation. The TPA single-Toxin assay produced the most significant increase in TR regulated translation.
Figure 1B:
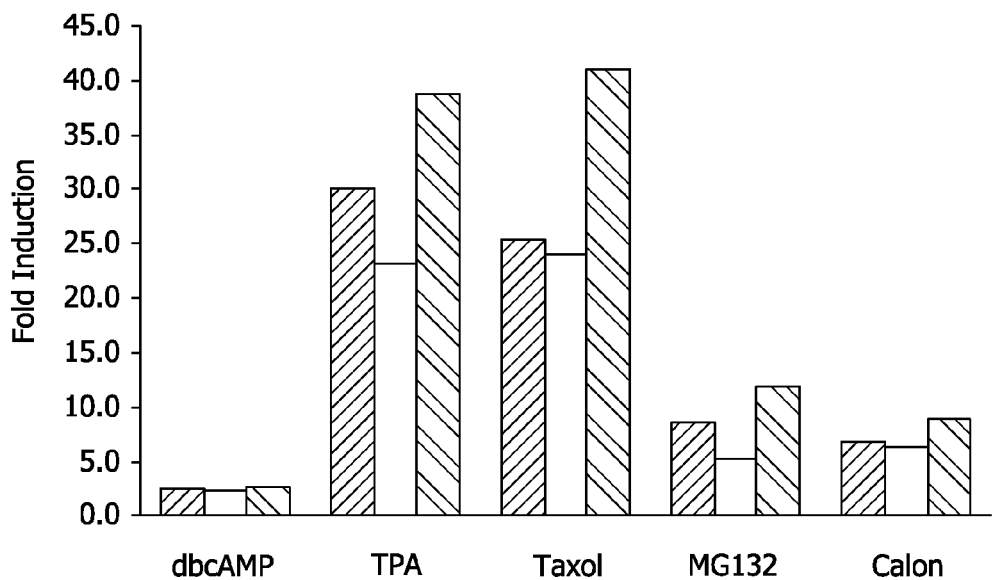
FIG. 1B shows a 5-Assay histogram of the TR-specific responses produced by triplicate samples of the HCT116 mTRdm-fLUC 12-16 subclone #38 cell line. These results emphasize the magnitude differences in cell responses.

In one test, the 5-Assay procedure (Table 3) was applied to HCT116 mTRdm-fLUC 12-16 subclone #30 cells (FIG. 1A). This subclone is a secondary subclone of the parental 12-16 cell line. 25,000 cells were plated in triplicate wells of a 96-well tray, cultured for 48 hr and treated for 6 hr with the defined toxin dissolved in fresh medium. Samples were then processed with Lysis buffer and read in a plate reader. A maximal TR-specific response was observed in TPA assays (range of 800-1200% increase in reporter activity). In a second application of the 5-Assay procedure, triplicate samples of HCT116 mTRdm-fLUC 12-16 subclone #38 cells were tested (FIG. 1B). Cells were processed as above. Maximal TR-specific toxin responses were observed in TPA and Taxol treated samples. No significant difference was observed between TPA and Taxol treated cells ($p > 0.05$).

Figure 1C:
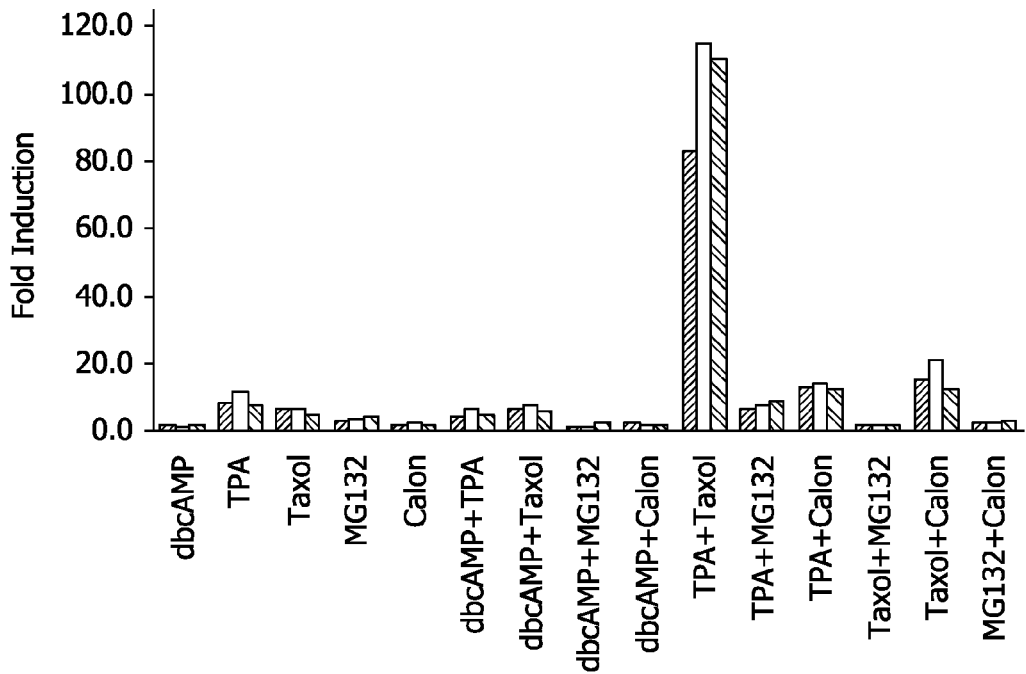
FIG. 1C shows a 15-Assay histogram of the HCT116 mTRdm-fLUC 12-16 subclone #30 cellular responses. As above, all assays were performed in triplicate.

Alternatively, toxins were applied in pairs (15-Assay method shown in Table 3). Triplicate samples of HCT116 mTRdm-fLUC 12-16 Sub#30 cells were cultured with the two-Toxin assays using a standard plate reader protocol (FIG. 1C). A clearly significant TR-mediated response ($p \ll 0.05$) was observed in cells treated with the TPA+Taxol two-Toxin assay compared to all other toxin assays (ranging from 8,000-

Figure 1D:
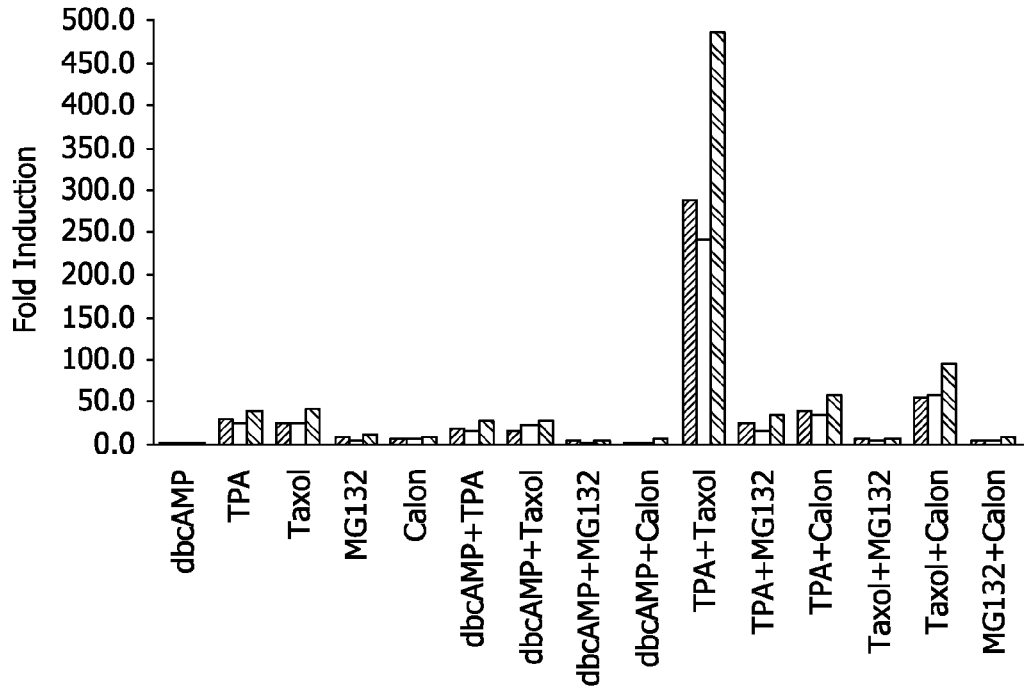
FIG. 1D displays a 15-Assay histogram of the HCT116 mTRdm-fLUC 12-16 subclone #38 cell line. As before, a large increase in TR-mediated translation was observed in the TPA+Taxol treated samples. This establishes that among the toxins tested, TPA or Taxol produce an optimal TR-specific response using a single-Toxin Assay procedure. However, a large increase in the TR-response observed in the combinatorial TPA+Taxol treatment establishes the TPA+Taxol assay is the optimal toxin assay for producing the largest TR-specific translational increase among the tested combinations of two toxins.

11,500% increase in reporter activity). Similarly, samples of HCT116 mTRdm-fLUC 12-16 Sub#38 cells were tested with the 15-Assay toxin screen (FIG. 1D). As before, a clearly significant difference (p<<0.05) was observed in cells treated with the TPA and Taxol two-Toxin combination.

These results established that TR-regulated translation correlated effectively with cell stress and death. When compared to standard cell death markers (not shown), these TR-specific responses were as early or earlier than caspase activation or mitochondrial dysfunction. Furthermore, the extreme TR responses observed in some assays (in particular, the TPA+Taxol two-Toxin response in FIGS. 1C and 1D) were unexpected. The magnitude of the response was not additive (10-fold plus 10-fold to yield 20-fold) but appeared to be a multiplicative process (10-fold times 10-fold to yield >100-fold). The 15-Assay results provided a previously unknown link between cap-independent translation, protein kinase C activation, microtubule disruption and cell stress/death.

Moreover, the toxin treatments did not produce significant variation in the TR-mediated response trends (compare FIGS. 1C and 1D); however, the magnitude of the TR-regulated responses appeared to vary even between these closely related subclones. Taken together, these results suggested that in addition to cellular variation in TR-specific responses, mechanical variation in the process of manipulating the toxin assay might play a role in regulating the extent of the responses. Therefore, the production of a preferred and highly informative assay involves the determination of "optimal" and "suboptimal" factors that affect the TR readout.

Example II

Application of Combinatorial Toxin Screens to TR-Responsive Cell Lines

Figure 2A:
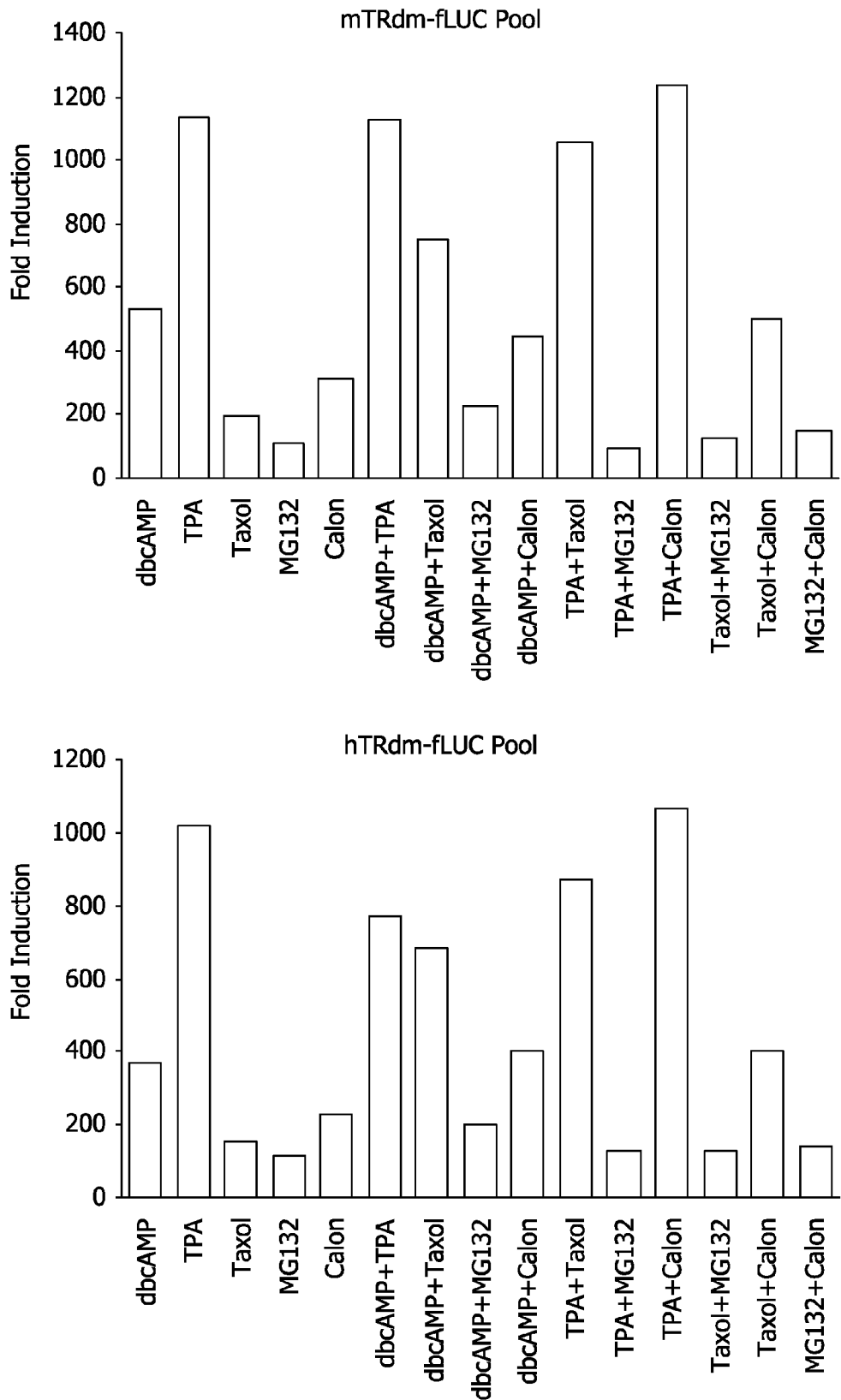
FIG. 2A Left panel shows a 15-Assay histogram of the TR responses produced by a human embryonic kidney HEK293 cell pool, stably transformed with the mTRdm-fLUC expression vector. The composition and concentration of the toxins in this figure are described in Table 3. Microplate reader analysis was used to determine fLUC protein activity which is expressed as the ratio of treated to untreated samples (i.e., Fold Induction). Right panel shows a 15-Assay histogram of the TR responses of a HEK293 cell pool expressing the human hTRdm-fLUC expression vector.
Figure 2B:
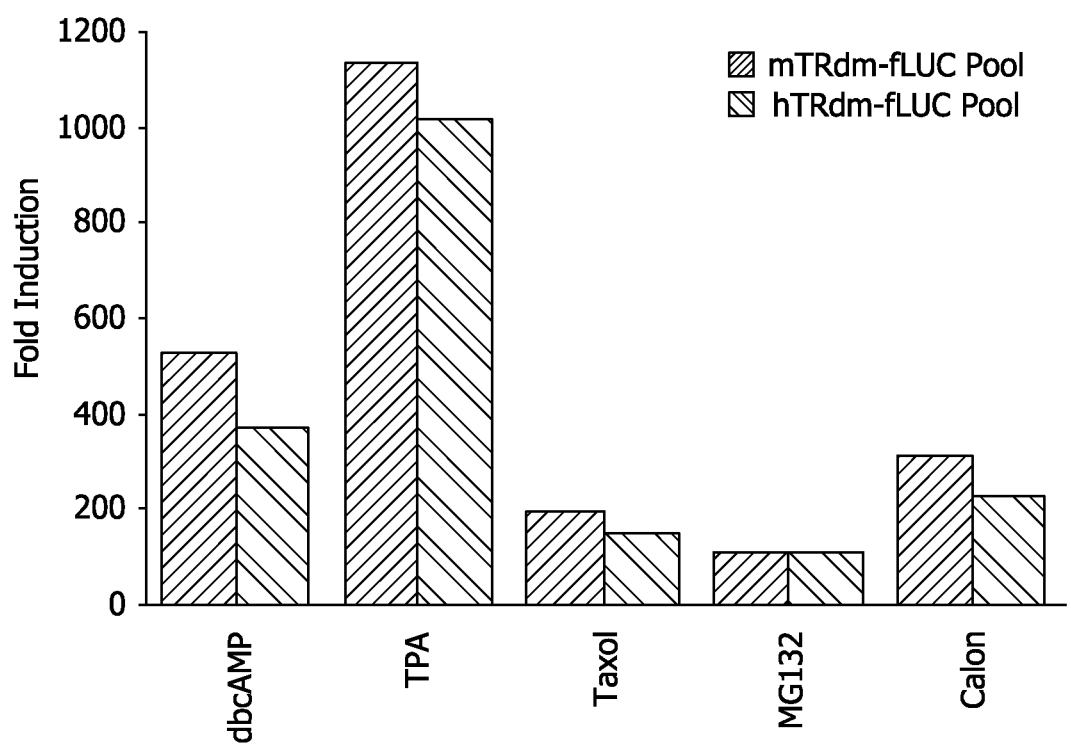
FIG. 2B shows a 5-Assay histogram of the TR responses produced by HEK293 cell pools stably transformed with the mouse mTRdm-fLUC (light bars) and human hTRdm-fLUC (dark bars) expression cassettes. This direct comparison shows no species-specific differences in the magnitude or toxin response to the TR sequences.

This example describes the application of toxins to pools of mammalian cells transformed with specialized TR cassettes. HEK293 cell pools expressing the mTRdm-fLUC and hTRdm-fLUC expression vectors were prepared. After propagation and cryogenic preservation, each pool was screened with the 15-Assay procedure (FIG. 2A). Since no significant differences were observed in the trend or magnitude of the TR-mediated response in HEK293 cells containing different species of TR expression cassette (FIG. 2B), other factors than the sequence of the TR expression cassette are likely to significantly contribute to TR response variation.

Example III

Use of Toxin Assay Procedures for Identifying and Assigning TR-responsive Cells to Classes A. Defining Variations in TR-Specific Responses and Assigning Class Designations to Cap-Independent and Cap-Dependent Responses In this Example, a definition of the primary variant in the toxin assays is reported. Triplicate samples of nine random subclones from the HEK293 hTRdm-fLUC pool were treated with no toxin (Control, labeled as UNT in the figure) or TPA (Sample) using a standard plate reader assay (FIG. 2C). The TR-response is expressed as a Fold Induction Value (Average of Sample Light Units (LU) values divided by the average of Control LU values). Examining the raw data found that individual sample variation was not significant in the triplicate assays. For samples with any value statistically out of the range of the remaining duplicate values, a questionable response was assigned and these samples were rescreened in a subsequent assay (marked with question marks). Subsequent testing established that this sample variation was the product of variable cell distribution between wells. So, the primary variable metric in this assay appeared to be difference in the Fold Induction value (which ranged from 4.1 to 17.4) and secondarily cell number per assay.

Figure 2D:
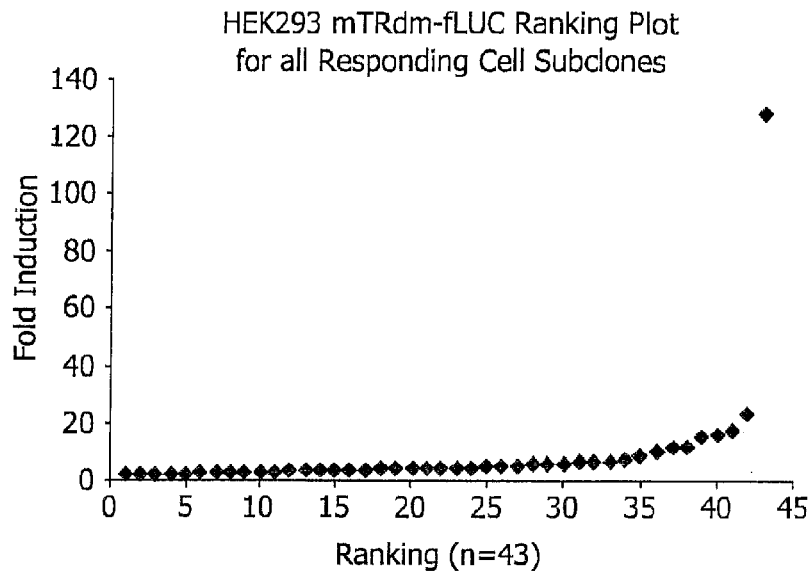
Figure 2D:
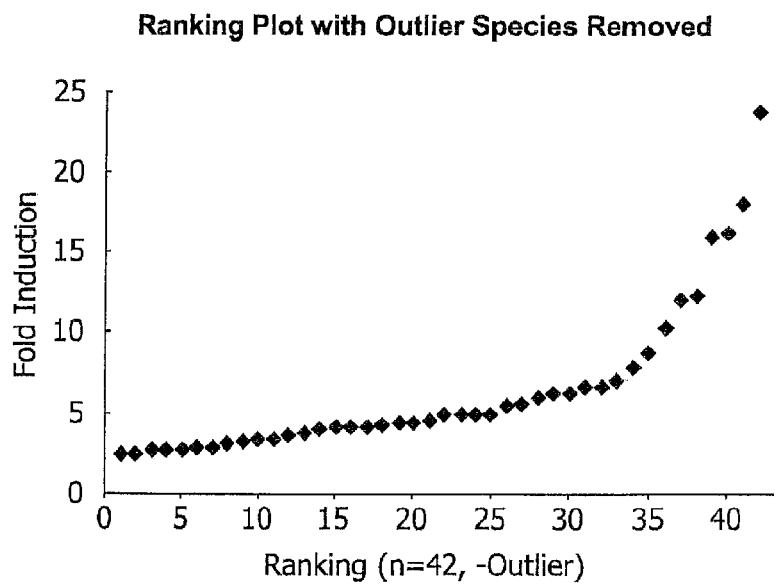

To further investigate the primary regulator of Fold Induction, a comprehensive analysis of HEK293 mTRdm-fLUC transformed cells was performed. For this example, 95 random colonies were isolated and assayed using a standard TPA single-Toxin treatment. 43 responding subclones were evaluated and the Fold-induction of each clone was presented (FIG. 2D). The entire group of responding clones was ordered by rank (lowest to highest value) and displayed on a graph versus Fold Induction (the largest statistically variable metric). This plot has been termed a Ranking Plot. The top panel shows a Ranking Plot for all responding cell subclones (FIG. 2D). In this analysis, the extremely large TR response in the highest responder (an Outlier species) compressed the remaining values. In the middle panel, the Ranking Plot was regraphed after removal of the Outlier to illustrate the three distinct Fold Induction trends. The first Fold Induction trend was associated with a group of cells that exhibit modest TR-specific translational responses, which have been termed Class I cells. Subsequent studies of Class I cells (for example, FIG. 10B) found that these cells were uniformly nonresponsive to toxin treatments. The second Fold Induction trend was produced by a group of cells that displayed statistically significant (p<0.05) increases in TR-specific reporter activity compared to the Class I cells. This group of responsive cells has been termed Class II cells. The remaining cell lines exhibited Fold Induction responses that are statistically different (p<0.05) from the Class I and Class II groups. These highly responsive cell lines have been termed Class III cells. For the HEK293 mTRdm-fLUC cell pool, 25 of 43 responders (58.1%) displayed a Class I phenotype, 13 of 43 responders (30.2%) exhibited a Class II phenotype and 5 of 43 (11.6%) responders were labeled Class III.

Figure 2E:
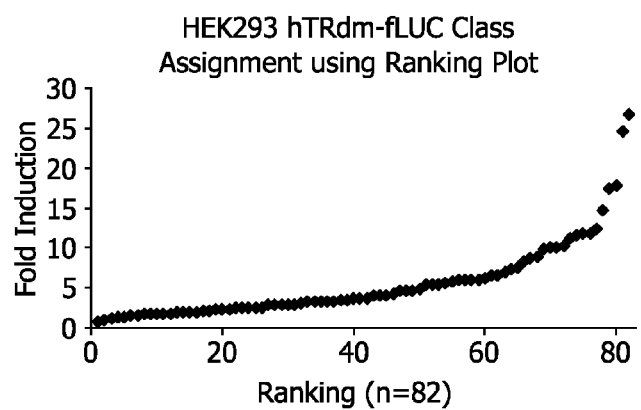
Figure 2F:
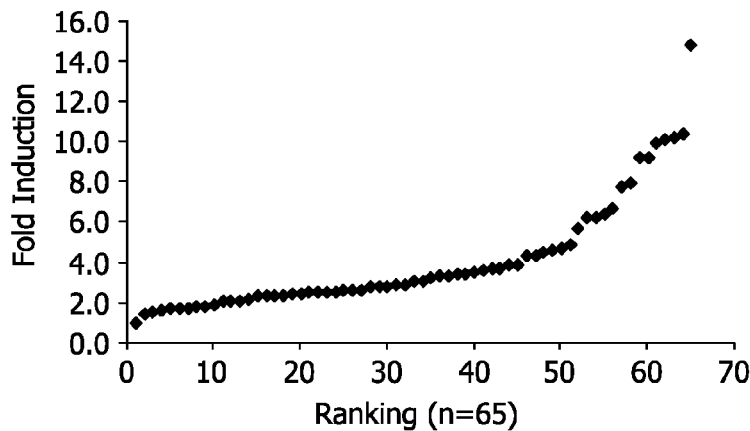

In a complementary analysis, 120 random HEK293 hTRdm-fLUC transformed colonies were recovered and assayed using the TPA single-Toxin assay. 82 responding subclones were evaluated and assigned to three trends (FIG. 2E). The first trend included 50 modestly responsive Class I clones, a second trend produced by 27 responsive Class II cell lines and the final Class III trend exhibited 5 subclones (6.1%). Furthermore, a similar analysis of HEK293 mTRplp-fLUC transformed cells found that 107 random HEK293 mTRplp-fLUC transformed colonies produced 65 responding subclones (FIG. 2F). For the HEK293 mTRplp-fLUC cell pool, 51 of 65 responders (78.5%) displayed a Class I phenotype, 13 of 65 (20%) displayed a Class II response and 1 of 65 (1.5%) were labeled Class III.

Figure 2G:
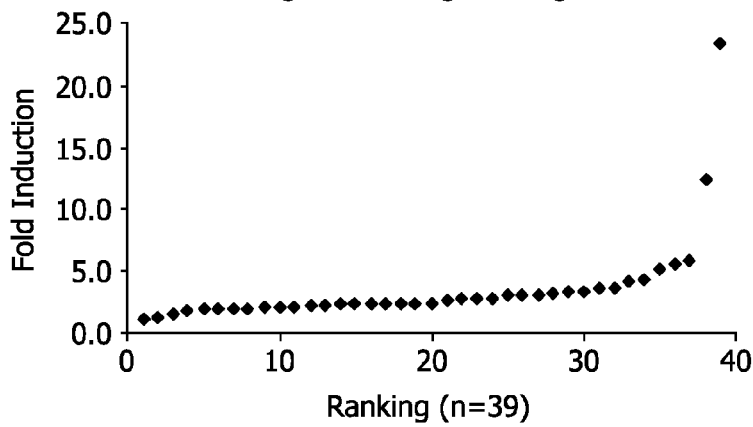

Although the cap-independent translation process is clearly linked to cell recovery from stress and death signals as described herein, it was believed that Fold Induction would be regulated by molecular processes that directly elevated or lowered ribosomal activity. Direct modification of the ribosomal proteins was expected to negatively and positively affect the rate of protein synthesis (for example, FIG. 33). To test this theory, this example provides a comprehensive analysis of HEK293 CMV-fLUC transformed cells (FIG. 2G). These cells constitutively express a gene cassette that has deleted all TR regulatory sequences. For this example, 71 random colonies were tested using the standard TPA toxin assay and 39 responding subclones were used to define Fold Induction values. For the HEK293 CMV-fLUC cell pool, 34 of 39 responders displayed a Class I phenotype, 4 of 39 showed a Class II response and 1 of 39 (2.6%) displayed a putative Class III phenotype.

These results support the concept that toxin treatment can induce cell stress and death, but can also directly impact the rate of ribosome activity in some sensitive cells. Therefore, Class designations can be applied to the cap-independent TR expressing cell lines and the cap-dependent constitutive expressing cell lines.

By compiling all of the available data (FIGS. 2-9), a definition for Class designation can be derived for both groups. Therefore, the class I cells are characterized by the expression of the reporter protein that is up to 500% greater than the expression of the reporter protein in the mammalian cells which have not been treated with the toxins, the class II cells are characterized by the expression of the reporter protein that is more than 500% to 1400% greater than the expression of the reporter protein in the mammalian cells which have not been treated with the toxins, and the class III cells are characterized by the expression of the reporter protein that is more than 1400% to about 75000% greater than the expression of the reporter protein in the mammalian cells which have not been treated with the toxins.

(A) Using a Suboptimal Toxin Assay to Assign Class Designations

Based upon the 5-Assay and 15-Assay methods, a "suboptimal" assay is defined as any assay that produces a minimal translational response.

Figure 7A:
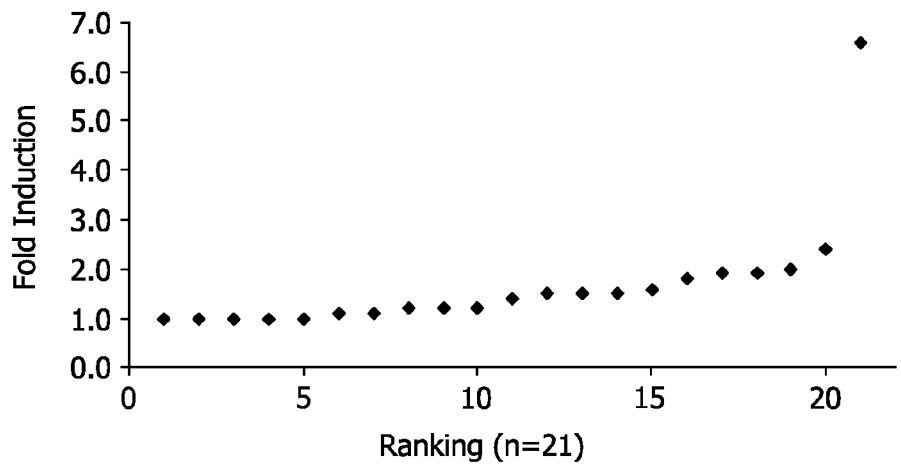
FIG. 7A The top panel is a Ranking Plot of the 21 TR responses produced by a primary screen of a human colorectal carcinoma HCT116 cell pool, stably transformed with the mouse mTRdm-fLUC (firefly luciferase) expression vector, following treatment with the dbcAMP (FIG. 7A-C) and the TPA (FIG. 7D-E)single-Toxin assays. The bottom table shows the Class designation for the HCT116 mTRdm-fLUC pool; 20 of 21 (95.2%) subclones showed a Class I response, 1 of 21 subclones (4.8%) exhibited a Class II response and 0 of 21 responders (0%) displayed a Class III phenotype.

In this example, an analysis of HCT116 mTRdm-fLUC transformed cells was performed using the suboptimal dbcAMP single-Toxin assay (Table 3). For this example, 80 random colonies were recovered and 21 responding subclones were evaluated (FIG. 7A). In particular, a small number of Class II and III cells were recovered from the expressing group. However, given the small number of responding clones in this test group (n=21) and the minimal translational response in the dbcAMP assay, it is unlikely that these results represent a significant distribution of the potential mTRdm-fLUC responses in HCT116 cells. The first trend included 20 modestly responsive Class I clones, the second trend contained 1 responsive Class II cell line and 0 subclones were detected for the Class III group.

This nonrandom distribution was verified in an expanded study (FIG. 7D) where 39 responding subclones were screened using the TPA single-Toxin assay. These larger numbers provided a different Class distribution and now included significant numbers of subclones with Class II (20.5%) and Class III (5.1%) phenotypes. In general, analyzing ~50-60 responding clones with an optimal toxin assay produces a random distribution of the Class phenotype, since adding additional subclones to the pool data do not significantly alter the Class ranking.

Figure 7B:
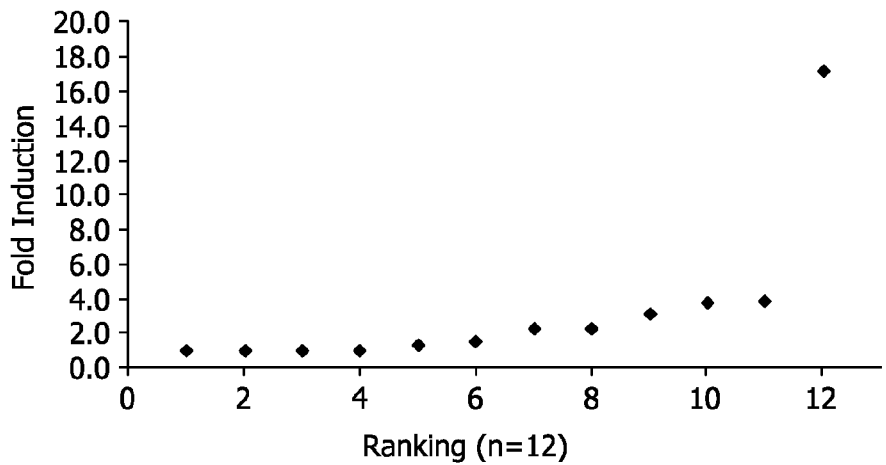
FIG. 7B The top panel is a Ranking Plot showing the 12 HCT116 mTRplp-fLUC subclone responses. The bottom table shows the Class designations for the HCT116 mTRplp-fLUC pool; 11 of 12 (91.7%) displayed a Class I phenotype, 0 of 12 (0%) displayed a Class II response and 1 of 12 (8.3%) exhibited a Class III response.

In a complementary study HCT116 mTRplp-fLUC transformed cells which express a gene cassette that operatively links the mTRplp sequence to the firefly luciferase reporter gene were evaluated (FIG. 7B). For this example, 91 random colonies were recovered and 12 responding subclones were evaluated and the Fold-induction values presented in a Ranking Plot. As above, the small number of responding clones in this cell pool are unlikely to represent a significant fraction of potential mTRplp-fLUC responses in HCT116 cells. For the HCT116 mTRplp-fLUC cell pool, 11 of 12 responders displayed a Class I phenotype, 0 of 12 displayed a Class II response and 1 of 12 (8.3%) were sufficiently large to be termed a Class III cell type.

Figure 7C:
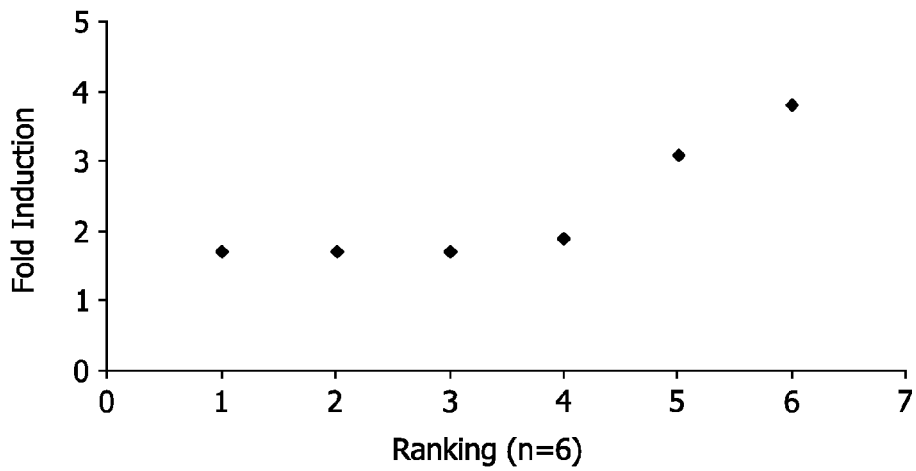
FIG. 7C The top panel is a Ranking Plot showing the 6 responses from the HCT116 CMV-fLUC subclones. The bottom table shows the Class designations for the HCT116 CMV-fLUC pool; 6 of 6 (100.0%) were labeled Class I cells, 0 of 6 (0%) exhibited a Class II response and 0 of 6 (0%) showed a Class III phenotype.

The next effort used 68 random colonies from a HCT116 CMV-fLUC transformed pool and the dbcAMP single-Toxin assay to define Class order (FIG. 7C). Only 6 responding subclones were recovered and the Fold-induction values shown in a Ranking Plot. As above, the small number of responding clones in this cell pool are unlikely to represent a significant fraction of potential CMV-fLUC responses in HCT116 cells. For this HCT116 CMV-fLUC cell pool, 6 of 6 responders displayed a Class I phenotype, and no Class II or Class III phenotypes were detected.

In another example of pool screening with an optimal toxin assay, 21 responding subclones from the HCT116 hTRdm-fLUC pool were treated with the TPA single-Toxin assay, and significant fractions of Class I (47.6%), Class II (33.4%) and Class III (19%) phenotypes were identified.

Figure 8A:
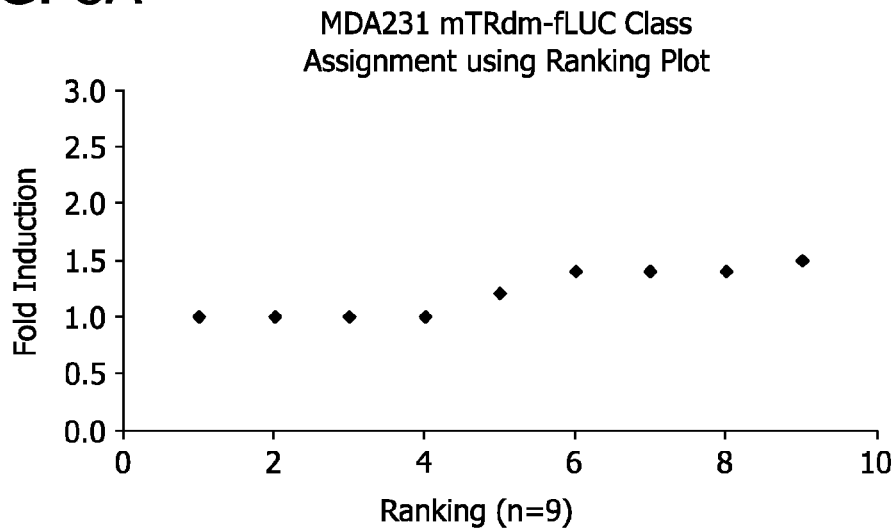
FIG. 8A The top panel is a Ranking plot of the 9 TR responses produced by a human breast adenocarcinoma MDA231 cell pool, stably transformed with the mouse mTRdm-fLUC (firefly luciferase) expression vector, following treatment with the dbcAMP single-Toxin assay. The bottom table shows the Class designation for the MDA231 mTRdm-fLUC pool; 9 of 9 (100.0%) subclones showed a Class I response, 0 of 9 subclones (0%) exhibited a Class II response and 0 of 9 responders (0%) displayed a Class III phenotype.

In a related experiment, the analysis of MDA231 mTRdm-fLUC transformed cells employed the suboptimal dbcAMP single-Toxin assay (FIG. 8A). For this example, 60 random colonies were recovered and only 9 responding subclones were available to define Class trends. However, this small number of responding clones is unlikely to represent a significant fraction of potential mTRdm-fLUC responses in MDA231 cells since no Class II or III phenotypes were observed.

Figure 8B:
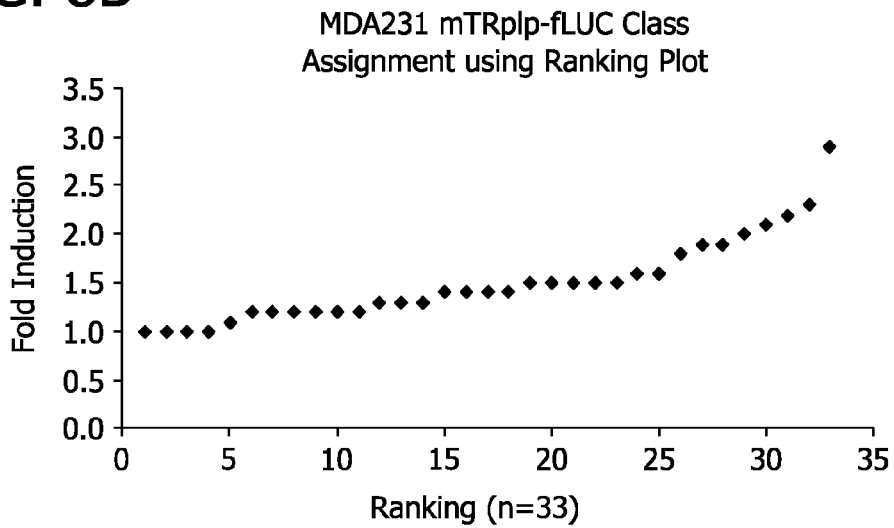
FIG. 8B The top panel is a Ranking Plot showing the 33 MDA231 mTRplp-fLUC subclone responses. The bottom table shows the Class designations for the MDA231 mTRplp-fLUC pool; 33 of 33 (100.0%) displayed a Class I phenotype, 0 of 33 (0%) displayed a Class II response and 0 of 33 (0%) exhibited a Class III response.

Further analysis of the MDA231 mTRplp-fLUC cell pool, which expresses a gene cassette that operatively links the mTRplp sequence to the firefly luciferase reporter gene, was used to isolate 83 random colonies which were evaluated using the suboptimal dbcAMP single-Toxin assay (FIG. 8B). Of the 33 responding subclones, all 33 responders were classified Class I and no Class II or Class III cells were detected.

Figure 8C:
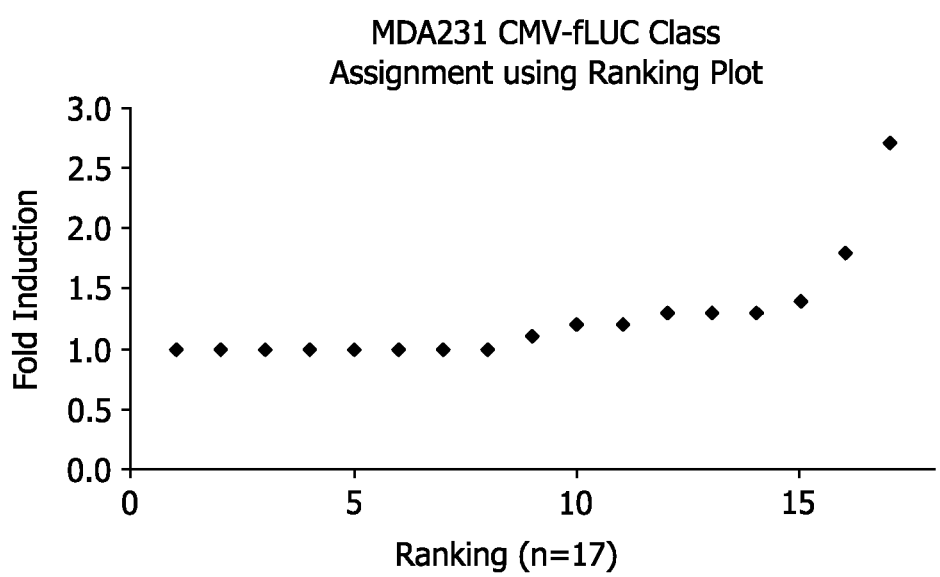
FIG. 8C The top panel is a Ranking Plot showing the 17 responses from the MDA231 CMV-fLUC subclones. The bottom table shows the Class designations for the MDA231 CMV-fLUC pool; 17 of 17 (100.0%) were labeled Class I cells, 0 of 17 (0%) exhibited a Class II response and 0 of 17 (0%) showed a Class III phenotype.

Finally, analysis of MDA231 CMV-fLUC transformed cell pool examined 60 random colonies and tested translational responses using the suboptimal dbcAMP single-Toxin assay (FIG. 8C). Of the 17 responding subclones, all 17 responders were placed into the Class I group and no Class II or Class III cells were detected.

In this example, the suboptimal toxin assay failed to produce a maximal translational response and when coupled with a minimal number of responding clones, an inappropriate Class distribution was produced. This was verified by subsequent studies (FIG. 10) where rescreening with an optimal toxin assay established a more accurate Class distribution. Thus, while not being bound to a particular theory, the most accurate Class distribution is obtained using an appropriate number of responding clones (at least about 40) using an optimal toxin assay.

(A) Using a Suboptimal Pool Size to Assign Class Designations

Figure 7D:
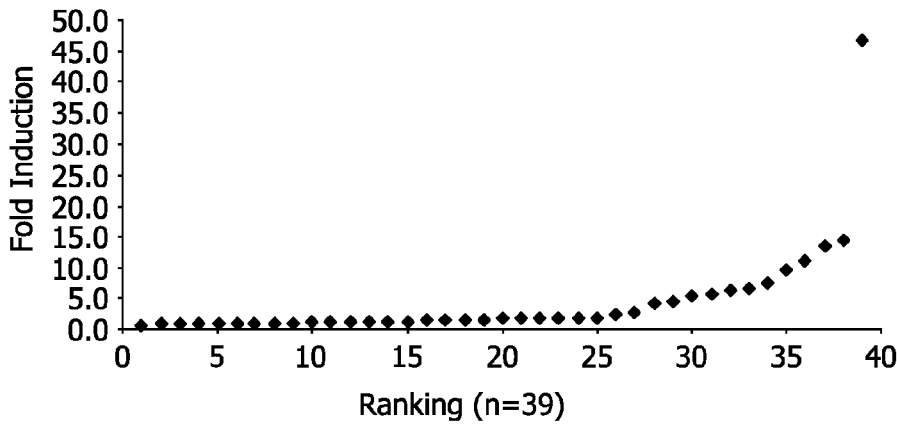
FIG. 7D The top panel is the Ranking Plot showing the 39 responses produced by the HCT116 mTRdm-fLUC subclones isolated in a secondary screen of the HCT116 transfected pool. The bottom table shows the Class designations for the secondary HCT116 mTRdm-fLUC pool; 29 of 39 (74.4%) were labeled Class I cells, 8 of 39 (20.5%) exhibited a Class II phenotype and 2 of 39 (5.1%) showed a Class III response.
Figure 7E:
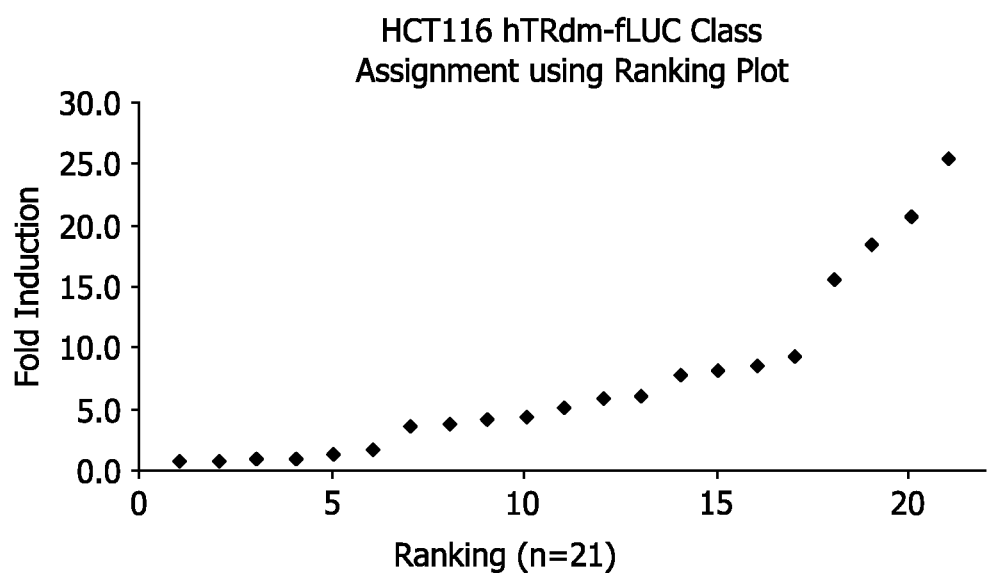
FIG. 7E The top panel is a Ranking Plot showing the 21 responses from the HCT116 hTRdm-fLUC subclones. The bottom table shows the Class designations for the HCT116 hTRdm-fLUC pool; 10 of 21 (47.6%) were classified as Class I, 7 of 21 (33.4%) exhibited a Class II response and 4 of 21 (19.0%) showed a Class III phenotype.

Any statistical measurement is dependent upon a lack of bias, a random distribution and a sufficiently large sample size. Given the random method used to isolate the colonies used for Class definitions and the fact that all clones are assayed, a lack of bias and a random distribution is achieved in these studies. As shown in FIG. 7D, increasing the sample size improves the ability to identify the Fold Induction trends and the ability to accurately assign magnitudes to Class designations.

In this example, the MCF7 mTRdm-fLUC transformed cell pool was used to recover 103 random colonies that were assayed using the TPA toxin assay (FIG. 5A). 11 responding subclones were recovered and analyzed even though the small number of responding clones are unlikely to represent a significant fraction of potential mTRdm-fLUC responses in MCF7 cells. The first trend included 6 modestly responsive Class I clones, a second trend contained only 4 responsive Class II cell lines and the final Class III trend included only 1 subclone (9.1%).

Figure 5B:
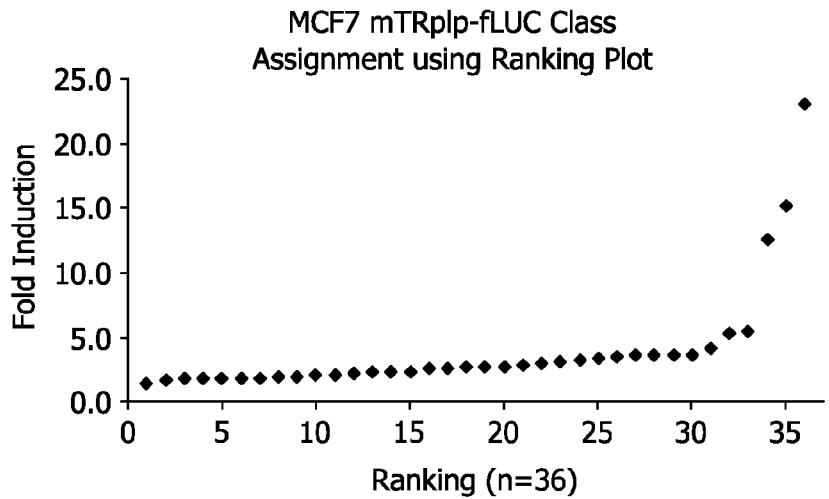
FIG. 5B The top panel is a Ranking Plot showing the 36 MCF7 mTRplp-fLUC subclone responses. The bottom table shows the Class designations for the MCF7 mTRplp-fLUC pool; 31 of 36 (86.1%) displayed a Class I phenotype, 3 of 36 (8.3%) displayed a Class II response and 2 of 36 (5.6%) exhibited a Class III response.
Figure 5C:
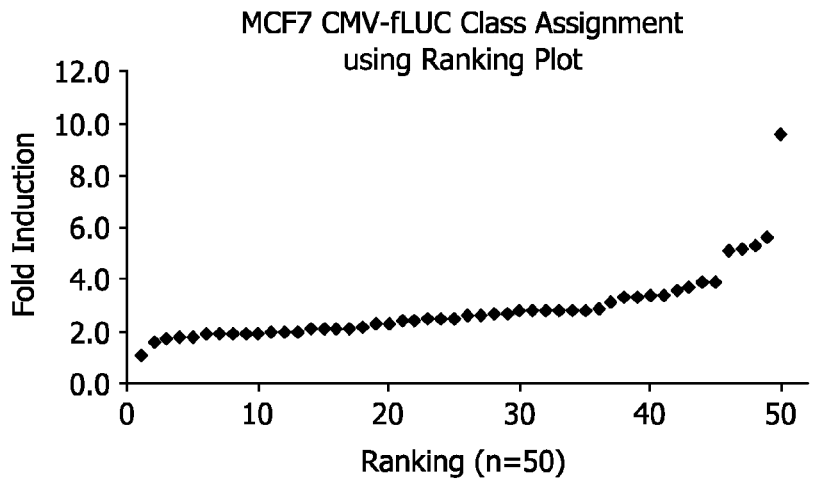
FIG. 5C The top panel is a Ranking Plot showing the 50 responses from the MCF7 CMV-fLUC subclones. The bottom table shows the Class designations for the MCF7 CMV-fLUC pool; 45 of (90.0%) were labeled Class I cells, 5 of 50 (10.0%) exhibited a Class II response and 0 of 79 (0%) showed a Class III phenotype.
Figure 5D:
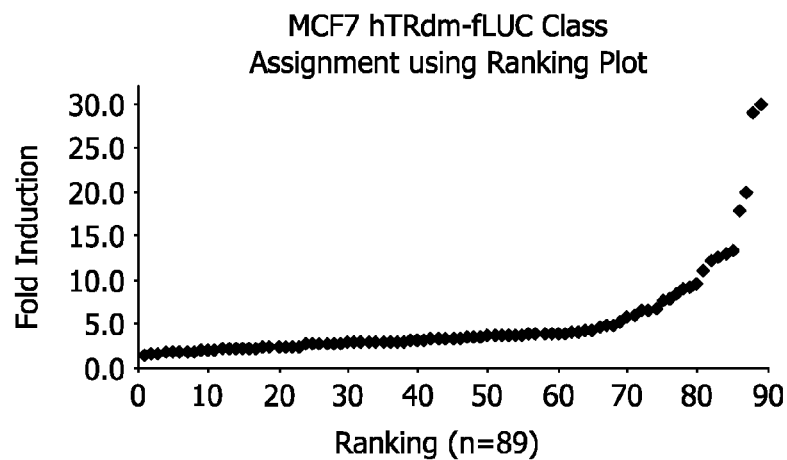
FIG. 5D The top panel is a Ranking Plot showing the 89 responses produced by the MCF7 hTRdm-fLUC subclones. The bottom table shows the Class designations for the MCF7 hTRdm-fLUC pool; 68 of 89 (76.4%) were labeled Class I cells, 17 of 89 (19.1%) exhibited a Class II phenotype and 4 of 89 (4.5%) showed a Class III response.
Figure 5E:
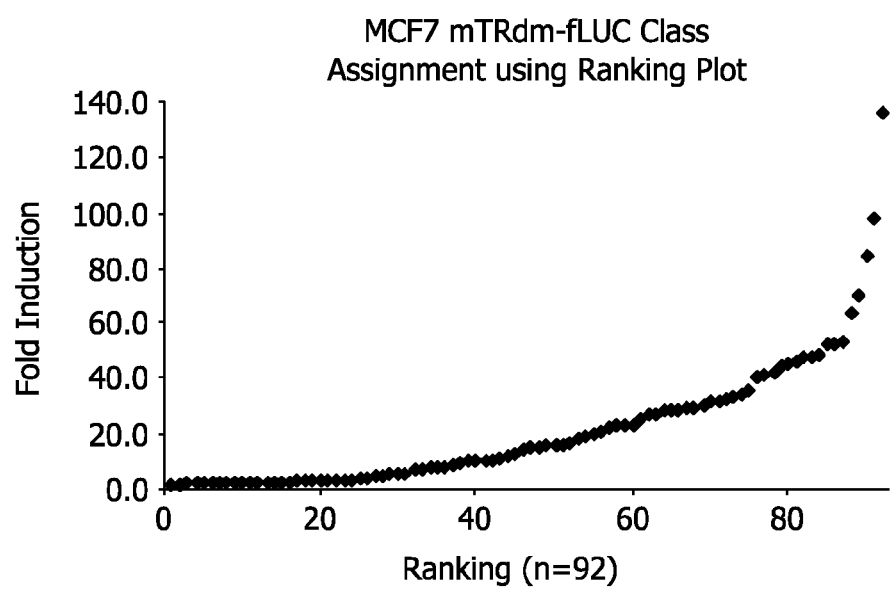
FIG. 5E The top panel is the Ranking Plot showing the 92 responses produced by the MCF7 mTRdm-fLUC subclones isolated in a secondary screen of the MCF7 transfected pool. The bottom table shows the Class designations for the secondary MCF7 mTRdm-fLUC pool; 27 of 92 (29.3%) were labeled Class I cells, 19 of 92 (20.7%) exhibited a Class II phenotype and 46 of 92 (50.0%) showed a Class III response.

In an example of the effect of sample size on Class distribution, FIG. 5E shows that increasing the pool size from 11 subclones to 92 subclones can significantly alter the Class ranking even when identical toxin assays are employed. The Class distribution changed so that 50.0% of the responding clones displayed a Class III phenotype compared to 9% in the smaller screening.

In complementary efforts, MCF7 mTRplp-fLUC transformed cells were used to isolate 106 random colonies (FIG. 5B). Of this number, 36 responding subclones were evaluated and placed into Classes. For the MCF7 mTRplp-fLUC cell pool, 31 of 36 responders (86.1%) displayed a Class I phenotype, 3 of 36 displayed a Class II response (8.3%) and 2 of 36 (5.6%) were labeled Class III. For the 89 responding clones in the MCF7 hTRdm-fLUC cell pool (FIG. 5D), 68 of 89 (76.4%) displayed a Class I phenotype which compares to the Class II (17 of 89; 19.1%) and Class III (4 of 89; 4.5%) distributions. Although the latter pool contained more than double the total number of subclones in the former pool, very similar Class distributions were detected. Similarly, cap-dependent changes were measured using the MCF7 CMV-fLUC transformed cells (FIG. 5C). For this example, 58 random colonies were tested using the standard TPA toxin assay. 50 responding subclones were assayed and the Fold-induction values shown in a Ranking Plot as above. In contrast to above, the larger number of responding subclones likely represents a significant fraction of potential CMV-fLUC responses in MCF7 cells. For this MCF7 CMV-fLUC cell pool, 45 of 50 responders displayed a Class I phenotype, 5 of 50 showed a Class II response and no Class III cells were detected.

In another example of small subclone count, the DU145 mTRdm-fLUC transformed cells were tested, 119 random colonies were recovered and assayed using the TPA toxin assay (FIG. 6A). 22 responding subclones were evaluated and a Ranking Plot was used to identify three putative Class trends. The first trend included 5 modestly responsive Class I clones (22.7%), a second trend produced by 13 responsive Class II cell lines (59.1%) and the final Class III trend exhibited 4 subclones (18.2%).

Figure 6A:
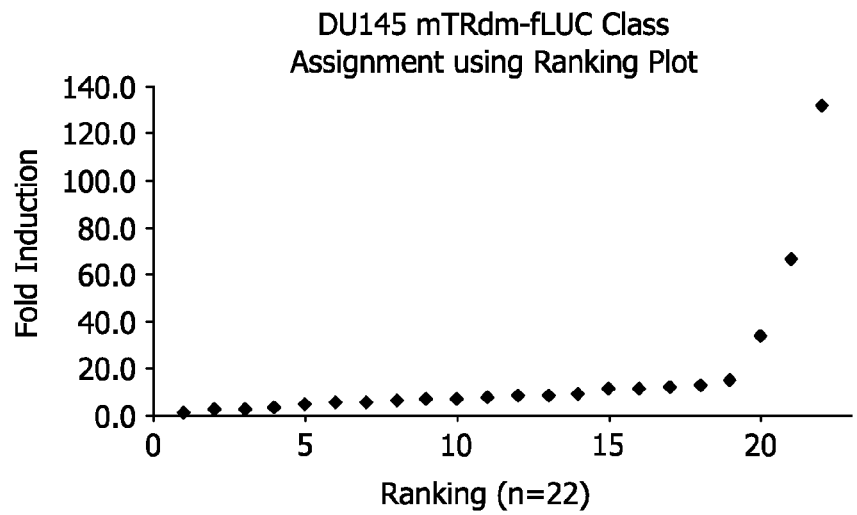
FIG. 6A The top panel is a Ranking plot of the 22 TR responses produced by a primary screen of a human prostate carcinoma DU145 cell pool, stably transformed with the mouse mTRdm-fLUC (firefly luciferase) expression vector, following treatment with the TPA toxin assay. The bottom table shows the Class designations for the DU145 mTRdm-fLUC pool; 5 of 22 (22.7%) subclones showed a Class I response, 13 of 22 subclones (59.1%) exhibited a Class II response and 4 of 22 responders (18.2%) displayed a Class III phenotype.
Figure 6B:
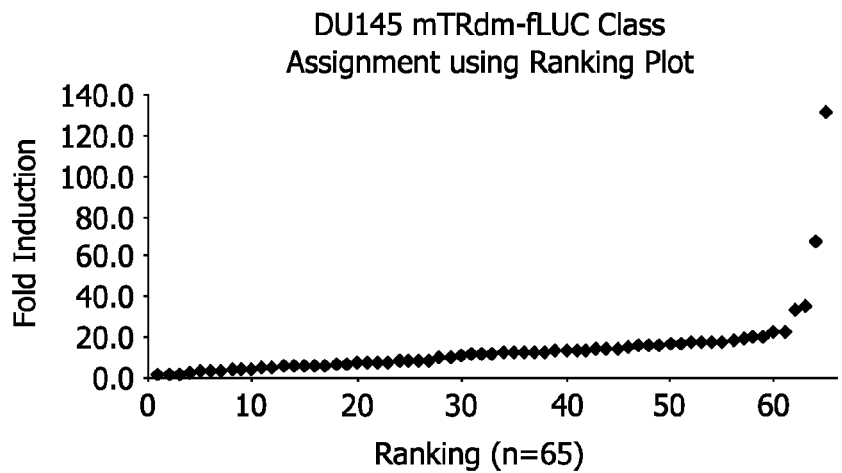
FIG. 6B The top panel is the Ranking Plot showing the 65 responses produced by the DU145 mTRdm-fLUC subclones isolated in a secondary screen of the DU145 transfected pool. The bottom table shows the Class designations for the secondary DU145 mTRdm-fLUC pool; 10 of 65 (15.4%) were labeled Class I cells, 33 of 65 (50.8%) exhibited a Class II phenotype and 22 of 65 (33.8%) showed a Class III response.

In this example, increasing the pool size to 65 subclones only reduced the Class I and II distributions by about 10% (FIG. 6B). However, each of these reductions was imported into the Class III group which increased from 18.2% to 33.8%. This effect was very similar to the trend observed in FIG. 5E which suggests that the nonrandom distribution in the small pools may have an undefined biological component involving increased viability which is overcome during the processing of a larger sample size.

Figure 6C:
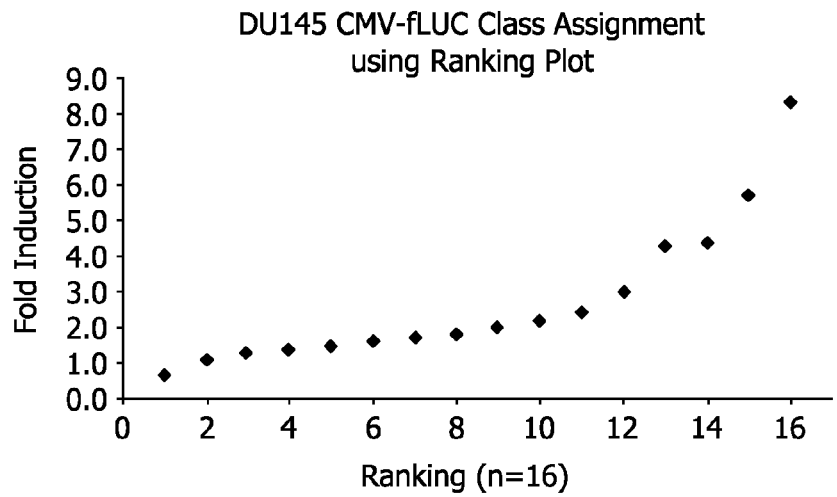
FIG. 6C The top panel is a Ranking Plot showing the 16 responses from a primary screen of the DU145 CMV-fLUC subclones. The bottom table shows the Class designations for the DU145 CMV-fLUC pool; 14 of 16 (87.5%) were labeled Class I cells, 2 of 16 (12.5%) exhibited a Class II response and 0 of 16 (0%) showed a Class III phenotype.
Figure 6D:
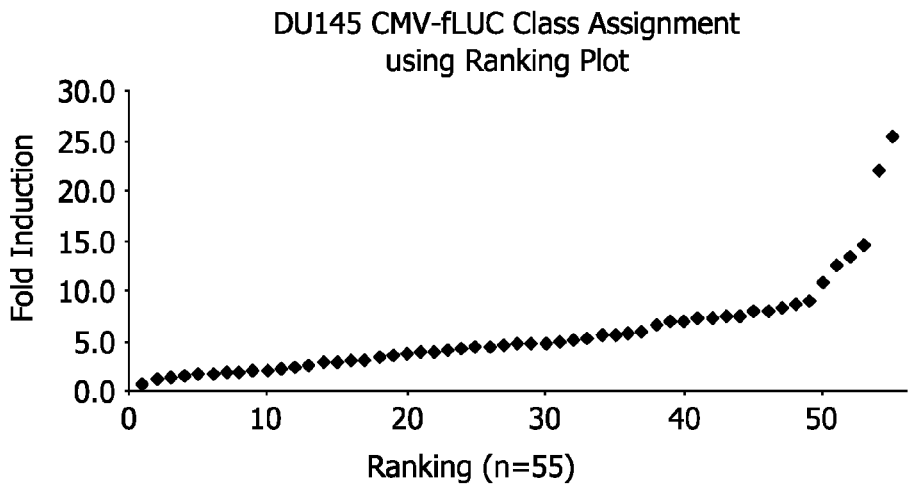
FIG. 6D The top panel is the Ranking Plot showing the 55 responses produced by the DU145 CMV-fLUC subclones isolated in a secondary screen of the DU145 transfected pool. The bottom table shows the Class designations for the secondary DU145 CMV-fLUC pool; 30 of 55 (54.5%) were labeled Class I cells, 22 of 55 (40.0%) exhibited a Class II phenotype and 3 of 55 (5.5%) showed a Class III response.

To further test this hypothesis, an initial analysis was performed of DU145 CMV-fLUC transformed cells using 78 random colonies identified 16 responding subclones (FIG. 6C). As above, the small number of responding clones in this cell pool is unlikely to represent a significant fraction of potential CMV-fLUC responses in DU145 cells. For this DU145 CMV-fLUC cell pool, 14 of 16 responders displayed a Class I phenotype (87.5%), 2 of 16 (12.5%) showed a Class II response and no Class III cells were detected.

A subsequent expansion of this pool size from 16 to 55 (FIG. 6D) resulted in a shift in the apparent Class grouping from 87.5% to 54.5% (Class I), 12.5% to 40% (Class II) and 0% to 5.5% (Class III). In these cases, the trend was to move from small sample sets dominated by the moderately responsive Class I cells to more randomly distributed pools with increased Class II and III fractions. So for these cell lines, the sampling error apparently resulted in small pools with non-responsive cell types which could be a measure of toxic effects during colony formation.

Figure 9A:
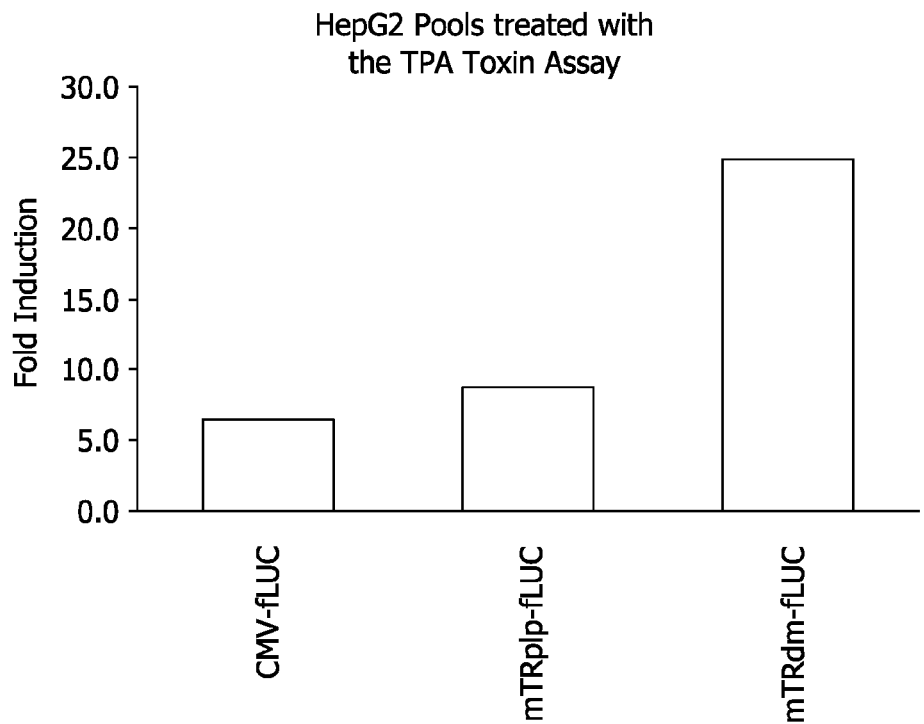
FIG. 9A shows a histogram of fLUC activity produced by human liver hepatocellular carcinoma HepG2 cell pools, stably transformed with the CMV-fLUC, mTRplp-fLUC and mTRdm-fLUC expression vectors (left to right), following treatment with the TPA single-Toxin assay.
Figure 9B:
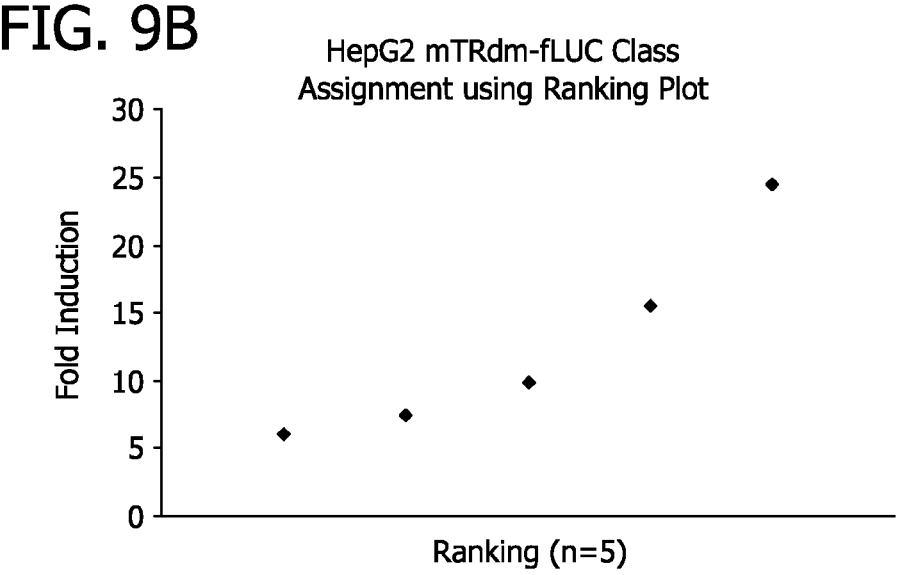
FIG. 9B The top panel is a Ranking plot of the 5 TR responses produced by a human liver hepatocellular carcinoma HepG2 cell pool, stably transformed with the mTRdm-fLUC (firefly luciferase) expression vector, following treatment with the TPA single-Toxin assay. The bottom table shows the Class designation for the HepG2 mTRdm-fLUC pool; 0 of 5 (0%) subclones showed a Class I response, 3 of 5 subclones (60.0%) exhibited a Class II response and 2 of 5 responders (40.0%) displayed a Class III phenotype.
Figure 9C:
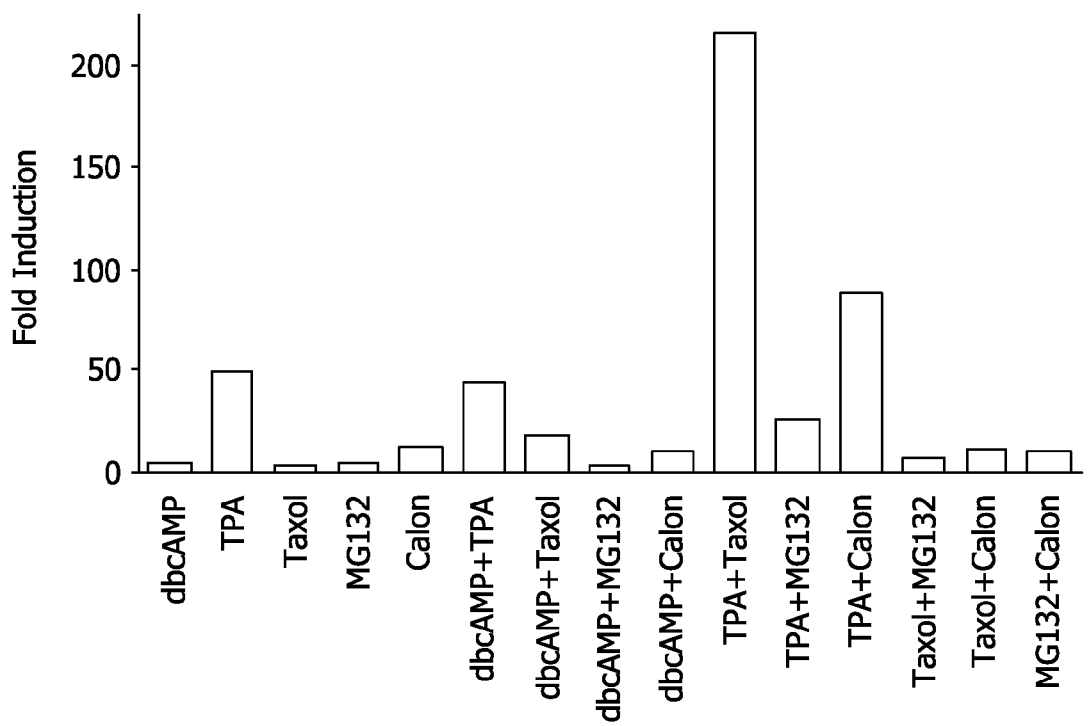
FIG. 9C shows a 15-Assay histogram of the TR responses produced by the HepG2 mTRdm-fLUC #16 subclone. The composition and concentration of the toxins in this figure are described in Table 3. Microplate reader analysis was used to determine fLUC protein activity which is expressed as the ratio of treated to untreated samples (i.e., Fold Induction). A large increase in fLUC activity was observed in the TPA+Taxol two-Toxin assay which established that the TPA+Taxol treatment was the optimal toxin assay for producing the largest magnitude TR-specific translational response.

However, sampling error is also likely to produce nonrandom distribution involving Class II and III cells. For slow growing cells, an enhanced growth phenotype associated with Class II and III cells might result in a small pool with minimal Class I representation. Support for this theory is shown in this final example (FIG. 9), where a small population of responsive subclones from the HepG2 mTRdm-fLUC pool (n=5) were recovered and analyzed. In contrast to the normal distribution produced in larger studies, each of the 5 recovered clones exhibited a Class II or III phenotype (FIG. 9B). This Class assignment was subsequently confirmed for subclone #16 using a 15-Assay procedure (FIG. 9C).

Figure 4A:
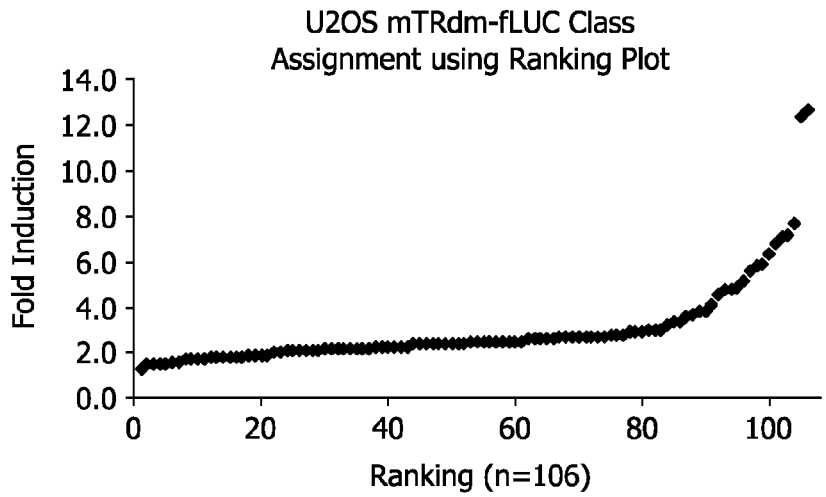
FIG. 4A The top panel is a Ranking plot of the 106 TR responses produced by a human bone osteosarcoma U2OS cell pool, stably transformed with the mouse mTRdm-fLUC (firefly luciferase) expression vector, following treatment with the TPA single-Toxin assay. The bottom table shows the Class designation for the U2OS mTRdm-fLUC pool; 95 of 106 (89.6%) subclones showed a Class I response, 11 of 106 subclones (10.4%) exhibited a Class II response and 0 of 106 responders (0%) displayed a Class III phenotype.
Figure 4B:
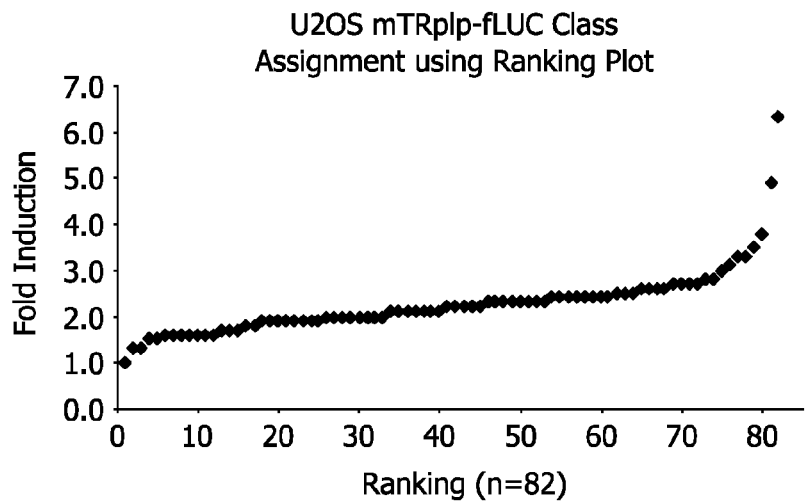
FIG. 4B The top panel is a Ranking Plot showing the 82 U2OS mTRplp-fLUC subclone responses. The bottom table shows the Class labels for the U2OS mTRplp-fLUC pool; 81 of 82 (98.8%) displayed a Class I phenotype, 1 of 82 (1.2%) displayed a Class II response and 0 of 82 (0%) exhibited a Class III response.

Lastly, sampling error can also be produced by low transfection efficiency and the preparation and use of an inadequately sized primary cell pool to isolate subcloned cell lines. An example of this type of sampling error might be displayed by the U2OS osteosarcoma cell line. Repeated transfection procedures resulted in only a modest number of stable colonies (<250) which when pooled apparently resulted in a nonrandom distribution of potential clone types. In this example, the U2OS mTRdm-fLUC transformed cell pool was used to isolate 122 random colonies which were assayed using the TPA toxin assay (FIG. 4A). Of the 106 responding subclones, 95 exhibited a Class I response (89.6%), 11 were Class II cell lines (10.4%) and no Class III subclones were detected.

In a related study, the U2OS mTRplp-fLUC transformed cell pool was used to recover 106 random colonies which were evaluated using the standard TPA toxin assay (FIG. 4B). 82 responding subclones produced 81 Class I subclones (98.8%), 1 Class II subclone (1.2%) and no Class III cells.

Finally, the U2OS CMV-fLUC transformed cell pool was used to isolate 83 random colonies which were tested using the standard TPA toxin assay. Of the 79 responding subclones 78 exhibited a Class I phenotype (98.7%), none were Class II and 1 of 79 (1.2%) displayed a Class III activity. Even though large numbers of individual subclones were examined (>80 in each effort), each U2OS study produced a nonrandom Class ranking with an overabundance of subclones displaying a Class I phenotype.

Therefore, small sample size can be a major error impacting Class assignment. A sampling error may be produced in an inadequately sized stably transformed primary cell pool or in a small subclone number tested for Class assignment (See above). In compiling all of the pool data sets, a random distribution can be produced by using a primary cell pool containing >500 primary transformants and screening a subclone group of 30-60 independent subclones (derived from subclones isolated from multiple independent dilution plates).

(A) Effect of Plating Condition on Fold Induction

Cell cultures can be plated for analysis using either maximal cell density (Confluence method) or a cell limiting procedure (Cell Counting method). It was believed that maximizing cell density would also maximize basal level or background translational activity, and that this could have a significant effect on the denominator of the Fold Induction calculations.

This example shows that plating untreated MDA231 cells expressing the CMV-fLuc, mTRdm-fLuc and mTRplp-fLuc expression cassettes using the cell confluence method increases the absolute number of cells in a well and generally raises the basal level reporter value compared to the subconfluent 25,000 cell counts (FIG. 13A). However in the TR expressing cell lines, 2 of 6 cell lines exhibited significant increases in basal level reporter protein activity using the Cell Count procedure versus the Confluence method (FIG. 13B). This suggests that for some cell lines, subconfluent cultures may exhibit some biological effect that regulates basal level TR-specific translation.

E. Establishing that Class Assignment is not a Product of the Reporter Protein

Figure 3A:
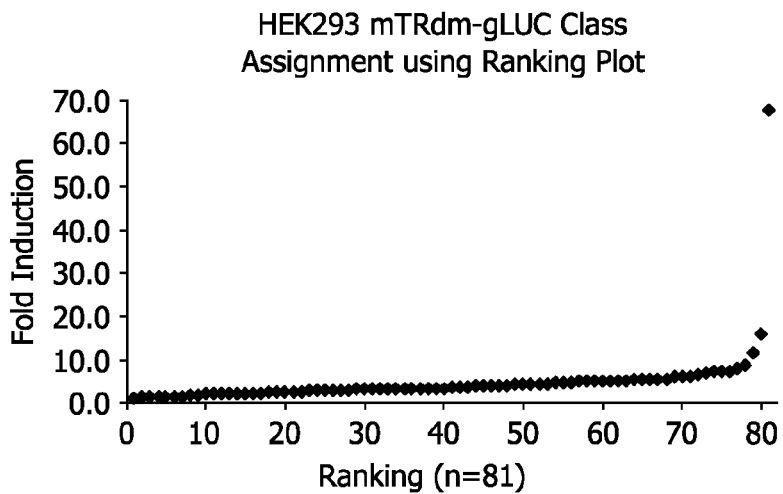
FIG. 3A The top panel is a Ranking plot of the 81 TR responses produced by an HEK293 cell pool, stably transformed with the mouse mTRdm-gLUC (*gaussia* luciferase) expression vector, following treatment with the TPA single-Toxin assay. The bottom table shows the Class designation for the HEK293 mTRdm-gLUC pool; 56 of 81 (69.1%) subclones showed a Class I response, 23 of 81 subclones (28.4%) exhibited a Class II response and 2 of 81 responders (2.5%) displayed a Class III phenotype.
Figure 3B:
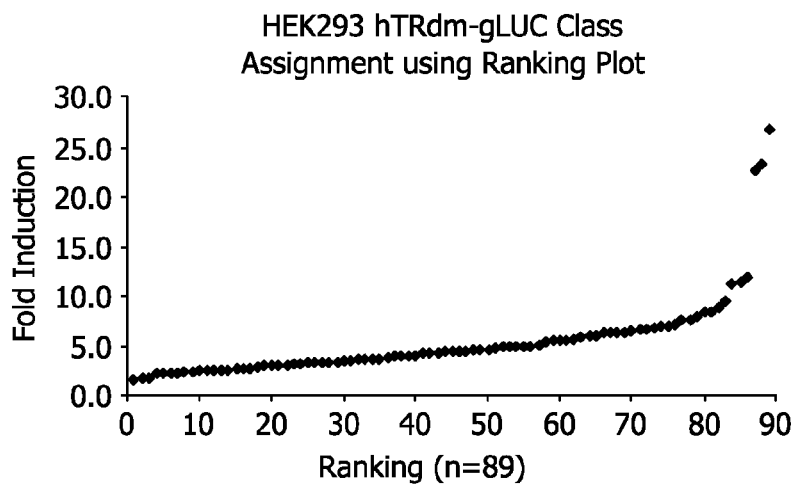
FIG. 3B The top panel is a Ranking Plot showing the 89 HEK293 hTRdm-gLUC subclone responses. The bottom table shows the Class assignments for the HEK293 hTRdm-gLUC pool; 56 of 89 (62.9%) displayed a Class I phenotype, 30 of 89 (33.7%) displayed a Class II response and 3 of 89 (3.4%) exhibited a Class III response.

In this example, the reporter sequence is tested for its effect on Fold Induction values and ultimately Class designations. This example employs alternative TR expression cassettes that operatively link the mTRdm sequence to the *gaussia* luciferase reporter gene. Using the HEK293 mTRdm-gLUC transformed cell pool, 129 random colonies were recovered and assayed using the TPA toxin assay (FIG. 3A). Of the 81 responding subclones three Class trends were detected. The first trend included 56 moderately responsive Class I clones (69.1%), a second trend produced by 23 responsive Class II cell lines (28.4%) and the final Class III trend exhibited 2 subclones (2.5%).

In a related study, HEK293 hTRdm-gLUC transformed cells were used to isolate 110 random colonies which were evaluated using the standard TPA toxin assay (FIG. 3B). 89 responding subclones were evaluated and 56 of 89 responders displayed a Class I phenotype (62.9%), 30 displayed a Class II response (33.7%) and 3 (3.4%) were labeled Class III.

Figure 3C:
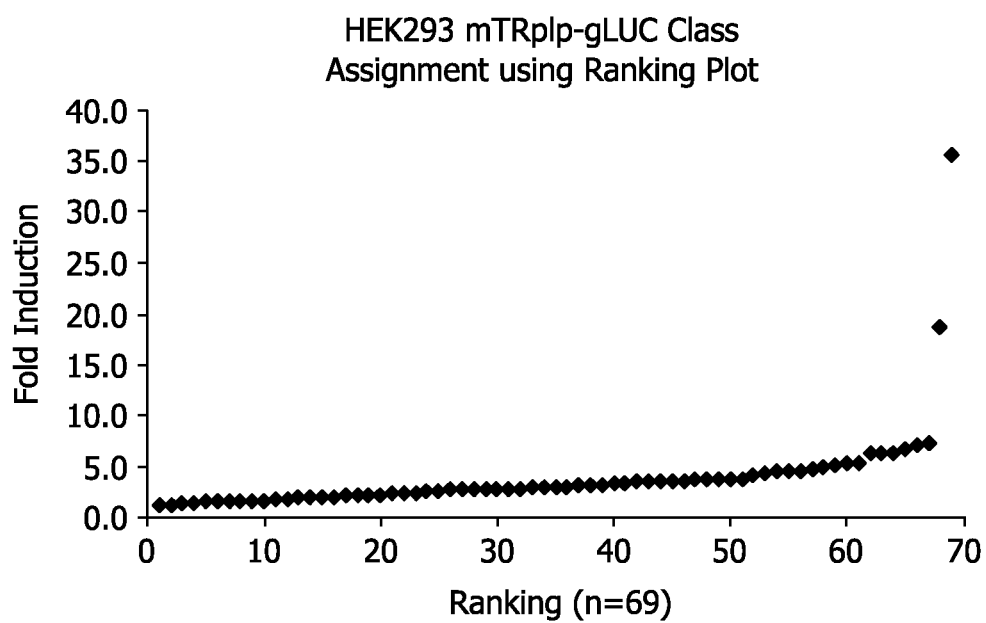
FIG. 3C The top panel is a Ranking Plot showing the 69 responses from the HEK293 mTRplp-gLUC subclones. The bottom table shows the Class designations for the HEK293 mTRplp-gLUC pool; 58 of 69 (84.1%) were labeled Class I cells, 9 of 69 (13.0%) exhibited a Class II response and 2 of 69 (2.9%) showed a Class III phenotype.

Finally, HEK293 mTRplp-gLUC transformed cells were used to isolate 104 random colonies that were tested with the TPA toxin assay (FIG. 3C). Of the 69 responding subclones from the HEK293 mTRplp-gLUC cell pool, 58 of 69 responders displayed a Class I phenotype (84.1%), 9 showed a Class II response (13.0%) and 2 of 69 (2.9%) displayed a Class III phenotype.

Comparing the HEK293 gLuc (FIG. 2) and fLuc studies (FIG. 2), it is clear that cells transformed with the expression vectors containing the gLuc reporter sequence did not display any significant differences in the HEK293 Class ranking. Therefore, Class ranking is a cell-based phenotype and not a product of the vector cassette.

Example IV

Application of the 15-Assay Procedure to Class Defined Cell Lines

Figure 4C:
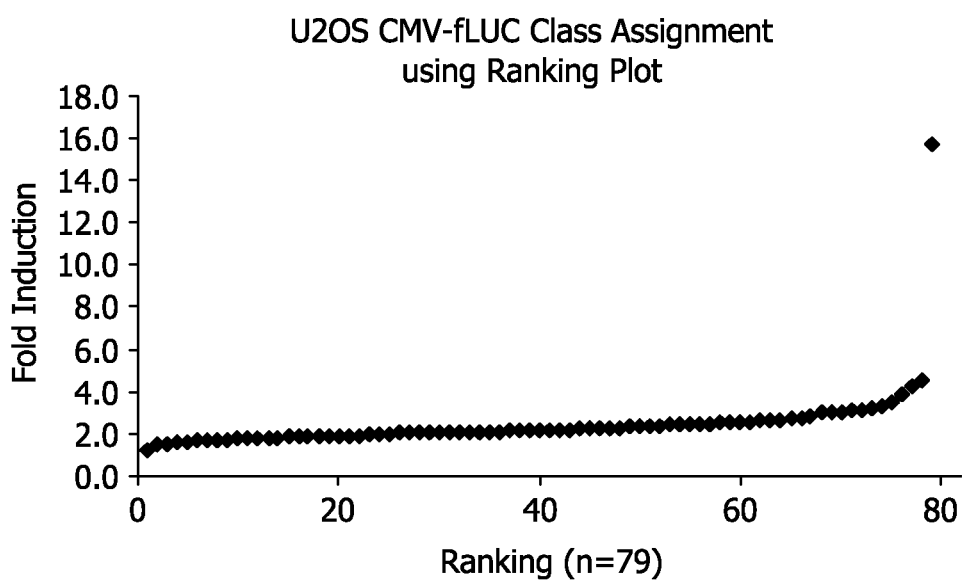
FIG. 4C The top panel is a Ranking Plot showing the 79 responses from the U2OS CMV-fLUC subclones. The bottom table shows the Class designations for the U2OS CMV-fLUC pool; 78 of 79 (98.7%) were labeled Class I cells, 0 of 79 (0%) exhibited a Class II response and 1 of 79 (1.2%) showed a Class III phenotype.

A. Verification that Class Designations Performed Using Optimal Conditions Retain Class Designation in Low Passage Cultures This example evaluates whether the Class designation is an inheritable phenotype that is maintained during cell passage. FIG. 4 contains the detailed analysis of the U2OS cell line which produced few Class III cells even though the screening assays were performed using optimized assay and culture conditions. It was difficult to determine if this was a result of a non-reproducible U2OS translational response or a sampling error. To examine this process in more detail, low passage (P5-P8) cell lines were reexamined using the 15-Assay Cell Count procedure (FIG. 10A). Although the U2OS mTRdm-fLUC #109 and #40 subclones exhibited an ~50% increase in translational response in the TPA+Taxol two-Toxin assay, the magnitude of the change did not alter the Class II designation.

(A) Verification that Class Designations Performed Using Suboptimal Conditions Can Switch Class Designation In this example, the 15-Assay method (FIG. 10B) was applied to the HCT116 mTRdm-fLUC 12-15, 7-5, 12-3 and 12-16 cell lines to reevaluate Class assignment. Initially each cell line was assigned a Class I designation using a small number of subclones screened with a suboptimal dbcAMP single-Toxin assay (FIG. 7). Whereas the HCT116 mTRdm-fLUC 12-15 and 12-3 subclones continued to express a Class I phenotype, the HCT116 mTRdm-fLUC 7-5 and 12-16 subclones showed clear Class III phenotypes (>1500% induction).

Figure 10C:
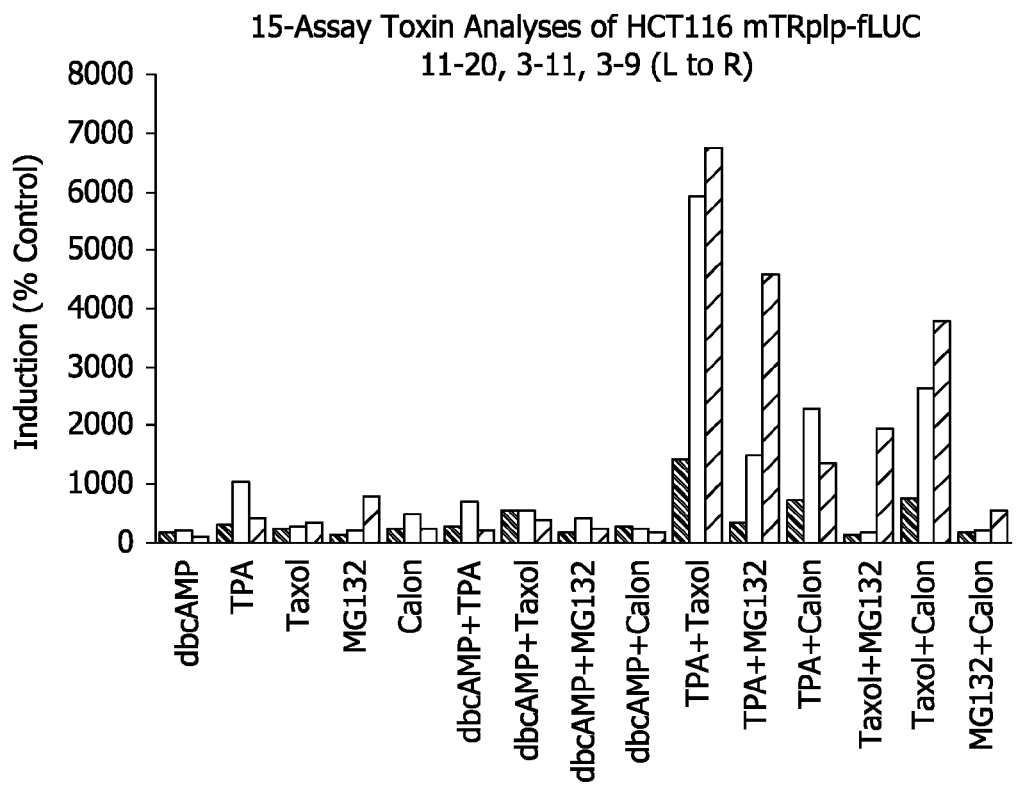
FIG. 10C shows a histogram of the reanalysis of three HCT116 mTRplp-fLUC subclones using the Cell Count plating procedure. These cells were assigned a Class I designation in FIG. 7B using a suboptimal single-Toxin assay. This histogram illustrates the enhanced TR responses produced by the HCT116 mTRplp-fLUC 11-20, 3-11 and 3-9 subclones (L to R) in the 15-Assay procedure. Whereas the HCT116 mTRplp-fLUC 11-20 subclone expressed a Class II phenotype in the TPA+Taxol two-Toxin assay, the HCT116 mTRplp-fLUC 3-11 and 3-9 subclones exhibited Class III responses in the TPA+Taxol two-Toxin assay.

In a related effort, the reanalysis of three HCT116 mTR-plp-fLUC subclones 11-20, 3-11 and 3-9 are shown in FIG. 10C. Initially each cell line was assigned a Class I designation (FIG. 7B) using the dbcAMP single-Toxin assay; however, reanalysis showed that the HCT116 mTRplp-fLUC 11-20 subclone expressed a Class II phenotype (>500% but <1400% induction), and the HCT116 mTRplp-fLUC 3-11 and 3-9 subclones exhibited Class III responses (>1400% induction) in the TPA+Taxol two-Toxin assay.

Figure 10D:
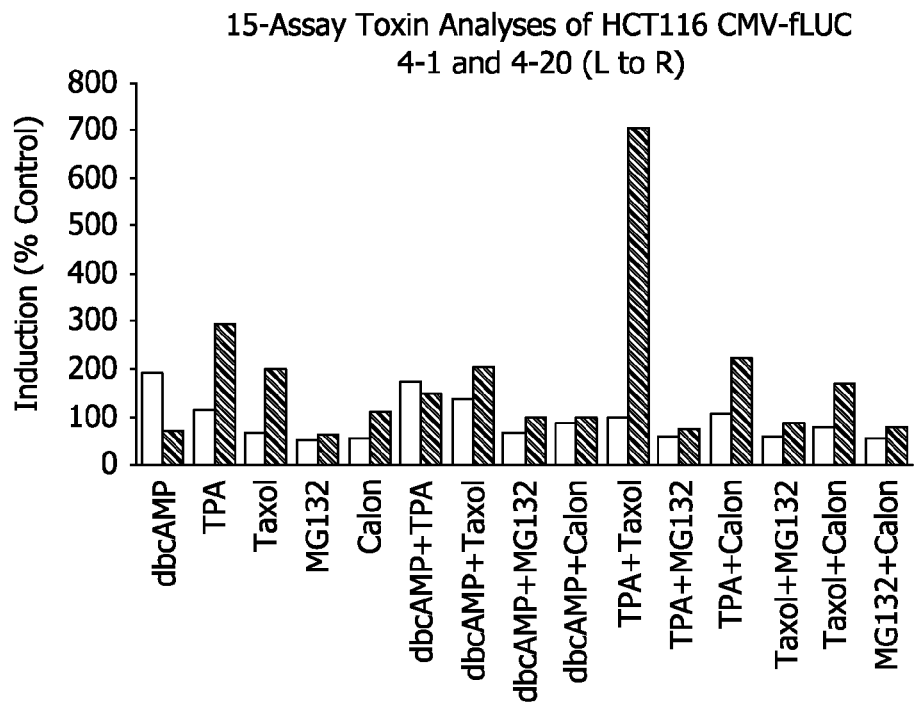
FIG. 10D shows a histogram of the reanalysis of two HCT116 CMV-fLUC subclones using the Cell Count plating procedure that had been assigned a Class I designation in FIG. 7C using a suboptimal single-Toxin assay. This histogram illustrates the fLUC activity produced by the HCT116 CMV-fLUC 4-1 and 4-20 subclones in the 15-Assay procedure (left to right). Whereas the HCT116 CMV-fLUC 4-1 subclone continued to express a Class I phenotype, the HCT116 CMV-fLUC 4-20 subclone exhibited a Class II response in the TPA+Taxol two-Toxin assay.

Similarly, application of the 15-Assay method to the HCT116 CMV-fLUC 4-1 and 4-20 subclones found that whereas the HCT116 CMV-fLUC 4-1 subclone continued to express a Class I phenotype, the HCT116 CMV-fLUC 4-20 subclone exhibited a Class II response in the TPA+Taxol two-Toxin assay (FIG. 10D).

Figure 10E:
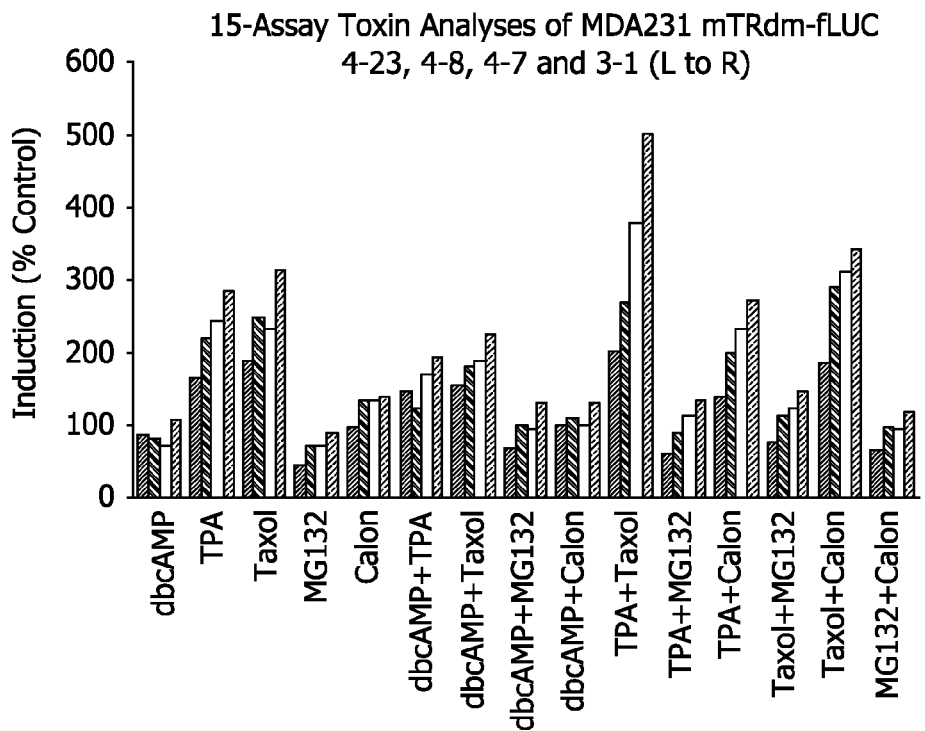
FIG. 10E shows a histogram of the reanalysis of four MDA231 mTRdm-fLUC subclones using the Cell Count plating procedure. These cells were previously assigned a Class I designation in FIG. 8A using a suboptimal single-Toxin assay. This histogram illustrates the TR responses produced by the MDA231 mTRdm-fLUC 4-23, 4-8, 4-7 and 3-1 subclones (left to right) in the 15-Assay protocol. Whereas the MDA231 mTRdm-fLUC 4-23, 4-8 and 4-7 subclones continued to display a Class I phenotype, the MDA231 mTRdm-fLUC 3-1 subclone exhibited a Class II response in the TPA+Taxol two-Toxin assay.

To confirm that Class switching is not a unique property of the HCT116 cell type, TR Class designation was examined in the MDA231 mTRdm-fLUC 4-23, 4-8, 4-7 and 3-1 subclones (FIG. 10E). Although initially assigned a Class I designation (FIG. 8A), subsequent reanalysis found that whereas the MDA231 mTRdm-fLUC 4-1, 4-8 and 4-7 subclones continues to express a Class I phenotype, the MDA231 mTRdm-fLUC 3-1 subclone exhibited a Class II response in the TPA+Taxol two-Toxin assay.

Further proof is provided by rescreens of the MDA231 mTRplp-fLUC 3-12, 5-2, 5-13 and 2-17 subclones (FIG. 10F). Although each cell line was assigned a Class I designation, subsequent tests show that while the 3-12, 5-2 and 5-13 subclones retained their Class I response, the 2-17 subclone exhibited Class II phenotype.

Finally, application of the 15-Assay method (FIG. 10G) to the MDA231 CMV-fLUC 1-21, 2-5 and 1-20 subclones found that although each subclone exhibited elevated translational activity in the two-Toxin assays none of these subclones changed Class and remained Class I cells.

Example V

Class Recovery in High Passage Cultures by Subcloning and Reselection

A. Protocol for Recovering a Class Defined Phenotype by Subcloning

This example examines the recovery and/or enhancement of the TR-specific Class designation by resubcloning. High passage number cell cultures accumulate alterations in many cellular processes. Chromosome loss and genome shuffling during mitosis can alter any recombinant expression system that does not confer a selective growth advantage to that cell. It is not uncommon for high passage number cell cultures to segregate selectable plasmids.

This example examines a method for recovering the Class phenotype using secondary subcloning to recover valuable cell traits. In this example, a comprehensive (n=113) collection of secondary subclones were isolated from the Class II MDA231 mTRplp-fLUC 2-17 cell line and assayed using the TPA or Taxol single-Toxin assays (FIG. 11A). In this pool, the majority of subclones continued to display Class II responses; however, a small number of cell lines exhibited an enhanced translational response in both assays and a Class III phenotype.

Similarly, a large series of secondary subclones was isolated from the Class III HCT116 mTRdm-fLUC 12-16 cell line and tested with the TPA or Taxol single-Toxin assays (FIG. 11B). While the vast majority of subclones displayed a Class III response, a significant fraction of the recovered cell lines exhibiting enhanced TR activity compared to the parental cell line with some subclones exhibiting three times the translational activity of the parental cell line.

In another example, 95 secondary subclones isolated from the Class III MCF7 mTRplp-fLUC #43 cell line were treated with the Taxol single-Toxin assay (FIG. 11C). Although most of the subclones in this high passage culture exhibited decreased translational responses, a fraction of the secondary subclones (~7%) exhibited a Class III phenotype with a higher reporter activity than the parental cell line.

Similarly, a number of secondary subclones isolated from the Class III MCF7 mTRdm-fLUC #64 cell line were assayed using the Taxol single-Toxin assay (FIG. 11D). A majority of the secondary subclones retained the Class III phenotype and a significant fraction (~35%) showed enhanced TR activity compared to the parental cell line.

Therefore, recovering a Class designation from a high passage cell culture can be accomplished by secondary subcloning. Furthermore, while not being bound to a theory, these data suggest that the accumulation of genetic variations in these high passage cultures generates a mixture of translational activities similar to the parental cell line. Although most of the secondary subclones continue to express the parental Class ranking, in many cases, enhancement of the TR phenotype can be observed. This suggests that secondary subcloning provides a method for recovery of cells expressing the original Class rank and also allows for the isolation of higher responding subclones.

(A) Protocol for Recovering a Class Defined Phenotype by Reselection

High passage number cells often segregate nonselected expression vectors. In many cases, this will result in the loss of the selectable antibiotic resistance gene which was used to generate the original cell pool. In this example, high passage number cultures of mTRdm-fLUC transformed HCT116 subclones 7-2 and 12-16 and two subclones of 12-16 termed Sub#30 and Sub#38 (light bars) were maintained in culture until evident loss of their TR-specific translational phenotype ((FIG. 12). Each high passage cell culture was reselected using the G418 antibiotic resistance marker in the TR expression cassette until no significant cell death was microscopically detectable. These reselected cell lines were examined using the TPA single-Toxin assay (FIG. 12B) and TPA+Taxol two-Toxin assay (FIG. 12A). Statistical analysis using the Student's T-test found significant statistical increases in translational activity (p<0.05) after the reselection process.

Example VI

Correlating TR-Specific Reporter Activity with TR-Derived Translation Products and Uses Thereof A. Verification that Toxin-Induced Increases in TR-Specific Activity are Produced by Increased Protein Production In this example, the extremely large TR-specific responses produced from the TR cassette in a number of toxin assays were examined to show that these increases in enzyme activity correlated with increases in protein concentration. For this test, the Class III HCT116 mTRdm-fLUC 7-5 cell line was subjected to a 15-Assay procedure and nondenatured cell lysates were generated for each assay. A defined fraction of each cell lysate (10%) was assayed for fLUC activity and compared to the same cell line assayed by direct measurement (FIG. 14A-14B). Although the 15-Assay trends did not change, the magnitude of the Fold Induction for TPA+Taxol two-Toxin assay changed in the cell extracts.

The remaining toxin treated cell samples (90% of total cells) were pelleted and a total protein sample was prepared using 1×SDS Lysis Buffer (50 mM TrisHCl (pH6.8), 2% SDS, 10% glycerol, 10 mM DTT, 5 mM EDTA, 1× Roche Protease Inhibitor Cocktail). The integrity and concentration of each protein sample was established by a Coomassie Blue stained 12% SDS-PAGE gel. Equivalent protein concentrations were resolved on a second SDS-PAGE gel, and fLUC protein levels were detected by Western Blot analysis using an anti-firefly luciferase primary antibody and an appropriately labeled secondary antibody (see above) (FIG. 14B). Although significant fLUC protein levels were observed in the MG132, TPA+Taxol, TPA+MG132 and Taxol/Calon assays, band intensities were consistent with the plate reader results shown in FIG. 14A.

As above, densitometric scanning of the Western blot (FIG. 14C) found no significant variation in the trend in TR-specific protein levels compared to the plate reader measurements indicating a strong correlation between the reporter protein activity measured by the plate reader procedures and TR-mediated protein synthesis. However, a statistically significant ($p<0.05$) increase in reporter protein level was detected in the Western blot analysis of lysates prepared from cells treated with the MG132 single-Toxin assay (a diffusible proteasomal inhibitor). While not being bound to any particular theory, this result suggests that the toxins affecting protein turnover may artificially lower TR-mediated responses in plate reader assays by reducing reporter protein activity via protein denaturation or modification.

(A) A Procedure for Employing Toxin-Regulated Increases in TR-Specific Activity for the Selective Expression of Recombinant Proteins The production of high concentrations of recombinant protein in human cell lines offer considerable advantage in biotechnology manufacturing processes. In this example, the human Class III HCT116 mTRdm-fLUC 12-16 cell line was examined as a potential resource for TR-regulated expression of recombinant protein.

To quantitate the amount of a recombinant protein in a cell line, the specific activity of the expressed protein was compared to a defined specific activity of purified protein. For this example, a dose response curve was generated using a serial dilution of recombinant firefly luciferase protein (Sigma; 1 mg; 4.6 mg/1 ml as determined by Bradford assay) (FIG. 15A).

A linear dose response was observed which produced a specific activity of $3\times10^{11}$ light units per mg of recombinant fLuc protein. Using Coomassie stained SDS-PAGE gels, it was verified that the recombinant fLUC protein stock was at least 98% pure and was at least 5 microgram of fLUC protein per microliter.

The Class III HCT116 mTRdm-fLUC 12-16 cell line was subjected to the 15-Assay toxin protocol (FIG. 15B). A confluent 12-well tray was treated with the indicated toxin dissolved in culture medium and incubated for 6 hrs. Cells from 3 wells were recovered in 1 ml of 1×PBS, 100 ul (1/10 of total cell number) transferred to a fresh microcentrifuge tube and centrifuged for 1 minute at 10,000 rpm. This cell pellet was resuspended in 40 ul of Luciferase Lysis Buffer, and the firefly Luciferase activity was determined using a standard plate reader procedure. The relative Light Units produced in each toxin assay were compared to the linear response observed in the recombinant protein serial dilution plot (FIG.

15A). These values were used to calculate an estimate for the amount of expressed protein in 3 wells of a 12-well tray (FIG. 15B). For example, assuming that each well of a 12-well tray contain an average of 400,000 cells, the specific activity of the TPA+Taxol assay converted to a conservative estimate of 442 femtogram (fg) of fLUC protein per cell.

The remaining cell pellets (90% of the toxin treated cells) were dissolved in 200 ul of 1×SDS buffer, and total protein samples were prepared. 5 ul of each sample was resolved on a 12% SDS-PAGE gel and developed by Western blot analysis using an anti-fLUC primary antibody (FIG. 15C). Although extremely high protein levels were observed in the MG132, TPA+Taxol and TPA+MG132 assays, the band intensities were consistent with the calculated fLUC reporter protein concentrations in cellular extracts, shown in FIG. 15B.

There are a number of advantages to using the TR expression system of the present invention to produce recombinant proteins. They include for example, 1) the ability to synthesize proteins in a human source (removal of issues concerning xenogenic proteins), 2) the inherent regulatory process provided by the use of cell-specific toxins to stimulate TR-specific translation, thereby allowing for regulated expression of potentially lethal proteins, 3) speed of the translational process (e.g., toxin treatments proceed for a relatively short amount of time, e.g., 6 hrs) and 4) applicability of the present expression system to a wide range of mammalian cells, thus essentially eliminating issues about protein processing, post-translational modification and turnover.

Example VII

Use of Toxin Assay Procedures and Responsive Cell Lines for Identifying and Defining Translational Regulation A. Use of a Procedure Employing Comparative Dose-Response Assays of PKC Activators to Detect Cap-Dependent and Cap-Independent Translational Regulation In addition to measuring cap-dependent and cap-independent translational effects, Class-specific translational activity and toxin-defined actions, the previously described materials and methods allow for a variety of applications designed to detect and characterize agents and processes that regulate ribosome activity. In this example, comparative dose response assays were used to detect cap-dependent and cap-independent translational regulation in MCF7 cells. The basis for this application was the observation that distinct translational responses are produced by compounds at different doses. When an assortment of compounds act on a common molecular target, they can be grouped into a genus of related drugs. By comparing individual species of a compound genus over a defined dose range, differences in translational regulation can be defined. Furthermore, these translational differences can often be linked to biological differences.

FIG. 27 illustrates the application of Dose Response procedures to differentiate compound-specific effects within the Protein Kinase C (PKC) activator genus in MCF7 breast cancer cells. This group was composed of the phorbol ester (TPA) and the macrolide lactones (Bryostatin 1 and Bryostatin 2). While previous studies showed that the Bryostatins can induce transient cell morphology changes and inhibit cell growth similarly to TPA, other traits such as inhibition of DNA synthesis and PKC translocation to the plasma membrane were much reduced. The macrolide lactones also display internal differences with Bryostatin 2 exhibiting an inhibition constant (Ki) that is 10× larger than the Ki of Bryostatin 1.

In this example (FIG. 27), the three PKC activators produced similar dose response trends in cap-dependent assays. Over a 1 nM to 250 nM range, each activator exhibited a linear increase in cap-dependent translation that peaked at a 100 nM dose. However, macrolide lactones produced translational increases that were generally 60-70% of the TPA translational response (FIG. 27B). In fact, a 25 fold increase in Bryostatin 2 concentration (2.5 uM) was needed to produce a translational magnitude similar to the 100 nM TPA assay (FIG. 27B).

In the cap-independent assays, a similar dose response trend was observed over a 1 nM to 250 nM range with a translational peak at a 100 nM dose. However, the magnitude of the Bryostatin increases were generally 30% of 100 nM TPA response. Another difference with the cap-dependent assay was the fact that increasing the Bryostatin 2 dose to 2.5 uM only resulted in ~50% of the 100 nM TPA response.

While the Bryostatin drugs exhibited similar responses in cap-dependent and cap-independent assays, a clear difference was detected between TPA and the Bryostatins. In each assay type, TPA exhibited an increased translational response that could only be replicated by Bryostatin 2 at very high concentrations in cap-dependent tests. For cap-independent assays, a larger magnitude difference was observed with TPA which could not be reproduced by Bryostatin 2 even at high doses. Therefore, comparative dose response assays show that the TPA activated translational responses differed significantly from the Bryostatins' translational responses, a fact which is consistent with the known biological activities of these compounds. In contrast, the Bryostatins showed highly similar dose response trends that only differed at a high dose (>500 nM), which is also consistent with their previously described biological effects.

(A) Use of a Procedure Employing Comparative Dose-Response Assays of Microtubule Disruptors to Detect Cap-Dependent and Cap-Independent Translational Regulation Another application of comparative dose response assays has been used to differentiate drug-specific phenotypes between the microtubule disruptor (MTD) drugs in HEK293 embryonic kidney cells (FIG. 29). Developed by plants to defend themselves against invasion by proliferating cells, alkaloids such as the MTD drugs arrest cells during mitosis by blocking microtubule function. As known in the art, dynamic cytoskeletal structures are important for normal cellular function. In the case of microtubules, interfering with the remodeling of the tubulin subunit protein can produce significant anti-proliferative activity by blocking cell cycle progression. However, drugs that disrupt microtubules exhibit significant biological differences after tubulin binding. For example, nocodazole and colchicine bind microtubules at nonidentical overlapping protein sequences and block microtubule assembly sites that prevent polymerization and promote depolymerization. Vinca alkaloids, such as vicristine and vinblastine, bind tubulin and induce its aggregation into insoluble crystals that prevent microtubule assembly. Finally, taxol binds and stabilizes intact microtubules, which interferes with their disassembly during cell division.

In this example, HEK293 cells were treated with various doses of MTD drugs to detect compound-specific translational regulation. Following 6 hr exposure, cap-dependent assays showed that nocodazole, colchicine and vincristine exhibited consistent increases in reporter protein activity between 100 nM and 5 uM doses. In contrast, significant changes in fLUC expression were only observed at the highest taxol doses (2.5 uM and 5 uM).

Highly similar cap-independent translational profiles were produced by each TR-expressing cell line (FIGS. 29B and C). As in the cap-dependent assays in FIG. 29A, colchicine and vincristine exhibited increased reporter activity in all doses larger than 100 nM. This contrasted with the nocodazole responses, where significant increases were observed only at concentrations larger than 250 nM. As before, taxol-specific translational increases were only observed at the 2.5 uM and 5 uM doses.

Despite the fact that colchicine and vincristine demonstrated similar translational responses in cap-dependent and cap-independent assays, nocodazole produced a distinct cap-independent response. Even though significant translational increases were observed at high taxol doses, this drug consistently produced the smallest translational response of the MTD drugs. Therefore, single-Toxin dose response assays can be used to compare drugs with identical molecular targets and detect differences in translational regulation. In these assays, these differences can be correlated with unique biological activities exhibited by each drug species.

C. Use of a Procedure Employing Combinatorial Toxin Assays of Topoisomerase I Inhibitors to Detect Cap-Dependent and Cap-Independent Translational Regulation This example illustrates the application of single-Toxin and two-Toxin Assays to differentiate compound-specific translational responses using Topoisomerase I inhibitors in MCF7 breast cancer cells (FIG. 28). Camptothecin and its chemically related analogs belong to a class of Topoisomerase I (TopoI) inhibitors that produce diminished DNA unwinding and inhibit DNA replication and transcription. Although structurally related to other TopoI inhibitors, irinotecan differs in that it requires the presence of hepatic or gastrointestinal carboxylesterase to be metabolized to an active form termed SN38. This metabolic activity is missing in MCF7 cells and provides a basis for detecting compound-specific translational regulation. These results also provide an example of drugs that selectively reduce ribosome activity, even though their molecular target does not alter protein translation.

FIG. 28A illustrates a cap-dependent dose response assay of MCF7 cells treated with varying dosages (10 nM to 10 uM range) of the following TopoI inhibitors: camptothecin, topotecan, irinotecan, and rubitecan. Camptothecin and rubitecan showed similar dose responses with increasing fLuc protein expression that peaked at ~1 uM but declined to basal expression levels at higher doses. While the altered irinotecan response might have been predicted based on its metabolic requirements, the lack of topotecan action on cap-dependent translation in the single-Toxin assays was unexpected.

Application of a two-Toxin dose response assay to examine cap-dependent regulation by TopoI inhibitors in the presence of the TPA translational activator (FIG. 28B) showed that camptothecin and rubitecan acted synergistically with TPA to increase fLUC protein activity up to a 1 uM dose but antagonized TPA activity at higher concentrations. Since similar doses inhibited translation in the single-Toxin assays (FIG. 28A), this effect might have represented a direct effect on translation. Irinotecan did not significantly alter the TPA-specific translational response in comparison with topotecan, which only showed TPA antagonism at high doses (i.e. 5 uM and 10 uM). These results placed camptothecin and rubitecan into a similar translational regulatory group, which phenotypically overlapped with the responses produced by topotecan but differed from irinotecan's responses.

In contrast to the cap-dependent assays, all four compounds increased cap-independent translation at low doses (10 nM and 100 nM) but only camptothecin, rubitecan, and topotecan reduced fLUC activity at higher doses (5 uM and 10 uM) (FIG. 28C). Particularly noticeable was the effect of high concentrations of camptothecan and rubitecan which resulted in fLUC levels below those in the untreated control cells (<100%). This differed from the high dose topotecan assays, which only reduced translational activity to control cell levels. As expected, these results differed from the ones obtained for irinotecan, which demonstrated a constant level of fLUC activity at all tested concentrations.

FIG. 28D illustrates the use of a two-Toxin dose response assay using varying dosages of the TopoI inhibitors in combination with the 100 nM TPA translational activator. All four inhibitors acted synergistically with TPA at low doses to increase protein translation. At concentrations higher than 100 nM, camptothecin, rubitecan, and topotecan antagonized the TPA response and reduced the fLUC expression. As before, the high dose camptothecin and rubitecan antagonized total fLUC translation, and resulted in reporter protein levels below untreated control cells (<100%). In comparison, the high dose topotecan response exhibited basal level expression of the reporter protein. The irinotecan two-Toxin assays displayed synergistic action with TPA, and enhanced fLUC activity at all tested doses.

While not being bound to a particular theory, these results show that in addition to their known action on topoisomerase 1, low doses of the TopoI drugs can stimulate protein synthesis alone or in combination with TPA. In contrast, high doses of TopoI drugs inhibited translational activity with the greatest magnitude changes occurring in stimulated TR expressing cell lines. As expected, MCF7 cells lacked an enzyme system to convert irinotecan to its active form and resulted in a distinct translational regulation profile. However, an unexpected result was the ability of low doses of the inactive precursor to enhance translational activity alone or in combination with TPA. This application provides a system to intelligently design and test molecular models of TopoI inhibitor drug structures that specifically regulate translational responses.

D. Use of a Procedure Employing Combinatorial Toxin Assays of Translation Elongation Inhibitors to Detect Cap-Dependent and Cap-Independent Translational Regulation In this example (FIG. 33), single-Toxin and two-Toxin dose responses were used to define translational responses associated with translation inhibitors. Inhibitors of protein biosynthesis generally act by interfering with translational initiation (assembly of the components or structures required for translation) or elongation (enzymatic process of peptide synthesis and chain movement within the ribosome). A variety of translational inhibitors exist that affect each of these stages. Due to the fact that cap-dependent and cap-independent translation display distinct translational initiation mechanisms, this example focused on translational inhibitors associated with peptide elongation. Since the majority of these enzymatic processes are common to cap-dependent and cap-independent translation, any significant differences in chain elongation reflect differences in peptide synthesis.

For this example, the group of elongation inhibitors included cycloheximide (blocks the translocation step in protein synthesis), anisomycin (blocks the enzymatic peptidyl transferase activity in the 80S ribosome), puromycin (causes premature peptide chain termination by blocking the ribosomal A site) and emetine (binds the S14 protein of the 40S ribosomal subunit and prevents EF2-dependent peptide translocation). Although each drug alters a common ribosomal activity, each may affect distinct biological processes.

A dose response single-Toxin assay was used to examine translation regulation in HEK293 cells (FIG. 33A). Although many common effects were noted in cap-dependent and cap-independent assays, one particular trait of the elongation inhibitors is their ability to block total protein synthesis. For example, translation inhibition stops reporter protein production, and protein turnover reduces reporter activity below the basal level. In this example, a 250 nM concentration of each inhibitor was sufficient to reduce protein synthesis below control cell levels in cap-dependent and cap-independent assays (FIG. 33A). Furthermore, any dose above 2.5 uM produced only minimal additional reductions in reporter protein activity supporting the theory that translation in these assays had ceased. Using these assays' results, the 30-40% decline in fLUC protein activity suggested that the fLUC protein exhibits a half-life in excess of 6 hr in HEK293 cells.

In addition to this generalized translation regulation, distinct inhibitor-specific and cell-specific responses were also observed. For example, puromycin required a 2.5 uM concentration to reduce cap-dependent and cap-independent reporter protein activity to levels produced by the other three inhibitors. This suggests that a generalized difference in the binding or activity of puromycin can be detected in these assays. Similarly, anisomycin and emetine exhibited distinct activities in the HEK293 CMV-fLUC #3 (top panel) and mTRdm-fLUC #45 (bottom panel) subclones (FIG. 33A). In these cell lines, low doses of anisomycin (~25 nM) and emetine (100 nM) were sufficient to reduce reporter protein levels below the levels of untreated control cells. Since this effect was not observed in the hTRdmfLuc #13 subclone (middle panel), it may be possible that cell-specific differences in translational regulation result in enhanced sensitivity (lack of resistance of cell translation) for these compounds.

In a second effort, a two-Toxin dose response assay was performed by varying the concentration of the elongation inhibitors in combination with the 100 nM TPA activator (FIG. 33B). This combinatorial assay was designed to examine protein synthesis in stimulated cells preferentially translating the TR transcript. As in the single-Toxin assays, cap-dependent translation was arrested by 2.5 uM puromycin (top panel) which contrasted with the cap-independent assays where a 10× increase in puromycin concentration (25 uM) was needed to prevent new protein synthesis. However even at this highest tested dose, immediate translation inhibition was not observed in any cell line (FIG. 33C).

Comparing the HEK293 mTRdm-fLUC #45 and hTRdm-fLUC #13 subclones showed that the former exhibited little or no reduction below untreated control cell levels for cyclohex-imide, puromycin and emetine in TPA activated cells. Statistical analysis (bottom table) confirmed the significance of this variation. While the fLUC protein turnover estimate remained consistent in the TPA treated HEK293 CMV-fLUC #3 and hTRdm-fLUC #13 subclones (at ~6 hr), the lack of any decline in protein levels in the mTRdm-fLUC #45 subclone was inconsistent with protein turnover in this time period. Since the single-Toxin assays showed that the HEK293 mTRdm-fLUC #45 subclone was sensitive to these three inhibitors, this result supports the theory that protein turnover is reduced following exposure to TPA.

Of the other inhibitor-specific and cell-specific effects detected in this combinatorial assay, the most obvious was the antagonism of the TPA response (50-300% declines compared to the TPA single-Toxin assay) by 10 nM anisomycin in the cap-dependent and cap-independent assays. A similar effect was not observed in unstimulated cells.

Since the majority of the enzymatic processes should be common to cap-dependent and cap-independent translation, the significant differences in chain elongation detected in the TPA+inhibitor two-Toxin assays evidence unexpected fundamental differences in peptide synthesis. It seems likely that these differences involve subtle changes in ribosome structure or activity.

E. Use of an Updated 15-Assay Procedure to Detect Cap-Dependent and Cap-Independent Translational Regulation Progress in moving new chemical agents from a research to pharmaceutical setting is hindered by the lack of high information toxicology and safety evaluation procedures. In particular, predictive toxicology in drug development can be enhanced by databases of responses containing clinically relevant assays. To address these needs, FIG. 30 demonstrates an example of an Updated 15-Assay procedure that employs test agents drawn from human relevant sources, such as clinical trials and human approved drugs (Table 3). This example also includes cell lines expressing an alternative reporter protein (gLUC). This reporter provides a unique readout of protein synthesis, transport, and secretion, which is not available in fLUC expression system. The methods and procedures described in this example show that an unlimited number of assay procedures can be developed using any combination of drugs or processes with known or unknown translational regulation properties.

Application of single-Toxin and two-Toxin assays in the Updated 15-Assay protocol was used to define cap-dependent translational responses in the HEK293 CMV-fLuc #3 subclone (FIG. 30A). Although significant increases in cap-dependent fLuc synthesis were observed in most TPA assays, no synergistic effects were detected. In fact, the TPA response was antagonized by Velcade, calcimycin, and particularly by High Dose (HD) Topotecan. Minimal changes in the remaining assays suggested that cap-dependent translation did not respond significantly to these agents.

FIG. 30B and FIG. 30C show translational responses produced by the HEK293 mTRdm-fLuc #13 and mTRdm-gLuc #79 subclones. Even though the fLuc protein is a cytosolic protein subject to intracellular protein degradation systems and gLuc is a secreted protein that escapes intracellular degradation and accumulates extracellularly, the cap-independent expression profiles for these two subclones showed a strong correlation and exhibited similar differences to the cap-dependent assays of FIG. 30A. Significant increases in TR-specific translation were observed in all TPA assays with the exception of the TPA+Topotecan (HD) two-Toxin assay.

In contrast to the cap-dependent antagonism observed in the TPA+calcimycin two-Toxin assay, both cap-independent assays displayed a synergistic response by TPA and calcimycin that produced the largest translational increase in the Updated 15-Assay procedure. This suggests that TR-mediated translation is regulated by PKC and calcium ion concentration in HEK293 cells. Since the MTD cholchicine should prevent gLUC transport and secretion, the dominant effect produced by TPA and calcimycin in the two-Toxin assays appears to indicate that microtubule activity in HEK293 cells is regulated by PKC activity and calcium ion concentration.

F. Use of a 15-Assay Procedure to Detect Cap-Dependent and Cap-Independent translational regulation by a control compound, Termed a 21-Assay Protocol The combinatorial process described in this example provides a system for testing translational regulation by unknown compounds. In this example, a 21-Assay setup is described that employs the single and pairwise combinatorial application of 5 toxins, as in a standard 15-Toxin assay, and the addition of a sixth substance. Inclusion of the sixth substance requires the expansion of the assay group to a total of 21 single- and two-Toxin assays. For this example, a control substance (taxol) was selected from the original 15-Assay system. The methods and procedures described in this example show that an unlimited number of assay procedures can be developed using any number or combination of drugs or processes to define known or unknown translational regulation activity.

FIG. 31 shows the 21-Assay procedure using the control taxol. Comparing FIG. 30A with FIG. 31A shows similar translational profiles for the CMV-fLUC #3 subclone with the exception of the TPA+taxol two-Toxin assay. In this assay, a significant synergistic effect was observed that exceeded the translational response produced by the TPA+colchicine two-Toxin assay. No additional significant changes were observed in the remaining assays.

As in FIG. 30, the cap-independent HEK293 mTRdm-fLuc #13 (FIG. 31B) and mTRdm-gLuc #79 (FIG. 31C) subclones produced similar response profiles. In contrast to FIG. 31A, taxol exhibited small synergistic increases in combination with TPA and calcimycin. Comparing colchicine and taxol responses in the 21-Assay protocol provided further evidence for the previously described difference in these MTD drugs shown in FIG. 29. In HEK293 cells, the reduced translational activity exhibited by taxol in the single-Toxin dose response assays resulted in a taxol-specific synergistic response in the two-Toxin assay system. This effect was likely produced by distinct biological activity of these tubulin protein binding drugs on microtubules.

G. Use of a 15-Assay Procedure to Detect Cap-Dependent and Cap-Independent translational regulation by an unknown compound, Termed a 21-Assay Protocol The combinatorial process described in this section provides a system for testing translational regulation by unknown compounds. In this example, the unknown compound was a fluoroquinolone antibiotic which acts by inhibiting bacterial DNA gyrase and blocking cell division. Since the mammalian enzyme equivalents exhibit minimal binding, these antibiotics generally exhibit low toxicity. However, long term chronic treatment and drug-drug interactions can produce significant toxicity and cell death. This example investigated whether chronic exposure to a fluoroquinolone antibiotic produced cap-dependent or cap-independent translational responses. For this example, the 21-Assay procedure was used to detect translational responses associated with chronic antibiotic treatment of HepG2 hepatocellular carcinoma and HEK293 embryonic kidney cells. The Mycoplasma Removal Agent (MRA) or 4-oxoquinoline-3-carboxylic acid derivative was an antibiotic commonly applied to cultured mammalian cells to treat mycoplasma contamination. MRA exhibits minimal toxicity and can be applied for extended culture periods.

In this example, the MRA treated cells (+MRA) were incubated with about 150 nM MRA for 7 days prior to the 21-Assay procedure.

For untreated cultures of the HepG2 mTRdm-fLuc #16 subclone (−MRA), significant increases in TR-mediated cap-independent fLuc synthesis were observed in most Single- and two-Toxin TPA assays (FIG. 32A Top panel). However, prolonged exposure to MRA antagonized the TPA effect and produced a particularly large decrease in fLUC expression in the TPA+colchicine two-Toxin assay, where the +MRA culture exhibited about a 2.5-fold decrease in fLUC activity compared to untreated, −MRA cells. The specificity of this translational response is shown in FIG. 32A (Bottom panel), where the TPA assay group has been removed. No significant MRA-specific effects were observed in the remaining 15 assays.

A cell-specific response was observed in the HEK293 mTRdm-fLuc #45 subclone subjected to chronic MRA culture conditions. In this assay (FIG. 32B), a near uniform decrease in fLUC expression was observed across all of the 21-Assay results. However, as in FIG. 32A, the greatest magnitude translation declines were observed in the TPA single- and two-Toxin assays. These results support the theory that prolonged exposure to fluoroquinolone antibiotics can measurably affect the TR translational response by antagonizing toxin-specific phenotypes, in particular the TPA toxin.

Thus, the application of the single- and combinatorial toxin assay procedures to unknown molecules and processes provides a platform for rapidly identifying and defining cap-dependent and cap-independent translational regulators, which can help facilitate drug discovery and design, as well as enhance the predictive value of preclinical testing.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying drawing[s] shall be interpreted as illustrative and not in a limiting sense.

What is claimed is:

1. A method for identifying a subpopulation of mammalian cells that has a modest cap-independent translational response, a cap-independent translational response, or a high cap-independent translational response, wherein the method comprises:

treating a subset of mammalian cells with at least one toxin to form toxin-treated cells, the mammalian cells being stably transformed with a nucleic acid expression cassette comprising a translation regulated (TR) element encoding a mammalian mRNA molecule that is at least 80% homologous to a human Proteolipid Protein (plp) gene of SEQ ID NO: 4, is selectively translated in stressed and/or dying cells and does not direct translation of a PIRP-L or PIRP-M peptide, and a nucleotide sequence operably linked to the TR element, which encodes a reporter gene and is translated from the TR element, wherein the reporter gene of the nucleic acid expression cassette consists of only one reporter gene;

measuring a level of a reporter protein encoded by the reporter gene in the toxin-treated cells as compared with a level of the reporter protein expressed by a reference standard, the reference standard being mammalian cells stably transformed with the nucleic expression cassette and not treated with the at least one toxin;

wherein the subpopulation of the mammalian cells is identified as being class I cells that have a modest cap-independent translational response if the level of the reporter protein is up to 500% greater than the level of the reporter protein in the reference standard, the subpopulation of the mammalian cells is identified as being class II cells that have a cap-independent translational response if the level of the reporter protein is more than 500% and not more than 1,400% greater than the level of the reporter protein in the reference standard, and the subpopulation of the mammalian cells is identified as being class III cells that have a high cap-independent translational response if the level of the reporter protein is more than 1,400% and not more than 75,000% greater than the level of the reporter protein in the reference standard;

the method further comprising isolating at least one cell from the mammalian cells to form a cell culture if the toxin-treated cells of the mammalian cells exhibit a level of the reporter protein that is characteristic of a desired subpopulation of the mammalian cells;

growing the cell culture to form a subpopulation of mammalian cells; and optionally treating with the at least one toxin the subpopulation of mammalian cells and repeating the measuring, isolating, and growing steps until the desired subpopulation of mammalian cells is identified.

2. A method for identifying whether or not mammalian cell translation is resistant to a substance or for determining whether or not a substance is toxic to mammalian cells, the method comprising:

stably transforming the mammalian cells with a nucleic acid expression cassette comprising a translation regulated (TR) element encoding a mammalian mRNA molecule that is at least 80% homologous to a human Proteolipid Protein (plp) gene of SEQ ID NO: 4, is selectively translated in stressed and/or dying cells and does not direct translation of a PIRP-L or PIRP-M peptide, and a nucleotide sequence operably linked to the TR element, which encodes a reporter gene and is translated from the TR element, wherein the reporter gene of the nucleic acid expression cassette consists of only one reporter gene;

treating a subset of stably transformed mammalian cells with at least one toxin to form toxin-treated cells;

measuring a level of a reporter protein encoded by the reporter gene in the toxin-treated cells as compared with a level of the reporter protein expressed by a reference standard, the reference standard being mammalian cells stably transformed with the nucleic expression cassette and not treated with the at least one toxin;

wherein the subpopulation of the mammalian cells is identified as being class I cells that have a modest cap-independent translational response if the level of the reporter protein is up to 500% greater than the level of the reporter protein in the reference standard, the subpopulation of the mammalian cells is identified as being class II cells that have a cap-independent translational response if the level of the reporter protein is more than 500% and not more than 1,400% greater than the level of the reporter protein in the reference standard, and the subpopulation of the mammalian cells is identified as being class III cells that have a high cap-independent translational response if the level of the reporter protein is more than 1,400% and not more than 75,000% greater than the level of the reporter protein in the reference standard;

the method further comprising isolating at least one cell from the mammalian cells to form a cell culture if the toxin-treated cells of the mammalian cells exhibit a level of the reporter protein that is characteristic of a desired subpopulation of the mammalian cells;

growing the cell culture to form a subpopulation of mammalian cells;

optionally treating with the at least one toxin the subpopulation of mammalian cells and repeating the measuring, isolating, and growing steps until the desired subpopulation of mammalian cells is identified;

contacting the desired subpopulation of the mammalian cells with the substance; and detecting presence or measuring levels of the reporter protein after the desired subpopulation of the mammalian cells is contacted with the substance, wherein the toxicity of the substance and resistance of mammalian cell translation to the substance correlates to the presence or the increase in the level of the reporter protein as compared to control mammalian cells that are not exposed to the substance, and lack of toxicity to the substance and lack of resistance of mammalian cell translation to the substance correlates to the absence or the decrease in the level of the reporter protein as compared to control mammalian cells that are not exposed to the substance.

3. The method of claim 1, wherein the level of the reporter protein in the mammalian cells is measured when mRNA translational activity is at its peak within about 6 to about 18 hours following treatment with the at least one toxin.

4. The method of claim 3, wherein the level of the reporter protein in the mammalian cells is measured at least 6 hours after the mammalian cells are treated with the at least one toxin.

5. The method of claim 4, wherein the level of the reporter protein in the toxin-treated cells is measured at a time from 6 hours to about 30 hours after the mammalian cells are treated with the at least one toxin.

6. The method of claim 1, wherein the mammalian cells are treated with a combination of at least two toxins, a combination of at least three toxins, or a combination of at least five toxins.

7. The method of claim 6 wherein the combination of at least two toxins, at least three toxins or at least five toxins is selected from the group consisting of cAMP, TPA, paclitaxel, MG132, thapsigargin, nocodazole, vinblastin, Calcium Ionophore A23167, colchicine, bortezomib, hycamtin and 4-oxoquinoline-3-carboxylic acid derivative antibiotic.

8. The method of claim 1, wherein the mammalian cells are cancer cells or cancer stem cells, the mammalian cells are human primary cells or murine primary cells, the mammalian cells are selected from the group consisting of HEK293, HT1080, NTERA-2D, HeLa, Caco2, HepG2, HCT116, MDA231, U2 OS, DU145, LNCaP, LoVo, MiaPaCa2, AsPC1, MCF-7, PC3, Capan-2, COLO201, COLO205, H4, HuTu80, and SK-N-MC, or the mammalian cells are embryonic stem cells.

9. The method of claim 1, wherein the reporter gene is selected from the group consisting of EGFP, GFP, EYFP, Firefly Luciferase, *Gaussia* Luciferase, *Renilla* Luciferase, LacZ, CAT, TK, and TKsr39.

10. The method of claim 1 wherein the TR element is murine or human.

11. The method of claim 10, wherein the TR element is selected from the group consisting of SEQ ID NO: 1 (mouse dm TR), SEQ ID NO: 2 (mouse plp TR), SEQ ID NO: 3 (human dm TR) and SEQ ID NO: 4 (human plp TR).

12. The method of claim 1, wherein the toxin is selected from the group consisting of cAMP, TPA, paclitaxel, MG132, thapsigargin, nocodazole, vinblastin, Calcium Ionophore A23167, colchicine, bortezomib, hycamtin and 4-oxoquinoline-3-carboxylic acid derivative antibiotic.

13. The method of claim 1, wherein the screening comprises microplate reader analysis, fluorescence microscopy, immunohistochemistry, ELISA, luminometer, FACS, or spectrophotometer, and wherein the isolating of the subpopulation of the mammalian cells comprises single colony isolation by subcloning.

14. A method for determining the ability of a substance to inhibit protein translation in mammalian cells, wherein the method comprises:
treating a subset of mammalian cells with at least one toxin to form toxin-treated cells, the mammalian cells being stably transformed with a nucleic acid expression cassette comprising a translation regulated (TR) element encoding a mammalian mRNA molecule that is at least 80% homologous to a human Proteolipid Protein (plp) gene of SEQ ID NO: 4, is selectively translated in stressed and/or dying cells and does not direct translation of a PIRP-L or PIRP-M peptide, and a nucleotide sequence operably linked to the TR element, which encodes a reporter gene and is translated from the TR element, wherein the reporter gene of the nucleic acid expression cassette consists of only one reporter gene;
measuring a level of a reporter protein encoded by the reporter gene in the toxin-treated cells as compared with a level of the reporter protein expressed by a reference standard, the reference standard being mammalian cells stably transformed with the nucleic expression cassette and not treated with the at least one toxin;
wherein the subpopulation of the mammalian cells is identified as being class I cells that have a modest cap-independent translational response if the level of the reporter protein is up to 500% greater than the level of the reporter protein in the reference standard,
the subpopulation of the mammalian cells is identified as being class II cells that have a cap-independent translational response if the level of the reporter protein is more than 500% and not more than 1,400% greater than the level of the reporter protein in the reference standard, and
the subpopulation of the mammalian cells is identified as being class III cells that have a high cap-independent translational response if the level of the reporter protein is more than 1,400% and not more than 75,000% greater than the level of the reporter protein in the reference standard;
the method further comprising isolating at least one cell from the mammalian cells to form a cell culture if the toxin-treated cells of the mammalian cells exhibit a level of the reporter protein that is characteristic of a desired subpopulation of the mammalian cells;
growing the cell culture to form a subpopulation of mammalian cells; and
optionally treating with the at least one toxin the subpopulation of mammalian cells and repeating the measuring, isolating, and growing steps until the desired subpopulation of mammalian cells is identified;
contacting the desired subpopulation of mammalian cells with the substance; and
determining the expression of the reporter protein produced by the desired subpopulation of mammalian cells after contact with the substance as compared to the expression of the reporter protein by the mammalian cells which have not been treated with the substance, wherein reduction in the expression of the reporter protein produced by the substance-treated cells as compared to the expression of the reporter protein produced by the mammalian cells which have not been treated with the substance indicates that the substance inhibits protein translation.

\* \* \* \* \*

SEQUENCE LISTING

<160> NUMBER OF SEQ ID NOS: 10

<210> SEQ ID NO 1
<211> LENGTH: 726
<212> TYPE: DNA
<213> ORGANISM: Artificial Sequence
<220> FEATURE:
<223> OTHER INFORMATION: Murine TRdm

<400> SEQUENCE: 1
ttgagtgagt tagagtagtg agctagttgt ctggtagggg cccccttttgc ttccctggtg      60 gccactggat tgtgtttctt tggagtggca ctgttctgtg gatgtggaca tgaagctctc     120
actggtacag aaaagctaat tgagacctat ttctccaaaa actaccagga ctatgagtat     180

```
ctcattaatg tgattcatgc tttccagtat gtcatctatg aactgcctc tttcttcttc      240 ctttatgggg ccctcctgct ggctgagggc ttctacacca ccggcgctgt caggcagatc      300
tttggcgact acaagaccac catctgcggc aagggcctga gcgcaacgtt tgtgggcatc      360
acctatgccc tgactgttgt atggctcctg gtgtttgcct gctcggctgt acctgtgtac      420
atttacttca atacctggac cacctgtcag tctattgcct ccctagcaa gacctctgcc       480 agtataggca gtctctgcgc tgatgccaga ttgtatggtt tctcccatg gaatgctttc       540 cctggcaagg tttgtggctc caaccttctg tccatctgca aaacagctga gttccaattg      600
accttccacc tgtttattgc tgcgtttgtg ggtgctgcgg ccacactagt ttccctgctc      660
accttcatga ttgctgccac ttacaacttc gccgtcctta aactcatggg ccgaggcacc      720
aagttc                                                                 726

<210> SEQ ID NO 2
<211> LENGTH: 831
<212> TYPE: DNA
<213> ORGANISM: Artificial Sequence
<220> FEATURE:
<223> OTHER INFORMATION: Murine TRp1p

<400> SEQUENCE: 2
ttgagtgagt tagagtagtg agctagttgt ctggtagggg cccccttttgc ttccctggtg      60 gccactggat tgtgtttctt tggagtggca ctgttctgtg gatgtggaca tgaagctctc     120
actggtacag aaaagctaat tgagacctat ttctccaaaa actaccagga ctatgagtat     180
ctcattaatg tgattcatgc tttccagtat gtcatctatg aactgcctc tttcttcttc     240 ctttatgggg ccctcctgct ggctgagggc ttctacacca ccggcgctgt caggcagatc     300
tttggcgact acaagaccac catctgcggc aagggcctga gcgcaacggt aacaggggc      360 cagaaggga ggggttccag aggccaacat caagctcatt ctttggagcg ggtgtgtcat      420
tgtttgggaa aatggctagg acatcccgac aagtttgtgg gcatcaccta tgccctgact     480
gttgtatggc tcctggtgtt tgcctgctcg gctgtacctg tgtacattta cttcaatacc     540
tggaccacct gtcagtctat tgccttccct agcaagacct ctgccagtat aggcagtctc    600
tgcgctgatg ccagattgta tggtgttctc ccatggaatg cttttccctgg caaggtttgt     660 ggctccaacc ttctgtccat ctgcaaaaca gctgagttcc aattgacctt ccacctgttt    720
attgctgcgt tgtgggtgc tgcggccaca ctagtttccc tgctcacctt catgattgct     780
gccacttaca acttcgccgt ccttaaactc atgggccgag gcaccaagtt c              831

<210> SEQ ID NO 3
<211> LENGTH: 726
<212> TYPE: DNA
<213> ORGANISM: Artificial Sequence
<220> FEATURE:
<223> OTHER INFORMATION: Human TRdm

<400> SEQUENCE: 3
ttgagtgagt tagagtagtg agctagttgt ctggtagggg cccccttttgc ttccctggtg      60 gccactggat tgtgtttctt tggggtggca ctgttctgtg gctgtggaca tgaagccctc     120
actggcacag aaaagctaat tgagacctat ttctccaaaa actaccaaga ctatgagtat     180
ctcatcaatg tgattcatgc tttccagtat gtcatctatg aactgcctc tttcttcttc     240 ctttatgggg ccctcctgct ggctgagggc ttctacacca ccggcgcagt caggcagatc     300
```

```
tttggcgact acaagaccac catctgcggc aagggcctga gcgcaacgtt tgtgggcatc    360
acctatgccc tgaccgttgt gtggctcctg gtgtttgcct gctctgctgt gcccgtgtac    420
atttacttca acacctggac cacctgcgac tctattgcct tccccagcaa gacctctgcc    480
agtataggca gtctctgtgc tgacgccaga ttgtatggtg ttctcccatg gaatgctttc    540
cctggcaagg tttgtggctc caaccttctg tccatctgca aaacagctga gttccaattg    600
accttccacc tgtttattgc tgcatttgtg ggggctgcag ccacactggt ttccctgctc    660
accttcatga ttgctgccac ttacaacttt gccgtcctta aactcatggg ccgaggcacc    720
aagttc                                                               726

<210> SEQ ID NO 4
<211> LENGTH: 831
<212> TYPE: DNA
<213> ORGANISM: Artificial Sequence
<220> FEATURE:
<223> OTHER INFORMATION: Human TRp1p

<400> SEQUENCE: 4
ttgagtgagt tagagtagtg agctagttgt ctggtagggg ccccctttgc ttccctggtg     60
gccactggat tgtgtttctt tggggtggca ctgttctgtg gctgtggaca tgaagccctc    120
actggcacag aaaagctaat tgagacctat ttctccaaaa actaccaaga ctatgagtat    180
ctcatcaatg tgattcatgc tttccagtat gtcatctatg aactgcctc tttcttcttc    240 ctttatgggg ccctcctgct ggctgagggc ttctacacca ccggcgcagt caggcagatc    300
tttggcgact acaagaccac catctgcggc aagggcctga gcgcaacggt aacaggggc    360 cagaaggga ggggttccag aggccaacat caagctcatt ctttggagcg ggtgtgtcat    420
tgtttgggaa aatggctagg acatcccgac aagtttgtgg gcatcaccta tgccctgacc    480
gttgtgtggc tcctggtgtt tgcctgctct gctgtgcccg tgtacattta cttcaacacc    540
tggaccacct gcgactctat tgccttcccc agcaagacct gccagtat aggcagtctc    600 tgtgctgacg ccagattgta tggtgttctc ccatggaatg ctttccctgg caaggtttgt    660
ggctccaacc ttctgtccat ctgcaaaaca gctgagttcc aattgacctt ccacctgttt    720
attgctgcat ttgtgggggc tgcagccaca ctggtttccc tgctcacctt catgattgct    780
gccacttaca actttgccgt ccttaaactc atgggccgag gcaccaagtt c             831

<210> SEQ ID NO 5
<211> LENGTH: 834
<212> TYPE: PRT
<213> ORGANISM: Artificial Sequence
<220> FEATURE:
<223> OTHER INFORMATION: PLP/DM20 Vertebrate Consensus Sequence

<400> SEQUENCE: 5

Ala Thr Gly Gly Gly Tyr Tyr Lys Gly Tyr Trp Asp Gly Ala Lys Lys
1               5                   10                  15

Gly Tyr Thr Gly Tyr Arg Tyr Asn Met Gly Met Thr Gly Tyr Met Thr
            20                  25                  30

Asx Arg Thr Trp Gly Gly Gly Tyr Met Cys Cys Met Thr Thr Tyr
        35                  40                  45

Gly Cys Tyr Thr Cys His Asx Thr Ser Arg Thr Asx Gly Cys Cys Ala
    50                  55                  60

Cys Trp Gly Lys Val Tyr Thr Val Thr Gly Tyr Thr Thr Tyr Lys Tyr
65                  70                  75                  80
```

```
Thr Gly Gly Arg Gly Thr Ser Gly Cys Val Cys Thr Val Thr Thr Cys
                 85                  90                  95
Thr Gly Tyr Gly Gly Met Thr Gly Tyr Gly Gly Arg Cys Ala Tyr Gly
            100                 105                 110
Ala Arg Gly Cys His Tyr Thr Val Ala Ser Tyr Gly Gly His Ala Cys
            115                 120                 125
Met Gly Ala Arg Met Ala Gly Tyr Thr Val Ala Thr Tyr Gly Ala Gly
            130                 135                 140
Ala Cys Met Thr Ala Tyr Thr Thr Tyr Thr Cys Cys Ala Ala Arg Ala
145                 150                 155                 160
Ala Tyr Thr Ala Cys Cys Ala Gly Ala Met Thr Ala Tyr Gly Ala
                165                 170                 175
Arg Thr Ala Tyr Cys Thr Cys Ala Thr Val Ala Tyr Gly Thr Ser
            180                 185                 190
Ala Thr Tyr Met Ala Tyr Gly Cys Tyr Thr Thr Tyr Cys Ala Gly Thr
            195                 200                 205
Ala Tyr Gly Thr Cys Ala Thr Cys Thr Ala Thr Gly Gly Ala Ala Tyr
210                 215                 220
Trp Gly Cys Cys Trp Tyr Tyr Thr Thr Cys Thr Thr Cys Thr Thr Tyr
225                 230                 235                 240
Cys Thr His Thr Trp Tyr Gly Gly Arg Arg Tyr Cys Cys Thr Val Cys
                245                 250                 255
Thr Lys Tyr Thr Gly Gly Cys Tyr Gly Ala Arg Gly Gly Met Thr Thr
            260                 265                 270
Cys Thr Ala Cys Ala Cys Ala Cys Met Arg Ser Tyr Gly Cys His
            275                 280                 285
Arg Thr Cys Ala Arg Gly Cys Ala Val Ala Thr Cys Tyr Thr His Gly
            290                 295                 300
Gly Ser Gly Ala Ser Thr Trp Cys Met Arg Arg Met Cys Cys Met Cys
305                 310                 315                 320
Met Arg Tyr Tyr Trp Lys Met Arg Arg Ser Arg Lys Gly Gly Ser
                325                 330                 335
Cys Thr Gly Ala Lys Tyr Lys Cys Trp Ala Cys Arg Gly Thr Arg Ala
            340                 345                 350
Cys Trp Gly Gly Arg Gly Gly Met Cys Met Lys Ala Ala Arg Gly Gly
            355                 360                 365
Gly Ala Gly Arg Arg Gly His Asp Cys Ser Met Gly Arg Gly Gly Met
            370                 375                 380
Met Val Val Cys Ala Lys Cys Val Ala Gly Tyr Tyr Cys Ala Tyr Trp
385                 390                 395                 400
Cys Tyr Trp Thr Arg Ser Ala Gly Cys Lys Ser Arg Thr Ser Thr Gly
                405                 410                 415
Thr Cys Arg Asx Thr Gly Tyr Thr Thr Gly Gly Ala Ala Ala Arg
            420                 425                 430
Thr Gly Gly Cys Thr Met Gly Gly Ala Cys Ala Tyr Cys Cys Tyr Gly
            435                 440                 445
Ala Tyr Ala Ala Gly Thr Thr Thr Gly Thr Ser Gly Gly Tyr Arg Thr
            450                 455                 460
Tyr Ala Cys Tyr Thr Ala Thr Arg Tyr Tyr His Thr Ser Ala Cys Tyr
465                 470                 475                 480
Arg Thr Tyr Lys Thr Val Thr Gly Gly Met Thr Met Cys Thr Arg Arg
                485                 490                 495
Tyr Ser Thr Thr Tyr Gly Cys Cys Thr Gly Cys Thr Cys Asp Gly Cys
```

```
            500             505             510
Tyr Gly Thr Asp Cys Cys Tyr Gly Thr Val Thr Ala Cys Ala Thr Tyr
        515             520             525
Thr Ala Tyr Thr Thr Tyr Ala Ala Tyr Ala Cys Thr Gly Gly Arg
    530             535             540
Tyr Cys Ala Cys Tyr Thr Gly Tyr Cys Ala Gly Thr Cys Thr Ala Thr
545             550             555             560
Tyr Gly Cys Cys Lys Tyr Cys Cys Cys His Arg Ser Ser Ala Ala Gly
            565             570             575
Ala Cys Tyr Trp Cys Trp Arg Cys Cys Ala Gly Tyr Arg Thr Met Arg
            580             585             590
Gly Tyr Ala Ser Asx Cys Thr Ser Thr Gly Tyr Lys Cys Asp Gly Ala
            595             600             605
Tyr Gly Ser Tyr Met Gly Val Ala Thr Gly Thr Ala Tyr Gly Gly Thr
            610             615             620
Gly Thr Tyr Cys Thr Ser Cys Cys Met Thr Gly Gly Ala Ala Tyr Gly
625             630             635             640
Cys Asx Thr Thr Tyr Cys Cys His Gly Gly Ser Ala Ala Arg Gly Thr
                645             650             655
Lys Thr Gly Tyr Gly Gly Ser Trp Cys Cys Ala Arg Cys Cys Thr Lys
            660             665             670
Cys Thr Asx Lys Cys Cys Ala Thr Cys Thr Gly Cys Ala Ala Arg Ala
            675             680             685
Cys Met Arg Ser Tyr Gly Ala Gly Thr Thr Cys Cys Ala Arg Ala Thr
            690             695             700
Gly Ala Cys Asn Thr Thr Tyr Cys Ala Tyr Cys Thr Asx Thr Thr Thr
705             710             715             720
Ala Thr Tyr Gly Cys Lys Gly Cys Val Thr Thr Tyr Gly Thr Gly Gly
                725             730             735
Gly Lys Gly Cys Trp Gly Cys Asn Gly Cys His Ala Cys Trp Cys Thr
            740             745             750
Asp Gly Thr Asx Lys Cys Met Cys Thr Gly Cys Thr Cys Ala Cys Tyr
            755             760             765
Thr Trp Tyr Ala Thr Gly Arg Thr His Gly Ser Tyr Gly Cys Met Trp
    770             775             780
Cys Trp Thr Trp Cys Ala Ala Cys Thr Trp Tyr Gly Cys Tyr Gly Thr
785             790             795             800
Ser Cys Thr Asx Met Arg Ala Ser Thr Asx Ala Tyr Lys Gly Gly Cys
                805             810             815
Cys Gly Arg Arg Gly Cys Trp Cys Met Ala Gly Thr Thr Tyr Thr
            820             825             830
Gly Ala

<210> SEQ ID NO 6
<211> LENGTH: 834
<212> TYPE: DNA
<213> ORGANISM: Mus musculus

<400> SEQUENCE: 6
atgggcttgt tagagtgttg tgctagatgt ctggtagggg ccccctttgc ttccctggtg    60
gccactggat tgtgtttctt tggagtggca ctgttctgtg atgtggaca tgaagctctc    120 actggtacag aaaagctaat tgagacctat ttctccaaaa actaccagga ctatgagtat    180
ctcattaatg tgattcatgc tttccagtat gtcatctatg gaactgcctc tttcttcttc    240
```

```
ctttatggggg ccctcctgct ggctgagggc ttctacacca ccggcgctgt caggcagatc    300
tttggcgact acaagaccac catctgcggc aagggcctga gcgcaacggt aacagggggc    360
cagaagggga ggggttccag aggccaacat caagctcatt ctttggagcg ggtgtgtcat    420
tgtttgggaa aatggctagg acatcccgac aagtttgtgg gcatcaccta tgccctgact    480
gttgtatggc tcctggtgtt tgcctgctcg gctgtacctg tgtacattta cttcaatacc    540
tggaccacct gtcagtctat tgccttccct agcaagacct ctgccagtat aggcagtctc    600
tgcgctgatg ccagaatgta tggtgttctc ccatggaatg cttttccctgg caaggtttgt    660 ggctccaacc ttctgtccat ctgcaaaaca gctgagttcc aaatgacctt ccacctgttt    720
attgctgcgt tgtgggtgc tgcggccaca ctagtttccc tgctcacctt catgattgct    780
gccacttaca acttcgccgt ccttaaactc atgggccgag gcaccaagtt ctga          834
```

```
<210> SEQ ID NO 7
<211> LENGTH: 729
<212> TYPE: DNA
<213> ORGANISM: Mus musculus

<400> SEQUENCE: 7
atgggcttgt tagagtgttg tgctagatgt ctggtagggg ccccctttgc ttccctggtg     60
gccactggat tgtgtttctt tggagtggca ctgttctgtg gatgtggaca tgaagctctc    120
actggtacag aaaagctaat tgagacctat ttctccaaaa actaccagga ctatgagtat    180
ctcattaatg tgattcatgc tttccagtat gtcatctatg gaactgcctc tttcttcttc    240 ctttatggggg ccctcctgct ggctgagggc ttctacacca ccggcgctgt caggcagatc    300
tttggcgact acaagaccac catctgcggc aagggcctga gcgcaacgtt tgtgggcatc    360
acctatgccc tgactgttgt atggctcctg gtgtttgcct gctcggctgt acctgtgtac    420
atttacttca atacctggac cacctgtcag tctattgcct tccctagcaa gacctctgcc    480
agtataggca gtctctgcgc tgatgccaga atgtatggtg ttctcccatg gaatgctttc    540
cctggcaagg tttgtggctc caaccttctg tccatctgca aaacagctga gttccaaatg    600
accttccacc tgtttattgc tgcgtttgtg ggtgctgcgg ccacactagt ttccctgctc    660
accttcatga ttgctgccac ttacaacttc gccgtcctta aactcatggg ccgaggcacc    720
aagttctga                                                             729
```

```
<210> SEQ ID NO 8
<211> LENGTH: 729
<212> TYPE: DNA
<213> ORGANISM: Homo sapiens

<400> SEQUENCE: 8
atgggcttgt tagagtgctg tgcaagatgt ctggtagggg ccccctttgc ttccctggtg     60
gccactggat tgtgtttctt tggggtggca ctgttctgtg gctgtggaca tgaagccctc    120
actggcacag aaaagctaat tgagacctat ttctccaaaa actaccaaga ctatgagtat    180
ctcatcaatg tgatccatgc cttccagtat gtcatctatg gaactgcctc tttcttcttc    240 ctttatggggg ccctcctgct ggctgagggc ttctacacca ccggcgcagt caggcagatc    300
tttggcgact acaagaccac catctgcggc aagggcctga gcgcaacgtt tgtgggcatc    360
acctatgccc tgaccgttgt gtggctcctg gtgtttgcct gctctgctgt gcccgtgtac    420
atttacttca acacctggac cacctgcgac tctattgcct tccccagcaa gacctctgcc    480
```

```
agtataggca gtctctgtgc tgacgccaga atgtatggtg ttctcccatg gaatgctttc      540
cctggcaagg tttgtggctc caaccttctg tccatctgca aaacagctga gttccaaatg      600
accttccacc tgtttattgc tgcatttgtg ggggctgcag ctacactggt ttccctgctc      660
accttcatga ttgctgccac ttacaacttt gccgtcctta aactcatggg ccgaggcacc      720
aagttctga                                                              729

<210> SEQ ID NO 9
<211> LENGTH: 850
<212> TYPE: DNA
<213> ORGANISM: Homo sapiens

<400> SEQUENCE: 9
atgggcttgt tagagtgctg tgcaagatgt ctggtagggg ccccctttgc ttccctggtg       60
gccactggat tgtgtttctt tggggtggca ctgttctgtg gctgtggaca tgaagccctc      120
actggcacag aaaagctaat tgagacctat ttctccaaaa actaccaaga ctatgagtat      180
ctcatcaatg tgatccatgc cttccagtat gtcatctatg aactgcctc tttcttcttc      240 ctttatgggg ccctcctgct ggctgagggc ttctacacca ccggcgcagt caggcagatc      300
tttggcgact acaagaccac catctgcggc aagggcctga gcgcaacggt aacaggggc      360 cagaagggga ggggttccag aggccaacat caagctcatt ctttggagcg gtgtgtcat      420 tgtttgggaa aatggctagg acatcccgac aagtttgtgg gcatcaccta tgccctgacc      480
gttgtgtggc tcctggtgtt tgcctgctct gctgtgcccg tgtacattta cttcaacacc      540
tggaccacct gcgactctat tgccttcccc agcaagacct ctgccagtat aggcagtctc      600
tgtgctgacg ccagaatgta tggtgttctc ccatggaatg cttttccctgg caaggtttgt      660 ggctccaacc ttctgtccat ctgcaaaaca gctgagttcc aaatgacctt ccacctgttt      720
attgctgcat tgtggggc tgcagctaca ctggtttccc tgctcacctt catgattgct      780
gccacttaca actttgccgt ccttaaactc atgggccgag gcaccaagtt ctgatacact      840
ggtttccctg                                                             850

<210> SEQ ID NO 10
<211> LENGTH: 834
<212> TYPE: DNA
<213> ORGANISM: Artificial Sequence
<220> FEATURE:
<223> OTHER INFORMATION: Mammalian PLP consensus sequence
<220> FEATURE:
<221> NAME/KEY: misc_feature
<222> LOCATION: (24)..(24)
<223> OTHER INFORMATION: n is a, c, g, or t

<400> SEQUENCE: 10
atgggcytgt tagagtgytg ygcnagatgy ctsgtagggg ccccctttgc ttccytggtg       60
gccactggat trtgtttctt tggrgtggca ctsttctgtg gmtgtggaca tgaagchytm      120
actggyacag aaaagytaat tgagacmtat ttctccaaaa aytaccaaga ctaygagtat      180
ctcatyaatg tgatycatgc yttccagtat gtcatctatg aactgcctc tttcttcttc      240 ctttatgggg ccctcctgct ggcygagggc ttctacacca ccggygcwgt caggcagatc      300
tttggcgact acaagaccac catctgcggs aagggcctga gygcaacggt aacaggggc      360 cagaagggga ggggttccag aggccaacat caagctcatt ctttggagcg gtgtgtcat      420 tgtttgggaa aatggctagg acatcccgac aagtttgtgg gcatcaccta tgccytgacy      480
gttgtrtggc tcctrgtgtt tgcctgctck gctgtrcctg tgtacattta yttcaayacc      540
```

```
tggaccacyt gycagtctat tgcckycccy agcaagacyt ctgccagyat aggcastctc    600
tgygctgatg ccagaatgta tggtgttctc ccatggaatg ctttyccwgg caargtktgt    660
ggctccaacc ttctgtccat ctgcaaaaca gctgagttcc aaatgacstt ccayctgttt    720
attgctgcvt tygtgggkgc tgcrgcyaca ctrgtktccc tgctcacctt catgattgct    780
gccacttaca acttygccgt cctkaaactc atgggccgag gcaccaagtt ctga          834
```